United States Patent
Kallen et al.

(10) Patent No.: US 12,036,277 B2
(45) Date of Patent: **\*Jul. 16, 2024**

(54) VACCINATION WITH mRNA-CODED ANTIGENS

(71) Applicant: CureVac SE, Tübingen (DE)

(72) Inventors: Karl-Josef Kallen, Tübingen (DE);
Thomas Kramps, Tübingen (DE);
Margit Schnee, Tübingen (DE);
Benjamin Petsch, Tübingen (DE);
Lothar Stitz, Rottenburg (DE)

(73) Assignee: CureVac SE, Tübingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/596,451

(22) Filed: Mar. 5, 2024

(65) Prior Publication Data

US 2024/0197857 A1 Jun. 20, 2024

Related U.S. Application Data

(63) Continuation of application No. 15/452,658, filed on Mar. 7, 2017, now Pat. No. 11,975,064, which is a continuation of application No. 15/015,458, filed on Feb. 4, 2016, which is a continuation of application No. 13/824,589, filed as application No. PCT/EP2012/000878 on Feb. 29, 2012, now abandoned.

(30) Foreign Application Priority Data

Mar. 2, 2011 (WO) .................. PCT/EP2011/001043

(51) Int. Cl.
*A61K 39/145* (2006.01)
*A61K 39/00* (2006.01)
*A61K 39/12* (2006.01)
*A61K 45/06* (2006.01)
*C12N 7/00* (2006.01)

(52) U.S. Cl.
CPC ............ *A61K 39/145* (2013.01); *A61K 39/00* (2013.01); *A61K 39/0011* (2013.01); *A61K 39/12* (2013.01); *A61K 45/06* (2013.01); *C12N 7/00* (2013.01); *A61K 2039/53* (2013.01); *A61K 2039/54* (2013.01); *A61K 2039/55* (2013.01); *A61K 2039/55505* (2013.01); *A61K 2039/5555* (2013.01); *A61K 2039/55555* (2013.01); *A61K 2039/572* (2013.01); *A61K 2039/585* (2013.01); *A61K 2039/6031* (2013.01); *A61K 2039/622* (2013.01); *A61K 2039/70* (2013.01); *C12N 2760/16134* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 8,592,385 B2 | 11/2013 | Kataoka et al. | |
| 9,254,265 B2 | 2/2016 | Geall et al. | |
| 9,872,900 B2 | 1/2018 | Ciaramella et al. | |
| 10,702,600 B1 | 7/2020 | Ciaramella et al. | |
| 10,933,127 B2 | 3/2021 | Ciaramella et al. | |
| 2005/0032730 A1 | 2/2005 | Von Der Mulbe et al. | |
| 2005/0059624 A1 | 3/2005 | Hoerr et al. | |
| 2005/0250723 A1 | 11/2005 | Hoerr et al. | |
| 2006/0188490 A1 | 8/2006 | Kretschmer et al. | |
| 2007/0105193 A1 | 5/2007 | Vilalta et al. | |
| 2007/0280929 A1 | 12/2007 | Hoerr et al. | |
| 2008/0025944 A1 | 1/2008 | Hoerr et al. | |
| 2008/0171711 A1 | 7/2008 | Hoerr et al. | |
| 2008/0175863 A1 | 7/2008 | Jin et al. | |
| 2008/0181911 A1 | 7/2008 | Hanon et al. | |
| 2008/0267873 A1 | 10/2008 | Hoerr et al. | |
| 2009/0136543 A1 | 5/2009 | Ballou et al. | |
| 2009/0246855 A1 | 10/2009 | Fouchier et al. | |
| 2009/0324584 A1 | 12/2009 | Hoerr et al. | |
| 2010/0048883 A1 | 2/2010 | Ketterer et al. | |
| 2010/0189729 A1 | 7/2010 | Hoerr et al. | |
| 2010/0203076 A1 | 8/2010 | Fotin-Mleczek et al. | |
| 2010/0239608 A1 | 9/2010 | Von Der Mülbe et al. | |
| 2010/0291156 A1 | 11/2010 | Barner et al. | |
| 2010/0305196 A1 | 12/2010 | Probst et al. | |
| 2011/0053829 A1 | 3/2011 | Baumhof et al. | |
| 2011/0250225 A1 | 10/2011 | Fotin-Mleczek et al. | |

(Continued)

FOREIGN PATENT DOCUMENTS

| | | |
|---|---|---|
| DE | 102004035227 | 2/2006 |
| DE | 102006007433 | 8/2007 |

(Continued)

OTHER PUBLICATIONS

"150318.P1194.3.1_E20 bRSV Calf study," CureVac Presentation, 2015.

(Continued)

*Primary Examiner* — Michael D Burkhart

(74) *Attorney, Agent, or Firm* — Parker Highlander PLLC

(57) ABSTRACT

The present invention relates to vaccines comprising at least one mRNA encoding at least one antigen for use in the treatment of a disease in an elderly patient preferably exhibiting an age of at least 50 years, more preferably of at least 55 years, 60 years, 65 years, 70 years, or older, wherein the treatment comprises vaccination of the patient and eliciting an immune response in said patient. The present invention is furthermore directed to kits and kits of parts comprising such a vaccine and/or its components and to methods applying such a vaccine or kit.

24 Claims, 10 Drawing Sheets

Figure 2:
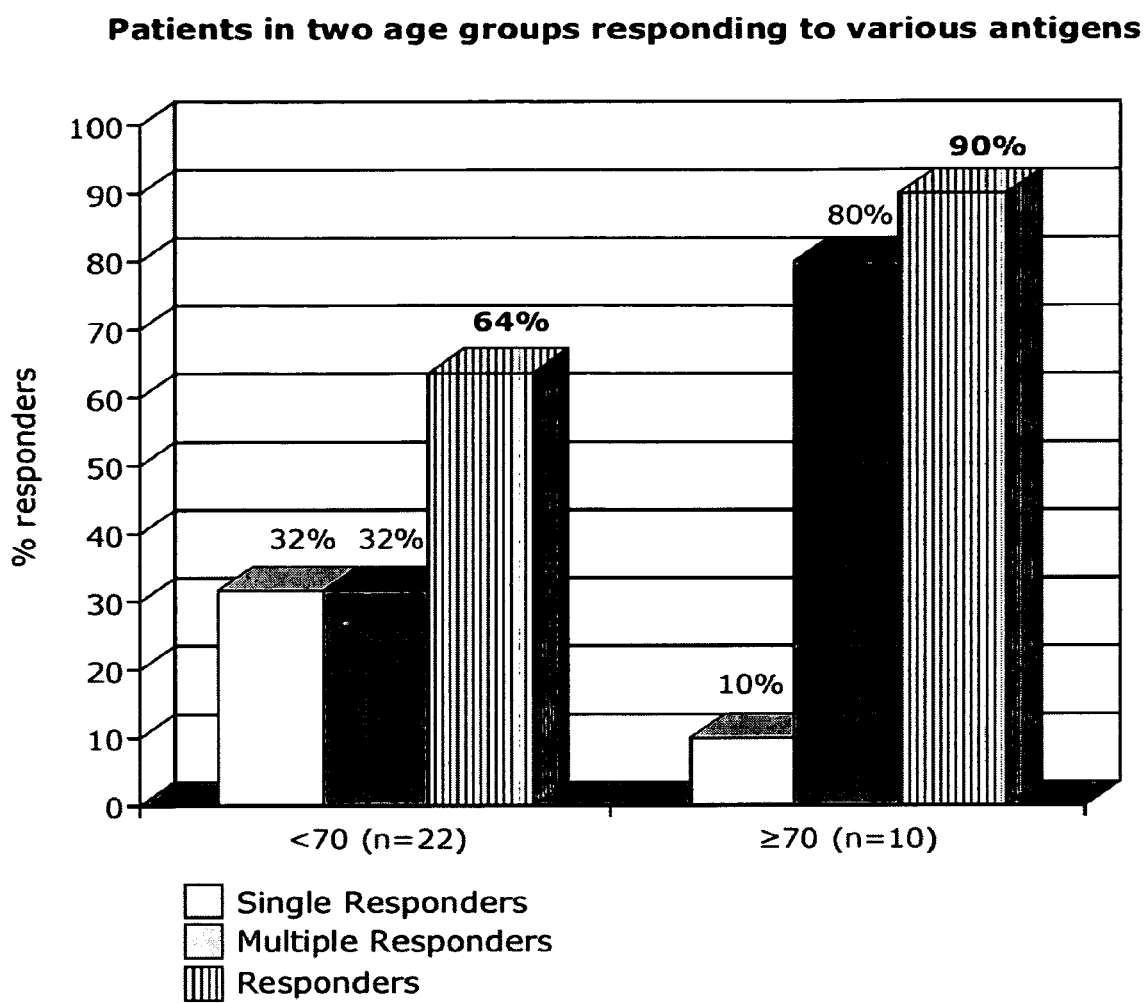

Specification includes a Sequence Listing.

(56) References Cited

U.S. PATENT DOCUMENTS

| | | |
|---|---|---|
| 2012/0021043 A1 | 1/2012 | Kramps et al. |
| 2012/0258046 A1 | 10/2012 | Mutzke |
| 2013/0129754 A1 | 5/2013 | Thess et al. |
| 2013/0142818 A1 | 6/2013 | Baumhof et al. |
| 2013/0259879 A1 | 10/2013 | Baumhof et al. |
| 2013/0280283 A1 | 10/2013 | Lorenz et al. |
| 2013/0295043 A1 | 11/2013 | Kallen et al. |
| 2013/0336998 A1 | 12/2013 | Kallen et al. |
| 2015/0037326 A1 | 2/2015 | Butler-Ransohoff et al. |
| 2015/0050302 A1 | 2/2015 | Thess |
| 2015/0057340 A1 | 2/2015 | Thess et al. |
| 2015/0093413 A1 | 4/2015 | Thess et al. |
| 2015/0118183 A1 | 4/2015 | Baumhof |
| 2015/0118264 A1 | 4/2015 | Baumhof et al. |
| 2015/0165006 A1 | 6/2015 | Thess et al. |
| 2015/0184195 A1 | 7/2015 | Thess et al. |
| 2015/0218554 A1 | 8/2015 | Thess |
| 2015/0306249 A1 | 10/2015 | Baumhof et al. |
| 2015/0320847 A1 | 11/2015 | Thess et al. |
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0235864 A1 | 8/2016 | Schlake et al. |
| 2016/0304883 A1 | 10/2016 | Grund et al. |
| 2016/0304938 A1 | 10/2016 | Wochner |
| 2016/0326575 A1 | 11/2016 | von der Mülbe |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |
| 2017/0114378 A1 | 4/2017 | Wochner et al. |
| 2017/0252430 A1 | 9/2017 | Fotin-Mleczek et al. |
| 2017/0326225 A1 | 11/2017 | Rauch et al. |
| 2018/0044687 A1 | 2/2018 | Thess et al. |
| 2018/0125952 A1 | 5/2018 | Fotin-Mleczek et al. |
| 2018/0126003 A1 | 5/2018 | Hoerr |
| 2018/0142275 A1 | 5/2018 | Roos et al. |
| 2018/0147146 A1 | 5/2018 | Eber et al. |
| 2018/0148727 A1 | 5/2018 | Grund et al. |
| 2018/0201967 A1 | 7/2018 | Eber et al. |
| 2018/0208957 A1 | 7/2018 | Roos et al. |
| 2018/0214537 A1 | 8/2018 | Mutzke et al. |
| 2018/0237786 A1 | 8/2018 | Schlake et al. |
| 2018/0237817 A1 | 8/2018 | Roos et al. |
| 2018/0243219 A1 | 8/2018 | Ketterer et al. |
| 2018/0296663 A1 | 10/2018 | Hipp et al. |
| 2018/0298372 A1 | 10/2018 | Funkner et al. |
| 2018/0312545 A1 | 11/2018 | Baumhof et al. |
| 2018/0371392 A1 | 12/2018 | Mayer et al. |
| 2019/0010485 A1 | 1/2019 | Yazdan Panah et al. |
| 2019/0017100 A1 | 1/2019 | Wochner et al. |
| 2019/0024096 A1 | 1/2019 | Schmid et al. |
| 2020/0197510 A1 | 6/2020 | Ciaramella et al. |
| 2021/0162037 A1 | 6/2021 | Jasny et al. |

FOREIGN PATENT DOCUMENTS

| | | |
|---|---|---|
| EP | 1083232 | 3/2001 |
| EP | 1905844 | 12/2002 |
| WO | WO 1998/019710 | 5/1998 |
| WO | WO 1998/047913 | 10/1998 |
| WO | WO 2002/098443 | 12/2002 |
| WO | WO 2003/059381 | 7/2003 |
| WO | WO 2003/068942 | 8/2003 |
| WO | WO 2006/046978 | 5/2006 |
| WO | WO 2006/078294 | 7/2006 |
| WO | WO 2007/031319 | 3/2007 |
| WO | WO 2007/069068 | 6/2007 |
| WO | WO 2007/099660 | 9/2007 |
| WO | WO 2008/014979 | 2/2008 |
| WO | WO 2008/022046 | 2/2008 |
| WO | WO 2009/030254 | 3/2009 |
| WO | WO 2009/030481 | 3/2009 |
| WO | WO 2009/046739 | 4/2009 |
| WO | WO 2009/046975 | 4/2009 |
| WO | WO 2009/079796 | 7/2009 |
| WO | WO 2009/095226 | 8/2009 |
| WO | WO 2010/037408 | 4/2010 |
| WO | WO 2010/037539 | 4/2010 |
| WO | WO 2010/088927 | 8/2010 |
| WO | WO 2011/026641 | 3/2011 |
| WO | WO 2012/013326 | 2/2012 |
| WO | WO 2012/019630 | 2/2012 |
| WO | WO 2012/019780 | 2/2012 |
| WO | WO 2012/113413 | 8/2012 |
| WO | WO 2013/182683 | 12/2013 |
| WO | WO 2015/024665 | 2/2015 |
| WO | WO 2015/024669 | 2/2015 |
| WO | WO 2016/184576 | 11/2016 |
| WO | WO 2017/021546 | 2/2017 |
| WO | WO 2017/025447 | 2/2017 |
| WO | WO 2017/064146 | 4/2017 |
| WO | WO 2017/081110 | 5/2017 |
| WO | WO 2017/109134 | 6/2017 |
| WO | WO 2017/137095 | 8/2017 |
| WO | WO 2017/140345 | 8/2017 |
| WO | WO 2017/140905 | 8/2017 |
| WO | WO 2017/149139 | 9/2017 |
| WO | WO 2017/162297 | 9/2017 |
| WO | WO 2017/182634 | 10/2017 |
| WO | WO 2017/186928 | 11/2017 |
| WO | WO 2017/191264 | 11/2017 |
| WO | WO 2017/191274 | 11/2017 |
| WO | WO 2017/203008 | 11/2017 |
| WO | WO 2017/212006 | 12/2017 |
| WO | WO 2017/212007 | 12/2017 |
| WO | WO 2017/212009 | 12/2017 |
| WO | WO 2019/008001 | 1/2019 |
| WO | WO 2019/232103 | 12/2019 |

OTHER PUBLICATIONS

"CureVac Advances Seasonal Flu Study to Phase 2 in Collaboration with GSK Following Selection of Promising mRNA Vaccine Candidate with Broad Coverage", press release, Sep. 12, 2023, pp. 1-3.

"CureVac Announces Solid Progress in Phase 2 COVID-19 and Seasonal Flu Clinical Development Programs in Collaboration with GSK", press release, Nov. 1, 2023, pp. 1-3.

"CureVac Final Data from Phase 2b/3 Trial of First-Generation COVID-19 Vaccine Candidate, CVnCoV, Demonstrates Protection in Age Group of 18 to 60", press release, Jun. 30, 2021.

"CureVac: Final Analysis of Pivotal Phase 2b/3 Herald Study", presentation, Jul. 1, 2021.

"Final Analysis of Phase 2b/3 Clinical Trial of First-Generation COVID-19 Vaccine Candidate, CVnCoV", transcript of conference call, Jul. 1, 2021.

"Immunogenicity and vaccine efficacy," In Atkinson et al. ed., Epidemiology and Prevention of Vaccine-Preventable Diseases, $12^{th}$ Ed., p. 159 and 309-311, 2011.

"Invivofectamine® 2.0 Reagent," Invitrogen Life Technologies, 2011.

"Licensure of a high-dose inactivated influenza vaccine for persons aged ≥65 years (fluzone high-dose) and guidance for use—United States, 2010," *Morbidity and Mortality Weekly Report*, 59(16):485-486, 2010.

"Lipofectamine™ 2000," Invitrogen life technologies, 2002.

"Messenger RNA", Wikipedia, Retrieved from the Internet: URL:https://en.wikipedia.org/wiki/Messenger_RNA.

"Moderna Announces Positive Phase 1/2 Data from mRNA-1083, the Company's Combination Vaccine Against Influenza and COVID-19", press release, Oct. 4, 2023, pp. 1-4.

"T helper cell," Wikipedia, located at https://en.wikipedia.org/wiki/T_helper_cell, 2020.

"The UK immunization programme", UK NHS Green Book, Chapter 11, 2011.

"Various forms of signal 3 induce the differentiation of naïve CD4T cells down distinct effector pathways," In Janeway's Immuno Biology, $7^{th}$ Ed., Chapter 8, pp. 352-353, 2008.

(56) References Cited

OTHER PUBLICATIONS

Adams et al., "Immunization of malignant melanoma patients with full-length NY-ESO-1 protein using TLR7 agonist imiquimod as vaccine adjuvant," *J Immunol.*, 181:776-784, 2008.

Aliprantis et al., "A phase 1, randomized, placebo-controlled study to evaluate the safety and immunogenicity of an mRNA-based RSV prefusion F protein vaccine in healthy younger and older adults," Human Vaccines & Immunotherapeutics, 17(5):1248-1261, 2020.

American Geriatrics Society, "A pocket guide to common immunizations for the older adult (>65 Years)", https://web.archive.org/web/20101226070627/https://www.americangeriatrics.org/file/documents/AGS_PocketGuide.pdf, 2010.

Anderson et al., "Safety and immunogenicity of SARS-CoV-2 mRNA-1273 vaccine in older adults," *N Engl J Med.*, 383:2427-2438, 2020.

Antohi et al., "The reactivity pattern of hemagglutinin-specific clonotypes from mice immunized as neonates or adults with naked DNA," *International Immunology*, 10(4):663-668, 1998.

Appeal Brief filed in U.S. Appl. No. 17/067,614, dated Apr. 18, 2022.

Appeal Brief filed in U.S. Appl. No. 17/067,709, filed Apr. 14, 2022.

Arulanandam et al., "IL-12 is a potent neonatal vaccine adjuvant," *Eur. J. Immunol.*, 29:256-264, 1999.

Arulanandam et al., "Neonatal administration of IL-12 enhances the protective efficacy of antiviral vaccines," *The Journal of Immunology*, 164:3698-3704, 2000.

Bahl et al., "Preclinical and clinical demonstration of immunogenicity by mRNA vaccines against H10N8 and H7N9 influenza viruses," *Molecular Therapy*, 25(6):1316-1327, 2017.

Belshe et al., "Live attenuated versus inactivated influenza vaccine in infants and young children," *N Engl J Med.*, 356(7):685-696, 2007.

Belshe, "The need for quadrivalent vaccine against seasonal influenza," *Vaccine*, 28(Suppl 4):D45-D53, 2010.

Bettinger et al., "Peptide-mediated RNA delivery: a novel approach for enhanced transfection of primary and post-mitotic cells," *Nucleic Acids Research*, 29(18):3882-3891, 2001.

Bolhassani et al., "Improvement of different vaccine delivery systems for cancer therapy," *Molecular Cancer*, 10(1):3, 2011.

Bona, "Cell-mediated immune responses in neonates," Neonatal Immunity. Humana Press: Totowa, N.J., pp. 241-251, 2005.

Bot et al., "Enhanced protection against influenza virus of mice immunized as newborns with a mixture of plasmids expressing hemagglutinin and nucleoprotein," *Vaccine*, 16(17):1675-1682, 1998.

Bot et al., "Genetic immunization of neonates," *Microbes and Infection*, 4(4):511-520, 2002.

Bot et al., "Induction of humoral and cellular immunity against influenza virus by immunization of newborn mice with a plasmid bearing a hemagglutinin gene," International Immunology, 9(11):1641-1650, 1997.

Bot et al., "Protective cellular immunity against influenza virus induced by plasmid inoculation of newborn mice," *Developmental Immunology*, 5:197-210, 1998.

Boudet, "Vaccines for the elderly: the quest for the ideal animal model," Journal of Comparative Pathology 142 (2010): S70-S73.

Brito et al., "Non-viral eNOS gene delivery and transfection with stents for the treatment of restenosis," *Biomed Eng. Online*, 9:56, 2010.

Burke et al., "Extracellular barriers to in vivo PEI and PEGylated PEI polyplex-mediated gene delivery to the liver," *Bioconjugate Chem.*, 19(3):693-704, 2008.

Carralot et al., "Polarization of immunity induced by direct injunction of naked sequence-stabilized mRNA vaccines," *Cell Mol Life Sci.*, 61(18):2418-2424, 2004.

Casciato et al., "Manual of Clinical Oncology," Lippincott Williams & Wilkins, 6th Edition, 2009.

CDC (US), "Recommended Immunization Schedules for Persons Aged 0-18 years—United States, 2011," 2011.

Chen et al., "Vaccination in the elderly: an immunological perspective," *Trends Immunol.*, 30(7):351-359, 2009.

Communication by European Patent Office in Opposition in European Application No. 12706489.7, dated Sep. 23, 2020.

Communication by Graf von Stosch in Opposition in European Application No. 12706489.7, dated Jul. 21, 2020.

Communication by Vossius & Partner in Opposition in European Application No. 12706489.7, dated Jul. 21, 2020.

Communication in Opposition in European Application No. 12706489.7 regarding Oral Proceedings of Mar. 22, 2021.

Communication in Opposition in European Application No. 12706489.7, mailed Mar. 23, 2021.

Communication in Opposition in European Application No. 12706489.7, mailed Mar. 24, 2021.

Communication in Opposition in European Application No. 12706489.7, mailed Aug. 12, 2020.

Communication in Opposition in European Application No. 12706489.7, mailed Dec. 18, 2019.

Communication in Opposition in European Application No. 12706489.7, mailed Jan. 21, 2021.

Communication in Opposition in European Application No. 12706489.7, mailed Jan. 22, 2021.

Communication in Opposition in European Application No. 12706489.7, Further Experimental Data in Aged Mice, dated Jul. 21, 2020.

Communication in Opposition in European Application No. 12706489.7, dated Jul. 26, 2018.

Communication in Opposition in European Application No. 12706489.7, Opposition Data, dated Jul. 26, 2018.

Communication in Opposition in European Application No. 12706489.7, dated Mar. 22, 2016.

Corbett et al., "Ontogeny of toll-like receptor mediated cytokine responses of human blood mononuclear cells," PLOS One, 5(11):e15041, 2010.

Corder et al., "A decade in review: A systematic review of universal influenza vaccines in clinical trials during the 2010 decade," Viruses, 12:1-22, 2020.

Cox et al., "Influenza Virus: Immunity and Vaccination Strategies. Comparison of the Immune Response to Inactivated and Live, Attenuated Influenza Vaccines," *Scand. J. Immunol.*, 59:1-15, 2004.

CureVac Investor Presentation, "Revolutionizing mRNA for life" pp. 1-52, Nov. 2023.

Danhier et al., "PLGA-based nanoparticles: an overview of biomedical applications," *J Control Release*, 161(2):505-522, 2012.

Database Uniprot, Accession No. A0A068IZQ2, Oct. 1, 2014.

Database Uniprot, Accession No. A0A097PG98, Jan. 7, 2015.

Database Uniprot, Accession No. A0A0N9RU18, Jan. 20, 2016.

Database Uniprot, Accession No. Q67043, Nov. 1, 1996.

Debus et al., "Delivery of messenger RNA using poly(ethylene imine)-poly(ethylene glycol)-copolymer blends for polyplex formation: biophysical characterization and in vitro transfection properties," *Journal of Controlled Release*, 148:334-343, 2010.

Decision on Appeal issued in U.S. Appl. No. 15/015,458, mailed Nov. 24, 2020.

Declaration Under 37 C.F.R. § 1.132 for U.S. Appl. No. 15/015,458, submitted Oct. 30, 2018.

Declaration Under 37 C.F.R. § 1.132 for U.S. Appl. No. 16/264,073, submitted Jun. 11, 2020.

Deering et al., "Nucleic acid vaccines: prospects for non-viral delivery of mRNA vaccines," *Expert Opinion on Drug Delivery*, 11(6): 885-899, 2014.

Deguchi. "Vaccination of influenza vaccine to the elderly subjects, high-risk subjects, medical care workers," *The Japanese Journal of Clinical and Experimental Medicine*, 81(12): 1938-1942, 2004.

Demirjian and Levy, "Safety and efficacy of neonatal vaccination," *Eur J. Immunol.*, 39(1):36-46, 2009.

Deshayes et al., "Cell-penetrating peptides: tools for intracellular delivery of therapeutics," *Cell Mol Life Sci.*, 62(16):1839-1849, 2005.

Dutta et al., "Men and mice: relating their ages," *Life Sciences*, 152:244-248, 2016.

Espeseth et al., "Modified mRNA/lipid nanoparticle-based vaccines expressing respiratory syncytial virus F protein variants are immunogenic and protective in rodent models of RSV infection", *NPJ Vaccines*, 5(16), 2020.

(56) References Cited

OTHER PUBLICATIONS

European Centre for Disease Prevention and Control, "Guidance: Priority Risk Groups for Influenza Vaccination", 2008.
Fajac et al., "Histidylated polylysine as a synthetic vector for gene transfer into immortalized cystic fibrosis airway surface and airway gland serous cells," *J Gene Med.*, 2(5):368-378, 2000.
Falsey et al., "Respiratory Syncytial Virus Infection in Elderly and High-Risk Adulst," N Engl J Med, 352:1749-1759, 2005.
Fillit et al., Brocklehurst's Textbook of Geriatric Medicine and Gerontology, Sounders/Elsevier, 2010.
Flurkey et al., "Mouse models in aging research," In Fox et al., eds. The Mouse in Biomedical Research, 2nd Edition. New York; Elsevier, vol. 3, Chapter 20, pp. 637-672, 2007.
Foerg et al., "On the biomedical promise of cell penetrating peptides: limits versus prospects," *J Pharm Sci.*, 97(1):144-162, 2008.
Form S-1 Registration Statement for Moderna, Inc., filed with the Securities and Exchange Commission on Nov. 9, 2018.
Fotin-Mleczek et al., "Messenger RNA-based vaccines with dual activity induce balanced TLR-7 dependent adaptive immune responses and provide antitumor activity," *Journal of Immunotherapy*, 34(1):1-15, 2011.
Fujita et al., "Calcium enhanced delivery of tetraarginine-PEG-lipid-coated DNA/protamine complexes," *International Journal of Pharmaceutics*, 368(1-2):186-192, 2009.
Fülöp et al., "Immunosupportive therapies in aging," *Clinical Interventions in Aging*, 2(1):33-54, 2007.
Gao et al., "Nonviral gene delivery: what we know and what is next," *AAPS J.*, 9(1):E92-104, 2007.
Garinot et al., "PEGylated PLGA-based nanoparticles targeting M cells for oral vaccintation," *Journal of Controlled Release*, 120(3):195-204, 2007.
Gervassi and Horton, "Is infant immunity actively suppressed or immature?" *Virology: Research and Treatment*, 4(5):1-9, 2014.
Giel-Peitraszuk Malgorzata et al., Database Biosis, DB Acc. No. Prev199800116011, 1997.
Goodwin et al., "Antibody response to influenza vaccination in the elderly: a quantitative review," *Vaccine*, 24:1159-1169, 2006.
Gorbalenya et al., "The species Severe acute respiratory syndrome-related coronavirus: classifying 2019-nCoV and naming it SARS-CoV-2," Nat. Microbiology, 5:536-544, 2020.
Gravekamp et al., "Cancer vaccines in old age," *Experimental Gerontology*, 42(5):441-450, 2007.
Grubeck-Loebenstein et al., "Immunosenescence and vaccine failure in the elderly," *Aging Clinical and Experimental Research*, 21:201-209, 2009.
Hamidi et al., "Pharmacokinetic consequences of pegylation," *Drug Deliv.*, 13(6):399-409, 2006.
Hassett et al., "Optimization of lipid nanoparticles for intramuscular administration of mRNA vaccines", *Mol. Ther. Nucleic Acids*, 15:1-11, 2019.
Heil et al., "Species-specific recognition of single-stranded RNA via toll-like receptor 7 and 8," *Science*, 303:1526-1529, 2004.
Hemmi et al., "A toll-like receptor recognizes bacterial DNA," *Nature*, 408(6813):740-745, 2000.
Hoerr et al., "In vivo application of RNA leads to induction of specific cytotoxic T lymphocytes and antibodies," *Eur. J. Immunol.*, 30(1):1-7, 2000.
Hoft et al., "Comparisons of the Humoral and Cellular Immune Responses Induced by Live Attenuated Influenza Vaccine and Inactivated Influenza Vaccine in Adults," *Clinical and Vaccine Immunology*, 24(1):e00414-16, 2017.
Ishii, "Influenza vaccination to the elderly patients, the dual activity induce balanced TLR-7 dependent adaptive immune responses and provide antitumor activity," *Journal of Immunotherapy*, 34(1):1-15, 2011.
Jiang et al., "SARS vaccine development," Emerging Infectious Diseases, 11(7):1016-1020, 2005.
Jing et al., "Aging is associated with a numerical and functional decline in plasmacytoid dendritic cells, whereas myeloid dendritic cells are relatively unaltered in human peripheral blood," *Human Immunology*, 70(10):777-784, 2009.
Johansson et al., "Intradermal electroporation of naked replicon RNA elicits strong immune responses," *PLOS One*, 7(1):e29732, 2012.
Katz et al., "Immunity to influenza: the challenges of protecting an aging population", *Immunologic Research*, 29(1-3):113-124, 2004.
Kim et al., "HIV Vaccines—Lessons learned and the way forward," Curr Opin HIV AIDS 5:428-434, 2010.
Koup and Douek, "Vaccine design for CD8 T lymphocyte responses," *Cold Spring Harb Prospect.*, 1(1):a007252, 2011.
Kovarik et al., "Optimization of vaccine response in early life: the role of delivery systems and immunomodulators," *Immunology and Cell Biology*, 76(3):222-236, 1998.
Krieg et al., "The role of CpG dinucleotides in DNA vaccines," *Trends in Microbiology*, 6(1):23-27, 1998.
Kudla et al., "High guanine and cytosine content increases mRNA levels in mammalian cells," PLoS Biology, 4, 2006.
Kusters et al., "Manufacturing vaccines for an emerging viral infection—specific issues associated with the development of a prototype SARS vaccine," Vaccine for Biodefense and Emerging and Neglected Diseases, 147-156, 2009.
Kuznik et al., "Recognition of nucleic acids by toll-like receptors and development of immunomodulatory drugs," *Current Medicinal Chemistry*, 17:1899-1914, 2010.
Kwok et al., "Formulation of highly soluble poly(ethylene glycol)-peptide DNA condensates," *J Pharm Sci.*, 88(10):996-1003, 1999.
La Gruta et al., "T Cell Mediated Immunity to Influenza: Mechanisms of Viral Control," *Trends in Immunology*, 35(8):396-402, 2014.
Lazzaro et al., "CD8 T-cell priming upon mRNA vaccination in restricted to bone-marrow derived antigen-presenting cells and may involve antigen transfer from myovytes," *Immunology*, 146:312-326, 2015.
Lochmann et al., "Drug delivery of oligonucleotides by peptides," *European Journal of Pharmaceutics and Biopharmaceutics*, 58(2):237-251, 2004.
Louten, "Virus structure and classification," Essential Human Virology, Chapter 2, pp. 19-29, 2016.
Lutz et al., "Unmodified mRNA in LNPs constitutes a competitive technology for prophylactic vaccines," *npj Vaccines*, 2:29, 2017.
MacLachlan, "Liposomal formulations for nucleic acid delivery," In Crooke, ed. Antisense Drug Technology: Principles, Strategies, and Applications, 2$^{nd}$ Edition, Chapter 9, pp. 237-270, 2007.
Maletto et al., "CpG-DNA stimulates cellular and humoral immunity and promotes Th1 differentiation in aged BALB/c mice," *Journal of Leukocyte Biology*, 72:447-454, 2002.
Martin et al., "Peptide-guided gene delivery," *AAPS J.*, 9(1):E18-29, 2007.
Martinez et al., "Combining DNA and protein vaccines for early life immunization against respiratory syncytial virus in mice," *Eur. J. Immunol.*, 29:3390-3400, 1999.
Mattner et al., "Vaccination with poly-I-arginine as immunostimulant for peptide vaccines: induction of potent and long-lasting t-cell response against cancer antigens," *Cancer Research*, 62:1477-1480, 2002.
McElhaney et al., "T Cell Responses Are Better Correlates of Vaccine Protection in the Elderly", *J. Immunol.*, 176(10):6333-6339, 2006.
Moderna R&D day and business updates, "Expanding the field of mRNA medicine," pp. 1-150, Sep. 13, 2023.
Moderna, Inc. Form S-1 Registration Statement, U.S. Securities and Exchange Commission, 2018.
Moingeon, "Strategies for designing vaccines eliciting Th1 responses in humans," *Journal of Biotechnology*, 98:189-198, 2002.
Naito et al., "High Risk Group of Influenza," *Jutendo Medical Journal*, 50(2):161-165, 2004.
Nakamura et al., "Octaarginin-modified multifunctional envelope-type nano device for siRNA," *J Control Release*, 119(3):360-367, 2007.
National Immunisation Office (Ireland), "Previous Immunisation Schedules", 2017.

(56) References Cited

OTHER PUBLICATIONS

Neu et al., "Recent advances in rational gene transfer vector design based on poly(ethylene imine) and its derivatives," *J Gene Med.*, 7(8):992-1009, 2005.
Nichol et al., "Effectiveness of influenza vaccine in the community-dwelling elderly", New Engl. J. Med., 357:1373-1381, 2007.
Nickol et al., "Effectiveness of influenza vaccine in the community-dwelling elderly," *N Engl J Med*, 357:1373-1381, 2007.
Notice of Allowance issued in U.S. Appl. No. 13/824,705, mailed Feb. 9, 2017.
Office Communication issued in U.S. Appl. No. 13/824,589, mailed Mar. 27, 2015.
Office Communication issued in U.S. Appl. No. 13/824,705, mailed Feb. 27, 2015.
Office Communication issued in U.S. Appl. No. 13/824,705, mailed Jul. 31, 2014.
Office Communication issued in U.S. Appl. No. 13/824,705, mailed Nov. 19, 2015.
Office Communication issued in U.S. Appl. No. 15/015,458, mailed Apr. 30, 2018.
Office Communication issued in U.S. Appl. No. 15/015,458, mailed Feb. 7, 2019.
Office Communication issued in U.S. Appl. No. 15/015,458, mailed Jan. 10, 2020.
Office Communication issued in U.S. Appl. No. 15/015,458, mailed Nov. 24, 2020.
Office Communication issued in U.S. Appl. No. 15/015,458, mailed Feb. 4, 2021.
Office Communication issued in U.S. Appl. No. 15/015,458, mailed Aug. 16, 2021.
Office Communication issued in U.S. Appl. No. 15/015,458, mailed Apr. 1, 2022.
Office Communication issued in U.S. Appl. No. 15/015,458, mailed Oct. 27, 2022.
Office Communication issued in U.S. Appl. No. 15/015,458, mailed Aug. 18, 2023.
Office Communication issued in U.S. Appl. No. 15/015,458, mailed Feb. 1, 2024.
Office Communication issued in U.S. Appl. No. 15/452,658, mailed Sep. 16, 2021.
Office Communication issued in U.S. Appl. No. 15/452,658, mailed Aug. 7, 2020.
Office Communication issued in U.S. Appl. No. 15/452,658, mailed Sep. 4, 2019.
Office Communication issued in U.S. Appl. No. 15/452,658, mailed Feb. 4, 2021.
Office Communication issued in U.S. Appl. No. 15/452,658, mailed Feb. 24, 2020.
Office Communication issued in U.S. Appl. No. 15/452,658, mailed May 2, 2018.
Office Communication issued in U.S. Appl. No. 15/452,658, mailed Feb. 7, 2019.
Office Communication issued in U.S. Appl. No. 15/452,658, mailed Nov. 30, 2023.
Office Communication issued in U.S. Appl. No. 15/452,658, mailed Feb. 28, 2023.
Office Communication issued in U.S. Appl. No. 16/264,073, mailed Apr. 5, 2019.
Office Communication issued in U.S. Appl. No. 16/264,073, mailed Aug. 16, 2021.
Office Communication issued in U.S. Appl. No. 16/264,073, mailed Dec. 11, 2019.
Office Communication issued in U.S. Appl. No. 16/264,073, mailed Feb. 4, 2021.
Office Communication issued in U.S. Appl. No. 16/264,073, mailed Jun. 26, 2020.
Office Communication issued in U.S. Appl. No. 16/910,845, mailed Jun. 9, 2022.
Office Communication issued in U.S. Appl. No. 16/910,845, mailed Sep. 20, 2021.
Office Communication issued in U.S. Appl. No. 17/067,614, mailed Apr. 1, 2021.
Office Communication issued in U.S. Appl. No. 17/067,614, mailed Dec. 10, 2020.
Office Communication issued in U.S. Appl. No. 17/067,614, mailed Jul. 20, 2022.
Office Communication issued in U.S. Appl. No. 17/067,614, mailed Oct. 18, 2021.
Office Communication issued in U.S. Appl. No. 17/067,709, mailed Jul. 14, 2021.
Office Communication issued in U.S. Appl. No. 17/067,709, mailed Jul. 19, 2022.
Office Communication issued in U.S. Appl. No. 17/067,709, mailed Mar. 10, 2021.
Office Communication issued in U.S. Appl. No. 17/067,709, mailed Nov. 27, 2020.
Office Communication issued in U.S. Appl. No. 17/067,709, mailed Oct. 18, 2021.
Office Communication issued in U.S. Appl. No. 17/090,885, mailed Feb. 18, 2021.
Ohfuji et al., "Target groups of influenza vaccination," *Japanese Journal of Public Health*, 54(6):361-367, 2007.
Opposition to European Patent No. EP 2680880 by Strawman Limited, filed Dec. 18, 2017.
Opposition to European Patent No. EP 2680881 by Strawman Limited, filed Dec. 18, 2017.
Oupicky et al., "Importance of lateral and steric stabilization of polyelectrolyte gene delivery vectors for extended systemic circulation," *Mol Ther.*, 5(4):463-472, 2002.
Oupicky et al., "Laterally stabilized complexes of DNA with linear reducible polycations: strategy for triggered intracellular activation of DNA delivery vectors," *J Am Chem Soc.*, 124(1):8-9, 2002.
Panda et al., "Age-associated decrease in TLR function in primary human dendritic cells predicts influenza vaccine response," *The Journal of Immunology*, 184:2518-2527, 2010.
Parker et al., "Enhanced gene transfer activity of peptide-targeted gene-delivery vectors," *J Drug Target*, 13(1):39-51, 2005.
Pascolo, "Vaccination with messenger RNA (mRNA)," *Handbook of Experimental Pharmacology*, 183:221-235, 2008.
Perlman et al., "Immunopathogenesis of coronavirus infections: Implications for SARS," Nature Reviews Immunology, 5:917-927, 2005.
Petsch et al., "Protective efficacy of in vitro synthesized, specific mRNA vaccines against influenza A virus infection," *Nature Biotechnology*, 30(12):1210-1216, 2012.
Petsch, Declaration Under 37 C.F.R. § 1.132, submitted in U.S. Appl. No. 13/824,705, executed Jul. 27, 2015.
Petsch, Declaration Under 37 C.F.R. § 1.132, submitted in U.S. Appl. No. 15/466,308, executed Jun. 8, 2018.
Philbin et al., "Developmental Biology of the Innate Immune Response: Implications for Neonatal and Infant Vaccine Development," Pediatric Research, 65:98R-105R, 2009.
Pichon et al., "Poly[Lys-(AEDTP)]: a cationic polymer that allows dissocation of pDNA/cationic polymer complexes in a reductive medium and enhances polyfection," Bioconjug Chem., 13(1):76-82, 2002.
Polack et al., "Safety and efficacy of the BNT162b2 mRNA covid-19 vaccine," *The New England Journal of Medicine*, 383(27):2603-2615, 2020.
Pomroy et al., "Solubilization of hydrophobic peptides by reversible cysteine PEGylation," *Biochem Biophys Res Commun.*, 245(2):618-621, 1998.
Radu et al., "Plasmid expressing the influenza HA gene protects old mice from lethal challenge with influenza virus," *Viral Immunology*, 12(3):217-226, 1999.
Read et al., "A versatile reducible polycation-based system for efficiency delivery of a broad range of nucleic acids," *Nucleic Acids Res.*, 33(9):e86, 2005.
Read et al., "RNA-based therapeutic strategies for cancer," *Expert Opinion on Therapeutic Patents*, 13(5):627-638, 2003.
Read et al., "Vectors based on reducible polycations facilitate intracellular release of nucleic acids," *J Gene Med*, 5(3):232-245, 2003.

(56) References Cited

OTHER PUBLICATIONS

Reichmuth et al., "mRNA vaccine delivery using lipid nanoparticles," *Therapeutic Delivery*, 7(5):319-334, 2016.
Reply Brief filed in U.S. Appl. No. 17/067,614, dated Sep. 20, 2022.
Response to Office Action for U.S. Appl. No. 15/015,458, submitted Oct. 30, 2018.
Richner et al., "Modified mRNA vaccines protect against Zika virus infection", *Cell*, 168(6):1114-1125, 2017.
Riedl et al., "The novel adjuvant IC31® strongly improves influenza vaccine-specific cellular and humoral immune responses in young adult and aged mice," *Vaccine*, 26:3461-3468, 2008.
Rittig et al., "Intradermal vaccinations with RNA coding for TAA generate CD8+ and CD4+ immune response and induce clinical benefit in vaccinated patients," *Molecular Therapy*, 19(5):990-999, 2010.
Sakae et al., "Highly efficient in vivo gene transfection by pasmid/ PEI complexes coated by anionic PEG derivatives bearing carboxy groups and RGD peptide," *Biomedicine and Pharmacotherapy*, 62(7):448-453, 2008.
Sarzotti et al., "Induction of protective CTL responses in newborn mice by a murine retrovirus," *Science*, 271(5256):1726-1728, 1996.
Scheel et al., "Therapeutic anti-tumor immunity triggered by injections of immunostimulating single-stranded RNA," *Eur J Immunol.*, 36(10):2807-2816, 2006.
Scheel et al., "Toll-like receptor-dependent activation of several human blood cell types by protamine-condensed mRNA," *Eur J Immunol.*, 35(5):1557-1566, 2005.
Shaw et al., "Dysregulation of human toll-like receptor function in aging," *Ageing Res Rev.*, 10(3):346-353, 2011.
Shiffman et al., "Portein dissociation from DNA in model systems and chromatin," *Nucleic Acids Res.*, 5(9):3409-3426, 1978.
Siegrist and Aspinall, "B-cell response to vaccination at the extremes of age," *Immunology*, 9:185-194, 2009.
Smith et al., "Identification of common biological pathways and drug targets across multiple respiratory viruses based on human host gene expression analysis," *PLoS One*, 7(3):e33174, 2012.
Sugaya, "Influenza vaccine", *The Journal of Pediatric Practice*, 64(11):1913-1918, 2004.
Sun et al., "Role of T Cell Immunity in Recovery From Influenza Virus Infection," *Curr Opin Virol.*, 3(4):425-429, 2013.
Takae et al., "PEG-detachable polyplex micelles based on disulfide-linked block catiomers as bioresponsive nonviral gene vectors," *J Am Chem Soc*, 130(18):6001-6009, 2008.
Third Party Observation issued in U.S. Appl. No. 15/015,458, mailed on Sep. 1, 2017.
Third Party Observation issued in U.S. Appl. No. 15/437,405, mailed on Oct. 20, 2017.
Third Party Observation issued in U.S. Appl. No. 15/452,658, mailed on Sep. 1, 2017.
Third Party Observation issued in U.S. Appl. No. 15/466,308, mailed on Oct. 20, 2017.
Third Party Observation issued in U.S. Appl. No. 16/910,845, mailed on Apr. 22, 2022.
Thompson and Locarnini, "Toll-like receptors, RIG-I-like RNA helicases and the antiviral innate immune response," *Immunology and Cell Biology*, 85(6):435-445, 2007.
Tönges et al., "Steraylated octaarginine and artificial virus-like particles for transfection of siRNA into primary rat neurons," *RNA*, 12(7):1431-1438, 2006.

Tummala et al., "Clinical immunology: immune senescence and the acquired immune deficiency of aging," Brocklehurst's Textbook of Geriatric Medicine and Gerontology, Sounders/Elsevier, Chapter 13, 2010.
U.S. Appl. No. 63/498,544, entitled Influenza Cocktail Vaccines, filed on Apr. 27, 2023.
UK Joint Committee on Vaccination and Immunisation, "Statement on varicella and herpes zoster vaccines", 2010.
Unicef, "Immunization Summary: A statistical reference containing data through 2011," 2013.
Unnamali et al., "Cationic oligopeptide-mediated delivery of dsRNA for post-transcriptional gene silencing in plant cells," *FEBS Lett.*, 566(1-3):307-310, 2004.
Van Duin et al., "Age-associated defect in human TLR-1/2 function," *J Immunol.*, 178:970-975, 2007.
Vives et al., "A truncated HIV-1 Tat protein basic domain rapidly translocates through the plasma membrane and accumulates in the cell nucleus," *J Biol Chem.*, 272925):16010-16017, 1997.
Wang et al., "An intracellular delivery method for siRNA by an arginine-rich peptide," *J Biochem Biophys Methods*, 70(4):579-586, 2007.
Weide et al., "Direct injection of protamine-protected mRNA: results of a phase 1/2 vaccination trial in metastatic melanoma patients," *J Immunother.*, 32(5):498-507, 2009.
Weinberger et al. "Biology of immune responses to vaccines in elderly persons," *Clinical Infection Diseases*, 46(7):1078-1084, 2008.
Widman et al., "RepliVAX WN, a single-cycle flavivirus vaccine to prevent West Nile disease, elicits durable protective immunity in hamsters," Vaccine, 27:5550-5553, 2009.
Wilschut, "Influenza vaccines: the virosome concept," *Immunology Letters*, 122:118-121, 2009.
Wong et al., "An mRNA vaccine for influenza," *Nature Biotechnology*, 30(12): 1202-1204, 2012.
Yager et al., "Age-associated decline in T cell repertoire diversity leads to holds in the repertoire and impaired immunity to influenza virus," *The Journal of Experimental Medicine*, 205(3):711-723, 2008.
Yamamoto et al., "Current prospects for mRNA gene delivery," *European Journal of Pharmaceutics and Biopharmaceutics*, 71:484-489, 2009.
Yamano et al., "Comparison of transfection efficiency of nonviral gene transfer reagents," *Mol Biotechnol.*, 46:287-300, 2010.
Yoshitomi et al., "Design of core—shell-type nanoparticles carrying stable radicals in the core", *Biomacromolecules*, 10:596-601, 2009.
Yu et al., "A new insight into hepatitis C vaccine development," J Biomed Biotechnol., 2010.
Zhang et al., "Delivery of telomerase reverse transcriptase small interfering RNA in complex with positively charged single-walled carbon nanotubes suppresses tumor growth," *Clinical Cancer Research*, 12:4933-4939, 2006.
Zhang et al., "Structural analysis reveals that toll-like receptor 7 is a dual receptor for guanosine and single-stranded RNA," *Immunity*, 45:737-748, 2016.
Zhang et al., "Type I interferons protect neonates from acute inflammation through interleukin 10-producing B cells," J Exp. Med., 204(5):1107-1118, 2007.
Zhong et al., "Toxicity of cationic liposome lipofectamine 2000 in human pancreatic cancer Capan-2 cells," *Nan Fang Yi Ke Da Xue Xue Bao*, 28(11):1981-1984, 2008, English abstract.
Zohra et al., "Effective delivery with enhanced translational activity synergistically accelerates mRNA-based transfection," *Biochem Biophys Res Commun.*, 358(1):373-378, 2007.

Survival of PR8 infected mice

Age: —△— 18 months  —○— 2 months black symbols: mRNA coding for PR8 H1 Hemagglutinin
grey symbols: control mRNA

Figure 1A

Weight kinetics of PR8 infected mice

Age: —△— 18 months  —○— 2 months black symbols: mRNA coding for PR8 H1 Hemagglutinin
grey symbols: control mRNA
In graph: Mean and standard deviation.

Figure 1B

PR8 H1 mRNA

AUGAAGGCCAACCUGCUCGUGCUGCUGUGCGCCCUCGCGGCCGCCGACGCCGA
CACCAUCUGCAUCGGCUACCACGCCAACAACAGCACCGACACGGUCGACACCG
UGCUGGAGAAGAACGUGACCGUCACCCACUCCGUGAACCUGCUCGAGGACAGC
CACAACGGGAAGCUGUGCCGGCUGAAGGGCAUCGCGCCCUCCAGCUGGGGAA
GUGCAACAUCGCCGGCUGGCUGCUCGGGAACCCGGAGUGCGACCCCUGCUGC
CCGUGCGCUCCUGGAGCUACAUCGUCGAGACGCCCAACUCCGAGAACGGCAUC
UGCUACCCGGGCGACUUCAUCGACUACGAGGAGCUCCGGGAGCAGCUGAGCUC
CGUGAGCUCCUUCGAGCGCUUCGAGAUCUUCCCCAAGGAGAGCUCCUGGCCCA
ACCACAACACCAACGGGGUGACCGCCGCCUGCAGCCACGAGGGCAAGUCCAGC
UUCUACCGGAACCUGCUCGGCUGACCGAGAAGGAGGGGUCCUACCCCAAGCU
GAAGAACAGCUACGUCAACAAGAAGGGCAAGGAGGUGCUCGUGCUGUGGGGA
UCCACCACCCGCCCAACUCCAAGGAGCAGCAGAACCUGUACCAGAACGAGAAC
GCGUACGUCAGCGUGGUGACGUCCAACUACAACCGCCGGUUCACCCCCGAGAU
CGCCGAGCGCCCCAAGGUCCGGGACCAGGCCGGCCGCAUGAACUACUACUGGA
CCCUCCUGAAGCCGGGCGACACCAUCAUCUUCGAGGCCAACGGGAACCUGAUC
GCCCCGAUGUACGCGUUCGCCCUCAGCCGGGGCUUCGGGAGCGGCAUCAUCAC
GUCCAACGCCAGCAUGCACGAGUGCAACACCAAGUGCCAGACCCCCUGGGCG
CCAUCAACUCCAGCCUGCCCUACCAGAACAUCCACCCGGUGACCAUCGGGGAG
UGCCCCAAGUACGUGCGCUCCGCCAAGCUCCGGAUGGUCACGGGCCUGCGCAA
CAACCCCAGCAUCCAGUCCCGGGGGCUGUUCGGCGCGAUCGCCGGGUUCAUCG
AGGGCGGCUGGACCGGGAUGAUCGACGGCUGGUACGGGUACCACCACCAGAAC
GAGCAGGGCAGCGGGUACGCCGCCGACCAGAAGUCCACCCAGAACGCCAUCAA
CGGCAUCACCAACAAGGUGAACACGGUGAUCGAGAAGAUGAACAUCCAGUUCA
CCGCGGUCGGCAAGGAGUUCAACAAGCUCGAGAAGCGCAUGGAGAACCUGAAC
AAGAAGGUGGACGACGGGUUCCUGGACAUCUGGACCUACAACGCCGAGCUCCU
GGUGCUGCUCGAGAACGAGCGGACCCUGGACUUCCACGACAGCAACGUCAAGA
ACCUGUACGAGAAGGUGAAGUCCCAGCUCAAGAACAACGCCAAGGAGAUCGGC
AACGGGUGCUUCGAGUUCUACCACAAGUGCGACAACGAGUGCAUGGAGAGCGU
CCGCAACGGCACGUACGACUACCCCAAGUACUCCGAGGAGAGCAAGCUGAACC
GGGAGAAGGUGGACGGGGUGAAGCUGGAGUCCAUGGGCAUCUACCAGAUCCUC
GCCAUCUACAGCACCGUCGCCUCCAGCCUGGUGCUGCUGGUGUCCCUCGGCGC
GAUCAGCUUCUGGAUGUGCAGCAACGGGUCCCUGCAGUGCCGCAUCUGCAUCU
GA

Elements in 3'UTR of mRNAs: alpha goblin 3'UTR, poly A, poly C
Vector used: pCV19

Figure 1C

Ovalbumin (control) mRNA
AUGGGCAGCAUCGGGGCCGCGUCGAUGGAGUUCUGCUUCGACGUGUUCAAGGA
GCUGAAGGUCCACCACGCCAACGAGAACAUCUUCUACUGCCCGAUCGCCAUCA
UGAGCGCGCUCGCCAUGGUGUACCUGGGCGCCAAGGACAGCACCCGGACGCAG
AUCAACAAGGUGGUCCGCUUCGACAAGCUGCCCGGCUUCGGGGACUCGAUCGA
GGCGCAGUGCGGCACCAGCGUGAACGUGCACAGCUCGCUCCGGGACAUCCUGA
ACCAGAUCACCAAGCCGAACGACGUCUACAGCUUCAGCCUGGCCUCGCGGCUC
UACGCCGAGGAGCGCUACCCGAUCCUGCCCGAGUACCUGCAGUGCGUGAAGGA
GCUCUACCGGGGCGGGCUGGAGCCGAUCAACUUCCAGACGGCGGCCGACCAGG
CCCGGGAGCUGAUCAACAGCUGGGUGGAGAGCCAGACCAACGGCAUCAUCCGC
AACGUCCUCCAGCCGUCGAGCGUGGACAGCCAGACCGCGAUGGUGCUGGUCAA
CGCCAUCGUGUUCAAGGGCCUGUGGGAGAAGACGUUCAAGGACGAGGACACCC
AGGCCAUGCCCUUCCGGGUGACCGAGCAGGAGUCGAAGCCGGUCCAGAUGAUG
UACCAGAUCGGGCUCUUCCGGGUGGCGAGCAUGGCCAGCGAGAAGAUGAAGAU
CCUGGAGCUGCCGUUCGCCUCGGGCACGAUGAGCAUGCUCGUGCUGCUGCCCG
ACGAGGUCAGCGGCCUCGAGCAGCUGGAGUCGAUCAUCAACUUCGAGAAGCUG
ACCGAGUGGACCAGCAGCAACGUGAUGGAGGAGCGCAAGAUCAAGGUGUACCU
CCCGCGGAUGAAGAUGGAGGAGAAGUACAACCUGACGUCGGUCCUGAUGGCGA
UGGGGAUCACCGACGUGUUCAGCAGCUCGGCCAACCUCAGCGGCAUCAGCUCG
GCCGAGAGCCUGAAGAUCAGCCAGGCGGUGCACGCCGCCCACGCGGAGAUCAA
CGAGGCCGGCCGGGAGGUCGUGGGGUCGGCCGAGGCGGGCGUGGACGCCGCCA
GCGUCAGCGAGGAGUUCCGCGCGGACCACCCGUUCCUGUUCUGCAUCAAGCAC
AUCGCCACCAACGCCGUGCUCUUCUUCGGCCGGUGCGUGUCGCCCUGA Elements in 3'UTR of mRNAs: alpha goblin 3'UTR, poly A, poly C
Vector used: pCV19

Figure 1D

Overview of immunological responders for different antigens

| Patient | Age | PSA | PSCA | PSMA | STEAP |
|---------|-----|-----|------|------|-------|
| 111-04 | 72 | ■ |  | ■ |  |
| 111-05 | 74 |  |  | ■ | ■ |
| 111-06 | 69 |  |  |  | ■ |
| 111-07 | 63 |  |  |  |  |
| 113-08 | 63 |  |  |  |  |
| 113-09 | 73 | ■ |  |  | ■ |
| 113-10 | 72 |  |  |  |  |
| 151-01 | 57 |  | ■ |  |  |
| 151-02 | 52 | ■ |  | ■ | ■ |
| 151-03 | 70 |  |  |  | ■ |
| 151-04 | 69 |  |  |  |  |
| 151-05 | 64 | ■ |  | ■ |  |
| 151-06 | 68 | ■ |  |  |  |
| 151-07 | 59 |  |  |  |  |
| 151-08 | 60 |  |  | ■ | ■ |
| 151-10 | 65 |  |  |  |  |
| 151-11 | 54 | ■ |  |  |  |
| 151-13 | 63 |  |  | ■ | ■ |
| 151-14 | 61 | ■ |  | ■ | ■ |
| 152-01 | 73 | ■ | ■ | ■ |  |
| 153-01 | 66 | ■ |  |  |  |
| 154-01 | 69 | ■ | ■ | ■ |  |
| 154-02 | 72 | ■ |  | ■ |  |
| 155-01 | 74 |  | ■ | ■ | ■ |
| 155-02 | 73 | ■ |  |  |  |
| 155-03 | 59 | ■ |  |  |  |
| 158-01 | 63 | ■ |  |  |  |
| 158-02 | 67 |  |  |  |  |
| 158-03 | 69 |  |  |  |  |
| 158-04 | 66 |  |  |  |  |
| 158-05 | 71 |  |  |  | ■ |
| 158-06 | 67 |  |  | ■ |  |

Figure 2 B

RNActive II KLK3(GC) = PSA

GGGAGAAAGCTTACCATGTGGGTGCCGGTCGTGTTCCTGACCCTCAGCGTGAC
GTGGATCGGCGCCGCGCCCCTGATCCTGTCGCGGATCGTGGGGGGCTGGGAGT
GCGAGAAGCACAGCCAGCCCTGGCAGGTGCTGGTGGCCAGCCGCGGCCGGGCC
GTGTGCGGCGGCGTGCTGGTGCACCCCAGTGGGTGCTGACCGCCGCCACTG
CATCCGGAACAAGAGCGTCATCCTGCTGGGCCGGCACAGCCTGTTCCACCCCG
AGGACACCGGCCAGGTGTTCCAGGTGAGCCACAGCTTCCCCCACCCCTGTAC
GACATGAGCCTCCTGAAGAACCGGTTCCTGCGGCCCGGCGACGACAGCAGCCA
CGACCTGATGCTGCTGCGGCTGAGCGAGCCCGCCGAGCTGACCGACGCCGTGA
AGGTGATGGACCTGCCGACCCAGGAGCCCGCCCTGGGCACCACCTGCTACGCC
AGCGGCTGGGGGAGCATCGAGCCCGAGGAGTTCCTCACCCCCAAGAAGCTGCA
GTGCGTGGACCTGCACGTGATCAGCAACGACGTGTGCGCCCAGGTGCACCCC
AGAAGGTGACCAAGTTCATGCTGTGCGCCGGCCGGTGGACCGGCGGCAAGAGC
ACCTGCAGCGGCGACAGCGGCGGCCCCTGGTCTGCAACGGCGTGCTGCAGGG
CATCACCAGCTGGGGCAGCGAGCCCTGCGCCCTGCCCGAGCGCCCCAGCCTGT
ACACCAAGGTGGTGCACTACCGGAAGTGGATCAAGGACACCATCGTGGCCAAC
CCGTGACCACTAGTTATAAGACTGACTAGCCCGATGGGCCTCCCAACGGGCCC
TCCTCCCCTCCTTGCACCGAGATTAATAAAAAAAAAAAAAAAAAAAAAAAAA
AAAAAAAAAAAAAAAAAAAAAAAAAAAAAAAAAAAAATATTCCCCCCCCCCC
CCCCCCCCCCCCCCCCCTCTAGACAATTGGAATT

Figure 2 C

RNActive II FOLH1(GC) = PSMA

GGGAGAAAGCTTACCATGTGGAACCTGCTCCACGAGACCGACAGCGCCGTGGCGACGG
CCCGGCGCCCGCGGTGGCTGTGCGCCGGCGCCCTGGTCCTGGCCGGGGGCTTCTTCCT
GCTGGGCTTCCTGTTCGGCTGGTTCATCAAGTCGAGCAACGAGGCCACCAACATCACC
CCCAAGCACAACATGAAGGCCTTCCTCGACGAGCTGAAGGCCGAGAACATCAAGAAGT
TCCTGTACAACTTCACCCAGATCCCCCACCTGGCCGGGACCGAGCAGAACTTCCAGCT
GGCCAAGCAGATCCAGAGCCAGTGGAAGGAGTTCGGCCTGGACTCGGTGGAGCTGGCG
CACTACGACGTGCTGCTCAGCTACCCCAACAAGACCCACCCCAACTACATCAGCATCA
TCAACGAGGACGGCAACGAGATCTTCAACACCAGCCTGTTCGAGCCCCGCCCCCCGG
CTACGAGAACGTGTCGGACATCGTGCCCCCCTTCAGCGCCTTCAGCCCGCAGGGCATG
CCCGAGGGGGACCTGGTGTACGTGAACTACGCCCGGACGGAGGACTTCTTCAAGCTGG
AGCGCGACATGAAGATCAACTGCAGCGGCAAGATCGTGATCGCCCGGTACGGCAAGGT
GTTCCGGGGCAACAAGGTGAAGAACGCCCAGCTGGCCGGGGCCAAGGGCGTGATCCTG
TACTCGGACCCCGCCGACTACTTCGCCCCCGGCGTGAAGAGCTACCCCGACGGCTGGA
ACCTGCCCGGCGGGGCGTCCAGCGCGGCAACATCCTCAACCTGAACGGCGCCGGCGA
CCCGCTGACCCCCGGGTACCCCGCGAACGAGTACGCCTACCGGCGGGCATCGCCGAG
GCCGTGGGCCTGCCCAGCATCCCCGTGCACCCGATCGGCTACTACGACGCCCAGAAGC
TGCTGGAGAAGATGGGCGGGAGCGCCCCGCCCGACTCGAGCTGGCGGGGCAGCCTGAA
GGTGCCCTACAACGTGGGCCCCGGCTTCACCGGGAACTTCTCGACCCAGAAGGTGAAG
ATGCACATCCACAGCACCAACGAGGTGACCCGCATCTACAACGTGATCGGCACCCTGC
GGGGCGCCGTGGAGCCCGACCGGTACGTGATCCTCGGCGGGCACCGCGACAGCTGGGT
GTTCGGCGGCATCGACCCCCAGAGCGGCGCCGCCGTGGTCCACGAGATCGTGCGGTCG
TTCGGCACCCTGAAGAAGGAGGGGTGGCGGCCCCGCCGGACGATCCTGTTCGCCAGCT
GGGACGCGGAGGAGTTCGGCCTGCTGGGCAGCACCGAGTGGGCCGAGGAGAACAGCCG
GCTGCTGCAGGAGCGGGGCGTGGCCTACATCAACGCCGACTCGAGCATCGAGGGCAAC
TACACCCTCCGCGTGGACTGCACCCCGCTGATGTACAGCCTGGTGCACAACCTGACCA
AGGAGCTGAAGAGCCCCGACGAGGGGTTCGAGGGCAAGTCGCTGTACGAGAGCTGGAC
CAAGAAGAGCCCCTCGCCCGAGTTCAGCGGCATGCCCCGGATCAGCAAGCTGGGCAGC
GGGAACGACTTCGAGGTGTTCTTCCAGCGGCTGGGCATCGCCTCGGGCCGCGCCCGGT
ACACCAAGAACTGGGAGACGAACAAGTTCAGCGGCTACCCCTCTACCACAGCGTGTA
CGAGACCTACGAGCTGGTGGAGAAGTTCTACGACCCCATGTTCAAGTACCACCTGACC
GTGGCCCAGGTGCGGGGCGGGATGGTGTTCGAGCTGGCCAACAGCATCGTGCTGCCCT
TCGACTGCCGCGACTACGCCGTCGTGCTGCGGAAGTACGCCGACAAGATCTACTCGAT
CAGCATGAAGCACCCCAGGAGATGAAGACCTACAGCGTGAGCTTCGACTCGCTGTTC
AGCGCGGTGAAGAACTTCACCGAGATCGCCAGCAAGTTCTCGGAGCGGCTCCAGGACT
TCGACAAGAGCAACCCGATCGTGCTGCGCATGATGAACGACCAGCTGATGTTCCTGGA
GCGGGCCTTCATCGACCCCTGGGCCTGCCCGACCGGCCTTCTACCGGCACGTGATC
TACGCCCCCAGCAGCCACAACAAGTACGCCGGCGAGTCGTTCCCGGGGATCTACGACG
CCCTGTTCGACATCGAGAGCAAGGTGGACCCAGCAAGGCCTGGGGCGAGGTGAAGCG
CCAGATCTACGTGGCCGCCTTCACCGTGCAGGCCGCGGCCGAGACCCTGAGCGAGGTG
GCCTGACCACTAGTTATAAGACTGACTAGCCCGATGGGCCTCCCAACGGGCCCTCCTC
CCTCCTTGCACCGAGATTAATAAAAAAAAAAAAAAAAAAAAAAAAAAAAAAAAAAAAA
AAAAAAAAAAAAAAAAAAAAAAAAAAATATTCCCCCCCCCCCCCCCCCCCCCCCC
CCCCTCTAGACAATTGGAATT

Figure 2 D

RNActiveII PSCA(GC)

GGGAGAAAGCTTACCATGAAGGCCGTGCTGCTCGCGCTGCTGATGGCCGGCCT
GGCCCTGCAGCCGGGGACCGCCCTGCTGTGCTACAGCTGCAAGGCCCAGGTCT
CGAACGAGGACTGCCTGCAGGTGGAGAACTGCACGCAGCTGGGCGAGCAGTGC
TGGACCGCCCGGATCCGCGCCGTGGGCCTGCTCACCGTGATCAGCAAGGGCTG
CAGCCTGAACTGCGTGGACGACAGCCAGGACTACTACGTGGGCAAGAAGAACA
TCACCTGCTGCGACACCGACCTGTGCAACGCCAGCGGCGCCCACGCCCTGCAG
CCCGCGGCCGCCATCCTGGCCCTGCTGCCCGCCCTGGGCCTGCTGCTCTGGGG
CCCCGGCCAGCTGTGACCACTAGTTATAAGACTGACTAGCCCGATGGGCCTCC
CAACGGGCCCTCCTCCCTCCTTGCACCGAGATTAATAAAAAAAAAAAAAAAA
AAAAAAAAAAAAAAAAAAAAAAAAAAAAAAAAAAAAAAAAAAAAAATATTC
CCCCCCCCCCCCCCCCCCCCCCCCCCCTCTAGACAATTGGAATT

Figure 2 E

RNActive II STEAP (GC) = STEAP1

GGGagaAAGCTTaccATGgagagccggaaggacatcaccaaccaggaggagct
gtggaagatgaagccgcgccggaacctcgaggaggacgactacctgcacaagg
acacgggcgagacctcgatgctgaagcggcccgtgctcctgcacctgcaccag
accgcccacgcggacgagttcgactgcccgagcgagctccagcacacgcagga
gctgttcccgcagtggcacctgcccatcaagatcgccgccatcatcgcgagcc
tcaccttcctgtacaccctgctccgcgaggtcatccaccgctggccacgtcg
caccagcagtacttctacaagatcccgatcctggtgatcaacaaggtgctccc
catggtcagcatcaccctgctggccctcgtgtacctgccgggggtgatcgcgg
ccatcgtccagctgcacaacggcaccaagtacaagaagttcccgcactggctc
gacaagtggatgctgacgcggaagcagttcggcctgctcagcttcttcttcgc
cgtgctgcacgcgatctactcgctgagctacccatgcggcgcagctaccggt
acaagctcctgaactgggcctaccagcaggtgcagcagaacaaggaggacgcc
tggatcgagcacgacgtctggcggatggagatctacgtgtcgctggggatcgt
gggcctcgcgatcctggccctgctcgccgtcaccagcatcccgagcgtgtcgg
acagcctgacctggcgcgagttccactacatccagagcaagctgggcatcgtg
tcgctcctgctggggacgatccacgcgctcatcttcgcctggaacaagtggat
cgacatcaagcagttcgtctggtacaccccgcccaccttcatgatcgccgtgt
cctgccgatcgtggtcctgatcttcaagagcatcctcttcctgccgtgcctg
cggaagaagatcctcaagatccggcacggctgggaggacgtgacgaagatcaa
caagaccgagatctgcagccagctgtgaccACTAGTTATAAgactgactagcc
cgAtgggcctcccaacgggccctcctcccctccttgcaccgagAttaaTAAAA
AAAAAAAAAAAAAAAAAAAAAAAAAAAAAAAAAAAAAAAAAAAAAAAAAAAAA
AAAAAatattCCCCCCCCCCCCCCCCCCCCCCCCCCCCCCtctagaCAATTG
gaatt

Figure 2 F

SEQUENCE LISTING

```
Sequence total quantity: 389
SEQ ID NO: 1            moltype = AA  length = 9
FEATURE                 Location/Qualifiers
REGION                  1..9
                        note = Description of Sequence: cationic or polycationic
                         peptide of formula (Ib): Cys Cys
source                  1..9
                        mol_type = protein
                        organism = synthetic construct
SEQUENCE: 1
CRRRRRRRC                                                                 9

SEQ ID NO: 2            moltype = AA  length = 10
FEATURE                 Location/Qualifiers
REGION                  1..10
                        note = Description of Sequence: cationic or polycationic
                         peptide of formula (Ib): Cys Cys
source                  1..10
                        mol_type = protein
                        organism = synthetic construct
SEQUENCE: 2
CRRRRRRRRC                                                                10

SEQ ID NO: 3            moltype = AA  length = 11
FEATURE                 Location/Qualifiers
REGION                  1..11
                        note = Description of Sequence: cationic or polycationic
                         peptide of formula (Ib): Cys Cys
source                  1..11
                        mol_type = protein
                        organism = synthetic construct
SEQUENCE: 3
CRRRRRRRRR C                                                              11

SEQ ID NO: 4            moltype = AA  length = 12
FEATURE                 Location/Qualifiers
REGION                  1..12
                        note = Description of Sequence: cationic or polycationic
                         peptide of formula (Ib): Cys Cys
source                  1..12
                        mol_type = protein
```

```
                       organism = synthetic construct
SEQUENCE: 4
CRRRRRRRR RC                                                                     12

SEQ ID NO: 5           moltype = AA   length = 13
FEATURE                Location/Qualifiers
REGION                 1..13
                       note = Description of Sequence: cationic or polycationic
                       peptide of formula (Ib): Cys
 Cys
source                 1..13
                       mol_type = protein
                       organism = synthetic construct
SEQUENCE: 5
CRRRRRRRRR RRC                                                                   13

SEQ ID NO: 6           moltype = AA   length = 14
FEATURE                Location/Qualifiers
REGION                 1..14
                       note = Description of Sequence: cationic or polycationic
                       peptide of formula (Ib): Cys
 Cys
source                 1..14
                       mol_type = protein
                       organism = synthetic construct
SEQUENCE: 6
CRRRRRRRRR RRRC                                                                  14

SEQ ID NO: 7           moltype = AA   length = 15
FEATURE                Location/Qualifiers
REGION                 1..15
                       note = Description of Sequence: cationic or polycationic
                       peptide of formula (Ib): Cys
 Cys
source                 1..15
                       mol_type = protein
                       organism = synthetic construct
SEQUENCE: 7
CRRRRRRRRR RRRRC                                                                 15

SEQ ID NO: 8           moltype = AA   length = 16
FEATURE                Location/Qualifiers
REGION                 1..16
                       note = Description of Sequence: cationic or polycationic
                       peptide of formula (Ib): Cys
 Cys
source                 1..16
                       mol_type = protein
                       organism = synthetic construct
SEQUENCE: 8
CRRRRRRRRR RRRRRC                                                                16

SEQ ID NO: 9           moltype = AA   length = 17
FEATURE                Location/Qualifiers
REGION                 1..17
                       note = Description of Sequence: cationic or polycationic
                       peptide of formula (Ib): Cys
 Cys
source                 1..17
                       mol_type = protein
                       organism = synthetic construct
SEQUENCE: 9
CRRRRRRRRR RRRRRRC                                                               17

SEQ ID NO: 10          moltype = AA   length = 18
FEATURE                Location/Qualifiers
REGION                 1..18
                       note = Description of Sequence: cationic or polycationic
                       peptide of formula (Ib): Cys
 Cys
source                 1..18
                       mol_type = protein
                       organism = synthetic construct
SEQUENCE: 10
```

```
CRRRRRRRRR RRRRRRRC                                                         18

SEQ ID NO: 11           moltype = AA  length = 19
FEATURE                 Location/Qualifiers
REGION                  1..19
                        note = Description of Sequence: cationic or polycationic
                         peptide of formula (Ib): Cys Cys
source                  1..19
                        mol_type = protein
                        organism = synthetic construct
SEQUENCE: 11
CRRRRRRRRR RRRRRRRRC                                                        19

SEQ ID NO: 12           moltype = AA  length = 20
FEATURE                 Location/Qualifiers
REGION                  1..20
                        note = Description of Sequence: cationic or polycationic
                         peptide of formula (Ib): Cys Cys
source                  1..20
                        mol_type = protein
                        organism = synthetic construct
SEQUENCE: 12
CRRRRRRRRR RRRRRRRRRC                                                       20

SEQ ID NO: 13           moltype = AA  length = 21
FEATURE                 Location/Qualifiers
REGION                  1..21
                        note = Description of Sequence: cationic or polycationic
                         peptide of formula (Ib): Cys Cys
source                  1..21
                        mol_type = protein
                        organism = synthetic construct
SEQUENCE: 13
CRRRRRRRRR RRRRRRRRRR C                                                     21

SEQ ID NO: 14           moltype = AA  length = 22
FEATURE                 Location/Qualifiers
REGION                  1..22
                        note = Description of Sequence: cationic or polycationic
                         peptide of formula (Ib): Cys Cys
source                  1..22
                        mol_type = protein
                        organism = synthetic construct
SEQUENCE: 14
CRRRRRRRRR RRRRRRRRRR RC                                                    22

SEQ ID NO: 15           moltype =    length =
SEQUENCE: 15
000

SEQ ID NO: 16           moltype =    length =
SEQUENCE: 16
000

SEQ ID NO: 17           moltype =    length =
SEQUENCE: 17
000

SEQ ID NO: 18           moltype =    length =
SEQUENCE: 18
000

SEQ ID NO: 19           moltype =    length =
SEQUENCE: 19
000

SEQ ID NO: 20           moltype =    length =
SEQUENCE: 20
000

SEQ ID NO: 21           moltype =    length =
SEQUENCE: 21
```

```
000

SEQ ID NO: 22          moltype =    length =
SEQUENCE: 22
000

SEQ ID NO: 23          moltype = AA   length = 4
FEATURE                Location/Qualifiers
REGION                 1..4
                       note = Exemplary aromatic amino acid component (AA)
source                 1..4
                       mol_type = protein
                       organism = synthetic construct
SEQUENCE: 23
WYWY                                                                    4

SEQ ID NO: 24          moltype = AA   length = 4
FEATURE                Location/Qualifiers
REGION                 1..4
                       note = Exemplary aromatic amino acid component (AA)
source                 1..4
                       mol_type = protein
                       organism = synthetic construct
SEQUENCE: 24
YWYW                                                                    4

SEQ ID NO: 25          moltype = AA   length = 4
FEATURE                Location/Qualifiers
REGION                 1..4
                       note = Exemplary aromatic amino acid component (AA)
source                 1..4
                       mol_type = protein
                       organism = synthetic construct
SEQUENCE: 25
WWWW                                                                    4

SEQ ID NO: 26          moltype =    length =
SEQUENCE: 26
000

SEQ ID NO: 27          moltype =    length =
SEQUENCE: 27
000

SEQ ID NO: 28          moltype =    length =
SEQUENCE: 28
000

SEQ ID NO: 29          moltype =    length =
SEQUENCE: 29
000

SEQ ID NO: 30          moltype =    length =
SEQUENCE: 30
000

SEQ ID NO: 31          moltype =    length =
SEQUENCE: 31
000

SEQ ID NO: 32          moltype = AA   length = 4
FEATURE                Location/Qualifiers
REGION                 1..4
                       note = Exemplary aromatic amino acid component (AA)
source                 1..4
                       mol_type = protein
                       organism = synthetic construct
SEQUENCE: 32
FYFY                                                                    4

SEQ ID NO: 33          moltype = AA   length = 4
FEATURE                Location/Qualifiers
REGION                 1..4
                       note = Exemplary aromatic amino acid component (AA)
source                 1..4
                       mol_type = protein
                       organism = synthetic construct
SEQUENCE: 33
YFYF                                                                    4
```

```
SEQ ID NO: 34           moltype = AA  length = 4
FEATURE                 Location/Qualifiers
REGION                  1..4
                        note = Exemplary aromatic amino acid component (AA)
source                  1..4
                        mol_type = protein
                        organism = synthetic construct
SEQUENCE: 34
FFFF                                                                        4

SEQ ID NO: 35           moltype =    length =
SEQUENCE: 35
000

SEQ ID NO: 36           moltype =    length =
SEQUENCE: 36
000

SEQ ID NO: 37           moltype =    length =
SEQUENCE: 37
000

SEQ ID NO: 38           moltype =    length =
SEQUENCE: 38
000

SEQ ID NO: 39           moltype =    length =
SEQUENCE: 39
000

SEQ ID NO: 40           moltype = AA  length = 4
FEATURE                 Location/Qualifiers
REGION                  1..4
                        note = Exemplary aromatic amino acid component (AA)
source                  1..4
                        mol_type = protein
                        organism = synthetic construct
SEQUENCE: 40
FWFW                                                                        4

SEQ ID NO: 41           moltype = AA  length = 4
FEATURE                 Location/Qualifiers
REGION                  1..4
                        note = Exemplary aromatic amino acid component (AA)
source                  1..4
                        mol_type = protein
                        organism = synthetic construct
SEQUENCE: 41
WFWF                                                                        4

SEQ ID NO: 42           moltype = AA  length = 4
FEATURE                 Location/Qualifiers
REGION                  1..4
                        note = Exemplary aromatic amino acid component (AA)
source                  1..4
                        mol_type = protein
                        organism = synthetic construct
SEQUENCE: 42
YYYY                                                                        4

SEQ ID NO: 43           moltype =    length =
SEQUENCE: 43
000

SEQ ID NO: 44           moltype =    length =
SEQUENCE: 44
000

SEQ ID NO: 45           moltype = AA  length = 4
FEATURE                 Location/Qualifiers
REGION                  1..4
                        note = Exemplary aromatic amino acid component (AA)
source                  1..4
                        mol_type = protein
                        organism = synthetic construct
SEQUENCE: 45
CWYC                                                                        4
```

```
SEQ ID NO: 46           moltype = AA   length = 4
FEATURE                 Location/Qualifiers
REGION                  1..4
                        note = Exemplary aromatic amino acid component (AA)
source                  1..4
                        mol_type = protein
                        organism = synthetic construct
SEQUENCE: 46
CYWC                                                                     4

SEQ ID NO: 47           moltype = AA   length = 4
FEATURE                 Location/Qualifiers
REGION                  1..4
                        note = Exemplary aromatic amino acid component (AA)
source                  1..4
                        mol_type = protein
                        organism = synthetic construct
SEQUENCE: 47
CWWC                                                                     4

SEQ ID NO: 48           moltype = AA   length = 4
FEATURE                 Location/Qualifiers
REGION                  1..4
                        note = Exemplary aromatic amino acid component (AA)
source                  1..4
                        mol_type = protein
                        organism = synthetic construct
SEQUENCE: 48
CYYC                                                                     4

SEQ ID NO: 49           moltype = AA   length = 5
FEATURE                 Location/Qualifiers
REGION                  1..5
                        note = Exemplary aromatic amino acid component (AA)
source                  1..5
                        mol_type = protein
                        organism = synthetic construct
SEQUENCE: 49
CWYWC                                                                    5

SEQ ID NO: 50           moltype = AA   length = 5
FEATURE                 Location/Qualifiers
REGION                  1..5
                        note = Exemplary aromatic amino acid component (AA)
source                  1..5
                        mol_type = protein
                        organism = synthetic construct
SEQUENCE: 50
CYWYC                                                                    5

SEQ ID NO: 51           moltype = AA   length = 5
FEATURE                 Location/Qualifiers
REGION                  1..5
                        note = Exemplary aromatic amino acid component (AA)
source                  1..5
                        mol_type = protein
                        organism = synthetic construct
SEQUENCE: 51
CWWWC                                                                    5

SEQ ID NO: 52           moltype = AA   length = 5
FEATURE                 Location/Qualifiers
REGION                  1..5
                        note = Exemplary aromatic amino acid component (AA)
source                  1..5
                        mol_type = protein
                        organism = synthetic construct
SEQUENCE: 52
CYYYC                                                                    5

SEQ ID NO: 53           moltype = AA   length = 6
FEATURE                 Location/Qualifiers
REGION                  1..6
                        note = Exemplary aromatic amino acid component (AA)
source                  1..6
                        mol_type = protein
                        organism = synthetic construct
SEQUENCE: 53
CWYWYC                                                                   6
```

```
SEQ ID NO: 54            moltype = AA   length = 6
FEATURE                  Location/Qualifiers
REGION                   1..6
                         note = Exemplary aromatic amino acid component (AA)
source                   1..6
                         mol_type = protein
                         organism = synthetic construct
SEQUENCE: 54
CYWYWC                                                                      6

SEQ ID NO: 55            moltype = AA   length = 6
FEATURE                  Location/Qualifiers
REGION                   1..6
                         note = Exemplary aromatic amino acid component (AA)
source                   1..6
                         mol_type = protein
                         organism = synthetic construct
SEQUENCE: 55
CWWWWC                                                                      6

SEQ ID NO: 56            moltype = AA   length = 6
FEATURE                  Location/Qualifiers
REGION                   1..6
                         note = Exemplary aromatic amino acid component (AA)
source                   1..6
                         mol_type = protein
                         organism = synthetic construct
SEQUENCE: 56
CYYYYC                                                                      6

SEQ ID NO: 57            moltype =     length =
SEQUENCE: 57
000

SEQ ID NO: 58            moltype = AA   length = 4
FEATURE                  Location/Qualifiers
REGION                   1..4
                         note = Exemplary aromatic amino acid component (AA)
source                   1..4
                         mol_type = protein
                         organism = synthetic construct
SEQUENCE: 58
CFYC                                                                        4

SEQ ID NO: 59            moltype = AA   length = 4
FEATURE                  Location/Qualifiers
REGION                   1..4
                         note = Exemplary aromatic amino acid component (AA)
source                   1..4
                         mol_type = protein
                         organism = synthetic construct
SEQUENCE: 59
CYFC                                                                        4

SEQ ID NO: 60            moltype = AA   length = 4
FEATURE                  Location/Qualifiers
REGION                   1..4
                         note = Exemplary aromatic amino acid component (AA)
source                   1..4
                         mol_type = protein
                         organism = synthetic construct
SEQUENCE: 60
CFFC                                                                        4

SEQ ID NO: 61            moltype = AA   length = 4
FEATURE                  Location/Qualifiers
REGION                   1..4
                         note = Exemplary aromatic amino acid component (AA)
source                   1..4
                         mol_type = protein
                         organism = synthetic construct
SEQUENCE: 61
CYYC                                                                        4

SEQ ID NO: 62            moltype = AA   length = 5
FEATURE                  Location/Qualifiers
REGION                   1..5
                         note = Exemplary aromatic amino acid component (AA)
```

```
source                   1..5
                         mol_type = protein
                         organism = synthetic construct
SEQUENCE: 62
CFYFC                                                                    5

SEQ ID NO: 63            moltype = AA  length = 5
FEATURE                  Location/Qualifiers
REGION                   1..5
                         note = Exemplary aromatic amino acid component (AA)
source                   1..5
                         mol_type = protein
                         organism = synthetic construct
SEQUENCE: 63
CYFYC                                                                    5

SEQ ID NO: 64            moltype = AA  length = 5
FEATURE                  Location/Qualifiers
REGION                   1..5
                         note = Exemplary aromatic amino acid component (AA)
source                   1..5
                         mol_type = protein
                         organism = synthetic construct
SEQUENCE: 64
CFFFC                                                                    5

SEQ ID NO: 65            moltype = AA  length = 5
FEATURE                  Location/Qualifiers
REGION                   1..5
                         note = Exemplary aromatic amino acid component (AA)
source                   1..5
                         mol_type = protein
                         organism = synthetic construct
SEQUENCE: 65
CYYYC                                                                    5

SEQ ID NO: 66            moltype = AA  length = 6
FEATURE                  Location/Qualifiers
REGION                   1..6
                         note = Exemplary aromatic amino acid component (AA)
source                   1..6
                         mol_type = protein
                         organism = synthetic construct
SEQUENCE: 66
CFYFYC                                                                   6

SEQ ID NO: 67            moltype = AA  length = 5
FEATURE                  Location/Qualifiers
REGION                   1..5
                         note = Exemplary aromatic amino acid component (AA)
source                   1..5
                         mol_type = protein
                         organism = synthetic construct
SEQUENCE: 67
CYFYF                                                                    5

SEQ ID NO: 68            moltype = AA  length = 6
FEATURE                  Location/Qualifiers
REGION                   1..6
                         note = Exemplary aromatic amino acid component (AA)
source                   1..6
                         mol_type = protein
                         organism = synthetic construct
SEQUENCE: 68
CFFFFC                                                                   6

SEQ ID NO: 69            moltype = AA  length = 4
FEATURE                  Location/Qualifiers
REGION                   1..4
                         note = Exemplary aromatic amino acid component (AA)
source                   1..4
                         mol_type = protein
                         organism = synthetic construct
SEQUENCE: 69
CFWC                                                                     4

SEQ ID NO: 70            moltype = AA  length = 4
FEATURE                  Location/Qualifiers
REGION                   1..4
```

```
                       note = Exemplary aromatic amino acid component (AA)
source                 1..4
                       mol_type = protein
                       organism = synthetic construct
SEQUENCE: 70
CWFC                                                                       4

SEQ ID NO: 71          moltype = AA  length = 4
FEATURE                Location/Qualifiers
REGION                 1..4
                       note = Exemplary aromatic amino acid component (AA)
source                 1..4
                       mol_type = protein
                       organism = synthetic construct
SEQUENCE: 71
CFFC                                                                       4

SEQ ID NO: 72          moltype = AA  length = 5
FEATURE                Location/Qualifiers
REGION                 1..5
                       note = Exemplary aromatic amino acid component (AA)
source                 1..5
                       mol_type = protein
                       organism = synthetic construct
SEQUENCE: 72
CFWFC                                                                      5

SEQ ID NO: 73          moltype = AA  length = 5
FEATURE                Location/Qualifiers
REGION                 1..5
                       note = Exemplary aromatic amino acid component (AA)
source                 1..5
                       mol_type = protein
                       organism = synthetic construct
SEQUENCE: 73
CWFWC                                                                      5

SEQ ID NO: 74          moltype = AA  length = 6
FEATURE                Location/Qualifiers
REGION                 1..6
                       note = Exemplary aromatic amino acid component (AA)
source                 1..6
                       mol_type = protein
                       organism = synthetic construct
SEQUENCE: 74
CFWFWC                                                                     6

SEQ ID NO: 75          moltype = AA  length = 6
FEATURE                Location/Qualifiers
REGION                 1..6
                       note = Exemplary aromatic amino acid component (AA)
source                 1..6
                       mol_type = protein
                       organism = synthetic construct
SEQUENCE: 75
CWFWFC                                                                     6

SEQ ID NO: 76          moltype =     length =
SEQUENCE: 76
000

SEQ ID NO: 77          moltype =     length =
SEQUENCE: 77
000

SEQ ID NO: 78          moltype =     length =
SEQUENCE: 78
000

SEQ ID NO: 79          moltype =     length =
SEQUENCE: 79
000

SEQ ID NO: 80          moltype =     length =
SEQUENCE: 80
000

SEQ ID NO: 81          moltype =     length =
SEQUENCE: 81
```

```
000

SEQ ID NO: 82            moltype =    length =
SEQUENCE: 82
000

SEQ ID NO: 83            moltype =    length =
SEQUENCE: 83
000

SEQ ID NO: 84            moltype = AA  length = 4
FEATURE                  Location/Qualifiers
REGION                   1..4
                         note = Exemplary hydrophilic (and preferably non charged
                          polar) amino acid component (AA)
source                   1..4
                         mol_type = protein
                         organism = synthetic construct
SEQUENCE: 84
STST                                                                       4

SEQ ID NO: 85            moltype = AA  length = 4
FEATURE                  Location/Qualifiers
REGION                   1..4
                         note = Exemplary hydrophilic (and preferably non charged
                          polar) amino acid component (AA)
source                   1..4
                         mol_type = protein
                         organism = synthetic construct
SEQUENCE: 85
TSTS                                                                       4

SEQ ID NO: 86            moltype = AA  length = 4
FEATURE                  Location/Qualifiers
REGION                   1..4
                         note = Exemplary hydrophilic (and preferably non charged
                          polar) amino acid component (AA)
source                   1..4
                         mol_type = protein
                         organism = synthetic construct
SEQUENCE: 86
SSSS                                                                       4

SEQ ID NO: 87            moltype = AA  length = 4
FEATURE                  Location/Qualifiers
REGION                   1..4
                         note = Exemplary hydrophilic (and preferably non charged
                          polar) amino acid component (AA)
source                   1..4
                         mol_type = protein
                         organism = synthetic construct
SEQUENCE: 87
TTTT                                                                       4

SEQ ID NO: 88            moltype =    length =
SEQUENCE: 88
000

SEQ ID NO: 89            moltype =    length =
SEQUENCE: 89
000

SEQ ID NO: 90            moltype =    length =
SEQUENCE: 90
000

SEQ ID NO: 91            moltype =    length =
SEQUENCE: 91
000

SEQ ID NO: 92            moltype =    length =
SEQUENCE: 92
000

SEQ ID NO: 93            moltype =    length =
SEQUENCE: 93
000

SEQ ID NO: 94            moltype =    length =
```

```
SEQUENCE: 94
000

SEQ ID NO: 95              moltype =    length =
SEQUENCE: 95
000

SEQ ID NO: 96              moltype = AA   length = 4
FEATURE                    Location/Qualifiers
REGION                     1..4
                           note = Exemplary hydrophilic (and preferably non charged
                            polar) amino acid component (AA)
source                     1..4
                           mol_type = protein
                           organism = synthetic construct
SEQUENCE: 96
QNQN                                                                            4

SEQ ID NO: 97              moltype = AA   length = 4
FEATURE                    Location/Qualifiers
REGION                     1..4
                           note = Exemplary hydrophilic (and preferably non charged
                            polar) amino acid component (AA)
source                     1..4
                           mol_type = protein
                           organism = synthetic construct
SEQUENCE: 97
NQNQ                                                                            4

SEQ ID NO: 98              moltype = AA   length = 4
FEATURE                    Location/Qualifiers
REGION                     1..4
                           note = Exemplary hydrophilic (and preferably non charged
                            polar) amino acid component (AA)
source                     1..4
                           mol_type = protein
                           organism = synthetic construct
SEQUENCE: 98
QQQQ                                                                            4

SEQ ID NO: 99              moltype = AA   length = 4
FEATURE                    Location/Qualifiers
REGION                     1..4
                           note = Exemplary hydrophilic (and preferably non charged
                            polar) amino acid component (AA)
source                     1..4
                           mol_type = protein
                           organism = synthetic construct
SEQUENCE: 99
NNNN                                                                            4

SEQ ID NO: 100             moltype =    length =
SEQUENCE: 100
000

SEQ ID NO: 101             moltype =    length =
SEQUENCE: 101
000

SEQ ID NO: 102             moltype =    length =
SEQUENCE: 102
000

SEQ ID NO: 103             moltype =    length =
SEQUENCE: 103
000

SEQ ID NO: 104             moltype =    length =
SEQUENCE: 104
000

SEQ ID NO: 105             moltype =    length =
SEQUENCE: 105
000

SEQ ID NO: 106             moltype =    length =
SEQUENCE: 106
000
```

| | | |
|---|---|---|
| SEQ ID NO: 107<br>SEQUENCE: 107<br>000 | moltype =    length = | |
| SEQ ID NO: 108<br>FEATURE<br>REGION<br><br>source<br><br><br>SEQUENCE: 108<br>SNSN | moltype = AA   length = 4<br>Location/Qualifiers<br>1..4<br>note = Exemplary hydrophilic (and preferably non charged<br> polar) amino acid component (AA)<br>1..4<br>mol_type = protein<br>organism = synthetic construct | <br><br><br><br><br><br><br><br><br>4 |
| SEQ ID NO: 109<br>FEATURE<br>REGION<br><br>source<br><br><br>SEQUENCE: 109<br>NSNS | moltype = AA   length = 4<br>Location/Qualifiers<br>1..4<br>note = Exemplary hydrophilic (and preferably non charged<br> polar) amino acid component (AA)<br>1..4<br>mol_type = protein<br>organism = synthetic construct | <br><br><br><br><br><br><br><br><br>4 |
| SEQ ID NO: 110<br>FEATURE<br>REGION<br><br>source<br><br><br>SEQUENCE: 110<br>SSSS | moltype = AA   length = 4<br>Location/Qualifiers<br>1..4<br>note = Exemplary hydrophilic (and preferably non charged<br> polar) amino acid component (AA)<br>1..4<br>mol_type = protein<br>organism = synthetic construct | <br><br><br><br><br><br><br><br><br>4 |
| SEQ ID NO: 111<br>FEATURE<br>REGION<br><br>source<br><br><br>SEQUENCE: 111<br>NNNN | moltype = AA   length = 4<br>Location/Qualifiers<br>1..4<br>note = Exemplary hydrophilic (and preferably non charged<br> polar) amino acid component (AA)<br>1..4<br>mol_type = protein<br>organism = synthetic construct | <br><br><br><br><br><br><br><br><br>4 |
| SEQ ID NO: 112<br>SEQUENCE: 112<br>000 | moltype =    length = | |
| SEQ ID NO: 113<br>SEQUENCE: 113<br>000 | moltype =    length = | |
| SEQ ID NO: 114<br>FEATURE<br>REGION<br><br>source<br><br><br>SEQUENCE: 114<br>CSTC | moltype = AA   length = 4<br>Location/Qualifiers<br>1..4<br>note = Exemplary hydrophilic (and preferably non charged<br> polar) amino acid component (AA)<br>1..4<br>mol_type = protein<br>organism = synthetic construct | <br><br><br><br><br><br><br><br><br>4 |
| SEQ ID NO: 115<br>FEATURE<br>REGION<br><br>source<br><br><br>SEQUENCE: 115<br>CTSC | moltype = AA   length = 4<br>Location/Qualifiers<br>1..4<br>note = Exemplary hydrophilic (and preferably non charged<br> polar) amino acid component (AA)<br>1..4<br>mol_type = protein<br>organism = synthetic construct | <br><br><br><br><br><br><br><br><br>4 |
| SEQ ID NO: 116 | moltype = AA   length = 4 | |

| | | |
|---|---|---|
| FEATURE | Location/Qualifiers | |
| REGION | 1..4 | |
| | note = Exemplary hydrophilic (and preferably non charged polar) amino acid component (AA) | |
| source | 1..4 | |
| | mol_type = protein | |
| | organism = synthetic construct | |
| SEQUENCE: 116 | | |
| CSSC | | 4 |

| | | |
|---|---|---|
| SEQ ID NO: 117 | moltype = AA length = 4 | |
| FEATURE | Location/Qualifiers | |
| REGION | 1..4 | |
| | note = Exemplary hydrophilic (and preferably non charged polar) amino acid component (AA) | |
| source | 1..4 | |
| | mol_type = protein | |
| | organism = synthetic construct | |
| SEQUENCE: 117 | | |
| CTTC | | 4 |

| | | |
|---|---|---|
| SEQ ID NO: 118 | moltype = AA length = 5 | |
| FEATURE | Location/Qualifiers | |
| REGION | 1..5 | |
| | note = Exemplary hydrophilic (and preferably non charged polar) amino acid component (AA) | |
| source | 1..5 | |
| | mol_type = protein | |
| | organism = synthetic construct | |
| SEQUENCE: 118 | | |
| CSTSC | | 5 |

| | | |
|---|---|---|
| SEQ ID NO: 119 | moltype = AA length = 5 | |
| FEATURE | Location/Qualifiers | |
| REGION | 1..5 | |
| | note = Exemplary hydrophilic (and preferably non charged polar) amino acid component (AA) | |
| source | 1..5 | |
| | mol_type = protein | |
| | organism = synthetic construct | |
| SEQUENCE: 119 | | |
| CTSTC | | 5 |

| | | |
|---|---|---|
| SEQ ID NO: 120 | moltype = AA length = 5 | |
| FEATURE | Location/Qualifiers | |
| REGION | 1..5 | |
| | note = Exemplary hydrophilic (and preferably non charged polar) amino acid component (AA) | |
| source | 1..5 | |
| | mol_type = protein | |
| | organism = synthetic construct | |
| SEQUENCE: 120 | | |
| CSSSC | | 5 |

| | | |
|---|---|---|
| SEQ ID NO: 121 | moltype = AA length = 5 | |
| FEATURE | Location/Qualifiers | |
| REGION | 1..5 | |
| | note = Exemplary hydrophilic (and preferably non charged polar) amino acid component (AA) | |
| source | 1..5 | |
| | mol_type = protein | |
| | organism = synthetic construct | |
| SEQUENCE: 121 | | |
| CTTTC | | 5 |

| | | |
|---|---|---|
| SEQ ID NO: 122 | moltype = AA length = 6 | |
| FEATURE | Location/Qualifiers | |
| REGION | 1..6 | |
| | note = Exemplary hydrophilic (and preferably non charged polar) amino acid component (AA) | |
| source | 1..6 | |
| | mol_type = protein | |
| | organism = synthetic construct | |
| SEQUENCE: 122 | | |
| CSTSTC | | 6 |

| | | |
|---|---|---|
| SEQ ID NO: 123 | moltype = AA length = 6 | |
| FEATURE | Location/Qualifiers | |
| REGION | 1..6 | |

| | |
|---|---|
| | note = Exemplary hydrophilic (and preferably non charged polar) amino acid component (AA) |
| source | 1..6 |
| | mol_type = protein |
| | organism = synthetic construct |
| SEQUENCE: 123 | |
| CTSTSC | 6 |
| | |
| SEQ ID NO: 124 | moltype = AA  length = 6 |
| FEATURE | Location/Qualifiers |
| REGION | 1..6 |
| | note = Exemplary hydrophilic (and preferably non charged polar) amino acid component (AA) |
| source | 1..6 |
| | mol_type = protein |
| | organism = synthetic construct |
| SEQUENCE: 124 | |
| CSSSSC | 6 |
| | |
| SEQ ID NO: 125 | moltype = AA  length = 6 |
| FEATURE | Location/Qualifiers |
| REGION | 1..6 |
| | note = Exemplary hydrophilic (and preferably non charged polar) amino acid component (AA) |
| source | 1..6 |
| | mol_type = protein |
| | organism = synthetic construct |
| SEQUENCE: 125 | |
| CTTTTC | 6 |
| | |
| SEQ ID NO: 126 | moltype =   length = |
| SEQUENCE: 126 | |
| 000 | |
| | |
| SEQ ID NO: 127 | moltype =   length = |
| SEQUENCE: 127 | |
| 000 | |
| | |
| SEQ ID NO: 128 | moltype = AA  length = 4 |
| FEATURE | Location/Qualifiers |
| REGION | 1..4 |
| | note = Exemplary hydrophilic (and preferably non charged polar) amino acid component (AA) |
| source | 1..4 |
| | mol_type = protein |
| | organism = synthetic construct |
| SEQUENCE: 128 | |
| CQNC | 4 |
| | |
| SEQ ID NO: 129 | moltype = AA  length = 4 |
| FEATURE | Location/Qualifiers |
| REGION | 1..4 |
| | note = Exemplary hydrophilic (and preferably non charged polar) amino acid component (AA) |
| source | 1..4 |
| | mol_type = protein |
| | organism = synthetic construct |
| SEQUENCE: 129 | |
| CNQC | 4 |
| | |
| SEQ ID NO: 130 | moltype = AA  length = 4 |
| FEATURE | Location/Qualifiers |
| REGION | 1..4 |
| | note = Exemplary hydrophilic (and preferably non charged polar) amino acid component (AA) |
| source | 1..4 |
| | mol_type = protein |
| | organism = synthetic construct |
| SEQUENCE: 130 | |
| CQQC | 4 |
| | |
| SEQ ID NO: 131 | moltype = AA  length = 4 |
| FEATURE | Location/Qualifiers |
| REGION | 1..4 |
| | note = Exemplary hydrophilic (and preferably non charged polar) amino acid component (AA) |
| source | 1..4 |
| | mol_type = protein |
| | organism = synthetic construct |

```
SEQUENCE: 131
CNNC                                                                4

SEQ ID NO: 132          moltype = AA  length = 5
FEATURE                 Location/Qualifiers
REGION                  1..5
                        note = Exemplary hydrophilic (and preferably non charged
                         polar) amino acid component (AA)
source                  1..5
                        mol_type = protein
                        organism = synthetic construct
SEQUENCE: 132
CQNQC                                                               5

SEQ ID NO: 133          moltype = AA  length = 5
FEATURE                 Location/Qualifiers
REGION                  1..5
                        note = Exemplary hydrophilic (and preferably non charged
                         polar) amino acid component (AA)
source                  1..5
                        mol_type = protein
                        organism = synthetic construct
SEQUENCE: 133
CNQNC                                                               5

SEQ ID NO: 134          moltype = AA  length = 5
FEATURE                 Location/Qualifiers
REGION                  1..5
                        note = Exemplary hydrophilic (and preferably non charged
                         polar) amino acid component (AA)
source                  1..5
                        mol_type = protein
                        organism = synthetic construct
SEQUENCE: 134
CQQQC                                                               5

SEQ ID NO: 135          moltype = AA  length = 5
FEATURE                 Location/Qualifiers
REGION                  1..5
                        note = Exemplary hydrophilic (and preferably non charged
                         polar) amino acid component (AA)
source                  1..5
                        mol_type = protein
                        organism = synthetic construct
SEQUENCE: 135
CNNNC                                                               5

SEQ ID NO: 136          moltype = AA  length = 6
FEATURE                 Location/Qualifiers
REGION                  1..6
                        note = Exemplary hydrophilic (and preferably non charged
                         polar) amino acid component (AA)
source                  1..6
                        mol_type = protein
                        organism = synthetic construct
SEQUENCE: 136
CQNQNC                                                              6

SEQ ID NO: 137          moltype = AA  length = 6
FEATURE                 Location/Qualifiers
REGION                  1..6
                        note = Exemplary hydrophilic (and preferably non charged
                         polar) amino acid component (AA)
source                  1..6
                        mol_type = protein
                        organism = synthetic construct
SEQUENCE: 137
CNQNQC                                                              6

SEQ ID NO: 138          moltype = AA  length = 6
FEATURE                 Location/Qualifiers
REGION                  1..6
                        note = Exemplary hydrophilic (and preferably non charged
                         polar) amino acid component (AA)
source                  1..6
                        mol_type = protein
                        organism = synthetic construct
SEQUENCE: 138
CQQQQC                                                              6
```

```
SEQ ID NO: 139          moltype = AA  length = 6
FEATURE                 Location/Qualifiers
REGION                  1..6
                        note = Exemplary hydrophilic (and preferably non charged
                         polar) amino acid component (AA)
source                  1..6
                        mol_type = protein
                        organism = synthetic construct
SEQUENCE: 139
CNNNNC                                                                     6

SEQ ID NO: 140          moltype =    length =
SEQUENCE: 140
000

SEQ ID NO: 141          moltype =    length =
SEQUENCE: 141
000

SEQ ID NO: 142          moltype = AA  length = 4
FEATURE                 Location/Qualifiers
REGION                  1..4
                        note = Exemplary hydrophilic (and preferably non charged
                         polar) amino acid component (AA)
source                  1..4
                        mol_type = protein
                        organism = synthetic construct
SEQUENCE: 142
CSNC                                                                       4

SEQ ID NO: 143          moltype = AA  length = 4
FEATURE                 Location/Qualifiers
REGION                  1..4
                        note = Exemplary hydrophilic (and preferably non charged
                         polar) amino acid component (AA)
source                  1..4
                        mol_type = protein
                        organism = synthetic construct
SEQUENCE: 143
CNSC                                                                       4

SEQ ID NO: 144          moltype = AA  length = 4
FEATURE                 Location/Qualifiers
REGION                  1..4
                        note = Exemplary hydrophilic (and preferably non charged
                         polar) amino acid component (AA)
source                  1..4
                        mol_type = protein
                        organism = synthetic construct
SEQUENCE: 144
CSSC                                                                       4

SEQ ID NO: 145          moltype = AA  length = 4
FEATURE                 Location/Qualifiers
REGION                  1..4
                        note = Exemplary hydrophilic (and preferably non charged
                         polar) amino acid component (AA)
source                  1..4
                        mol_type = protein
                        organism = synthetic construct
SEQUENCE: 145
CNNC                                                                       4

SEQ ID NO: 146          moltype = AA  length = 5
FEATURE                 Location/Qualifiers
REGION                  1..5
                        note = Exemplary hydrophilic (and preferably non charged
                         polar) amino acid component (AA)
source                  1..5
                        mol_type = protein
                        organism = synthetic construct
SEQUENCE: 146
CSNSC                                                                      5

SEQ ID NO: 147          moltype = AA  length = 5
FEATURE                 Location/Qualifiers
REGION                  1..5
                        note = Exemplary hydrophilic (and preferably non charged
```

```
                          polar) amino acid component (AA)
source                    1..5
                          mol_type = protein
                          organism = synthetic construct
SEQUENCE: 147
CNSNC                                                                        5

SEQ ID NO: 148            moltype = AA  length = 5
FEATURE                   Location/Qualifiers
REGION                    1..5
                          note = Exemplary hydrophilic (and preferably non charged
                          polar) amino acid component (AA)
source                    1..5
                          mol_type = protein
                          organism = synthetic construct
SEQUENCE: 148
CSSSC                                                                        5

SEQ ID NO: 149            moltype = AA  length = 5
FEATURE                   Location/Qualifiers
REGION                    1..5
                          note = Exemplary hydrophilic (and preferably non charged
                          polar) amino acid component (AA)
source                    1..5
                          mol_type = protein
                          organism = synthetic construct
SEQUENCE: 149
CNNNC                                                                        5

SEQ ID NO: 150            moltype = AA  length = 6
FEATURE                   Location/Qualifiers
REGION                    1..6
                          note = Exemplary hydrophilic (and preferably non charged
                          polar) amino acid component (AA)
source                    1..6
                          mol_type = protein
                          organism = synthetic construct
SEQUENCE: 150
CSNSNC                                                                       6

SEQ ID NO: 151            moltype = AA  length = 6
FEATURE                   Location/Qualifiers
REGION                    1..6
                          note = Exemplary hydrophilic (and preferably non charged
                          polar) amino acid component (AA)
source                    1..6
                          mol_type = protein
                          organism = synthetic construct
SEQUENCE: 151
CNSNSC                                                                       6

SEQ ID NO: 152            moltype = AA  length = 6
FEATURE                   Location/Qualifiers
REGION                    1..6
                          note = Exemplary hydrophilic (and preferably non charged
                          polar) amino acid component (AA)
source                    1..6
                          mol_type = protein
                          organism = synthetic construct
SEQUENCE: 152
CSSSSC                                                                       6

SEQ ID NO: 153            moltype = AA  length = 6
FEATURE                   Location/Qualifiers
REGION                    1..6
                          note = Exemplary hydrophilic (and preferably non charged
                          polar) amino acid component (AA)
source                    1..6
                          mol_type = protein
                          organism = synthetic construct
SEQUENCE: 153
CNNNNC                                                                       6

SEQ ID NO: 154            moltype =     length =
SEQUENCE: 154
000

SEQ ID NO: 155            moltype =     length =
SEQUENCE: 155
```

```
SEQ ID NO: 156         moltype =    length =
SEQUENCE: 156
000

SEQ ID NO: 157         moltype =    length =
SEQUENCE: 157
000

SEQ ID NO: 158         moltype =    length =
SEQUENCE: 158
000

SEQ ID NO: 159         moltype =    length =
SEQUENCE: 159
000

SEQ ID NO: 160         moltype =    length =
SEQUENCE: 160
000

SEQ ID NO: 161         moltype =    length =
SEQUENCE: 161
000

SEQ ID NO: 162         moltype = AA  length = 4
FEATURE                Location/Qualifiers
REGION                 1..4
                       note = Exemplary lipophilic amino acid component (AA)
source                 1..4
                       mol_type = protein
                       organism = synthetic construct
SEQUENCE: 162
LVLV                                                                      4

SEQ ID NO: 163         moltype = AA  length = 4
FEATURE                Location/Qualifiers
REGION                 1..4
                       note = Exemplary lipophilic amino acid component (AA)
source                 1..4
                       mol_type = protein
                       organism = synthetic construct
SEQUENCE: 163
VLVL                                                                      4

SEQ ID NO: 164         moltype = AA  length = 4
FEATURE                Location/Qualifiers
REGION                 1..4
                       note = Exemplary lipophilic amino acid component (AA)
source                 1..4
                       mol_type = protein
                       organism = synthetic construct
SEQUENCE: 164
LLLL                                                                      4

SEQ ID NO: 165         moltype = AA  length = 4
FEATURE                Location/Qualifiers
REGION                 1..4
                       note = Exemplary lipophilic amino acid component (AA)
source                 1..4
                       mol_type = protein
                       organism = synthetic construct
SEQUENCE: 165
VVVV                                                                      4

SEQ ID NO: 166         moltype =    length =
SEQUENCE: 166
000

SEQ ID NO: 167         moltype =    length =
SEQUENCE: 167
000

SEQ ID NO: 168         moltype =    length =
SEQUENCE: 168
000

SEQ ID NO: 169         moltype =    length =
```

```
SEQUENCE: 169
000

SEQ ID NO: 170          moltype =   length =
SEQUENCE: 170
000

SEQ ID NO: 171          moltype =   length =
SEQUENCE: 171
000

SEQ ID NO: 172          moltype =   length =
SEQUENCE: 172
000

SEQ ID NO: 173          moltype =   length =
SEQUENCE: 173
000

SEQ ID NO: 174          moltype =   length =
SEQUENCE: 174
000

SEQ ID NO: 175          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 175
AIAI                                                                        4

SEQ ID NO: 176          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 176
IIII                                                                        4

SEQ ID NO: 177          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 177
AAAA                                                                        4

SEQ ID NO: 178          moltype =   length =
SEQUENCE: 178
000

SEQ ID NO: 179          moltype =   length =
SEQUENCE: 179
000

SEQ ID NO: 180          moltype =   length =
SEQUENCE: 180
000

SEQ ID NO: 181          moltype =   length =
SEQUENCE: 181
000

SEQ ID NO: 182          moltype =   length =
SEQUENCE: 182
000

SEQ ID NO: 183          moltype =   length =
SEQUENCE: 183
000

SEQ ID NO: 184          moltype =   length =
SEQUENCE: 184
```

```
000

SEQ ID NO: 185        moltype =    length =
SEQUENCE: 185
000

SEQ ID NO: 186        moltype = AA   length = 4
FEATURE               Location/Qualifiers
REGION                1..4
                      note = Exemplary lipophilic amino acid component (AA)
source                1..4
                      mol_type = protein
                      organism = synthetic construct
SEQUENCE: 186
MAMA                                                                     4

SEQ ID NO: 187        moltype = AA   length = 4
FEATURE               Location/Qualifiers
REGION                1..4
                      note = Exemplary lipophilic amino acid component (AA)
source                1..4
                      mol_type = protein
                      organism = synthetic construct
SEQUENCE: 187
AMAM                                                                     4

SEQ ID NO: 188        moltype = AA   length = 4
FEATURE               Location/Qualifiers
REGION                1..4
                      note = Exemplary lipophilic amino acid component (AA)
source                1..4
                      mol_type = protein
                      organism = synthetic construct
SEQUENCE: 188
MMMM                                                                     4

SEQ ID NO: 189        moltype =    length =
SEQUENCE: 189
000

SEQ ID NO: 190        moltype =    length =
SEQUENCE: 190
000

SEQ ID NO: 191        moltype = AA   length = 4
FEATURE               Location/Qualifiers
REGION                1..4
                      note = Exemplary lipophilic amino acid component (AA)
source                1..4
                      mol_type = protein
                      organism = synthetic construct
SEQUENCE: 191
CLVC                                                                     4

SEQ ID NO: 192        moltype = AA   length = 4
FEATURE               Location/Qualifiers
REGION                1..4
                      note = Exemplary lipophilic amino acid component (AA)
source                1..4
                      mol_type = protein
                      organism = synthetic construct
SEQUENCE: 192
CVLC                                                                     4

SEQ ID NO: 193        moltype = AA   length = 4
FEATURE               Location/Qualifiers
REGION                1..4
                      note = Exemplary lipophilic amino acid component (AA)
source                1..4
                      mol_type = protein
                      organism = synthetic construct
SEQUENCE: 193
CLLC                                                                     4

SEQ ID NO: 194        moltype = AA   length = 4
FEATURE               Location/Qualifiers
REGION                1..4
                      note = Exemplary lipophilic amino acid component (AA)
source                1..4
```

```
                        mol_type = protein
                        organism = synthetic construct
SEQUENCE: 194
CVVC                                                                    4

SEQ ID NO: 195          moltype = AA   length = 5
FEATURE                 Location/Qualifiers
REGION                  1..5
                        note = Exemplary lipophilic amino acid component (AA)
source                  1..5
                        mol_type = protein
                        organism = synthetic construct
SEQUENCE: 195
CLVLC                                                                   5

SEQ ID NO: 196          moltype = AA   length = 5
FEATURE                 Location/Qualifiers
REGION                  1..5
                        note = Exemplary lipophilic amino acid component (AA)
source                  1..5
                        mol_type = protein
                        organism = synthetic construct
SEQUENCE: 196
CVLVC                                                                   5

SEQ ID NO: 197          moltype = AA   length = 5
FEATURE                 Location/Qualifiers
REGION                  1..5
                        note = Exemplary lipophilic amino acid component (AA)
source                  1..5
                        mol_type = protein
                        organism = synthetic construct
SEQUENCE: 197
CLLLC                                                                   5

SEQ ID NO: 198          moltype = AA   length = 5
FEATURE                 Location/Qualifiers
REGION                  1..5
                        note = Exemplary lipophilic amino acid component (AA)
source                  1..5
                        mol_type = protein
                        organism = synthetic construct
SEQUENCE: 198
CVVVC                                                                   5

SEQ ID NO: 199          moltype = AA   length = 6
FEATURE                 Location/Qualifiers
REGION                  1..6
                        note = Exemplary lipophilic amino acid component (AA)
source                  1..6
                        mol_type = protein
                        organism = synthetic construct
SEQUENCE: 199
CLVLVC                                                                  6

SEQ ID NO: 200          moltype = AA   length = 6
FEATURE                 Location/Qualifiers
REGION                  1..6
                        note = Exemplary lipophilic amino acid component (AA)
source                  1..6
                        mol_type = protein
                        organism = synthetic construct
SEQUENCE: 200
CVLVLC                                                                  6

SEQ ID NO: 201          moltype = AA   length = 6
FEATURE                 Location/Qualifiers
REGION                  1..6
                        note = Exemplary lipophilic amino acid component (AA)
source                  1..6
                        mol_type = protein
                        organism = synthetic construct
SEQUENCE: 201
CLLLLC                                                                  6

SEQ ID NO: 202          moltype = AA   length = 6
FEATURE                 Location/Qualifiers
REGION                  1..6
                        note = Exemplary lipophilic amino acid component (AA)
```

```
source                 1..6
                       mol_type = protein
                       organism = synthetic construct
SEQUENCE: 202
CVVVVC                                                                 6

SEQ ID NO: 203         moltype =   length =
SEQUENCE: 203
000

SEQ ID NO: 204         moltype =   length =
SEQUENCE: 204
000

SEQ ID NO: 205         moltype = AA   length = 4
FEATURE                Location/Qualifiers
REGION                 1..4
                       note = Exemplary lipophilic amino acid component (AA)
source                 1..4
                       mol_type = protein
                       organism = synthetic construct
SEQUENCE: 205
CIAC                                                                   4

SEQ ID NO: 206         moltype = AA   length = 4
FEATURE                Location/Qualifiers
REGION                 1..4
                       note = Exemplary lipophilic amino acid component (AA)
source                 1..4
                       mol_type = protein
                       organism = synthetic construct
SEQUENCE: 206
CAIC                                                                   4

SEQ ID NO: 207         moltype = AA   length = 4
FEATURE                Location/Qualifiers
REGION                 1..4
                       note = Exemplary lipophilic amino acid component (AA)
source                 1..4
                       mol_type = protein
                       organism = synthetic construct
SEQUENCE: 207
CIIC                                                                   4

SEQ ID NO: 208         moltype = AA   length = 4
FEATURE                Location/Qualifiers
REGION                 1..4
                       note = Exemplary lipophilic amino acid component (AA)
source                 1..4
                       mol_type = protein
                       organism = synthetic construct
SEQUENCE: 208
CAAC                                                                   4

SEQ ID NO: 209         moltype = AA   length = 5
FEATURE                Location/Qualifiers
REGION                 1..5
                       note = Exemplary lipophilic amino acid component (AA)
source                 1..5
                       mol_type = protein
                       organism = synthetic construct
SEQUENCE: 209
CIAIC                                                                  5

SEQ ID NO: 210         moltype = AA   length = 5
FEATURE                Location/Qualifiers
REGION                 1..5
                       note = Exemplary lipophilic amino acid component (AA)
source                 1..5
                       mol_type = protein
                       organism = synthetic construct
SEQUENCE: 210
CAIAC                                                                  5

SEQ ID NO: 211         moltype = AA   length = 5
FEATURE                Location/Qualifiers
REGION                 1..5
                       note = Exemplary lipophilic amino acid component (AA)
source                 1..5
```

```
                         mol_type = protein
                         organism = synthetic construct
SEQUENCE: 211
CIIIC                                                                          5

SEQ ID NO: 212           moltype = AA   length = 5
FEATURE                  Location/Qualifiers
REGION                   1..5
                         note = Exemplary lipophilic amino acid component (AA)
source                   1..5
                         mol_type = protein
                         organism = synthetic construct
SEQUENCE: 212
CAAAC                                                                          5

SEQ ID NO: 213           moltype = AA   length = 6
FEATURE                  Location/Qualifiers
REGION                   1..6
                         note = Exemplary lipophilic amino acid component (AA)
source                   1..6
                         mol_type = protein
                         organism = synthetic construct
SEQUENCE: 213
CIAIAC                                                                         6

SEQ ID NO: 214           moltype = AA   length = 6
FEATURE                  Location/Qualifiers
REGION                   1..6
                         note = Exemplary lipophilic amino acid component (AA)
source                   1..6
                         mol_type = protein
                         organism = synthetic construct
SEQUENCE: 214
CAIAIC                                                                         6

SEQ ID NO: 215           moltype = AA   length = 6
FEATURE                  Location/Qualifiers
REGION                   1..6
                         note = Exemplary lipophilic amino acid component (AA)
source                   1..6
                         mol_type = protein
                         organism = synthetic construct
SEQUENCE: 215
CIIIIC                                                                         6

SEQ ID NO: 216           moltype = AA   length = 6
FEATURE                  Location/Qualifiers
REGION                   1..6
                         note = Exemplary lipophilic amino acid component (AA)
source                   1..6
                         mol_type = protein
                         organism = synthetic construct
SEQUENCE: 216
CAAAAC                                                                         6

SEQ ID NO: 217           moltype =    length =
SEQUENCE: 217
000

SEQ ID NO: 218           moltype = AA   length = 4
FEATURE                  Location/Qualifiers
REGION                   1..4
                         note = Exemplary lipophilic amino acid component (AA)
source                   1..4
                         mol_type = protein
                         organism = synthetic construct
SEQUENCE: 218
CMAC                                                                           4

SEQ ID NO: 219           moltype = AA   length = 4
FEATURE                  Location/Qualifiers
REGION                   1..4
                         note = Exemplary lipophilic amino acid component (AA)
source                   1..4
                         mol_type = protein
                         organism = synthetic construct
SEQUENCE: 219
CAMC                                                                           4
```

```
SEQ ID NO: 220               moltype = AA   length = 4
FEATURE                      Location/Qualifiers
REGION                       1..4
                             note = Exemplary lipophilic amino acid component (AA)
source                       1..4
                             mol_type = protein
                             organism = synthetic construct
SEQUENCE: 220
CMMC                                                                             4

SEQ ID NO: 221               moltype = AA   length = 4
FEATURE                      Location/Qualifiers
REGION                       1..4
                             note = Exemplary lipophilic amino acid component (AA)
source                       1..4
                             mol_type = protein
                             organism = synthetic construct
SEQUENCE: 221
CAAC                                                                             4

SEQ ID NO: 222               moltype = AA   length = 5
FEATURE                      Location/Qualifiers
REGION                       1..5
                             note = Exemplary lipophilic amino acid component (AA)
source                       1..5
                             mol_type = protein
                             organism = synthetic construct
SEQUENCE: 222
CMAMC                                                                            5

SEQ ID NO: 223               moltype = AA   length = 5
FEATURE                      Location/Qualifiers
REGION                       1..5
                             note = Exemplary lipophilic amino acid component (AA)
source                       1..5
                             mol_type = protein
                             organism = synthetic construct
SEQUENCE: 223
CAMAC                                                                            5

SEQ ID NO: 224               moltype = AA   length = 5
FEATURE                      Location/Qualifiers
REGION                       1..5
                             note = Exemplary lipophilic amino acid component (AA)
source                       1..5
                             mol_type = protein
                             organism = synthetic construct
SEQUENCE: 224
CMMMC                                                                            5

SEQ ID NO: 225               moltype = AA   length = 5
FEATURE                      Location/Qualifiers
REGION                       1..5
                             note = Exemplary lipophilic amino acid component (AA)
source                       1..5
                             mol_type = protein
                             organism = synthetic construct
SEQUENCE: 225
CAAAC                                                                            5

SEQ ID NO: 226               moltype = AA   length = 6
FEATURE                      Location/Qualifiers
REGION                       1..6
                             note = Exemplary lipophilic amino acid component (AA)
source                       1..6
                             mol_type = protein
                             organism = synthetic construct
SEQUENCE: 226
CMAMAC                                                                           6

SEQ ID NO: 227               moltype = AA   length = 6
FEATURE                      Location/Qualifiers
REGION                       1..6
                             note = Exemplary lipophilic amino acid component (AA)
source                       1..6
                             mol_type = protein
                             organism = synthetic construct
SEQUENCE: 227
CAMAMC                                                                           6
```

```
SEQ ID NO: 228        moltype = AA  length = 6
FEATURE               Location/Qualifiers
REGION                1..6
                      note = Exemplary lipophilic amino acid component (AA)
source                1..6
                      mol_type = protein
                      organism = synthetic construct
SEQUENCE: 228
CMMMMC                                                                    6

SEQ ID NO: 229        moltype = AA  length = 6
FEATURE               Location/Qualifiers
REGION                1..6
                      note = Exemplary lipophilic amino acid component (AA)
source                1..6
                      mol_type = protein
                      organism = synthetic construct
SEQUENCE: 229
CAAAAC                                                                    6

SEQ ID NO: 230        moltype =    length =
SEQUENCE: 230
000

SEQ ID NO: 231        moltype =    length =
SEQUENCE: 231
000

SEQ ID NO: 232        moltype =    length =
SEQUENCE: 232
000

SEQ ID NO: 233        moltype =    length =
SEQUENCE: 233
000

SEQ ID NO: 234        moltype =    length =
SEQUENCE: 234
000

SEQ ID NO: 235        moltype =    length =
SEQUENCE: 235
000

SEQ ID NO: 236        moltype =    length =
SEQUENCE: 236
000

SEQ ID NO: 237        moltype =    length =
SEQUENCE: 237
000

SEQ ID NO: 238        moltype = AA  length = 4
FEATURE               Location/Qualifiers
REGION                1..4
                      note = Exemplary weak basic amino acid component (AA)
source                1..4
                      mol_type = protein
                      organism = synthetic construct
SEQUENCE: 238
DHDH                                                                      4

SEQ ID NO: 239        moltype = AA  length = 4
FEATURE               Location/Qualifiers
REGION                1..4
                      note = Exemplary weak basic amino acid component (AA)
source                1..4
                      mol_type = protein
                      organism = synthetic construct
SEQUENCE: 239
HDHD                                                                      4

SEQ ID NO: 240        moltype = AA  length = 4
FEATURE               Location/Qualifiers
REGION                1..4
                      note = Exemplary weak basic amino acid component (AA)
source                1..4
                      mol_type = protein
```

-continued

```
                            organism = synthetic construct
SEQUENCE: 240
DDDD                                                                    4

SEQ ID NO: 241              moltype = AA  length = 4
FEATURE                     Location/Qualifiers
REGION                      1..4
                            note = Exemplary weak basic amino acid component (AA)
source                      1..4
                            mol_type = protein
                            organism = synthetic construct
SEQUENCE: 241
HHHH                                                                    4

SEQ ID NO: 242              moltype =   length =
SEQUENCE: 242
000

SEQ ID NO: 243              moltype =   length =
SEQUENCE: 243
000

SEQ ID NO: 244              moltype = AA  length = 4
FEATURE                     Location/Qualifiers
REGION                      1..4
                            note = Exemplary weak basic amino acid component (AA)
source                      1..4
                            mol_type = protein
                            organism = synthetic construct
SEQUENCE: 244
CDHC                                                                    4

SEQ ID NO: 245              moltype = AA  length = 4
FEATURE                     Location/Qualifiers
REGION                      1..4
                            note = Exemplary weak basic amino acid component (AA)
source                      1..4
                            mol_type = protein
                            organism = synthetic construct
SEQUENCE: 245
CHDC                                                                    4

SEQ ID NO: 246              moltype = AA  length = 4
FEATURE                     Location/Qualifiers
REGION                      1..4
                            note = Exemplary weak basic amino acid component (AA)
source                      1..4
                            mol_type = protein
                            organism = synthetic construct
SEQUENCE: 246
CDDC                                                                    4

SEQ ID NO: 247              moltype = AA  length = 4
FEATURE                     Location/Qualifiers
REGION                      1..4
                            note = Exemplary weak basic amino acid component (AA)
source                      1..4
                            mol_type = protein
                            organism = synthetic construct
SEQUENCE: 247
CHHC                                                                    4

SEQ ID NO: 248              moltype = AA  length = 5
FEATURE                     Location/Qualifiers
REGION                      1..5
                            note = Exemplary weak basic amino acid component (AA)
source                      1..5
                            mol_type = protein
                            organism = synthetic construct
SEQUENCE: 248
CDHDC                                                                   5

SEQ ID NO: 249              moltype = AA  length = 5
FEATURE                     Location/Qualifiers
REGION                      1..5
                            note = Exemplary weak basic amino acid component (AA)
source                      1..5
                            mol_type = protein
                            organism = synthetic construct
```

```
SEQUENCE: 249
CHDHC                                                               5

SEQ ID NO: 250          moltype = AA  length = 5
FEATURE                 Location/Qualifiers
REGION                  1..5
                        note = Exemplary weak basic amino acid component (AA)
source                  1..5
                        mol_type = protein
                        organism = synthetic construct
SEQUENCE: 250
CDDDC                                                               5

SEQ ID NO: 251          moltype = AA  length = 5
FEATURE                 Location/Qualifiers
REGION                  1..5
                        note = Exemplary weak basic amino acid component (AA)
source                  1..5
                        mol_type = protein
                        organism = synthetic construct
SEQUENCE: 251
CHHHC                                                               5

SEQ ID NO: 252          moltype = AA  length = 6
FEATURE                 Location/Qualifiers
REGION                  1..6
                        note = Exemplary weak basic amino acid component (AA)
source                  1..6
                        mol_type = protein
                        organism = synthetic construct
SEQUENCE: 252
CDHDHC                                                              6

SEQ ID NO: 253          moltype = AA  length = 6
FEATURE                 Location/Qualifiers
REGION                  1..6
                        note = Exemplary weak basic amino acid component (AA)
source                  1..6
                        mol_type = protein
                        organism = synthetic construct
SEQUENCE: 253
CHDHDC                                                              6

SEQ ID NO: 254          moltype = AA  length = 6
FEATURE                 Location/Qualifiers
REGION                  1..6
                        note = Exemplary weak basic amino acid component (AA)
source                  1..6
                        mol_type = protein
                        organism = synthetic construct
SEQUENCE: 254
CDDDDC                                                              6

SEQ ID NO: 255          moltype = AA  length = 6
FEATURE                 Location/Qualifiers
REGION                  1..6
                        note = Exemplary weak basic amino acid component (AA)
source                  1..6
                        mol_type = protein
                        organism = synthetic construct
SEQUENCE: 255
CHHHHC                                                              6

SEQ ID NO: 256          moltype = AA  length = 4
FEATURE                 Location/Qualifiers
REGION                  1..4
                        note = Description of sequence: signal peptide,
                          localization signal or sequence or nuclear localization
                          signal
source                  1..4
                        mol_type = protein
                        organism = synthetic construct
SEQUENCE: 256
KDEL                                                                4

SEQ ID NO: 257          moltype = AA  length = 4
FEATURE                 Location/Qualifiers
REGION                  1..4
                        note = Description of sequence: signal peptide,
```

```
                        localization signal or sequence or nuclear localization
                        signal
source                  1..4
                        mol_type = protein
                        organism = synthetic construct
SEQUENCE: 257
DDEL                                                                         4

SEQ ID NO: 258          moltype = AA   length = 4
FEATURE                 Location/Qualifiers
REGION                  1..4
                        note = Description of sequence: signal peptide,
                        localization signal or sequence or nuclear localization
                        signal
source                  1..4
                        mol_type = protein
                        organism = synthetic construct
SEQUENCE: 258
DEEL                                                                         4

SEQ ID NO: 259          moltype = AA   length = 4
FEATURE                 Location/Qualifiers
REGION                  1..4
                        note = Description of sequence: signal peptide,
                        localization signal or sequence or nuclear localization
                        signal
source                  1..4
                        mol_type = protein
                        organism = synthetic construct
SEQUENCE: 259
QEDL                                                                         4

SEQ ID NO: 260          moltype = AA   length = 4
FEATURE                 Location/Qualifiers
REGION                  1..4
                        note = Description of sequence: signal peptide,
                        localization signal or sequence or nuclear localization
                        signal
source                  1..4
                        mol_type = protein
                        organism = synthetic construct
SEQUENCE: 260
RDEL                                                                         4

SEQ ID NO: 261          moltype = AA   length = 8
FEATURE                 Location/Qualifiers
REGION                  1..8
                        note = Description of sequence: signal peptide,
                        localization signal or sequence or nuclear localization
                        signal
source                  1..8
                        mol_type = protein
                        organism = synthetic construct
SEQUENCE: 261
GQNLSTSN                                                                     8

SEQ ID NO: 262          moltype = AA   length = 7
FEATURE                 Location/Qualifiers
REGION                  1..7
                        note = Description of sequence: signal peptide,
                        localization signal or sequence or nuclear localization
                        signal
source                  1..7
                        mol_type = protein
                        organism = synthetic construct
SEQUENCE: 262
PKKKRKV                                                                      7

SEQ ID NO: 263          moltype = AA   length = 7
FEATURE                 Location/Qualifiers
REGION                  1..7
                        note = Description of sequence: signal peptide,
                        localization signal or sequence or nuclear localization
                        signal
source                  1..7
                        mol_type = protein
                        organism = synthetic construct
SEQUENCE: 263
PQKKIKS                                                                      7
```

```
SEQ ID NO: 264          moltype = AA  length = 5
FEATURE                 Location/Qualifiers
REGION                  1..5
                        note = Description of sequence: signal peptide,
                         localization signal or sequence or nuclear localization
                         signal
source                  1..5
                        mol_type = protein
                        organism = synthetic construct
SEQUENCE: 264
QPKKP                                                                       5

SEQ ID NO: 265          moltype = AA  length = 4
FEATURE                 Location/Qualifiers
REGION                  1..4
                        note = Description of sequence: signal peptide,
                         localization signal or sequence or nuclear localization
                         signal
source                  1..4
                        mol_type = protein
                        organism = synthetic construct
SEQUENCE: 265
RKKR                                                                        4

SEQ ID NO: 266          moltype = AA  length = 12
FEATURE                 Location/Qualifiers
REGION                  1..12
                        note = Description of sequence: signal peptide,
                         localization signal or sequence or nuclear localization
                         signal
source                  1..12
                        mol_type = protein
                        organism = synthetic construct
SEQUENCE: 266
RKKRRQRRRA HQ                                                              12

SEQ ID NO: 267          moltype = AA  length = 16
FEATURE                 Location/Qualifiers
REGION                  1..16
                        note = Description of sequence: signal peptide,
                         localization signal or sequence or nuclear localization
                         signal
source                  1..16
                        mol_type = protein
                        organism = synthetic construct
SEQUENCE: 267
RQARRNRRRR WRERQR                                                          16

SEQ ID NO: 268          moltype = AA  length = 19
FEATURE                 Location/Qualifiers
REGION                  1..19
                        note = Description of sequence: signal peptide,
                         localization signal or sequence or nuclear localization
                         signal
source                  1..19
                        mol_type = protein
                        organism = synthetic construct
SEQUENCE: 268
MPLTRRRPAA SQALAPPTP                                                       19

SEQ ID NO: 269          moltype = AA  length = 8
FEATURE                 Location/Qualifiers
REGION                  1..8
                        note = Description of sequence: signal peptide,
                         localization signal or sequence or nuclear localization
                         signal
source                  1..8
                        mol_type = protein
                        organism = synthetic construct
SEQUENCE: 269
GAALTILV                                                                    8

SEQ ID NO: 270          moltype = AA  length = 8
FEATURE                 Location/Qualifiers
REGION                  1..8
                        note = Description of sequence: signal peptide,
                         localization signal or sequence or nuclear localization
                         signal
```

```
source              1..8
                    mol_type = protein
                    organism = synthetic construct
SEQUENCE: 270
GAALTLLG                                                                  8

SEQ ID NO: 271      moltype = AA   length = 15
FEATURE             Location/Qualifiers
REGION              1..15
                    note = Description of sequence: signal peptide,
                    localization signal or sequence or nuclear localization
                    signal
source              1..15
                    mol_type = protein
                    organism = synthetic construct
SEQUENCE: 271
MDDQRDLISN NEQLP                                                         15

SEQ ID NO: 272      moltype = AA   length = 32
FEATURE             Location/Qualifiers
REGION              1..32
                    note = Description of sequence: signal peptide,
                    localization signal or sequence or nuclear localization
                    signal
REGION              7..8
                    note = misc_feature - Xaa can be any naturally occurring
                    amino acid
SITE                32
                    note = misc_feature - Xaa can be any naturally occurring
                    amino acid
source              1..32
                    mol_type = protein
                    organism = synthetic construct
SEQUENCE: 272
MLFNLRXXLN NAAFRHGHNF MVRNFRCGQP LX                                       32

SEQ ID NO: 273      moltype = AA   length = 8
FEATURE             Location/Qualifiers
REGION              1..8
                    note = Description of sequence: signal peptide,
                    localization signal or sequence or nuclear localization
                    signal
source              1..8
                    mol_type = protein
                    organism = synthetic construct
SEQUENCE: 273
GCVCSSNP                                                                  8

SEQ ID NO: 274      moltype = AA   length = 8
FEATURE             Location/Qualifiers
REGION              1..8
                    note = Description of sequence: signal peptide,
                    localization signal or sequence or nuclear localization
                    signal
source              1..8
                    mol_type = protein
                    organism = synthetic construct
SEQUENCE: 274
GQTVTTPL                                                                  8

SEQ ID NO: 275      moltype = AA   length = 8
FEATURE             Location/Qualifiers
REGION              1..8
                    note = Description of sequence: signal peptide,
                    localization signal or sequence or nuclear localization
                    signal
source              1..8
                    mol_type = protein
                    organism = synthetic construct
SEQUENCE: 275
GQELSQHE                                                                  8

SEQ ID NO: 276      moltype = AA   length = 8
FEATURE             Location/Qualifiers
REGION              1..8
                    note = Description of sequence: signal peptide,
                    localization signal or sequence or nuclear localization
                    signal
source              1..8
```

```
                        mol_type = protein
                        organism = synthetic construct
SEQUENCE: 276
GNSPSYNP                                                                 8

SEQ ID NO: 277          moltype = AA   length = 8
FEATURE                 Location/Qualifiers
REGION                  1..8
                        note = Description of sequence: signal peptide,
                         localization signal or sequence or nuclear localization
                         signal
source                  1..8
                        mol_type = protein
                        organism = synthetic construct
SEQUENCE: 277
GVSGSKGQ                                                                 8

SEQ ID NO: 278          moltype = AA   length = 8
FEATURE                 Location/Qualifiers
REGION                  1..8
                        note = Description of sequence: signal peptide,
                         localization signal or sequence or nuclear localization
                         signal
source                  1..8
                        mol_type = protein
                        organism = synthetic construct
SEQUENCE: 278
GQTITTPL                                                                 8

SEQ ID NO: 279          moltype = AA   length = 8
FEATURE                 Location/Qualifiers
REGION                  1..8
                        note = Description of sequence: signal peptide,
                         localization signal or sequence or nuclear localization
                         signal
source                  1..8
                        mol_type = protein
                        organism = synthetic construct
SEQUENCE: 279
GQTLTTPL                                                                 8

SEQ ID NO: 280          moltype = AA   length = 8
FEATURE                 Location/Qualifiers
REGION                  1..8
                        note = Description of sequence: signal peptide,
                         localization signal or sequence or nuclear localization
                         signal
source                  1..8
                        mol_type = protein
                        organism = synthetic construct
SEQUENCE: 280
GQIFSRSA                                                                 8

SEQ ID NO: 281          moltype = AA   length = 8
FEATURE                 Location/Qualifiers
REGION                  1..8
                        note = Description of sequence: signal peptide,
                         localization signal or sequence or nuclear localization
                         signal
source                  1..8
                        mol_type = protein
                        organism = synthetic construct
SEQUENCE: 281
GQIHGLSP                                                                 8

SEQ ID NO: 282          moltype = AA   length = 8
FEATURE                 Location/Qualifiers
REGION                  1..8
                        note = Description of sequence: signal peptide,
                         localization signal or sequence or nuclear localization
                         signal
source                  1..8
                        mol_type = protein
                        organism = synthetic construct
SEQUENCE: 282
GARASVLS                                                                 8

SEQ ID NO: 283          moltype = AA   length = 8
FEATURE                 Location/Qualifiers
```

```
SEQ ID NO: 283            moltype = AA   length = 8
FEATURE                   Location/Qualifiers
REGION                    1..8
                          note = Description of sequence: signal peptide,
                            localization signal or sequence or nuclear localization
                            signal
source                    1..8
                          mol_type = protein
                          organism = synthetic construct
SEQUENCE: 283
GCTLSAEE                                                                          8

SEQ ID NO: 284            moltype = AA   length = 8
FEATURE                   Location/Qualifiers
REGION                    1..8
                          note = Description of sequence: signal peptide,
                            localization signal or sequence or nuclear localization
                            signal
source                    1..8
                          mol_type = protein
                          organism = synthetic construct
SEQUENCE: 284
GAQVSSQK                                                                          8

SEQ ID NO: 285            moltype = AA   length = 8
FEATURE                   Location/Qualifiers
REGION                    1..8
                          note = Description of sequence: signal peptide,
                            localization signal or sequence or nuclear localization
                            signal
source                    1..8
                          mol_type = protein
                          organism = synthetic construct
SEQUENCE: 285
GAQLSRNT                                                                          8

SEQ ID NO: 286            moltype = AA   length = 8
FEATURE                   Location/Qualifiers
REGION                    1..8
                          note = Description of sequence: signal peptide,
                            localization signal or sequence or nuclear localization
                            signal
source                    1..8
                          mol_type = protein
                          organism = synthetic construct
SEQUENCE: 286
GNAAAAKK                                                                          8

SEQ ID NO: 287            moltype = AA   length = 8
FEATURE                   Location/Qualifiers
REGION                    1..8
                          note = Description of sequence: signal peptide,
                            localization signal or sequence or nuclear localization
                            signal
source                    1..8
                          mol_type = protein
                          organism = synthetic construct
SEQUENCE: 287
GNEASYPL                                                                          8

SEQ ID NO: 288            moltype = AA   length = 8
FEATURE                   Location/Qualifiers
REGION                    1..8
                          note = Description of sequence: signal peptide,
                            localization signal or sequence or nuclear localization
                            signal
source                    1..8
                          mol_type = protein
                          organism = synthetic construct
SEQUENCE: 288
GSSKSKPK                                                                          8

SEQ ID NO: 289            moltype = RNA   length = 20
FEATURE                   Location/Qualifiers
misc_feature              1..20
                          note = nucleic acid sequence according to formula (II)
source                    1..20
                          mol_type = other RNA
                          organism = synthetic construct
SEQUENCE: 289
ggtttttttt tttttttggg                                                            20
```

```
SEQ ID NO: 290          moltype = RNA  length = 20
FEATURE                 Location/Qualifiers
misc_feature            1..20
                        note = nucleic acid sequence according to formula (II)
source                  1..20
                        mol_type = other RNA
                        organism = synthetic construct
SEQUENCE: 290
gggggttttt tttttggggg                                                    20

SEQ ID NO: 291          moltype = RNA  length = 40
FEATURE                 Location/Qualifiers
misc_feature            1..40
                        note = nucleic acid sequence according to formula (II)
source                  1..40
                        mol_type = other RNA
                        organism = synthetic construct
SEQUENCE: 291
gggggttttt tttttttttt tttttttttt tttttggggg                              40

SEQ ID NO: 292          moltype = RNA  length = 39
FEATURE                 Location/Qualifiers
misc_feature            1..39
                        note = nucleic acid sequence according to formula (II)
source                  1..39
                        mol_type = other RNA
                        organism = synthetic construct
SEQUENCE: 292
gtgtgtgtgt gttttttttt tttttttgtg tgtgtgtgt                               39

SEQ ID NO: 293          moltype = RNA  length = 39
FEATURE                 Location/Qualifiers
misc_feature            1..39
                        note = nucleic acid sequence according to formula (II)
source                  1..39
                        mol_type = other RNA
                        organism = synthetic construct
SEQUENCE: 293
ggttggttgg tttttttttt tttttttggt tggttggtt                               39

SEQ ID NO: 294          moltype = RNA  length = 20
FEATURE                 Location/Qualifiers
misc_feature            1..20
                        note = nucleic acid sequence according to formula (II)
source                  1..20
                        mol_type = other RNA
                        organism = synthetic construct
SEQUENCE: 294
gggggggggt ttggggggggg                                                   20

SEQ ID NO: 295          moltype = RNA  length = 20
FEATURE                 Location/Qualifiers
misc_feature            1..20
                        note = nucleic acid sequence according to formula (II)
source                  1..20
                        mol_type = other RNA
                        organism = synthetic construct
SEQUENCE: 295
ggggggggtt ttgggggggg                                                    20

SEQ ID NO: 296          moltype = RNA  length = 20
FEATURE                 Location/Qualifiers
misc_feature            1..20
                        note = nucleic acid sequence according to formula (II)
source                  1..20
                        mol_type = other RNA
                        organism = synthetic construct
SEQUENCE: 296
gggggggttt tttggggggg                                                    20

SEQ ID NO: 297          moltype = RNA  length = 20
FEATURE                 Location/Qualifiers
misc_feature            1..20
                        note = nucleic acid sequence according to formula (II)
source                  1..20
                        mol_type = other RNA
                        organism = synthetic construct
SEQUENCE: 297
```

```
gggggggtttt ttttggggggg                                            20

SEQ ID NO: 298          moltype = RNA   length = 20
FEATURE                 Location/Qualifiers
misc_feature            1..20
                        note = nucleic acid sequence according to formula (II)
source                  1..20
                        mol_type = other RNA
                        organism = synthetic construct
SEQUENCE: 298
ggggggtttt ttttggggggg                                             20

SEQ ID NO: 299          moltype = RNA   length = 20
FEATURE                 Location/Qualifiers
misc_feature            1..20
                        note = nucleic acid sequence according to formula (II)
source                  1..20
                        mol_type = other RNA
                        organism = synthetic construct
SEQUENCE: 299
gggggttttt tttttggggg                                              20

SEQ ID NO: 300          moltype = RNA   length = 20
FEATURE                 Location/Qualifiers
misc_feature            1..20
                        note = nucleic acid sequence according to formula (II)
source                  1..20
                        mol_type = other RNA
                        organism = synthetic construct
SEQUENCE: 300
gggggtttt tttttggggg                                               20

SEQ ID NO: 301          moltype = RNA   length = 20
FEATURE                 Location/Qualifiers
misc_feature            1..20
                        note = nucleic acid sequence according to formula (II)
source                  1..20
                        mol_type = other RNA
                        organism = synthetic construct
SEQUENCE: 301
ggggttttt tttttggggg                                               20

SEQ ID NO: 302          moltype = RNA   length = 20
FEATURE                 Location/Qualifiers
misc_feature            1..20
                        note = nucleic acid sequence according to formula (II)
source                  1..20
                        mol_type = other RNA
                        organism = synthetic construct
SEQUENCE: 302
ggggttttt ttttttggg                                                20

SEQ ID NO: 303          moltype = RNA   length = 20
FEATURE                 Location/Qualifiers
misc_feature            1..20
                        note = nucleic acid sequence according to formula (II)
source                  1..20
                        mol_type = other RNA
                        organism = synthetic construct
SEQUENCE: 303
ggggttttt ttttttggg                                                20

SEQ ID NO: 304          moltype = RNA   length = 20
FEATURE                 Location/Qualifiers
misc_feature            1..20
                        note = nucleic acid sequence according to formula (II)
source                  1..20
                        mol_type = other RNA
                        organism = synthetic construct
SEQUENCE: 304
ggggtttt tttttttgg                                                 20

SEQ ID NO: 305          moltype = RNA   length = 20
FEATURE                 Location/Qualifiers
misc_feature            1..20
                        note = nucleic acid sequence according to formula (II)
source                  1..20
                        mol_type = other RNA
                        organism = synthetic construct
```

```
SEQUENCE: 305
ggttttttttt ttttttttgg                                              20

SEQ ID NO: 306          moltype = RNA  length = 20
FEATURE                 Location/Qualifiers
misc_feature            1..20
                        note = nucleic acid sequence according to formula (II)
source                  1..20
                        mol_type = other RNA
                        organism = synthetic construct
SEQUENCE: 306
gttttttttt ttttttttttg                                              20

SEQ ID NO: 307          moltype = RNA  length = 22
FEATURE                 Location/Qualifiers
misc_feature            1..22
                        note = nucleic acid sequence according to formula (II)
source                  1..22
                        mol_type = other RNA
                        organism = synthetic construct
SEQUENCE: 307
gggggggggg tttggggggg gg                                            22

SEQ ID NO: 308          moltype = RNA  length = 22
FEATURE                 Location/Qualifiers
misc_feature            1..22
                        note = nucleic acid sequence according to formula (II)
source                  1..22
                        mol_type = other RNA
                        organism = synthetic construct
SEQUENCE: 308
ggggggggggt tttggggggg gg                                           22

SEQ ID NO: 309          moltype = RNA  length = 22
FEATURE                 Location/Qualifiers
misc_feature            1..22
                        note = nucleic acid sequence according to formula (II)
source                  1..22
                        mol_type = other RNA
                        organism = synthetic construct
SEQUENCE: 309
ggggggggtt tttggggggg gg                                            22

SEQ ID NO: 310          moltype = RNA  length = 22
FEATURE                 Location/Qualifiers
misc_feature            1..22
                        note = nucleic acid sequence according to formula (II)
source                  1..22
                        mol_type = other RNA
                        organism = synthetic construct
SEQUENCE: 310
gggggggggtt ttttgggggg gg                                           22

SEQ ID NO: 311          moltype = RNA  length = 22
FEATURE                 Location/Qualifiers
misc_feature            1..22
                        note = nucleic acid sequence according to formula (II)
source                  1..22
                        mol_type = other RNA
                        organism = synthetic construct
SEQUENCE: 311
ggggggggttt tttttggggg gg                                           22

SEQ ID NO: 312          moltype = RNA  length = 22
FEATURE                 Location/Qualifiers
misc_feature            1..22
                        note = nucleic acid sequence according to formula (II)
source                  1..22
                        mol_type = other RNA
                        organism = synthetic construct
SEQUENCE: 312
gggggggttt tttttttgggg gg                                           22

SEQ ID NO: 313          moltype = RNA  length = 22
FEATURE                 Location/Qualifiers
misc_feature            1..22
                        note = nucleic acid sequence according to formula (II)
source                  1..22
                        mol_type = other RNA
```

```
                        organism = synthetic construct
SEQUENCE: 313
ggggggggttt tttttttggg gg                                              22

SEQ ID NO: 314          moltype = RNA   length = 22
FEATURE                 Location/Qualifiers
misc_feature            1..22
                        note = nucleic acid sequence according to formula (II)
source                  1..22
                        mol_type = other RNA
                        organism = synthetic construct
SEQUENCE: 314
gggggtttt ttttttggg gg                                                 22

SEQ ID NO: 315          moltype = RNA   length = 22
FEATURE                 Location/Qualifiers
misc_feature            1..22
                        note = nucleic acid sequence according to formula (II)
source                  1..22
                        mol_type = other RNA
                        organism = synthetic construct
SEQUENCE: 315
ggggggtttt ttttttttgg gg                                               22

SEQ ID NO: 316          moltype = RNA   length = 22
FEATURE                 Location/Qualifiers
misc_feature            1..22
                        note = nucleic acid sequence according to formula (II)
source                  1..22
                        mol_type = other RNA
                        organism = synthetic construct
SEQUENCE: 316
gggggttttt tttttttgg gg                                                22

SEQ ID NO: 317          moltype = RNA   length = 22
FEATURE                 Location/Qualifiers
misc_feature            1..22
                        note = nucleic acid sequence according to formula (II)
source                  1..22
                        mol_type = other RNA
                        organism = synthetic construct
SEQUENCE: 317
gggggttttt ttttttttg gg                                                22

SEQ ID NO: 318          moltype = RNA   length = 22
FEATURE                 Location/Qualifiers
misc_feature            1..22
                        note = nucleic acid sequence according to formula (II)
source                  1..22
                        mol_type = other RNA
                        organism = synthetic construct
SEQUENCE: 318
gggttttttt ttttttttg gg                                                22

SEQ ID NO: 319          moltype = RNA   length = 22
FEATURE                 Location/Qualifiers
misc_feature            1..22
                        note = nucleic acid sequence according to formula (II)
source                  1..22
                        mol_type = other RNA
                        organism = synthetic construct
SEQUENCE: 319
ggttttttt tttttttttt gg                                                22

SEQ ID NO: 320          moltype = RNA   length = 24
FEATURE                 Location/Qualifiers
misc_feature            1..24
                        note = nucleic acid sequence according to formula (II)
source                  1..24
                        mol_type = other RNA
                        organism = synthetic construct
SEQUENCE: 320
gggggggggg gtttggggggg gggg                                            24

SEQ ID NO: 321          moltype = RNA   length = 24
FEATURE                 Location/Qualifiers
misc_feature            1..24
                        note = nucleic acid sequence according to formula (II)
source                  1..24
```

```
                    mol_type = other RNA
                    organism = synthetic construct
SEQUENCE: 321
gggggggggg ttttggggg gggg                                              24

SEQ ID NO: 322          moltype = RNA   length = 24
FEATURE                 Location/Qualifiers
misc_feature            1..24
                    note = nucleic acid sequence according to formula (II)
source                  1..24
                    mol_type = other RNA
                    organism = synthetic construct
SEQUENCE: 322
gggggggggt ttttggggg gggg                                              24

SEQ ID NO: 323          moltype = RNA   length = 24
FEATURE                 Location/Qualifiers
misc_feature            1..24
                    note = nucleic acid sequence according to formula (II)
source                  1..24
                    mol_type = other RNA
                    organism = synthetic construct
SEQUENCE: 323
ggggggggt tttttgggg gggg                                               24

SEQ ID NO: 324          moltype = RNA   length = 24
FEATURE                 Location/Qualifiers
misc_feature            1..24
                    note = nucleic acid sequence according to formula (II)
source                  1..24
                    mol_type = other RNA
                    organism = synthetic construct
SEQUENCE: 324
ggggggggtt tttttgggg gggg                                              24

SEQ ID NO: 325          moltype = RNA   length = 24
FEATURE                 Location/Qualifiers
misc_feature            1..24
                    note = nucleic acid sequence according to formula (II)
source                  1..24
                    mol_type = other RNA
                    organism = synthetic construct
SEQUENCE: 325
gggggggtt tttttggg gggg                                                24

SEQ ID NO: 326          moltype = RNA   length = 24
FEATURE                 Location/Qualifiers
misc_feature            1..24
                    note = nucleic acid sequence according to formula (II)
source                  1..24
                    mol_type = other RNA
                    organism = synthetic construct
SEQUENCE: 326
gggggggtt tttttttgg gggg                                               24

SEQ ID NO: 327          moltype = RNA   length = 24
FEATURE                 Location/Qualifiers
misc_feature            1..24
                    note = nucleic acid sequence according to formula (II)
source                  1..24
                    mol_type = other RNA
                    organism = synthetic construct
SEQUENCE: 327
ggggggttt tttttttgg gggg                                               24

SEQ ID NO: 328          moltype = RNA   length = 24
FEATURE                 Location/Qualifiers
misc_feature            1..24
                    note = nucleic acid sequence according to formula (II)
source                  1..24
                    mol_type = other RNA
                    organism = synthetic construct
SEQUENCE: 328
ggggggttt tttttttg gggg                                                24

SEQ ID NO: 329          moltype = RNA   length = 24
FEATURE                 Location/Qualifiers
misc_feature            1..24
                    note = nucleic acid sequence according to formula (II)
```

```
source                  1..24
                        mol_type = other RNA
                        organism = synthetic construct
SEQUENCE: 329
gggggtttt tttttttttg gggg                                              24

SEQ ID NO: 330          moltype = RNA  length = 24
FEATURE                 Location/Qualifiers
misc_feature            1..24
                        note = nucleic acid sequence according to formula (II)
source                  1..24
                        mol_type = other RNA
                        organism = synthetic construct
SEQUENCE: 330
gggggtttt tttttttttt gggg                                              24

SEQ ID NO: 331          moltype = RNA  length = 24
FEATURE                 Location/Qualifiers
misc_feature            1..24
                        note = nucleic acid sequence according to formula (II)
source                  1..24
                        mol_type = other RNA
                        organism = synthetic construct
SEQUENCE: 331
ggggttttt tttttttttt gggg                                              24

SEQ ID NO: 332          moltype = RNA  length = 24
FEATURE                 Location/Qualifiers
misc_feature            1..24
                        note = nucleic acid sequence according to formula (II)
source                  1..24
                        mol_type = other RNA
                        organism = synthetic construct
SEQUENCE: 332
gggttttttt tttttttttt tggg                                             24

SEQ ID NO: 333          moltype = RNA  length = 32
FEATURE                 Location/Qualifiers
misc_feature            1..32
                        note = nucleic acid sequence according to formula (II)
source                  1..32
                        mol_type = other RNA
                        organism = synthetic construct
SEQUENCE: 333
gttttttttt tttttttttt tttttttttt tg                                    32

SEQ ID NO: 334          moltype = RNA  length = 34
FEATURE                 Location/Qualifiers
misc_feature            1..34
                        note = nucleic acid sequence according to formula (II)
source                  1..34
                        mol_type = other RNA
                        organism = synthetic construct
SEQUENCE: 334
ggttttttt tttttttttt tttttttttt ttgg                                   34

SEQ ID NO: 335          moltype = RNA  length = 36
FEATURE                 Location/Qualifiers
misc_feature            1..36
                        note = nucleic acid sequence according to formula (II)
source                  1..36
                        mol_type = other RNA
                        organism = synthetic construct
SEQUENCE: 335
gggttttttt tttttttttt tttttttttt tttggg                                36

SEQ ID NO: 336          moltype = RNA  length = 37
FEATURE                 Location/Qualifiers
misc_feature            1..37
                        note = nucleic acid sequence according to formula (II)
source                  1..37
                        mol_type = other RNA
                        organism = synthetic construct
SEQUENCE: 336
ggggttttt tttttttttt tttttttttt ttttggg                                37

SEQ ID NO: 337          moltype = RNA  length = 39
FEATURE                 Location/Qualifiers
misc_feature            1..39
```

```
                    note = nucleic acid sequence according to formula (II)
source              1..39
                    mol_type = other RNA
                    organism = synthetic construct
SEQUENCE: 337
gggggttttt tttttttttt tttttttttt tttttgggg                            39

SEQ ID NO: 338      moltype = RNA   length = 41
FEATURE             Location/Qualifiers
misc_feature        1..41
                    note = nucleic acid sequence according to formula (II)
source              1..41
                    mol_type = other RNA
                    organism = synthetic construct
SEQUENCE: 338
ggggggtttt tttttttttt tttttttttt tttttgggg g                          41

SEQ ID NO: 339      moltype = RNA   length = 43
FEATURE             Location/Qualifiers
misc_feature        1..43
                    note = nucleic acid sequence according to formula (II)
source              1..43
                    mol_type = other RNA
                    organism = synthetic construct
SEQUENCE: 339
gggggggttt tttttttttt tttttttttt ttttttggg ggg                        43

SEQ ID NO: 340      moltype = RNA   length = 45
FEATURE             Location/Qualifiers
misc_feature        1..45
                    note = nucleic acid sequence according to formula (II)
source              1..45
                    mol_type = other RNA
                    organism = synthetic construct
SEQUENCE: 340
ggggggggtt tttttttttt tttttttttt tttttttgg ggggg                      45

SEQ ID NO: 341      moltype = RNA   length = 47
FEATURE             Location/Qualifiers
misc_feature        1..47
                    note = nucleic acid sequence according to formula (II)
source              1..47
                    mol_type = other RNA
                    organism = synthetic construct
SEQUENCE: 341
gggggggggt tttttttttt tttttttttt ttttttttg ggggggg                    47

SEQ ID NO: 342      moltype =    length =
SEQUENCE: 342
000

SEQ ID NO: 343      moltype =    length =
SEQUENCE: 343
000

SEQ ID NO: 344      moltype =    length =
SEQUENCE: 344
000

SEQ ID NO: 345      moltype = RNA   length = 10
FEATURE             Location/Qualifiers
misc_feature        1..10
                    note = nucleic acid sequence according to formula (II)
source              1..10
                    mol_type = other RNA
                    organism = synthetic construct
SEQUENCE: 345
ggtttttgg                                                             10

SEQ ID NO: 346      moltype = RNA   length = 11
FEATURE             Location/Qualifiers
misc_feature        1..11
                    note = nucleic acid sequence according to formula (II)
source              1..11
                    mol_type = other RNA
                    organism = synthetic construct
SEQUENCE: 346
ggttttttg g                                                           11
```

```
SEQ ID NO: 347           moltype = RNA   length = 12
FEATURE                  Location/Qualifiers
misc_feature             1..12
                         note = nucleic acid sequence according to formula (II)
source                   1..12
                         mol_type = other RNA
                         organism = synthetic construct
SEQUENCE: 347
ggtttttttt gg                                                              12

SEQ ID NO: 348           moltype = RNA   length = 13
FEATURE                  Location/Qualifiers
misc_feature             1..13
                         note = nucleic acid sequence according to formula (II)
source                   1..13
                         mol_type = other RNA
                         organism = synthetic construct
SEQUENCE: 348
ggtttttttt tgg                                                             13

SEQ ID NO: 349           moltype = RNA   length = 14
FEATURE                  Location/Qualifiers
misc_feature             1..14
                         note = nucleic acid sequence according to formula (II)
source                   1..14
                         mol_type = other RNA
                         organism = synthetic construct
SEQUENCE: 349
ggtttttttt ttgg                                                            14

SEQ ID NO: 350           moltype = RNA   length = 15
FEATURE                  Location/Qualifiers
misc_feature             1..15
                         note = nucleic acid sequence according to formula (II)
source                   1..15
                         mol_type = other RNA
                         organism = synthetic construct
SEQUENCE: 350
ggtttttttt tttgg                                                           15

SEQ ID NO: 351           moltype = RNA   length = 16
FEATURE                  Location/Qualifiers
misc_feature             1..16
                         note = nucleic acid sequence according to formula (II)
source                   1..16
                         mol_type = other RNA
                         organism = synthetic construct
SEQUENCE: 351
ggtttttttt ttttgg                                                          16

SEQ ID NO: 352           moltype = RNA   length = 17
FEATURE                  Location/Qualifiers
misc_feature             1..17
                         note = nucleic acid sequence according to formula (II)
source                   1..17
                         mol_type = other RNA
                         organism = synthetic construct
SEQUENCE: 352
ggtttttttt tttttgg                                                         17

SEQ ID NO: 353           moltype = RNA   length = 18
FEATURE                  Location/Qualifiers
misc_feature             1..18
                         note = nucleic acid sequence according to formula (II)
source                   1..18
                         mol_type = other RNA
                         organism = synthetic construct
SEQUENCE: 353
ggtttttttt ttttttgg                                                        18

SEQ ID NO: 354           moltype = RNA   length = 19
FEATURE                  Location/Qualifiers
misc_feature             1..19
                         note = nucleic acid sequence according to formula (II)
source                   1..19
                         mol_type = other RNA
                         organism = synthetic construct
SEQUENCE: 354
ggtttttttt tttttttgg                                                       19
```

| | | |
|---|---|---|
| SEQ ID NO: 355
SEQUENCE: 355
000 | moltype =   length = | |
| SEQ ID NO: 356
FEATURE
misc_feature source | moltype = RNA   length = 10
Location/Qualifiers
1..10
note = nucleic acid sequence according to formula (II)
1..10
mol_type = other RNA
organism = synthetic construct | |
| SEQUENCE: 356
gggttttggg | | 10 |
| SEQ ID NO: 357
FEATURE
misc_feature source | moltype = RNA   length = 11
Location/Qualifiers
1..11
note = nucleic acid sequence according to formula (II)
1..11
mol_type = other RNA
organism = synthetic construct | |
| SEQUENCE: 357
gggtttttgg g | | 11 |
| SEQ ID NO: 358
FEATURE
misc_feature source | moltype = RNA   length = 12
Location/Qualifiers
1..12
note = nucleic acid sequence according to formula (II)
1..12
mol_type = other RNA
organism = synthetic construct | |
| SEQUENCE: 358
gggttttttg gg | | 12 |
| SEQ ID NO: 359
FEATURE
misc_feature source | moltype = RNA   length = 13
Location/Qualifiers
1..13
note = nucleic acid sequence according to formula (II)
1..13
mol_type = other RNA
organism = synthetic construct | |
| SEQUENCE: 359
gggttttttt ggg | | 13 |
| SEQ ID NO: 360
FEATURE
misc_feature source | moltype = RNA   length = 14
Location/Qualifiers
1..14
note = nucleic acid sequence according to formula (II)
1..14
mol_type = other RNA
organism = synthetic construct | |
| SEQUENCE: 360
gggttttttt tggg | | 14 |
| SEQ ID NO: 361
FEATURE
misc_feature source | moltype = RNA   length = 15
Location/Qualifiers
1..15
note = nucleic acid sequence according to formula (II)
1..15
mol_type = other RNA
organism = synthetic construct | |
| SEQUENCE: 361
gggttttttt ttggg | | 15 |
| SEQ ID NO: 362
FEATURE
misc_feature source | moltype = RNA   length = 16
Location/Qualifiers
1..16
note = nucleic acid sequence according to formula (II)
1..16
mol_type = other RNA
organism = synthetic construct | |
| SEQUENCE: 362
gggttttttt tttggg | | 16 |
| SEQ ID NO: 363
FEATURE
misc_feature | moltype = RNA   length = 17
Location/Qualifiers
1..17
note = nucleic acid sequence according to formula (II) | |

| | |
|---|---|
| source | 1..17<br>mol_type = other RNA<br>organism = synthetic construct |
| SEQUENCE: 363 | |
| gggttttttt ttttggg | 17 |
| | |
| SEQ ID NO: 364<br>FEATURE<br>misc_feature | moltype = RNA length = 18<br>Location/Qualifiers<br>1..18<br>note = nucleic acid sequence according to formula (II) |
| source | 1..18<br>mol_type = other RNA<br>organism = synthetic construct |
| SEQUENCE: 364 | |
| gggttttttt tttttggg | 18 |
| | |
| SEQ ID NO: 365<br>FEATURE<br>misc_feature | moltype = RNA length = 19<br>Location/Qualifiers<br>1..19<br>note = nucleic acid sequence according to formula (II) |
| source | 1..19<br>mol_type = other RNA<br>organism = synthetic construct |
| SEQUENCE: 365 | |
| gggttttttt ttttttggg | 19 |
| | |
| SEQ ID NO: 366<br>FEATURE<br>misc_feature | moltype = RNA length = 57<br>Location/Qualifiers<br>1..57<br>note = nucleic acid sequence according to formula (II) |
| source | 1..57<br>mol_type = other RNA<br>organism = synthetic construct |
| SEQUENCE: 366 | |
| gggttttttt tttttttgg gttttttttt tttttgggt tttttttttt ttttggg | 57 |
| | |
| SEQ ID NO: 367<br>FEATURE<br>misc_feature | moltype = RNA length = 42<br>Location/Qualifiers<br>1..42<br>note = nucleic acid sequence according to formula (II) |
| source | 1..42<br>mol_type = other RNA<br>organism = synthetic construct |
| SEQUENCE: 367 | |
| gggttttttt tttttttgg ggggttttttt tttttttg gg | 42 |
| | |
| SEQ ID NO: 368<br>FEATURE<br>misc_feature | moltype = RNA length = 51<br>Location/Qualifiers<br>1..51<br>note = nucleic acid sequence according to formula (III) |
| source | 1..51<br>mol_type = other RNA<br>organism = synthetic construct |
| SEQUENCE: 368 | |
| gggtttgggt ttgggtttgg gtttgggttt gggtttgggt tgggtttgg g | 51 |
| | |
| SEQ ID NO: 369<br>FEATURE<br>misc_feature | moltype = RNA length = 20<br>Location/Qualifiers<br>1..20<br>note = nucleic acid sequence according to formula (II) -<br>Short GU rich |
| source | 1..20<br>mol_type = other RNA<br>organism = synthetic construct |
| SEQUENCE: 369 | |
| ggtttttttt tttttttggg | 20 |
| | |
| SEQ ID NO: 370<br>FEATURE<br>misc_feature | moltype = RNA length = 57<br>Location/Qualifiers<br>1..57<br>note = nucleic acid sequence according to formula (III) |
| source | 1..57<br>mol_type = other RNA<br>organism = synthetic construct |
| SEQUENCE: 370 | |
| cccttttttt ttttttttcc ctttttttttt tttttcccct tttttttttt ttttccc | 57 |
| | |
| SEQ ID NO: 371<br>FEATURE | moltype = RNA length = 51<br>Location/Qualifiers |

```
misc_feature               1..51
                           note = nucleic acid sequence according to formula (III)
source                     1..51
                           mol_type = other RNA
                           organism = synthetic construct
SEQUENCE: 371
ccctttccct tcccttttcc ctttccctttt ccctttccct tcccttttcc c            51

SEQ ID NO: 372             moltype = RNA  length = 42
FEATURE                    Location/Qualifiers
misc_feature               1..42
                           note = nucleic acid sequence according to formula (III)
source                     1..42
                           mol_type = other RNA
                           organism = synthetic construct
SEQUENCE: 372
ccctttttt tttttttcc ccctttttt ttttttttc cc                           42

SEQ ID NO: 373             moltype = RNA  length = 60
FEATURE                    Location/Qualifiers
misc_feature               1..60
                           note = nucleic acid sequence according to formula (IV)
source                     1..60
                           mol_type = other RNA
                           organism = synthetic construct
SEQUENCE: 373
tagcgaagct cttggaccta ggttttttt tttttttggg tgcgttccta gaagtacacg    60

SEQ ID NO: 374             moltype = RNA  length = 120
FEATURE                    Location/Qualifiers
misc_feature               1..120
                           note = nucleic acid sequence according to formula (IV)
source                     1..120
                           mol_type = other RNA
                           organism = synthetic construct
SEQUENCE: 374
tagcgaagct cttggaccta ggttttttt tttttttggg tgcgttccta gaagtacacg    60
atcgcttcga gaacctggat ccaaaaaaaa aaaaaaaccc acgcaaggat cttcatgtgc   120

SEQ ID NO: 375             moltype = RNA  length = 229
FEATURE                    Location/Qualifiers
misc_feature               1..229
                           note = nucleic acid sequence according to formula (IV)
source                     1..229
                           mol_type = other RNA
                           organism = synthetic construct
SEQUENCE: 375
gggagaaagc tcaagcttgg agcaatgccc gcacattgag gaaaccgagt tgcatatctc    60
agagtattgg ccccgtgta ggttattctt gacagacagt ggagcttatt cactcccagg   120
atccgagtcg catactacgg tactggtgac agacctaggt cgtcagttga ccagtccgcc   180
actagacgtg agtccgtcaa agcagttaga tgttacactc tattagatc              229

SEQ ID NO: 376             moltype = RNA  length = 547
FEATURE                    Location/Qualifiers
misc_feature               1..547
                           note = nucleic acid sequence according to formula (IV)
source                     1..547
                           mol_type = other RNA
                           organism = synthetic construct
SEQUENCE: 376
gggagaaagc tcaagcttgg agcaatgccc gcacattgag gaaaccgagt tgcatatctc    60
agagtattgg ccccgtgta ggttattctt gacagacagt ggagcttatt cactcccagg   120
atccgagtcg catactacgg tactggtgac agacctaggt cgtcagttga ccagtccgcc   180
actagacgtg agtccgtcaa agcagttaga tgttacactc tattagatcc cggattacag   240
ctggaaggag caggagtagt gttcttgctc taagtaccga gtgtgcccaa tacccgatca   300
gcttattaac gaacggctcc tcctcttaga ctgcagcgta agtgcggaat ctggggatca   360
aattactgac tgcctggatt accctcggac atataacctt gtagcacgct gttgctgtat   420
aggtgaccaa cgcccactcg agtagaccag ctctcttagt ccggacaatg ataggaggcg   480
cggtcaatct acttctggct agttaagaat aggctgcacc gacctctata agtagcgtgt   540
cctctag                                                            547

SEQ ID NO: 377             moltype = RNA  length = 1083
FEATURE                    Location/Qualifiers
misc_feature               1..1083
                           note = nucleic acid sequence according to formula (IV)
source                     1..1083
                           mol_type = other RNA
                           organism = synthetic construct
SEQUENCE: 377
```

```
gggagaaagc tcaagcttgg agcaatgccc gcacattgag gaaaccgagt tgcatatctc    60
agagtattgg cccccgtgta ggttattctt gacagacagt ggagcttatt cactcccagg   120
atccgagtcg catactacgg tactggtgac agacctaggt cgtcagttga ccagtccgcc   180
actagacgtg agtccgtcaa agcagttaga tgttacactc tattagatct cggattacag   240
ctggaaggag caggagtagt gttcttgctc taagtaccga gtgtgcccaa tacccgatca   300
gcttattaac gaacggctcc tcctcttaga ctgcagcgta agtgcggaat ctggggatca   360
aattactgac tgcctggatt accctcggac atataacctt gtagcacgct gttgctgtat   420
aggtgaccaa cgcccactcg agtagaccag ctctcttagt ccggacaatg ataggaggcg   480
cggtcaatct acttctggct agttaagaat aggctgcacc gacctctata agtagcgtgt   540
cctctagagc tacgcaggtt cgcaataaaa gcgttgatta gtgtgcatag aacagacctc   600
ttattcggtg aaacgccaga atgctaaatt ccaataactc ttcccaaaac gcgtacggcc   660
gaagacgcgc gcttatcttg tgtacgttct cgcacatgga agaatcagcg ggcatggtgg   720
tagggcaata ggggagctgg gtagcagcga aaaagggccc ctgcgcacgt agcttcgctg   780
ttcgtctgaa acaacccggc atccgttgta gcgatcccgt tatcagtgtt attcttgtgc   840
gcactaagat tcatggtgta gtcgacaata acagcgtctt ggcagattct ggtcacgtgc   900
cctatgcccg ggcttgtgcc tctcaggtgc acagcgatac ttaaagcctt caaggtactc   960
gacgtgggta ccgattcgtg acacttccta agattattcc actgtgttag ccccgcaccg  1020
ccgacctaaa ctggtccaat gtatacgcat cgctgagcg gatcgataat aaaagcttga  1080
att                                                                 1083

SEQ ID NO: 378           moltype = RNA  length = 229
FEATURE                  Location/Qualifiers
misc_feature             1..229
                         note = nucleic acid sequence according to formula (IV)
source                   1..229
                         mol_type = other RNA
                         organism = synthetic construct
SEQUENCE: 378
gggagaaagc tcaagcttat ccaagtaggc tggtcacctg tacaacgtag ccggtatttt    60
ttttttttt ttttttttga ccgtctcaag gtccaagtta gtctgccctat aaaggtgcgg   120
atccacagct gatgaaagac ttgtgcggta cggttaatct ccccttttt tttttttttt   180
tttttagtaa atgcgtctac tgaatccagc gatgatgctg gcccagatc              229

SEQ ID NO: 379           moltype = RNA  length = 546
FEATURE                  Location/Qualifiers
misc_feature             1..546
                         note = nucleic acid sequence according to formula (IV)
source                   1..546
                         mol_type = other RNA
                         organism = synthetic construct
SEQUENCE: 379
gggagaaagc tcaagcttat ccaagtaggc tggtcacctg tacaacgtag ccggtatttt    60
ttttttttt ttttttttga ccgtctcaag gtccaagtta gtctgccctat aaaggtgcgg   120
atccacagct gatgaaagac ttgtgcggta cggttaatct ccccttttt tttttttttt   180
tttttagtaa atgcgtctac tgaatccagc gatgatgctg gcccagatct cgaccacaa   240
gtgcatatag tagtcatcga gggtcgcctt tttttttttt tttttttttt tggcccagtt   300
ctgagacttc gctagagact acagttacag ctgcagtagt aaccactgcg gctattgcag   360
gaaatcccgt tcaggttttt ttttttttt ttttttccgc tcactatgat taagaaccag   420
gtggagtgtc actgctctcg aggtctcacg agagcgctcg atacagtcct tggaagaatc   480
tttttttttt tttttttttt ttgtgcgacg atcacagaga acttctattc atgcaggtct   540
gctcta                                                              546

SEQ ID NO: 380           moltype = RNA  length = 1083
FEATURE                  Location/Qualifiers
misc_feature             1..1083
                         note = nucleic acid sequence according to formula (IV)
source                   1..1083
                         mol_type = other RNA
                         organism = synthetic construct
SEQUENCE: 380
gggagaaagc tcaagcttat ccaagtaggc tggtcacctg tacaacgtag ccggtatttt    60
ttttttttt ttttttttga ccgtctcaag gtccaagtta gtctgccctat aaaggtgcgg   120
atccacagct gatgaaagac ttgtgcggta cggttaatct ccccttttt tttttttttt   180
tttttagtaa atgcgtctac tgaatccagc gatgatgctg gcccagatct cgaccacaa   240
gtgcatatag tagtcatcga gggtcgcctt tttttttttt tttttttttt tggcccagtt   300
ctgagacttc gctagagact acagttacag ctgcagtagt aaccactgcg gctattgcag   360
gaaatcccgt tcaggttttt ttttttttt ttttttccgc tcactatgat taagaaccag   420
gtggagtgtc actgctctcg aggtctcacg agagcgctcg atacagtcct tggaagaatc   480
tttttttttt tttttttttt ttgtgcgacg atcacagaga acttctattc atgcaggtct   540
gctctagaac gaactgacct gacgcctgaa cttatgagcg tgcgtatttt ttttttttt   600
tttttttttc ctcccaacaa atgtcgatca atagctgggc tgttggagac gcgtcagcaa   660
atgccgtggc tccataggac gtgtagactt ctattttttt tttttttttt ttttcccggg   720
accacaaata atattcttgc ttggttgggc gcaagggccc cgtatcaggt cataaacggg   780
tacatgttgc acaggtcct tttttttttt tttttttttt ttcgctgagt tattccggtc   840
tcaaaagacg gcagacgtca gtcgacaaca cggtctaaag cagtgctaca atctgccgtg   900
ttcgtgtttt ttttttttt tttttgtgaa acctacacgg cgtgcactgt agttcgcaat   960
tcataggtga ccggctcaga gttatgcctt ggttgaaaac tgcccagcat acttttttt  1020
tttttttttt ttcatattcc catgctaagc aagggatgcc gcgagtcatg ttaagcttga  1080
att                                                                1083
```

-continued

```
SEQ ID NO: 381          moltype = RNA  length = 59
FEATURE                 Location/Qualifiers
misc_feature            1..59
                        note = nucleic acid sequence according to formula (V)
source                  1..59
                        mol_type = other RNA
                        organism = synthetic construct
SEQUENCE: 381
tagcgaagct cttggaccta cctttttttt tttttccct gcgttcctag aagtacacg    59

SEQ ID NO: 382          moltype = RNA  length = 120
FEATURE                 Location/Qualifiers
misc_feature            1..120
                        note = nucleic acid sequence according to formula (V)
source                  1..120
                        mol_type = other RNA
                        organism = synthetic construct
SEQUENCE: 382
tagcgaagct cttggaccta cctttttttt tttttttccc tgcgttccta gaagtacacg    60
atcgcttcga gaacctggat ggaaaaaaaa aaaaaaaggg acgcaaggat cttcatgtgc   120

SEQ ID NO: 383          moltype = RNA  length = 15
FEATURE                 Location/Qualifiers
misc_feature            1..15
                        note = Description of sequence: generic stabilizing
                         sequence of the formula (C/U)CCANxCCC(U/A)PyxUC(C/U)CC
variation               1
                        note = /replace="cytosine" /replace="uracile"
misc_feature            1
                        note = nucleic acid = cytosine or uracil
misc_feature            5
                        note = Nx = a, g, c or u or any other nucleic acid
variation               5
                        note = /replace="cytosine" /replace="uracile"
                         /replace="guanosine" /replace="adonosine", or any other
                         nucleic acid
misc_feature            5
                        note = repeat_unit - x = any nucleotide
misc_feature            9
                        note = nucleic acid = uracil or adenosine
variation               9
                        note = /replace="uracile" /replace="adonosine"
misc_feature            10
                        note = Py = pyrimidine
misc_feature            10
                        note = repeat_unit - x = any nucleotide
variation               10
                        note = /replace="pyrimidine"
misc_feature            13
                        note = nucleic acid = cytosine or uracil
variation               13
                        note = /replace="cytosine" /replace="uracile"
source                  1..15
                        mol_type = other RNA
                        organism = synthetic construct
SEQUENCE: 383
nccancccnn tcncc                                                    15

SEQ ID NO: 384          moltype = RNA  length = 1698
FEATURE                 Location/Qualifiers
misc_feature            1..1698
                        note = PR8 H1 mRNA
source                  1..1698
                        mol_type = other RNA
                        organism = synthetic construct
SEQUENCE: 384
atgaaggcca acctgctcgt gctgctgtgc gccctcgcgg ccgccgacgc cgacaccatc    60
tgcatcggct accacgccaa caacagcacc gacacggtcg acaccgtgct ggagaagaac   120
gtgaccgtca cccactccgt gaacctgctc gaggacagcc acaacgggaa gctgtgccgg   180
ctgaagggca tcgcgcccct ccagctgggg aagtgcaaca tcgccggctg gctgctcggg   240
aacccggagt gcgaccccct gctgccgtg cgctcctgga gctacatcgt cgagacgccc   300
aactccgaga acggcatctg ctaccggggc gacttcatcg actacgagga gctccggag    360
cagctgagct ccgtgagctc cttcgagcgc ttcgagatct tccccaagga gagctcctgg   420
cccaaccaca caccaacgg ggtgaccgcc gcctgcagcc acgagggcaa gtccagcttc    480
taccggaacc tgctctggct gaccgagaag gaggggtcct accccaagct gaagaacagc   540
tacgtcaaca gaagggcaa ggaggtgctc gtgctgtggg ggatccacca cccgcccaac    600
tccaaggagc agcagaacct gtaccagaac gagaacgcgt acgtcagcgt ggtgacgtcc   660
aactacaacc gccggttcac ccccgagatc gccgagcgcc caaggtccg ggaccaggcc    720
```

```
ggccgcatga actactactg gaccctcctg aagccgggcg acaccatcat cttcgaggcc    780
aacgggaacc tgatcgcccc gatgtacgcg ttcgccctca gccggggctt cgggagcggc    840
atcatcacgt ccaacgccag catgcacgag tgcaacacca agtgccagac ccccctgggc    900
gccatcaact ccagcctgcc ctaccagaac atccacccgg tgaccatcgg ggagtgcccc    960
aagtacgtgc gctccgccaa gctccggat g tcacgggctc tgcgcaacaa ccccagcatc   1020
cagtcccggg ggctgttcgg cgcgatcgcc gggttcatcg agggcggctg gaccgggatg   1080
atcgacggct ggtacgggta ccaccaccag aacgagcagg gcagcgggta cgccgccgac   1140
cagaagtcca cccagaacgc catcaacggc atcaccaaca aggtgaacac ggtgatcgag   1200
aagatgaaca tccagttcac cgcggtcggc aaggagttca acaagctcga gaagcgcatg   1260
gagaacctga acaagaaggt ggacgacggg ttcctggaca tctggacctc caacgccgag   1320
ctcctggtgc tgctcgagaa cgagcggacc ctggacttcc acgacagcaa cgtcaagaac   1380
ctgtacgaga aggtcgaagt ccagctcaag aacaacgcca aggagatcgg caacgggtgc   1440
ttcgagttct accacaagtg cgacaacgag tgcatggaga gcgtccgcaa cggcacgtac   1500
gactacccca agtactccga ggagagcaag ctgaaccggg agaaggtgaa cggggtgaag   1560
ctggagtcca tgggcatcta ccagatcctc gccatctaca gcaccgtcgc ctccagcctg   1620
gtgctgctgg tgtccctcgg cgcgatcagc ttctggatgt gcagcaacgg gtccctgcag   1680
tgccgcatct gcatctga                                                 1698

SEQ ID NO: 385         moltype = RNA   length = 1161
FEATURE                Location/Qualifiers
misc_feature           1..1161
                       note = Ovalbumin (control) mRNA
source                 1..1161
                       mol_type = other RNA
                       organism = synthetic construct
SEQUENCE: 385
atgggcagca tcggggccgc gtcgatggag ttctgcttcg acgtgttcaa ggagctgaag     60
gtccaccacg ccaacgagaa catcttctac tgcccgatcg ccatcatgag cgcgctcgcc    120
atggtgtacc tgggcgccaa ggacagcacc cggacgcaga tcaacaaggt ggtccgcttc    180
gacaagctgc ccggcttcgg ggactcgatc gaggcgagt gcggcaccag cgtgaacgtg    240
cacagctcgc tccgggacat cctgaaccag atcaccaagc gaacgacgt ctacagcttc    300
agcctggcct cgcggctcta cgccgaggag cgctacccga tcctgccga gtacctgcag    360
tgcgtgaagg agctctaccg ggggcggctg gagccgatca acttccagac ggcggccgac    420
caggcccggg agctgatcaa cagctgggtg gagagccaga ccaacggcat catccgcaac    480
gtcctccagc cgtcgagcgt ggacagccag accggcgatg tgctggtcaa cgccatcgtg    540
ttcaagggcc tgtgggagaa gacgttcaag gacgaggaca cccaggccat gcccttccgg    600
gtgaccgagc aggagtcgaa gccggtccag atgatgtacc agatcgggct cttccgggtg    660
gcgagcatgg ccagcgagaa gatgaagatc ctggagctgc cgttcgcctc gggcacgatg    720
agcatgctcg tgctgctgcc cgacgaggtc agcggcctgg agcagctgga gtcgatcatc    780
aacttcgaga agctgaccga gtggaccagc agcaacgtga tggaggagcg caagatcaag    840
gtgtacctcc cgcggatgaa gatggaggag aagtacaacc tgacgtcggt cctgatggcg    900
atggggatca ccgacgtgtt cagcagctcg gccaacctca gcggcatcag ctcggccgag    960
agcctgaaga tcagccaggc ggtgcacgcc cccacgcggg agatcaacga gccggccggg   1020
gaggtcgtgg ggtcggccga ggcgggcgtg gacgccgcca gcgtcagcga ggagttccgc   1080
gcggaccacc cgttcctgtt ctgcatcaag cacatcgcca ccaacgccgt gctcttcttc   1140
ggccggtgcg tgtcgccctg a                                             1161

SEQ ID NO: 386         moltype = DNA   length = 990
FEATURE                Location/Qualifiers
misc_feature           1..990
                       note = RNAcriveII KLK3(GC) = PSA
source                 1..990
                       mol_type = other DNA
                       organism = synthetic construct
SEQUENCE: 386
gggagaaagc ttaccatgtg ggtgccggtc gtgttcctga ccctcagcgt gacgtggatc     60
ggcgccgcgc ccctgatcct gtcgcggatc gtgggggggct gggagtgcga gaagcacagc    120
cagccctggc aggtgctggt ggccagccgc ggccggccg tgtgcggcgg cgtgctggtc    180
caccccagt gggtgctgac cgccgcccac tgcatccgga acaagagcgt catcctgctg    240
ggccggcaca gcctgttcca ccccgaggac accggccagg tgttccaggt gagccacagc    300
ttcccccacc cctgtacga catgagcctc ctgaagaacc ggttcctgcg gccccggcgac   360
gacagcagcc acgacctgat gctgctgcgg ctgagcgagc ccgccgagct gaccgacgcc    420
gtgaaggtga tggacctgcc gacccaggag cccgccctgg gcaccacctg ctacgccagc    480
ggctggggga gcatcgagcc cgaggagttc ctcacccccca agaagctgca gtgcgtgcac    540
ctgcacgtga tcagcaacga cgtgtgcgcc caggtgcacc cccagaaggt gaccaagttc    600
atgctgtgcg ccggccggtg gaccggcggc aagagcacct gcagcggcga cagcggcggc    660
cccctggtct gcaacggcgt gctgcagggc atcaccagct ggggcagcga gccctgcgcc    720
ctgcccgagc gcccccagcct gtacaccaag gtggtgcact accggaagtg gatcaaggac    780
accatcgtgg ccaacccgtg accactagtt ataagactag ctagcccgat gggcctcca     840
acggccctc ctccctcct tgcaccgaga ttaataaaaa aaaaaaaaa aaaaaaaaa         900
aaaaaaaaaa aaaaaaaaa aaaaaaaaa aaaaaaaaat attccccccc cccccccccc      960
cccccccccc ccctctagac aattggaatt                                     990

SEQ ID NO: 387         moltype = DNA   length = 2457
FEATURE                Location/Qualifiers
misc_feature           1..2457
                       note = RNAcriveII FOLH1(GC) = PSMA
source                 1..2457
                       mol_type = other DNA
```

```
                          organism = synthetic construct
SEQUENCE: 387
gggagaaagc ttaccatgtg gaacctgctc cacgagaccg acagcgccgt ggcgacggcc   60
cggcgcccgc ggtggctgtg cgccggcgcc ctggtcctgg ccgggggctt cttcctgctg  120
ggcttcctgt tcggctggtt catcaagtcg agcaacgagg ccaccaacat caccccccaag 180
cacaacatga aggccttcct cgacgagctg aaggccgaga acatcaagaa gttcctgtac  240
aacttcaccc agatccccca cctggccggg accgagcaga acttccagct ggccaagcag  300
atccagagcc agtggaagga gttcggcctg gactcggtgg agctggcgca ctacgacgtg  360
ctgctcagct accccaacaa gacccacccc aactacatca gcatcatcaa cgaggacggc  420
aacgagatct tcaacaccag cctgttcgag cccccgcccc ccggctacga gaacgtgtcg  480
gacatcgtgc ccccttcag cgccttcagc ccgcagggca tgcccgaggg ggacctggtg  540
tacgtgaact acgccggac ggaggacttc ttcaagctgg agcgcgacat gaagatcaac  600
tgcagcggca agatcgtgat cgcccggtac ggcaaggtgt tccggggcaa caaggtgaag  660
aacgcccagc tggccggggc caagggcgtg atcctgtact cggaccccgc cgactacttc  720
gcccccggcg tgaagagcta ccccgacggc tggaacctgc ccggcggggg cgtccagcgc  780
ggcaacatcc tcaacctgaa cggcgccggc gacccgctga ccccgggta ccccgcgaac  840
gagtacgcct accggcgggg catcgccgag gccgtgggcc tgcccagcat ccccgtgcac  900
ccgatcgcct actacgacgc ccagaagctc tggagagaga tgggcgggag cgccccgccc  960
gactcgagct ggcggggcag cctgaaggtg ccctacaacg tgggcccggg cttcaccggg 1020
aacttctcga cccagaaggt gaagatgcac atccacagca ccaacgaggt gacccgcatc 1080
tacaacgtga tcggcaccct gcggggcgcc gtggagcccg accggtacgt gatcctcggc 1140
gggcaccgcg acagctgggt gttcggcggc atcgacccc agagcggcgc cgccgtggtc 1200
cacgagatcg tgcggtcgtt cggcacccctg aagaaggagg ggtgcgcc ccgccggacg 1260
atcctgttcg ccagctggga cgcggaggag ttcggcctgc tgggcagcac cgagtgggcc 1320
gaggagaaca gccggctgct gcaggagcgg ggcgtggcct acatcaacgc cgactcgagc 1380
atcgagggca actacaccct ccgcgtggac tgcaccccgc tgatgtacag cctggtgcac 1440
aacctgacca aggagctgaa gagccccgac gaggggttcg agggcaagtc gctgtacgag 1500
agctggacca agaagagccc ctcgcccgag ttcagcggca tgccccggat cagcaagctg 1560
ggcagcggga acgacttcga ggtgttcttc cagcggctgg gcatcgcctc gggccgcgcc 1620
cggtacacca agaactggga gacgaacaag ttcagcggct accccctcta ccacagcgtg 1680
tacgagacct acgagctggt ggagaagttc tacgacccca tgttcaagta ccacctgacc 1740
gtggcccagg tgcgggcgg gatggtgttc gagctggcca acagcatcgt gctgccctc  1800
gactgccgcg actacgccgt cgtgctgcgg aagtacgccg acaagatcta ctcgatcagc 1860
atgaagcacc cccaggagat gaagacctac agcgtgagct cgactcgct gttcagcgcg 1920
gtgaagaact tcaccgagat cgccagcaag ttctcggagg ggctccagga cttcgacaag 1980
agcaacccga tcgtgctgcg catgatgaac gaccagctga tgttcctgga gcgggccttc 2040
atcgacccc tgggcctgcc cgaccggccc ttctaccggc acgtgatcta cgcccccagc 2100
agccacaaca agtacgccgg cgagtcgttc ccggggatct acgacgccct gttcgacatc 2160
gagagcaagg tggacccag caaggcctgg ggcgaggtga agcgcagat ctacgtgcgc 2220
gccttcaccg tgcaggccgc ggccgagacc ctgagcgagg tggcctgacc actagttata 2280
agactgacta gcccgatggg cctcccaacg ggccctcctc cctccttgc accgagatta  2340
ataaaaaaaa aaaaaaaaaa aaaaaaaaaa aaaaaaaaaa aaaaaaaaa aaaaaaaaaa  2400
aaaaaatatt cccccccccc cccccccccc cccccccccc tctagacaat tggaatt    2457

SEQ ID NO: 388          moltype = DNA  length = 576
FEATURE                 Location/Qualifiers
misc_feature            1..576
                        note = RNActiveII PSCA(GC)
source                  1..576
                        mol_type = other DNA
                        organism = synthetic construct
SEQUENCE: 388
gggagaaagc ttaccatgaa ggccgtgctg ctcgcgctgc tgatggccgg cctggccctg   60
cagccgggga ccgccctgct gtgctacagc tgcaaggccc aggtctcgaa cgaggactgc  120
ctgcaggtgg agaactgcac gcagtgggc gagcagtgac ggaccgcccg gatccgcgcc  180
gtgggcctgc tcaccgtgat cagcaagggc tgcagcctga actgcgtgga cgacagccag  240
gactactacg tgggcaagaa gaacatcacc tgctgcgaca ccgacctgtg caacgccagc  300
ggcgcccacg ccctgcagcc cgcggccgcc atcctggccc tgctgccgc cctgggcctg  360
ctgctctggg gccccggcca gctgtgacca ctagttataa gactgactag cccgatgggc  420
ctcccaacgg gccctcctcc cctccttgca ccgagattaa taaaaaaaaa aaaaaaaaaa  480
aaaaaaaaaa aaaaaaaaaa aaaaaaaaaa aaaaaaaaaa aaaatattc cccccccccc  540
cccccccccc cccccccct ctagacaatt ggaatt                             576

SEQ ID NO: 389          moltype = DNA  length = 1224
FEATURE                 Location/Qualifiers
misc_feature            1..1224
                        note = RNActive II STEAP (GC) = STEAP1
source                  1..1224
                        mol_type = other DNA
                        organism = synthetic construct
SEQUENCE: 389
gggagaaagc ttaccatgga gagccggaag gacatcacca ccaggagga gctgtggaag   60
atgaagccgc gccggaacct cgaggaggac gactacctgc acaaggacac gggcgagacc  120
tcgatgctga agcggcccgt gctcctgcac ctgcaccaga ccgccacgc ggacgagttc  180
gactgcccga gcgagctcca gcacacgcag agctgttcc gcagtggca cctgcccatc  240
aagatcgccg ccatcatcgc gagcctcacc ttcctgtaca cctgctccg cgaggtcatc  300
cacccgctgg ccacgtcgca ccagcagtac ttctacaaga tcccgatcct ggtgatcaac  360
aaggtgctcc ccatggtcag catcacctg ctggccctcg tgtacctgcc ggggtgatc  420
gcggccatcc tccagctgca caacggcacc aagtacaaga agttccccca ctggctcgac  480
```

```
aagtggatgc tgacgcggaa gcagttcggc ctgctcagct tcttcttcgc cgtgctgcac    540
gcgatctact cgctgagcta ccccatgcgg cgcagctacc ggtacaagct cctgaactgg    600
gcctaccagc aggtgcagca gaacaaggag gacgcctgga tcgagcacga cgtctggcgg    660
atggagatct acgtgtcgct ggggatcgtg ggcctcgcga tcctggccct gctcgccgtc    720
accagcatcc cgagcgtgtc ggacagcctg acctggcgcg agttccacta catccagagc    780
aagctgggca tcgtgtcgct cctgctgggg acgatccacg cgctcatctt cgcctggaac    840
aagtggatcg acatcaagca gttcgtctgg tacaccccgc ccaccttcat gatcgccgtg    900
ttcctgccga tcgtggtcct gatcttcaag agcatcctct tcctgccgtg cctgcggaag    960
aagatcctca agatccggca cggctgggag gacgtgacga agatcaacaa gaccgagatc   1020
tgcagccagc tgtgaccact agttataaga ctgactagcc cgatgggcct cccaacgggc   1080
cctcctcccc tccttgcacc gagattaata aaaaaaaaaa aaaaaaaaaa aaaaaaaaaa   1140
aaaaaaaaaa aaaaaaaaaa aaaaaaaaaa aaatattccc cccccccccc cccccccccc   1200
cccccctct agacaattgg aatt                                           1224
```

VACCINATION WITH mRNA-CODED ANTIGENS

This application is a continuation of U.S. application Ser. No. 15/452,658, filed Mar. 7, 2017, which is a continuation of U.S. application Ser. No. 15/015,458, filed on Feb. 4, 2016, which was a continuation of U.S. application Ser. No. 13/824,589, filed Jul. 23, 2013, now abandoned, which is a national phase application under 35 U.S.C. § 371 of International Application No. PCT/EP2012/000878, filed Feb. 29, 2012, which claims benefit of International Application No. PCT/EP2011/001043, filed Mar. 2, 2011, the entire contents of each of which are hereby incorporated by reference.

This application contains a Sequence Listing XML, which has been submitted electronically and is hereby incorporated by reference in its entirety. Said Sequence Listing XML, created on Feb. 26, 2024, is named CRVCP0100USC5.xml and is 416,390 bytes in size.

The present invention relates to vaccines comprising at least one mRNA encoding at least one antigen for use in the treatment of a disease in an elderly patient preferably exhibiting an age of at least 50 years, more preferably of at least 55 years, 60 years, 65 years, 70 years, or older, wherein the treatment comprises vaccination of the patient and eliciting an immune response in said patient. The present invention is furthermore directed to kits and kits of parts comprising such a vaccine and/or its components and to methods applying such a vaccine or kit.

As evidenced over the last decades human beings reach an ever older age and even unexpected maximal ages. This, however, is accompanied by an apparent increase of the emergence of many diseases associated with aging. As widely reviewed by Fülöp et al. (Fülöp et al., Clinical Interventions in Aging, 2007:2(1), 33-54) the incidence of infections, cancers, and chronic inflammatory diseases such as atherosclerosis and neurodegenerative diseases increases with age. Although one still does not know what the exact cause of aging is, it may be recognized that changes of the immune system play an important role both in the aging process and in the increase of age-related diseases.

The primary role of the immune system is to protect the organism against pathogens, but age-associated alterations to immunity increase the susceptibility of the elderly to infectious diseases but also cancers and autoimmune disorders. Evidently, the immune system is a complex interactive system composed of many different players. However, these components are not all altered in the same manner and do not contribute equally to aging. One may perhaps conceptualize immunosenescence as a dysregulation of a homeostatically constantly adapting system, the inputs and outputs of which are still only crudely defined, let alone the pathways linking these. At the whole organism level, many studies have documented changes in endocrine and neural function, cardiovascular, muscle, and skeletal health, as well as regulation of glucose metabolism. It must be borne in mind that these diverse physiological changes also affect the immune system, although very few investigations address these issues, especially in humans. Although numerous studies on age-associated immune alterations exist (collectively known as "immunosenescence") the exact nature of these is still controversial because of differences between species, the lack of definition of physiological aging rendering difficult the exclusion of some latent disease states, nutritional, genetic, and environmental differences, amongst other factors. However, the clinical consequences of the decreased immune response with aging seem quite clear. These are mainly the increased incidence and severity of infections, but also cancers and autoimmune disorders. Many elderly subjects actually die from infections even if the cause of death given by the attending physician is very different.

The exact nature of these changes is still controversial, but the use of screening procedures, such as the SENIEUR protocol to exclude underlying illness, helped to better characterize the changes actually related to physiological aging rather than pathology (see Fülöp et al. (2007, supra)). The hallmark of immunosenescence is the overwhelming decrease in T cell function with aging. In this context, it is generally agreed that the most marked changes occur in the cellular immune response reflecting profound alterations in T cells. Much of this is due to thymic involution as well as changes in the proportions of T cell subpopulations resulting from antigen exposure, and altered T cell activation pathways. There are also changes in the other parts of the immune system, but they are much less marked, and may often be secondary to changes in the T cells (not only the T cell-dependent B cells, but also innate components sensitive to T cell feedback, especially antigen-presenting cells). Such age-related changes of the immune response are multifactorial, but it is reasonable to think that the extra-cellular milieu is very important. Furthermore, a body of data indicates that innate immune responses, including the critical bridge between innate and adaptive immunity, and antigen presenting capacity are not completely resistant to senescence processes. The consequences of all these alterations are an increased incidence of infections, as well as possibly cancers, autoimmune disorders, and chronic inflammatory diseases (see Fülöp et al. (2007, supra)).

Profound alterations in T cells as mentioned above in particular concern CD4+ T and CD8+ T cells. Whereas the function of aged CD4+ T cells has been extensively investigated and distinct defects defined, the impact of aging on CD8+ T cell function is poorly understood. It has been suggested that apparent declines in CD8+ T cell effector function may instead be the consequence of age-associated changes in the composition of the CD8+ T cell pool, consistent with reports that naive CD8+ T cells from aged mice are fully functional. The ability of individuals to generate effective T cell responses to newly encountered infections and to respond to vaccination requires the maintenance of a diverse repertoire of T cells. Thus, it has been speculated that declining T cell repertoire diversity associated with aging is a contributing factor to the impaired ability of aged individuals to mount effective immune responses to infections and vaccines. The functional diversity of the αβTCR repertoire in the spleens of young mice has been estimated to be ~2×10$^6$ clones, with ~10 cells per clone. However, several age-associated changes are thought to lead to reductions in both the size and diversity of the naive T cell repertoire. Fewer T cells are produced in the thymus, leading to reduced numbers of naive T cells in the periphery. The naive T cell repertoire also becomes increasingly constrained by the progressive accumulation of peripheral T cells exhibiting a memory phenotype, believed to be the result of the accumulated antigen experience of the individual. The diversity of the memory repertoire is further compromised by the development of age-associated CD8+ T cell clonal expansions, which can comprise 70-80% or more of the total CD8+ T cell compartment in some aged animals. Collectively, declining numbers and diversity of naive T cells emerging from the aged thymus, progressive increase in the proportion of antigen-experienced compared with naive T cells, and the development of large clonal expansions result in substantially reduced diversity among CD8+ T cells in aged mice (see Yager et al., JEM, Vol. 205, Mar. 17, 2008).

In this context, Yager et al. (2008, supra) show in a study with a well-characterized influenza virus model the impact of aging on the diversity of the antiviral CD8+ T cell response. The data of Yager et al. (2008, supra) provide experimental evidence that the age-associated decline in CD8+ T cell repertoire diversity can greatly impact the response to new infections, and the development of heterosubtypic immunity. Importantly, perturbations in the repertoire of T cells specific for influenza virus epitopes for which there is a low precursor frequency and limited TCR diversity, lead to the selective development of holes in the repertoire for a typically immunodominant viral epitope. T cell repertoire is frequently characterized by either exhaustive sequence analysis of individual cells or spectratype analysis of bulk populations of T cells, and different information is obtained by the two techniques.

Further to alterations in the CD4+ and CD8+ T cell response a shift from Th1 cytokines (including IFN-γ) to Th2 cytokines (including IL-10) with aging has been observed and associated with reduced CTL activity and diminished protection against influenza virus challenge. To be noted, influenza is cleared by CTL through granule-mediated killing of virus-infected host cells. In this process, granzyme B (GrB) is regarded as a key cytolytic mediator and an early marker of the CTL response to influenza infection. Virus-specific CTL are recruited to influenza-infected lungs by a Th1 response, specifically due to the production of IFN-γ. Although influenza specific Th2 cytokines including IL-10 do not promote recovery from influenza infection, these cytokines continue to be expressed in high levels at the site of influenza infection. Thus, a balance between Th1 and Th2 cytokines also appears to be important for viral clearance (see McElhaney et al., The Journal of Immunology, 2006, 176: 6333-6339).

Not only immunosenescence in T cell responses but also in B-cell responses appear to exhibit a severe impact on immunoprotection in elderly patients. B-cell responses in later life are mainly characterized by their serological profiles (see Claire-Anne Siegrist and Richard Aspinall, Nature Reviews|Immunology, Volume 9, March 2009, pp. 185-194). As discussed by Siegrist and Aspinall (2009), successful recovery from viral and bacterial infections typically requires a good humoral immune response, as shown by the increased levels of specific antibodies following infection. Surviving to old age requires a successful response to a wide range of potential pathogens and the generation of a prodigious 'reservoir' of immunological memory. Measurable titres of serum antibody are stable and have the capacity to be maintained for prolonged periods. Antibody responses to viruses, such as varicella-zoster, measles and mumps, have half-lives of 50 years or more, whereas antibody responses to non-replicating protein antigens, such as tetanus and diphtheria toxins, decline with half-lives of 10-20 years. This suggests that the persistence of antigen contributes to the continued production of antibody, as indicated by studies in mice. Unfortunately, the capacity to respond to new potential pathogens does not increase at an exponential rate throughout life. Indeed, an inability to respond to new antigens can be found in elderly patients, albeit for mechanistically different reasons. Evidence for this in older individuals comes from the measurement of changes in specific antibody levels at defined times after vaccination. As an example, the ability of influenza vaccine to induce protection is related to age, with an efficacy between 70% and 90% in those under 65 years of age, but of 30% to 40% at best for those over 65 years of age. Similarly, responses to pneumococcal polysaccharides and hepatitis B vaccines are compromised by old age, and antibody responses are of shorter duration in healthy older people (see Siegrist and Aspinall (2009, supra)).

Epidemiological studies furthermore have shown that populations of older individuals have increasing titres of autoantibody as they age. These autoantibody titres are not usually associated with autoimmune disease, possibly because of the low affinity of the antibodies. More than half of healthy older individuals have antibodies for non-organ specific autoantigens (such as nucleoprotein or IgG), which might result from their generation as a byproduct of responses to other antigens. Indeed, an early study showed that shortly after vaccination with tetanus toxoid, there was a significant increase in the frequency of B cells producing rheumatoid factor, accompanied by an increase in plasma levels of IgM rheumatoid factor. There is also an age-dependent increase in the prevalence of organ specific antibodies (such as thyroid-specific antibodies). The increase does not seem to be exponential, as studies showed that the prevalence of organ-specific auto antibodies in centenarians is similar to that found in individuals under 50 years of age. Further changes in the serological profile in older individuals were revealed by the presence of a single spike on electrophoresis gels within the region of the gel that is associated with immunoglobulins. These paraproteins are produced by a clone of plasma cells with a defined single specificity—a condition known as benign monoclonal gammopathy. The prevalence of this condition increases with age, with 3.2% of individuals over 50 years of age suffering from the disease, 5.3% of those over 70 years of age and 7.5% of those over 85 years of age. The differences in the serum antibody profile between these age groups include the increase in the amount of serum immunoglobulin between elderly individuals, the increased presence of autoantibodies and low affinity antibodies in the elderly and the occurrence of an over-representation of specific classes of antibody from individual B-cell clones in some older individuals (see Siegrist et al. (2009, supra).

Alterations in T cell responses and also in B-cell responses as discussed above exhibit a significant effect not only on immunoprotection towards pathogens but also to vaccination strategies in elderly patients when combating infectious diseases but possibly also cancers and autoimmune disorders. Accordingly, it was not surprising that similar observations were also made in the treatment of elderly cancer patients, preferably when using vaccines of the art.

One previous approach to overcome theses deficiencies in the context of virus-based influenza vaccines refers to the administration of hemagglutinin (HA) and/or nucleoprotein (NP) influenza viral genes (see Radu et al., Viral Immunology, Vol. 12, Number 3, 1999). Radu et al. (1999) discuss the finding that despite the greater antibody- and cell-mediated immune responses and complete protection afforded by the recombinant vaccinia vaccines to old mice, concerns about the toxicity of such vaccinia based vaccines have prevented their development as human vaccines. Accordingly, Radu et al. (1999) suggest that immunization with a recombinant vaccinia virus expressing the influenza hemagglutinin gene may overcome the age-associated defects in the immune response of old-mice and may elicit complete protection from influenza challenge in old mice. Radu et al. (1999) provided DNA-based plasmid vaccines expressing hemagglutinin (HA) and nucleoprotein (NP) influenza viral genes and argue that such DNA-based plasmid vaccines (pHA and pNP, respectively) have been shown to be safe and effective in inducing protective immunity to influenza in various animal species. They conclude that old and adult mice vaccinated with pHA were protected to a comparable extend from lethal challenge with live WSN influenza virus. They furthermore conclude that continuous production of antigen after DNA vaccination primes B and T cells in old and young mice to a comparable extent although the diversity of the antibody response in old mice was limited compared to adult mice. Such a strategy however, even though promising at the time of carrying out the above experiments, still requires administration of DNA based vectors, which have been encountered as dangerous due to unwanted insertion into the genome. Such DNA based vectors may even lead to interruption of functional genes and cancer or the formation of anti-DNA antibodies and are therefore out of focus as of today.

One further more actual strategy to combat e.g. infectious diseases with vaccines in elderly patients is based on the delivery of current vaccines or new vaccine candidates in combination with adjuvants. However, there are only few adjuvants approved for human use. One major adjuvant approved for human use is e.g. Alum, an aluminium salt based adjuvant. However, although approved for human use, such aluminium salts failed to provide satisfactory augmentation of immune responses for seasonal influenza vaccines in early human clinical trials, an effect, which may be expected likewise during other vaccination strategies. Further licensed adjuvanted influenza vaccines include to date Fluad® (Novartis Vaccines), containing MF59 in combination with a subunit vaccine formulation, and the virosomal vaccines Inflexal®V (Berna Biotech, a Crucell company) and Invivac® (Solvay). Although animal studies and human clinical trials revealed a higher immunogenicity profile—defined as increased antibody responses—with the MF59-adjuvanted influenza vaccine, MF59 is not a potent adjuvant for the induction of type 1 driven cellular immune responses. Unlike Fluad®, the virosomal vaccines represent reconstituted influenza virus envelopes containing the functional influenza surface proteins haemagglutinin and neuraminidase in their phospholipid bilayer. The immunogenicity and local tolerability of virosome-based influenza vaccines has been shown in several studies. However, the development of virosomal formulations is very complex and the costs of goods are high.

In this context, Riedl et al. (see Riedl. et al., Vaccine 26 (2008), 3461-3468) reported the development of a synthetic two component adjuvant IC31® with characteristics that are likely to contribute to improved influenza vaccines. IC31® is a mixture of a novel immunostimulatory oligodeoxynucleotide containing deoxy-Inosine/deoxy-Cytosine (ODN1a) and the peptide KLKL5KLK (KLK). Apart from effective vaccine depot formation mediated by KLK, IC31® induces activation of antigen presenting cells and strongly stimulates both T and B cell responses with type 1 dominance when combined with different types of antigens. In these studies the immunostimulatory effect of IC31® on seasonal subunit influenza vaccines was investigated. Riedl et al. (2008, supra) present evidence for antigen dose-sparing and induction of type 1 humoral and cellular responses that are long lasting and apparent even in aged animals. As shown in their experiments no immune enhancement was found at day 21 or 80 by measuring HI antibodies upon single vaccination of aged mice with low amounts of influenza vaccine in combination with IC31®. However, boosting on day 21 with the same amount of IC31®-containing influenza vaccine dramatically increased HI titres against all three strains 3 weeks post booster immunisation compared to administration of the vaccine alone. Although the immune response was significantly increased, the strategy as outlined by Riedl et al. (2008, supra) still requires booster administrations following administration of IC31® improved influenza vaccines. Furthermore, the effect appears to be at least in part dependent on prior exposition of the patient to be treated to specific influenza strains and thus may not resemble an immune response to an entirely novel pathogen.

It may also not reflect the requirements of vaccination strategies as e.g. in the treatment of cancer or autoimmune diseases.

Investigations have also been carried out with respect to cancer vaccines. Gravekamp (see Claudia Gravekamp, Exp Gerontol. 2007 May; 42(5): 441-450) reviews the current knowledge of T cell unresponsiveness in cancer patients and elderly, the results of cancer vaccination in preclinical models and in clinical trials, and recent data of cancer vaccination at old age in preclinical models. Finally, Gravekamp (2007, supra) proposes experimental approaches to provide cancer vaccines more effective at older age. They developed a DNA vaccine of Mage-b and tested this vaccine at young and old age in a syngeneic mouse tumour model, 4TO7cg. This mouse tumour model is moderately metastatic (range: 2-20 metastases per mouse) and overexpresses Mage-b in primary tumour and metastases (Sypniewska et al., 2005). Preventive vaccination of young and old mice with pcDNA3.1-Mage-b protected 90% of the young mice from metastases, while only 60% of the old mice remained free of metastases. Analysis of spleen cells of tumour-bearing mice after in vitro restimulation, showed high levels of IL-2 and IFN-γ at young age but undetectable levels at old age, indicating a poor immune response in old mice. Gravekamp (2007, supra) also repeated this vaccine study in a much more aggressive metastatic model 4T1 (range: 5-300 metastases per mouse), also overexpressing Mage-b, and mixed the pcDNA3.1-Mage-b DNA vaccine with plasmid DNA secreting GM-CSF. To recruit APC more effectively to the peritoneal cavity (pc), thioglycollate was injected into the pc, prior to each vaccination. Although the effect in the young mice was stronger than in the old, a significant reduction in the frequency of metastases was observed in both young and old mice. However, when analyzing the draining lymph nodes of tumour-bearing mice, moderate levels of IL-2 and IFN-γ still were detected after restimulation at young age but not at old age. FACS analysis of the draining lymph nodes of Mage-b vaccinated tumour-bearing mice at young and old age after restimulation, also showed CD4+ and CD8+ responses (intracellular IL-2 and/or IFN-γ production) at young age but not at old age. At old age macrophages and NK cells were more active (intracellular production of IFN-γ and IL-2 receptor expression), suggesting that the innate immune response may have contributed to the antitumour response in mice. Gravekamp (2007, supra) thus show that cancer vaccines may not be very effective in cancer patients, which are usually elderly, unless the vaccines are optimized for older age.

Summarizing the above, there is an urgent need for vaccines optimized for patients of older age. More precisely, vaccines are required, which lead to good immune response and do not bear the problems shown in the prior art or at least diminish these problems to a significant extent. Furthermore, it is highly envisaged to provide vaccines, which allow inducing Th1 immune responses in elderly patients, preferably without leading to a shift from Th1 to Th2 immune responses subsequent to administration. Likewise, the administration of DNA based vaccines should be avoided due to possible insertion of DNA into the genome, possible interruption of genes and formation of anti-DNA antibodies.

The object underlying the present invention is solved by the subject matter of the attached claims, more preferably as outlined in the following.

According to a first embodiment, the object underlying the present invention is solved by a vaccine comprising at least one mRNA encoding at least one antigen for use in the prophylaxis and/or treatment of a disease in an elderly patient exhibiting an age of at least 50 years, more preferably of at least 55 years, 60 years, 65 years, 70 years, or older, wherein the treatment comprises vaccination of the patient and eliciting an immune response in said patient.

Without being bound to theory RNA vaccines elegantly integrate adjuvanticity and antigen expression, thereby mimicking relevant aspects of viral infections. This increases their efficacy compared to other inactivated (dead) vaccines, that require the use of advanced adjuvants in the elderly, simplifying handling and production. RNA can address a range of dedicated immunologic pattern recognition receptors, including toll-like receptors 3, 7, and 8, RIG-I, MDA5, PKR, and others that may act synergistically and serve to enhance the induction of antigen-specific adaptive B and T cell responses. Importantly, by antigen synthesis in transfected host cells, mRNA vaccines directly introduce antigen into cellular antigen processing and presentation pathways, granting access to MHC molecules and triggering T cell responses, irrespective of the hosts MHC haplotype. This enables the induction of polyclonal T cell responses that may act synergistically with other immune responses, including B cells. Also, presenting the full spectrum of MHC-binding epitopes may circumvent limitations imposed by "holes" in the elderly T cell repertoire. Also, endogenous production of antigen ensures faithful posttranslational modification (e.g. proteolytic processing, glycosylation, etc.) that may positively impact immunogenicity. Also, RNA vaccines exhibit safety features that make them superior for use in the elderly. For example, the increased reactogenicity of live attenuated vaccines generally prevents use in this highly relevant target group, i.e. persons of at least 50 years of age, but also persons suffering from chronic conditions such as asthma or from a severe disease, such as cancer. However, considering the short persistence and traceless decay of the vaccine vector within a matter of days the observed good immunogenicity is unexpected and contrasts claims for plasmid DNA vaccines that variously linked efficacy to the persistent expression of antigen.

The at least one mRNA of the inventive vaccine as defined in the first embodiment of the present invention, encoding at least one antigen, may be selected from any antigen, known to a skilled person, preferably suitable to elicit an antigen-specific immune response in a patient. According to the present invention, the term "antigen" refers to a substance which is recognized by the immune system and is capable of triggering an antigen-specific immune response, e.g. by formation of antibodies or antigen-specific T cells as part of an adaptive immune response. In this context, the first step of an adaptive immune response is the activation of naïve antigen-specific T cells or different immune cells able to induce an antigen-specific immune response by antigen-presenting cells. This occurs in the lymphoid tissues and organs through which naïve T cells are constantly passing. The three cell types that can serve as antigen-presenting cells are dendritic cells, macrophages, and B cells. Each of these cells has a distinct function in eliciting immune responses. Tissue dendritic cells take up antigens by phagocytosis and macropinocytosis and are stimulated by contact with e.g. a foreign antigen to migrate to the local lymphoid tissue, where they differentiate into mature dendritic cells. Macrophages ingest particulate antigens such as bacteria and are induced by infectious agents or other appropriate stimuli to express MHC molecules. The unique ability of B cells to bind and internalize soluble protein antigens via their receptors may also be important to induce T cells. Presenting the antigen on MHC molecules leads to activation of T cells which induces their proliferation and differentiation into armed effector T cells. The most important function of effector T cells is the killing of infected cells by CD8+ cytotoxic T cells and the activation of macrophages by TH1 cells which together make up cell-mediated immunity, and the activation of B cells by both TH2 and TH1 cells to produce different classes of antibody, thus driving the humoral immune response. T cells recognize an antigen by their T cell receptors which do not recognize and bind antigen directly, but instead recognize short peptide fragments e.g. of pathogens' protein antigens, which are bound to MHC molecules on the surfaces of other cells.

In the context of the present invention, antigens as encoded by the at least one mRNA of the inventive vaccine typically comprise any antigen, falling under the above definition, more preferably protein and peptide antigens. In accordance with the invention, antigens as encoded by the at least one mRNA of the inventive vaccine may be antigens generated outside the cell, more typically antigens not derived from the host organism (e.g. a human) itself (i.e. non-self antigens) but rather derived from host cells outside the host organism, e.g. pathogenic antigens, particularly viral antigens, bacterial antigens, fungal antigens, protozoological antigens, animal antigens (preferably selected from animals or organisms as disclosed herein), allergy antigens, etc. Antigens as encoded by the at least one mRNA of the inventive vaccine may be furthermore antigens generated inside the cell, the tissue or the body, e.g. by secretion of proteins, their degradation, metabolism, etc. Such antigens include antigens derived from the host organism (e.g. a human) itself, e.g. tumour antigens, self-antigens or auto-antigens, such as auto-immune self-antigens, etc., but also (non-self) antigens as defined above, which have been originally been derived from host cells outside the host organism, but which are fragmented or degraded inside the body, tissue or cell, e.g. by (protease) degradation, metabolism, etc.

Pathogenic antigens particularly comprise e.g. antigens from influenza, preferably influenza A, influenza B, influenza C or thogotovirus, preferably influenza antigens haemagglutinin (HA) and/or neuraminidase (NA), preferably influenza antigens derived from haemagglutinin subtypes H1, H2, H3, H4, H5, H6, H7, H8, H9, H10, H11, H12, H13, H14 or H15, and/or neuraminidase subtypes N1, N2, N3, N4, N5, N6, N7, N8 or N9, or preferably selected from influenza-A subtypes H1N1, H1N2, H2N2, H2N3, H3N1, H3N2, H3N3, H5N1, H5N2, H7N7 or H9N2, or any further combination, or from matrix protein 1 (M1), ion channel protein M2 (M2), nucleoprotein (NP), etc; or e.g. antigens from respiratory syncytial virus (RSV), including F-protein, G-protein, etc.

One further class of antigens as encoded by the at least one mRNA of the inventive vaccine comprises allergy antigens. Allergy antigens are typically antigens, which cause an allergy in a human and may be derived from either a human or other sources. Such allergy antigens may be selected from antigens derived from different sources, e.g.

from animals, plants, fungi, bacteria, etc. Allergens in this context also include antigens derived from e.g. grasses, pollens, molds, drugs, or numerous environmental triggers, etc. Allergy antigens typically belong to different classes of compounds, such as proteins or peptides and their fragments, carbohydrates, polysaccharides, sugars, lipids, phospholipids, etc. Of particular interest in the context of the present invention are antigens, which are encoded by the at least one mRNA of the inventive vaccine, i.e. protein or peptide antigens and their fragments or epitopes, or nucleic acids and their fragments, particularly nucleic acids and their fragments, encoding such protein or peptide antigens and their fragments or epitopes.

Particularly preferred, antigens derived from animals, which are encoded by the at least one mRNA of the inventive vaccine, may include antigens derived from, without being limited thereto, insects, such as mite (e.g. house dust mites), mosquito, bee (e.g. honey bee, bumble bee), cockroach, tick, moth (e.g. silk moth), midge, bug, flea, wasp, caterpillar, fruit fly, migratory locust, grasshopper, ant aphide, from crustaceans, such as shrimps, crab, krill, lobster, prawn, crawfish, scampi, from birds, such as duck, goose, seagull, turkey, ostrich, chicken, from fishes, such as eel, herring, carp, seabream, codfish, halibut, catfish, beluga, salmon, flounder, mackerel, cuttlefish, perch, form molluscs, such as scallop, octopus, abalone, snail, whelk, squid, clam, mussel, from spiders, from mammals, such as cow, rabbit, sheep, lion, jaguar, leopard, rat, pig, buffalo, dog, loris, hamster, guinea pig, fallow deer, horse, cat, mouse, ocelot, serval, from arthropod, such as spider, or silverfish, from worms, such as nematodes, from trichinella species, or roundworm, from amphibians, such as frogs, or from sea squirt, etc. Antigens derived from animals may also comprise antigens contained in animal products, preferably contained in animal products derived from animals as defined above, e.g. milk, eggs, meat, etc., but also from excrements or precipitates of any kind, derived from any of these animals.

Most preferably, antigens derived from animals, which are encoded by the at least one mRNA of the inventive vaccine, may include antigens derived from such animals, causing a disease as defined herein, preferably an infectious disease or an autoimmune disease as defined herein, or any further disease as defined herein.

Antigens derived from plants, which are encoded by the at least one mRNA of the inventive vaccine, may include antigens derived from, without being limited thereto, fruits, such as kiwi, pineapple, jackfruit, papaya, lemon, orange, mandarin, melon, sharon fruit, strawberry, lychee, apple, cherry paradise apple, mango, passion fruit, plum, apricot, nectarine, pear, passion fruit, raspberry, grape, from vegetables, such as garlic, onion, leek, soya bean, celery, cauliflower, turnip, paprika, chickpea, fennel, zucchini, cucumber, carrot, yam, bean, pea, olive, tomato, potato, lentil, lettuce, avocado, parsley, horseradish, chirimoya, beet, pumkin, spinach, from spices, such as mustard, coriander, saffron, pepper, aniseed, from crop, such as oat, buckwheat, barley, rice, wheat, maize, rapeseed, sesame, from nuts, such as cashew, walnut, butternut, pistachio, almond, hazelnut, peanut, brazil nut, pecan, chestnut, from trees, such as alder, hornbeam, cedar, birch, hazel, beech, ash, privet, oak, plane tree, cypress, palm, from flowers, such as ragweed, carnation, forsythia, sunflower, lupine, chamomile, lilac, passion flower, from grasses, such as quack grass, common bent, brome grass, Bermuda grass, sweet vernal grass, rye grass, or from other plants, such as opium poppy, pellitory, ribwort, tobacco, asparagus, mugwort, cress, etc.

Antigens derived from fungi, which are encoded by the at least one mRNA of the inventive vaccine, may include antigens derived from, without being limited thereto, e.g. *Alternia* sp., *Aspergillus* sp., *Beauveria* sp., *Candida* sp., *Cladosporium* sp., *Endothia* sp., *Curcularia* sp., *Embellisia* sp., *Epicoccum* sp., *Fusarium* sp., *Malassezia* sp., *Penicillum* sp., *Pleospora* sp., *Saccharomyces* sp., etc.

Antigens derived from bacteria, which are encoded by the at least one mRNA of the inventive vaccine, may include antigens derived from, without being limited thereto, e.g. *Bacillus tetani, Staphylococcus aureus, Streptomyces griseus*, etc.

One further class of antigens as encoded by the at least one mRNA of the inventive vaccine comprises tumour antigens. "Tumour antigens" are preferably located on the surface of the (tumour) cell. Tumour antigens may also be selected from proteins, which are overexpressed in tumour cells compared to a normal cell. Furthermore, tumour antigens also include antigens expressed in cells which are (were) not themselves (or originally not themselves) degenerated but are associated with the supposed tumour. Antigens which are connected with tumour-supplying vessels or (re)formation thereof, in particular those antigens which are associated with neovascularization, e.g. growth factors, such as VEGF, bFGF etc., are also included herein. Antigens connected with a tumour furthermore include antigens from cells or tissues, typically embedding the tumour. Further, some substances (usually proteins or peptides) are expressed in patients suffering (knowingly or not-knowingly) from a cancer disease and they occur in increased concentrations in the body fluids of said patients. These substances are also referred to as "tumour antigens", however they are not antigens in the stringent meaning of an immune response inducing substance. The class of tumour antigens can be divided further into tumour-specific antigens (TSAs) and tumour-associated-antigens (TAAs). TSAs can only be presented by tumour cells and never by normal "healthy" cells. They typically result from a tumour specific mutation. TAAs, which are more common, are usually presented by both tumour and healthy cells. These antigens are recognized and the antigen-presenting cell can be destroyed by cytotoxic T cells. Additionally, tumour antigens can also occur on the surface of the tumour in the form of, e.g., a mutated receptor. In this case, they can be recognized by antibodies. According to the invention, the terms "cancer diseases" and "tumour diseases" are used synonymously herein.

Examples of tumour antigens as encoded by the at least one mRNA of the inventive vaccine may comprise e.g. antigens selected from the group comprising, without being limited thereto, 5T4, 707-AP (707 alanine proline), 9D7, AFP (alpha-fetoprotein), AlbZIP HPG1, alpha5beta1-Integrin, alpha5beta6-Integrin, alpha-methylacyl-coenzyme A racemase, ART4 (adenocarcinoma antigen recognized by T cells 4), B7H4, BAGE-1 (B antigen), BCL-2, BING-4, CA 15-3/CA 27-29, CA 19-9, CA 72-4, CA125, calreticulin, CAMEL (CTL-recognized antigen on melanoma), CASP-8 (caspase-8), cathepsin B, cathepsin L, CD19, CD20, CD22, CD25, CD30, CD33, CD40, CD52, CD55, CD56, CD80, CEA (carcinoembryonic antigen), CLCA2 (calcium-activated chloride channel-2), CML28, Coactosin-like protein, Collagen XXIII, COX-2, CT-9/BRD6 (bromodomain testis-specific protein), Cten (C-terminal tensin-like protein), cyclin B1, cyclin D1, cyp-B (cyclophilin B), CYPB1 (cytochrom P450 1B1), DAM-10/MAGE-B1 (differentiation antigen melanoma 10), DAM-6/MAGE-B2 (differentiation antigen melanoma 6), EGFR/Her1, EMMPRIN (tumour cell-associated extracellular matrix metalloproteinase inducer/), EpCam (epithelial cell adhesion molecule), EphA2 (ephrin type-A receptor 2), EphA3 (ephrin type-A receptor 3), ErbB3, EZH2 (enhancer of Zeste homolog 2), FGF-5 (fibroblast growth factor-5), FN (fibronectin), Fra-1 (Fos-related antigen-1), G250/CAIX (glycoprotein 250), GAGE-1 (G antigen 1), GAGE-2 (G antigen 2), GAGE-3 (G antigen 3), GAGE-4 (G antigen 4), GAGE-5 (G antigen 5), GAGE-6 (G antigen 6), GAGE-7b (G antigen 7b), GAGE-8 (G antigen 8), GDEP (gene differentially expressed in prostate), GnT-V (N-acetylglucosaminyltransferase V), gp100 (glycoprotein 100 kDa), GPC3 (glypican 3), HAGE (helicase antigen), HAST-2 (human signet ring tumour-2), hepsin, Her2/neu/ErbB2 (human epidermal receptor-2/neurological), HERV-K-MEL, HNE (human neutrophil elastase), homeobox NKX 3.1, HOM-TES-14/SCP-1, HOM-TES-85, HPV-E6, HPV-E7, HST-2, hTERT (human telomerase reverse transcriptase), iCE (intestinal carboxyl esterase), IGF-1R, IL-13Ra2 (interleukin 13 receptor alpha 2 chain), IL-2R, IL-5, immature laminin receptor, kallikrein 2, kallikrein 4, Ki67, KIAA0205, KK-LC-1 (Kita-kyushu lung cancer antigen 1), KM-HN-1, LAGE-1 (L antigen), livin, MAGE-A1 (melanoma antigen-A1), MAGE-A10 (melanoma antigen-A10), MAGE-A12 (melanoma antigen-A12), MAGE-A2 (melanoma antigen-A2), MAGE-A3 (melanoma antigen-A3), MAGE-A4 (melanoma antigenA4), MAGE-A6 (melanoma antigen-A6), MAGE-A9 (melanoma-antigen-A9), MAGE-B1 (melanoma-antigen-B1), MAGE-B10 (melanoma-antigen-B10), MAGE-B16 (melanomaantigen-B16), MAGE-B17 (melanoma-antigen-B17), MAGE-B2 (melanoma-antigen-B2), MAGE-B3 (melanoma-antigen-B3), MAGE-B4 (melanoma-antigen-B4), MAGE-B5 (melanoma-antigen-B5), MAGE-B6 (melanoma-antigen-B6), MAGE-C1 (melanoma-antigen-C1), MAGE-C2 (melanoma-antigen-C2), MAGE-C3 (melanoma-antigen-C3), MAGE-D1 (melanoma-antigen-D1), MAGE-D2 (melanoma-antigen-D2), MAGE-D4 (melanoma-antigen-D4), MAGE-E1 (melanoma-antigen-E1), MAGE-E2 (melanoma-antigen-E2), MAGE-F1 (melanoma-antigen-F1), MAGE-H1 (melanoma-antigen-H1), MAGEL2 (MAGE-like 2), mammaglobin A, MART-1/Melan-A (melanoma antigen recognized by T cells-1/melanoma antigen A), MART-2 (melanoma antigen recognized by T cells-2), matrix protein 22, MC1R (melanocortin 1 receptor), M-CSF (macrophage colony-stimulating factor gene), mesothelin, MG50/PXDN, MMP 11 (M-phase phosphoprotein 11), MN/CA IX-antigen, MRP-3 (multidrug resistance-associated protein 3), MUC1 (mucin 1), MUC2 (mucin 2), NA88-A (NA cDNA clone of patient M88), N-acetylglucosaminyltransferase-V, Neo-PAP (Neo-poly(A) polymerase), NGEP, NMP22, NPM/ALK (nucleophosmin/anaplastic lymphoma kinase fusion protein), NSE (neuron-specific enolase), NY-ESO-1 (New York esophageous 1), NYESO-B, OA1 (ocular albinism type 1 protein), OFA-iLRP (oncofetal antigen-immature laminin receptor), OGT (O-linked N-acetylglucosamine transferase gene), OS-9, osteocalcin, osteopontin, p15 (protein 15), p15, p190 minor bcr-abl, p53, PAGE-4 (prostate GAGElike protein-4), PAI-1 (plasminogen acitvator inhibitor 1), PAI-2 (plasminogen acitvator inhibitor 2), PAP (prostate acic phosphatase), PART-1, PATE, PDEF, Pim-1-Kinase, Pin1 (Propyl isomerase), POTE, PRAME (preferentially expressed antigen of melanoma), prostein, proteinase-3, PSA (prostate-specific antigen), PSCA, PSGR, PSM, PSMA (prostate-specific membrane antigen), RAGE-1 (renal antigen), RHAMM/CD168 (receptor for hyaluronic acid mediated motility), RU1 (renal ubiquitous 1), RU2 (renal ubiquitous 1), S-100, SAGE (sarcoma antigen), SART-1 (squamous antigen rejecting tumour 1), SART-2 (squamous antigen rejecting tumour 1), SART-3 (squamous antigen rejecting tumour 1), SCC (squamous cell carcinoma antigen), Sp17 (sperm protein 17), SSX-1 (synovial sarcoma X breakpoint 1), SSX2/HOM-MEL-40 (synovial sarcoma X breakpoint), SSX-4 (synovial sarcoma X breakpoint 4), STAMP-1, STEAP (six transmembrane epithelial antigen prostate), surviving, survivin-2B (intron 2-retaining survivin), TA-90, TAG-72, TARP, TGFb (TGFbeta), TGFbRII (TGFbeta receptor II), TGM-4 (prostate-specific transglutaminase), TRAG-3 (taxol resistant associated protein 3), TRG (testin-related gene), TRP-1 (tyrosine related protein 1), TRP-2/6b (TRP2/novel exon 6b), TRP-2/INT2 (TRP-2/intron 2), Trp-p8, Tyrosinase, UPA (urokinase-type plasminogen activator), VEGF (vascular endothelial growth factor), VEGFR-2/FLK-1 (vascular endothelial growth factor receptor-2), WT1 (Wilm' tumour gene), or may comprise e.g. mutant antigens expressed in cancer diseases selected from the group comprising, without being limited thereto, alpha-actinin-4/m, ARTC1/m, bcr/abl (breakpoint cluster region-Abelson fusion protein), beta-Catenin/m (beta-Catenin), BRCA1/m, BRCA2/m, CASP-5/m, CASP-8/m, CDC27/m (cell-division-cycle 27), CDK4/m (cyclin-dependent kinase 4), CDKN2A/m, CML66, COA-1/m, DEK-CAN (fusion protein), EFTUD2/m, ELF2/m (Elongation factor 2), ETV6-AML1 (Ets variant gene6/acute myeloid leukemia 1 gene fusion protein), FN1/m (fibronectin 1), GPNMB/m, HLA-A*0201-R1701 (arginine to isoleucine exchange at residue 170 of the alpha-helix of the alpha2-domain in the HLA-A2 gene), HLA-A11/m, HLA-A2/m, HSP70-2M (heat shock protein 70-2 mutated), KIAA0205/m, K-Ras/m, LDLR-FUT (LDR-Fucosyltransferase fusion protein), MART2/m, ME1/m, MUM-1/m (melanoma ubiquitous mutated 1), MUM-2/m (melanoma ubiquitous mutated 2), MUM-3/m (melanoma ubiquitous mutated 3), Myosin class I/m, neo-PAP/m, NFYC/m, N-Ras/m, OGT/m, OS-9/m, p53/m, Pml/RARa (promyelocytic leukemia/retinoic acid receptor alpha), PRDX5/m, PTPRK/m (receptor-type protein-tyrosine phosphatase kappa), RBAF600/m, SIRT2/m, SYT-SSX-1 (synaptotagmin I/synovial sarcoma X fusion protein), SYT-SSX-2 (synaptotagmin I/synovial sarcoma X fusion protein), TEL-AML1 (translocation Ets-family leukemia/acute myeloid leukemia 1 fusion protein), TGFbRII (TGFbeta receptor II), TPI/m (triosephosphate isomerase). According to a specific aspect, however, mRNAs encoding antigens gp100, MAGE-A1, MAGE-A3, MART-1/melan-A, survivin, and/or tyrosinase, more preferably mRNAs encoding antigens gp100, MAGE-A1, MAGE-A3, MART-1/melan-A, survivin, and/or tyrosinase, wherein the mRNAs have been complexed with or stabilized with protamine (e.g. in a ratio of about 80 µg mRNA and 128 µg protamine), may be excluded from the scope of invention. In a preferred aspect the tumour antigens as encoded by the at least one mRNA of the inventive vaccine are selected from the group consisting of 5T4, 707-AP, 9D7, AFP, AlbZIP HPG1, alpha-5-beta-1-integrin, alpha-5-beta-6-integrin, alpha-actinin-4/m, alpha-methylacyl-coenzyme A racemase, ART-4, ARTC1/m, B7H4, BAGE-1, BCL-2, bcr/abl, beta-catenin/m, BING-4, BRCA1/m, BRCA2/m, CA 15-3/CA 27-29, CA 19-9, CA72-4, CA125, calreticulin, CAMEL, CASP-8/m, cathepsin B, cathepsin L, CD19, CD20, CD22, CD25, CDE30, CD33, CD40, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMM-PRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gp100, GPC3, GPNMB/m, HAGE, HAST-2, hepsin, Her2/neu, HERV-K-MEL, HLAA*0201-R171, HLA-A11/m, HLA-A2/m, HNE, homeobox NKX3.1, HOM-TES-14/SCP-1, HOM-TES-85, HPV-E6, HPV-E7, HSP70-2M, HST-2, hTERT, ICE, IGF-1R, IL-13Ra2, IL-2R, IL-5, immature laminin receptor, kallikrein-2, kallikrein-4, Ki67, KIAA0205, KIAA0205/m, KK-LC-1, K-Ras/m, LAGE-A1, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGEB4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MC1R, M-CSF, ME1/m, mesothelin, MG50/PXDN, MMP11, MN/CA IX-antigen, MRP-3, MUC-1, MUC-2, MUM-1/m, MUM-2/m, MUM-3/m, myosin class I/m, NA88-A, Nacetylglucosaminyltransferase-V, Neo-PAP, Neo-PAP/m, NFYC/m, NGEP, NMP22, NPM/ALK, N-Ras/m, NSE, NY-ESO-1, NY-ESO-B, OA1, OFA-iLRP, OGT, OGT/m, OS-9, OS-9/m, osteocalcin, osteopontin, p15, p190 minor bcr-abl, p53, p53/m, PAGE-4, PAI-1, PAI-2, PART-1, PATE, PDEF, Pim-1-Kinase, Pin-1, Pml/PARalpha, POTE, PRAME, PRDX5/m, prostein, proteinase-3, PSA, PSCA, PSGR, PSM, PSMA, PTPRK/m, RAGE-1, RBAF600/m, RHAMM/CD168, RU1, RU2, S-100, SAGE, SART-1, SART-2, SART-3, SCC, SIRT2/m, Sp17, SSX-1, SSX-2/HOM-MEL-40, SSX-4, STAMP-1, STEAP, survivin, survivin-2B, SYT-SSX-1, SYT-SSX-2, TA-90, TAG-72, TARP, TEL-AML1, TGFbeta, TGFbetaRII, TGM-4, TPI/m, TRAG-3, TRG, TRP-1, TRP-2/6b, TRP/INT2, TRP-p8, tyrosinase, UPA, VEGF, VEGFR-2/FLK-1, and WT1.

According to a particularly preferred aspect, tumour antigens as encoded by the at least one mRNA of the inventive vaccine are selected from the group consisting of MAGE-A1 (e.g. MAGE-A1 according to accession number M77481), MAGE-A2, MAGE-A3, MAGE-A6 (e.g. MAGE-A6 according to accession number NM_005363), MAGE-C1, MAGE-C2, melan-A (e.g. melan-A according to accession number NM_005511), GP100 (e.g. GP100 according to accession number M77348), tyrosinase (e.g. tyrosinase according to accession number NM_000372), survivin (e.g. survivin according to accession number AF077350), CEA (e.g. CEA according to accession number NM_004363), Her-2/neu (e.g. Her-2/neu according to accession number M11730), WT1 (e.g. WT1 according to accession number NM_000378), PRAME (e.g. PRAME according to accession number NM_006115), EGFRI (epidermal growth factor receptor 1) (e.g. EGFRI (epidermal growth factor receptor 1) according to accession number AF288738), MUC1, mucin-1 (e.g. mucin-1 according to accession number NM_002456), SEC61G (e.g. SEC61G according to accession number NM_014302), hTERT (e.g. hTERT accession number NM_198253), 5T4 (e.g. 5T4 according to accession number NM_006670), NY-Eso-1 (e.g. NY-Eso1 according to accession number NM_001327), TRP-2 (e.g. TRP-2 according to accession number NM_001922), STEAP, PCA, PSA, PSMA, etc.

Particularly preferred are antigens derived from Influenza A virus (HA, NA, NP, M2, M1 antigens), influenza B virus (HA, NA antigens), respiratory syncytial virus (F, G, M, SH antigens), parainfluenza virus (glycoprotein antigens), varicella-zoster virus/herpes zoster, human papillomavirus (L1, L2, E6, E7), human immunodeficiency virus (gp120, gag, env antigens), SARS CoV (spike protein), *Staphylococcus aureus* (IsdA, IsdB, toxin antigens), Bordetella pertussis (toxin), polio virus (VP1-4), *Plasmodium* (NANP, CSP protein, ssp2, ama1, msp142 antigens), *Streptococcus pneumoniae* (Pht, PcsB, StkP antigens), *Corynebacterium diphtheriae, Clostridium tetani*, Measles, Mumps, Rubella, Rabies virus (G, N antigens), *Staphylococcus aureus* (toxin antigen), *Clostridium difficile* (toxin antigen), *Mycobacterium tuberculosis* (dormant antigens), *Candida albicans*.

Antigens as encoded by the at least one mRNA of the inventive vaccine may furthermore comprise fragments of such antigens as mentioned herein, particularly of protein or peptide antigens. Fragments of such antigens in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule, i.e. the fragments are typically not recognized in their native form.

Fragments of antigens as defined herein may also comprise epitopes of those antigens. Epitopes (also called "antigen determinants") are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form.

According to a further particularly preferred aspect, the tumour antigens as encoded by at least one mRNA of the inventive vaccine may form a cocktail of antigens, e.g. in an active (immunostimulatory) composition or a kit of parts (wherein preferably each antigen is contained in one part of the kit), preferably for eliciting an (adaptive) immune response for the treatment of a disease or disorder as defined herein. For this purpose, the inventive vaccine may comprise at least one mRNA, wherein each mRNA may encode at least one, preferably two, three, four or even more (preferably different) antigens as mentioned herein. Alternatively, the inventive vaccine may contain at least one, two, three, four or even more (preferably different) mRNAs, wherein each mRNA encodes at least one antigen as mentioned herein.

Such a cocktail of antigens, as encoded by the least one mRNA of the inventive vaccine may be used e.g. in the treatment of e.g. prostate cancer (PCa), preferably in the treatment of neoadjuvant and/or hormone-refractory prostate cancers, and diseases or disorders related thereto. For this purpose, the inventive vaccine may comprise at least one mRNA, wherein each mRNA may encode at least one, preferably two, three, four or even more (preferably different) antigens as mentioned herein. Alternatively, the inventive vaccine may contain at least one, two, three, four or even more (preferably different) mRNAs, wherein each mRNA encodes at least one antigen as mentioned herein. Preferably, the antigens are selected from PSA (Prostate- Specific Antigen)=KLK3 (Kallikrein-3), PSMA (Prostate-Specific Membrane Antigen), PSCA (Prostate Stem Cell Antigen), and/or STEAP (Six Transmembrane Epithelial Antigen of the Prostate).

Furthermore, such a cocktail of antigens, as encoded by the at least one mRNA of the inventive vaccine may be used in the treatment of e.g. non-small cell lung cancers (NSCLC), preferably selected from the three main sub-types squamous cell lung carcinoma, adenocarcinoma and large cell lung carcinoma, or of disorders related thereto. For this purpose, the inventive vaccine may comprise at least one mRNA, wherein each mRNA may encode at least one, preferably two, three, four, five, six, seven, eight, nine, ten eleven or twelve (preferably different) antigens as mentioned herein. Alternatively, the inventive vaccine may contain at least one, preferably two, three, four, five, six, seven, eight, nine, ten, eleven or twelve (preferably different) mRNAs, wherein each mRNA encodes at least one antigen as mentioned herein. Preferably, such antigens are selected from hTERT, WT1, MAGE-A2, 5T4, MAGE-A3, MUC1, Her-2/neu, NY-ESO-1, CEA, Survivin, MAGE-C1, and/or MAGE-C2.

In the above aspects, each of the above defined antigens may be encoded by one (monocistronic) mRNA. In other words, in this case the at least one mRNA of the inventive vaccine may comprise at least two (three, four, etc.) (monocistronic) mRNAs, wherein each of these at least two (three, four, etc.) (monocistronic) mRNAs may encode, e.g. just one (preferably different) antigen, preferably selected from one of the above mentioned antigen combinations.

According to a particularly preferred aspect, the at least one mRNA of the inventive vaccine may comprise (at least) one bi- or even multicistronic mRNA, preferably mRNA, i.e. (at least) one mRNA which carries, e.g. two or even more of the coding sequences of at least two (preferably different) antigens, preferably selected from one of the above mentioned antigen combinations. Such coding sequences, e.g. of the at least two (preferably different) antigens, of the (at least) one bi- or even multicistronic mRNA may be separated by at least one IRES (internal ribosomal entry site) sequence, as defined below. Thus, the term "encoding at least two (preferably different) antigens" may mean, without being limited thereto, that the (at least) one (bi- or even multicistronic) mRNA, may encode e.g. at least two, three, four, five, six, seven, eight, nine, ten, eleven or twelve or more (preferably different) antigens of the above mentioned group(s) of antigens, or their fragments or variants, etc. In this context, a so-called IRES (internal ribosomal entry site) sequence as defined herein can function as a sole ribosome binding site, but it can also serve to provide a bi- or even multicistronic RNA as defined herein which codes for several proteins, which are to be translated by the ribosomes independently of one another. Examples of IRES sequences which can be used according to the invention are those from picornaviruses (e.g. FMDV), pestiviruses (CFFV), polioviruses (PV), encephalomyocarditis viruses (ECMV), foot and mouth disease viruses (FMDV), hepatitis C viruses (HCV), classical swine fever viruses (CSFV), mouse leukemia virus (MLV), simian immunodeficiency viruses (SIV) or cricket paralysis viruses (CrPV).

According to a further particularly preferred aspect, the at least one mRNA of the inventive vaccine may comprise a mixture of at least one monocistronic mRNA as defined herein, and at least one bi- or even multicistronic RNA, preferably mRNA, as defined herein. The at least one monocistronic RNA and/or the at least one bi- or even multicistronic RNA preferably encode different antigens, or their fragments or variants, the antigens preferably being selected from one of the above mentioned antigens, more preferably in one of the above mentioned combinations. However, the at least one monocistronic RNA and the at least one bi- or even multicistronic RNA may preferably also encode (in part) identical antigens selected from one of the above mentioned antigens, preferably in one of the above mentioned combinations, provided that the at least one mRNA of the inventive vaccine as a whole provides at least two (preferably different) antigens, as defined herein. Such an aspect may be advantageous e.g. for a staggered, e.g. time dependent, administration of one or several of the at least one mRNA of the inventive vaccine to a patient in need thereof. The components of such a vaccine may be contained in (different parts of) a kit of parts composition or may be e.g. administered separately as components of the same inventive vaccine as defined according to the present invention.

In a further preferred embodiment the at least one mRNA of the inventive vaccine (or any further nucleic acid as defined herein) may also occur in the form of a modified nucleic acid.

According to a first aspect, the at least one mRNA of the inventive vaccine (or any further nucleic acid as defined herein) may be provided as a "stabilized nucleic acid" that is essentially resistant to in vivo degradation (e.g. by an exo- or endo-nuclease).

In this context, the at least one mRNA of the inventive vaccine (or any further nucleic acid as defined herein) may contain backbone modifications, sugar modifications or base modifications. A backbone modification in connection with the present invention is a modification in which phosphates of the backbone of the nucleotides contained in the at least one mRNA of the inventive vaccine (or any further nucleic acid as defined herein) are chemically modified. A sugar modification in connection with the present invention is a chemical modification of the sugar of the nucleotides of the at least one mRNA of the inventive vaccine (or any further nucleic acid as defined herein). Furthermore, a base modification in connection with the present invention is a chemical modification of the base moiety of the nucleotides of the at least one mRNA of the inventive vaccine (or any further nucleic acid as defined herein).

According to a further aspect, the at least one mRNA of the inventive vaccine (or any further nucleic acid as defined herein) can contain a lipid modification. Such a lipid-modified nucleic acid typically comprises a nucleic acid as defined herein, e.g. an mRNA or any further nucleic acid. Such a lipid-modified mRNA of the inventive vaccine (or any further lipid-modified nucleic acid as defined herein) typically further comprises at least one linker covalently linked with that nucleic acid molecule, and at least one lipid covalently linked with the respective linker. Alternatively, the lipid-modified mRNA of the inventive vaccine (or any further lipid-modified nucleic acid as defined herein) comprises at least one nucleic acid molecule as defined herein, e.g. an mRNA or any further nucleic acid, and at least one (bifunctional) lipid covalently linked (without a linker) with that nucleic acid molecule. According to a third alternative, the lipid-modified mRNA of the inventive vaccine (or any further lipid-modified nucleic acid as defined herein) comprises a nucleic acid molecule as defined herein, e.g. an mRNA or any further nucleic acid, at least one linker covalently linked with that nucleic acid molecule, and at least one lipid covalently linked with the respective linker, and also at least one (bifunctional) lipid covalently linked (without a linker) with that nucleic acid molecule.

The at least one mRNA of the inventive vaccine (or any further nucleic acid as defined herein) may likewise be stabilized in order to prevent degradation of the mRNA (or any further nucleic acid molecule) by various approaches. It is known in the art that instability and (fast) degradation of RNA in general may represent a serious problem in the application of RNA based compositions. This instability of RNA is typically due to RNA-degrading enzymes, "RNAases" (ribonucleases), wherein contamination with such ribonucleases may sometimes completely degrade RNA in solution. Accordingly, the natural degradation of RNA in the cytoplasm of cells is very finely regulated and RNase contaminations may be generally removed by special treatment prior to use of said compositions, in particular with diethyl pyrocarbonate (DEPC). A number of mechanisms of natural degradation are known in this connection in the prior art, which may be utilized as well. E.g., the terminal structure is typically of critical importance particularly for an mRNA. As an example, at the 5' end of naturally occurring mRNAs there is usually a so-called "cap structure" (a modified guanosine nucleotide), and at the 3' end is typically a sequence of up to 200 adenosine nucleotides (the so-called poly-A tail).

According to another aspect, the at least one mRNA of the inventive vaccine may be modified and thus stabilized by modifying the G/C content of the mRNA, preferably of the coding region thereof.

In a particularly preferred aspect of the present invention, the G/C content of the coding region of the at least one mRNA of the inventive vaccine is modified, particularly increased, compared to the G/C content of the coding region of its particular wild type coding sequence, i.e. the unmodified mRNA. The encoded amino acid sequence of the mRNA is preferably not modified compared to the coded amino acid sequence of the particular wild type mRNA.

The modification of the G/C-content of the at least one mRNA of the inventive vaccine is based on the fact that the sequence of any mRNA region to be translated is important for efficient translation of that mRNA. Thus, the composition and the sequence of various nucleotides are important. In particular, sequences having an increased G (guanosine)/C (cytosine) content are more stable than sequences having an increased A (adenosine)/U (uracil) content. According to the invention, the codons of the coding sequence or mRNA are therefore varied compared to its wild type coding sequence or mRNA, while retaining the translated amino acid sequence, such that they include an increased amount of G/C nucleotides. In respect to the fact that several codons code for one and the same amino acid (so-called degeneration of the genetic code), the most favourable codons for the stability can be determined (so-called alternative codon usage).

Preferably, the G/C content of the coding region of the at least one mRNA of the inventive vaccine is increased by at least 7%, more preferably by at least 15%, particularly preferably by at least 20%, compared to the G/C content of the coded region of the wild type mRNA. According to a specific aspect at least 5%, 10%, 20%, 30%, 40%, 50%, 60%, more preferably at least 70%, even more preferably at least 80% and most preferably at least 90%, 95% or even 100% of the substitutable codons in the region coding for a protein or peptide as defined herein or its fragment or variant thereof or the whole sequence of the wild type mRNA sequence or coding sequence are substituted, thereby increasing the G/C content of said sequence.

In this context, it is particularly preferable to increase the G/C content of the at least one mRNA of the inventive vaccine to the maximum (i.e. 100% of the substitutable codons), in particular in the region coding for a protein, compared to the wild type sequence.

According to the invention, a further preferred modification of the at least one mRNA of the inventive vaccine, especially if the nucleic acid is in the form of an mRNA or codes for an mRNA, is based on the finding that the translation efficiency is also determined by a different frequency in the occurrence of tRNAs in cells. Thus, if so-called "rare codons" are present in the at least one mRNA of the inventive vaccine to an increased extent, the corresponding modified mRNA is translated to a significantly poorer degree than in the case where codons coding for relatively "frequent" tRNAs are present.

Preferably, the coding region of the at least one mRNA of the inventive vaccine is modified compared to the corresponding region of the wild type mRNA or coding sequence such that at least one codon of the wild type sequence which codes for a tRNA which is relatively rare in the cell is exchanged for a codon which codes for a tRNA which is relatively frequent in the cell and carries the same amino acid as the relatively rare tRNA. By this modification, the sequences of the at least one mRNA of the inventive vaccine, especially if the nucleic acid is in the form of an mRNA or codes for an mRNA, is modified such that codons for which frequently occurring tRNAs are available are inserted. In other words, according to the invention, by this modification all codons of the wild type sequence which code for a tRNA which is relatively rare in the cell can in each case be exchanged for a codon which codes for a tRNA which is relatively frequent in the cell and which, in each case, carries the same amino acid as the relatively rare tRNA.

Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons which use for the particular amino acid the tRNA which occurs the most frequently, e.g. the Gly codon, which uses the tRNA which occurs the most frequently in the (human) cell, are particularly preferred.

According to the invention, it is particularly preferable to link the sequential G/C content which is increased, in particular maximized, in the modified at least one mRNA of the inventive vaccine with the "frequent" codons without modifying the amino acid sequence of the protein encoded by the coding region of the mRNA. This preferred aspect allows provision of a particularly efficiently translated and stabilized (modified) at least one mRNA of the inventive vaccine.

According to a further preferred aspect of the invention, the at least one mRNA of the inventive vaccine as defined herein or any further nucleic acid molecule as defined herein preferably has at least one 5' and/or 3' stabilizing sequence. These stabilizing sequences in the 5' and/or 3' untranslated regions have the effect of increasing the half-life of the nucleic acid in the cytosol. These stabilizing sequences can have 100% sequence identity to naturally occurring sequences which occur in viruses, bacteria and eukaryotes, but can also be partly or completely synthetic. The untranslated sequences (UTR) of the (alpha-)globin gene, e.g. from *Homo sapiens* or *Xenopus laevis* may be mentioned as an example of stabilizing sequences which can be used in the present invention for a stabilized nucleic acid. Another example of formula a stabilizing sequence has the general (C/U)CCAN$_x$CCC(U/A)Py$_x$UC(C/U)CC (SEQ ID NO: 383), which is contained in the 3'UTR of the very stable RNA which codes for (alpha-)globin, type(I)-collagen, 15-lipoxygenase or for tyrosine hydroxylase (cf. Holcik et al., Proc. Natl. Acad. Sci. USA 1997, 94: 2410 to 2414). Such stabilizing sequences can of course be used individually or in combination with one another and also in combination with other stabilizing sequences known to a person skilled in the art.

Nevertheless, substitutions, additions or eliminations of bases are preferably carried out with the at least one mRNA of the inventive vaccine or any further nucleic acid molecule as defined herein, especially if the nucleic acid is in the form of an mRNA, using a DNA matrix for preparation of the nucleic acid molecule by techniques of the well known site directed mutagenesis or with an oligonucleotide ligation strategy (see e.g. Maniatis et al., Molecular Cloning: A Laboratory Manual, Cold Spring Harbor Laboratory Press, 3rd ed., Cold Spring Harbor, N Y, 2001). In such a process, for preparation of the at least one mRNA of the inventive vaccine as defined herein a corresponding DNA molecule may be transcribed in vitro. This DNA matrix preferably comprises a suitable promoter, e.g. a T7 or SP6 promoter, for in vitro transcription, which is followed by the desired nucleotide sequence for the at least one mRNA to be prepared and a termination signal for in vitro transcription. The DNA molecule, which forms the matrix of the at least one mRNA of interest, may be prepared by fermentative proliferation and subsequent isolation as part of a plasmid which can be replicated in bacteria. Plasmids which may be mentioned as suitable for the present invention are e.g. the plasmids pT7 Ts (GenBank accession number U26404; Lai et al., Development 1995, 121: 2349 to 2360), pGEM® series, e.g. pGEM®-1 (GenBank accession number X65300; from Promega) and pSP64 (GenBank accession number X65327); cf. also Mezei and Storts, Purification of PCR Products, in: Griffin and Griffin (ed.), PCR Technology: Current Innovation, CRC Press, Boca Raton, F L, 2001.

Nucleic acid molecules used according to the invention and as defined herein, e.g. the at least one mRNA of the inventive vaccine or any further nucleic acid molecule as defined herein, may be modified as outlined above for the at least one mRNA of the inventive vaccine.

Additionally, nucleic acid molecules used according to the invention and as defined herein, e.g. the at least one mRNA of the inventive vaccine or any further nucleic acid molecule as defined herein, may be prepared using any method known in the art, including synthetic methods such as e.g. solid phase synthesis, as well as in vitro methods, such as in vitro transcription reactions.

According to one preferred aspect of the present invention the at least one mRNA of the inventive vaccine may be administered naked without being associated with any further vehicle, transfection or complexation agent for increasing the transfection efficiency of the at least one mRNA.

In a further preferred aspect of the present invention the at least one mRNA of the inventive vaccine is associated with a vehicle, transfection or complexation agent for increasing the transfection efficiency of the at least one mRNA. Particularly preferred agents in this context suitable for increasing the transfection efficiency are cationic or polycationic compounds, including protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, prolin-rich peptides, arginine-rich peptides, lysinerich peptides, MPG-peptide(s), Pep-1, L-oligomers, Calcitonin peptide(s), Antennapedia-derived peptides (particularly from Drosophila antennapedia), pAntp, plsI, FGF, Lactoferrin, Transportan, Buforin-2, Bac715-24, SynB, SynB(1), pVEC, hCT-derived peptides, SAP, or histones. Additionally, preferred cationic or polycationic proteins or peptides may be selected from the following proteins or peptides having the following total formula: $(Arg)_l;(Lys)_m;(His)_n;(Orn)_o;(Xaa)_x$, wherein l+m+n+o+x=8-15, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide. Particularly preferred cationic peptides in this context are e.g. $Arg_7$, $Arg_8$, $Arg_9$, $H_3R_9$, $R_9H_3$, $H_3R_9H_3$, $YSSR_9SSY$, $(RKH)_4$, $Y(RKH)_2R$, etc. Further preferred cationic or polycationic compounds, which can be used as transfection agent may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioacetyl)diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl]trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as β-amino-acid-polymers or reversed polyamides, etc., modified polyethylenes, such as PVP (poly(N-ethyl4-vinylpyridinium bromide)), etc., modified acrylates, such as pDMAEMA (poly (dimethylaminoethyl methylacrylate)), etc., modified amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole); etc.

The at least one mRNA of the inventive vaccine encoding at least one antigen may also be complexed with a polymeric carrier formed by disulfide-crosslinked cationic components. The term "cationic component" typically refers to a charged molecule, which is positively charged (cation) at a pH value of about 1 to 9, preferably of a pH value of or below 9, of or below 8, of or below 7, most preferably at physiological pH values, e.g. about 7.3 to 7.4. Accordingly, a cationic peptide, protein or polymer according to the present invention is positively charged under physiological conditions, particularly under physiological salt conditions of the cell in vivo. The definition "cationic" may also refer to "polycationic" components.

In this context the cationic components, which form basis for the polymeric carrier of the inventive vaccine by disulfide-crosslinkage, are typically selected from any suitable cationic or polycationic peptide, protein or polymer suitable for this purpose, particular any cationic or polycationic peptide, protein or polymer capable to complex a nucleic acid as defined according to the present invention, and thereby preferably condensing the nucleic acid. The cationic or polycationic peptide, protein or polymer, is preferably a linear molecule, however, branched cationic or polycationic peptides, proteins or polymers may also be used.

Each cationic or polycationic protein, peptide or polymer of the polymeric carrier, which may be used to complex the at least one mRNA of the inventive vaccine contains at least one —SH moiety, most preferably at least one cysteine residue or any further chemical group exhibiting an —SH moiety, capable to form a disulfide linkage upon condensation with at least one further cationic or polycationic protein, peptide or polymer as cationic component of the polymeric carrier as mentioned herein.

Each cationic or polycationic protein, peptide or polymer or any further component of the polymeric carrier, which may be used to complex the at least one mRNA of the inventive vaccine is preferably linked to its neighbouring component(s) (cationic proteins, peptides, polymers or other components) via disulfide-crosslinking. Preferably, the disulfide-crosslinking is a (reversible) disulfide bond (—S—S—) between at least one cationic or polycationic protein, peptide or polymer and at least one further cationic or polycationic protein, peptide or polymer or other component of the polymeric carrier. The disulfide-crosslinking is typically formed by condensation of —SH-moieties of the components of the polymeric carrier particularly of the cationic components. Such an —SH-moiety may be part of the structure of the cationic or polycationic protein, peptide or polymer or any further component of the polymeric carrier prior to disulfide-crosslinking or may be added prior to disulfide-crosslinking by a modification as defined below. In this context, the sulphurs adjacent to one component of the polymeric carrier, necessary for providing a disulfide bond, may be provided by the component itself, e.g. by a —SH moiety as defined herein or may be provided by modifying the component accordingly to exhibit a —SH moiety. These —SH-moieties are typically provided by each of the components, e.g. via a cysteine or any further (modified) amino acid of the component, which carries a —SH moiety. In the case that the cationic component or any further component of the polymeric carrier is a peptide or protein it is preferred that the —SH moiety is provided by at least one cysteine residue. Alternatively, the component of the polymeric carrier may be modified accordingly with a —SH moiety, preferably via a chemical reaction with a compound carrying a —SH moiety, such that each of the components of the polymeric carrier carries at least one such —SH moiety. Such a compound carrying a —SH moiety may be e.g. an (additional) cysteine or any further (modified) amino acid or compound of the component of the polymeric carrier, which carries a —SH moiety. Such a compound may also be any non-amino compound or moiety, which contains or allows to introduce a —SH moiety into the component as defined herein. Such non-amino compounds may be attached to the component of the polymeric carrier according to the present invention via chemical reactions or binding of compounds, e.g. by binding of a 3-thio propionic acid or 2-iminothiolane (Traut's reagent), by amide formation (e.g. carboxylic acids, sulphonic acids, amines, etc.), by Michael addition (e.g maleinimide moieties, $\alpha,\beta$ unsatured carbonyls, etc.), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g halogenalkans, thiols, alcohols, amines, hydrazines, hydrazides, sulphonic acid esters, oxyphosphonium salts) or other chemical moieties which can be utilized in the attachment of further components. In some cases the —SH moiety may be masked by protecting groups during chemical attachment to the component. Such protecting groups are known in the art and may be removed after chemical coupling. In each case, the —SH moiety, e.g. of a cysteine or of any further (modified) amino acid or compound, may be present at the terminal ends or internally at any position of the component of the polymeric carrier. As defined herein, each of the components of the polymeric carrier typically exhibits at least one —SH-moiety, but may also contain two, three, four, five, or even more —SH-moieties. Additionally to binding of cationic components a —SH moiety may be used to attach further components of the polymeric carrier of the inventive vaccine as defined herein, particularly an amino acid component, e.g. antigen epitopes, antigens, antibodies, cell penetrating peptides (e.g. TAT), ligands, etc.

As defined above, the polymeric carrier, which may be used to complex the at least one mRNA of the inventive vaccine may be formed by disulfide-crosslinked cationic (or polycationic) components.

According to one first alternative, at least one cationic (or polycationic) component of the polymeric carrier, which may be used to complex the at least one mRNA of the inventive vaccine may be selected from cationic or polycationic peptides or proteins. Such cationic or polycationic peptides or proteins preferably exhibit a length of about 3 to 100 amino acids, preferably a length of about 3 to 50 amino acids, more preferably a length of about 3 to 25 amino acids, e.g. a length of about 3 to 10, 5 to 15, 10 to 20 or 15 to 25 amino acids. Alternatively or additionally, such cationic or polycationic peptides or proteins may exhibit a molecular weight of about 0.01 kDa to about 100 kDa, including a molecular weight of about 0.5 kDa to about 100 kDa, preferably of about 10 kDa to about 50 kDa, even more preferably of about 10 kDa to about 30 kDa.

In the specific case that the cationic component of the polymeric carrier, which may be used to complex the at least one mRNA of the inventive vaccine comprises a cationic or polycationic peptide or protein, the cationic properties of the cationic or polycationic peptide or protein or of the entire polymeric carrier, if the polymeric carrier is entirely composed of cationic or polycationic peptides or proteins, may be determined upon its content of cationic amino acids. Preferably, the content of cationic amino acids in the cationic or polycationic peptide or protein and/or the polymeric carrier is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 15% to 75%, even more preferably in the range of about 20% to 50%, e.g. 20, 30, 40 or 50%, or in a range formed by any two of the afore mentioned values, provided, that the content of all amino acids, e.g. cationic, lipophilic, hydrophilic, aromatic and further amino acids, in the cationic or polycationic peptide or protein, or in the entire polymeric carrier, if the polymeric carrier is entirely composed of cationic or polycationic peptides or proteins, is 100%.

Preferably, such cationic or polycationic peptides or proteins of the polymeric carrier, which comprise or are additionally modified to comprise at least one —SH moiety, are selected from, without being restricted thereto, cationic peptides or proteins such as protamine, nucleoline, spermine or spermidine, oligo- or poly-L-lysine (PLL), basic polypeptides, oligo or poly-arginine, cell penetrating peptides (CPPs), chimeric CPPs, such as Transportan, or MPG peptides, HIV-binding peptides, Tat, HIV-1 Tat (HIV), Tat-derived peptides, members of the penetratin family, e.g. Penetratin, Antennapedia-derived peptides (particularly from *Drosophila antennapedia*), pAntp, plsI, etc., antimicrobial-derived CPPs e.g. Buforin-2, Bac715-24, SynB, SynB(1), pVEC, hCT-derived peptides, SAP, MAP, PpTG20, Loligomere, FGF, Lactoferrin, histones, VP22 derived or analog peptides, Pestivirus Erns, HSV, VP22 (Herpes simplex), MAP, KALA or protein transduction domains (PTDs, PpT620, prolin-rich peptides, arginine-rich peptides, lysine-rich peptides, Pep-1, L-oligomers, Calcitonin peptide(s), etc.

Alternatively or additionally, such cationic or polycationic peptides or proteins of the polymeric carrier, which comprise or are additionally modified to comprise at least one —SH moiety, are selected from, without being restricted thereto, following cationic peptides having the following sum formula (I):

$$\{(Arg)_l;(Lys)_m;(His)_n;(Orn)_o;(Xaa)_x\};$$

wherein l+m+n+o+x=3-100, and l, m, n or o independently of each other is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90 and 91-100 provided that the overall content of Arg (Arginine), Lys (Lysine), His (Histidine) and Orn (Ornithine) represents at least 10% of all amino acids of the oligopeptide; and Xaa is any amino acid selected from native (=naturally occurring) or non-native amino acids except of Arg, Lys, His or Orn; and x is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90, provided, that the overall content of Xaa does not exceed 90% of all amino acids of the oligopeptide. Any of amino acids Arg, Lys, His, Orn and Xaa may be positioned at any place of the peptide. In this context cationic peptides or proteins in the range of 7-30 amino acids are particular preferred. Even more preferred peptides of this formula are oligoarginines such as e.g. $Arg_7$, $Arg_8$, $Arg_9$, $Arg_{12}$, $His_3$ $Arg_9$, $Arg_9His_3$, $His_3Arg_9His_3$, $His_3Arg_9His_6$, $His_6Arg_9His_3$, $His_6Arg_4His_6$, $TyrSer_2Arg_9Ser_2$ Tyr, $(Arg-LysHis)_4$, $Tyr(ArgLysHis)_2Arg$, etc.

According to a particular preferred embodiment, such cationic or polycationic peptides or proteins of the polymeric carrier having the empirical sum formula (I) as shown above, may, without being restricted thereto, comprise at least one of the following subgroup of formulae:

$Arg_7Arg_8$, $Arg_9$, $Arg_{10}$, $Arg_{11}$, $Arg_{12}$, $Arg_{13}$, $Arg_{14}$, $Arg_{15-30}$;

$Lys_7$, $Lys_8$, $Lys_9$, $Lys_{10}$, $Lys_{11}$, $Lys_{12}$, $Lys_{13}$, $Lys_{14}$, $Lys_{15-30}$;

$His_7$, $His_8$, $His_9$, $His_{10}$, $His_{11}$, $His_{12}$, $His_{13}$, $His_{14}$, $His_{15-30}$;

$Orn_7$, $Orn_8$, $Orn_9$, $Orn_{10}$, $Orn_{11}$, $Orn_{12}$, $Orn_{13}$, $Orn_{14}$, $Orn_{15-30}$;

According to a further particularly preferred embodiment, cationic or polycationic peptides or proteins of the polymeric carrier, having the empirical sum formula (I) as shown above and which comprise or are additionally modified to comprise at least one —SH moiety, may be preferably selected from, without being restricted thereto, at least one of the following subgroup of formulae. The following formulae (as with empirical formula (I)) do not specify any amino acid order, but are intended to reflect empirical formulae by exclusively specifying the (number of) amino acids as components of the respective peptide. Accordingly, as an example, empirical formula $Arg_{(7-29)}Lys$, is intended to mean that peptides falling under this formula contain 7 to 19 Arg residues and 1 Lys residue of whatsoever order. If the peptides contain 7 Arg residues and 1 Lys residue, all variants having 7 Arg residues and 1 Lys residue are encompassed. The Lys residue may therefore be positioned anywhere in the e.g. 8 amino acid long sequence composed of 7 Arg and 1 Lys residues. The subgroup preferably comprises:

$Arg_{(4-29)}Lys_1$, $Arg_{(4-29)}His_1$, $Arg_{(4-29)}Orn_1$, $Lys_{(4-29)}His_1$, $Lys_{(4-29)}Orn_1$, $His_{(4-29)}Orn_1$, $Arg_{(3-28)}Lys_2$, $Arg_{(3-28)}His_2$, $Arg_{(3-28)}Orn_2$, $Lys_{(3-28)}His_2$, $Lys_{(3-28)}Orn_2$, $His_{(3-28)}Orn_2$, $Arg_{(2-27)}Lys_3$, $Arg_{(2-27)}His_3$, $Arg_{(2-27)}Orn_3$, $Lys_{(2-27)}His_3$, $Lys_{(2-27)}Orn_3$, $His_{(2-27)}Orn_3$, $Arg_{(1-26)}Lys_4$, $Arg_{(1-26)}His_4$, $Arg_{(1-26)}Orn_4$, $Lys_{(1-26)}His_4$, $Lys_{(1-26)}Orn_4$, $His_{(1-26)}Orn_4$, $Arg_{(3-28)}Lys_1His_1$, $Arg_{(3-28)}Lys_1Orn_1$, $Arg_{(3-28)}His_1Orn_1$, $Arg_1Lys_{(3-28)}His_1$, $Arg_1Lys_{(3-28)}Orn_1$, $Lys_{(3-28)}His_1Orn_1$, $Arg_1Lys_1His_{(3-28)}$, $Arg_1His_{(3-28)}Orn_1$, $Lys_1His_{(3-28)}Orn_1$;

$Arg_{(2-27)}Lys_2His_1$, $Arg_{(2-27)}Lys_1His_2$, $Arg_{(2-27)}Lys_2Orn_1$, $Arg_{(2-27)}Lys_1Orn_2$, $Arg_{(2-27)}His_2Orn_1$, $Arg_{(2-27)}His_1Orn_2$, $Arg_2Lys_{(2-27)}His_1$, $Arg_1Lys_{(2-27)}His_2$, $Arg_1Lys_{(2-27)}Orn_1$, $Arg_1Lys_{(2-27)}Orn_2$, $Lys_{(2-27)}His_2Orn_1$, $Lys_{(2-27)}His_1Orn_2$, $Arg_2Lys_1His_{(2-27)}$, $Arg_1Lys_2His_{(2-27)}$, $Arg_1His_{(2-27)}Orn_1$, $Arg_1His_{(2-27)}Orn_2$, $Lys_2His_{(2-27)}Orn_1$, $Lys_1His_{(2-27)}Orn_2$;

$Arg_{(1-26)}Lys_3$ $His_1$, $Arg_{(1-26)}Lys_2His_2$, $Arg_{(1-26)}Lys_1His_3$, $Arg_{(1-26)}Lys_1Orn_1$, $Arg_{(1-26)}Lys_2Orn_2$, $Arg_{(1-26)}Lys_1Orn_3$, $Arg_{(1-26)}His_3Orn_1$, $Arg_{(1-26)}His_2Orn_2$, $Arg_{(1-26)}His_1Orn_3$, $Arg_3Lys_{(1-26)}His_1$, $Arg_2Lys_{(1-26)}His_2$, $Arg_1Lys_{(1-26)}His_3$, $Arg_3Lys_{(1-26)}Orn_1$, $Arg_2Lys_{(1-26)}Orn_2$, $Arg_1Lys_{(1-26)}Orn_3$, $Lys_{(1-26)}His_3Orn_1$, $Lys_{(1-26)}His_2Orn_2$, $Lys_{(1-26)}His_1Orn_3$, $Arg_3Lys_1His_{(1-26)}$, $Arg_2Lys_2His_{(1-26)}$, $Arg_1Lys_3His_{(1-26)}$, $Arg_3His_{(1-26)}Orn_1$, $Arg_2His_{(1-26)}Orn_2$, $Arg_1His_{(1-26)}Orn_3$, $Lys_3$ $His_{(1-26)}$ $Orn$, $Lys_2His_{(1-26)}Orn_2$, $Lys_1His_{(1-26)}Orn_3$;

$Arg_{(2-27)}Lys_2His_1Orn_1$, $Arg_1Lys_{(2-27)}His_1Orn_1$, $Arg_1Lys_1His_{(2-27)}Orn_1$, $Arg_1Lys_1His_1Orn_{(2-27)}$;

$Arg_{(1-26)}Lys_2His_1Orn_1$, $Arg_{(1-26)}Lys_1His_2Orn_1$, $Arg_{(1-26)}Lys_1His_1Orn_2$, $Arg_2Lys_{(1-26)}$ $His_1Orn_1$, $Arg_1Lys_{(1-26)}His_2Orn_1$, $Arg_1Lys_{(1-26)}His_1Orn_2$, $Arg_2Lys_1His_{(1-26)}Orn_1$, $Arg_1Lys_2His_{(1-26)}Orn_1$, $Arg_1Lys_1His_{(1-26)}Orn_2$, $Arg_2Lys_1His_1Orn_{(1-26)}$, $Arg_1Lys_2His_1Orn_{(1-26)}$, $Arg_1Lys_1His_2Orn_{(1-26)}$;

According to a further particular preferred embodiment, cationic or polycationic peptides or proteins of the polymeric carrier, having the empirical sum formula (I) as shown above and which comprise or are additionally modified to comprise at least one —SH moiety, may be, without being restricted thereto, selected from the subgroup consisting of generic formulas $Arg_7$ (also termed as $R_7$), $Arg_9$ (also termed $R_9$), $Arg_{12}$ (also termed as $R_{12}$).

According to a one further particular preferred embodiment, the cationic or polycationic peptide or protein of the polymeric carrier, when defined according to formula $\{(Arg)_i;(Lys)_m;(His)_n;(Orn)_o;(Xaa)_x\}$ (formula (I)) as shown above and which comprises or is additionally modified to comprise at least one —SH moiety, may be, without being restricted thereto, selected from subformula (Ia):

$$\{(Arg)_i;(Lys)_m;(His)_n;(Orn)_o;(Xaa')_x(Cys)_y\} \quad \text{formula (Ia)}$$

wherein $(Arg)_i;(Lys)_m;(His)_n;(Orn)_o;$ and x are as defined herein, Xaa' is any amino acid selected from native (=naturally occurring) or non-native amino acids except of Arg, Lys, His, Orn or Cys and y is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide.

This embodiment may apply to situations, wherein the cationic or polycationic peptide or protein of the polymeric carrier, e.g. when defined according to empirical formula $(Arg)_i;(Lys)_m;(His)_n;(Orn)_o;(Xaa)_x$ (formula (I)) as shown above, comprises or has been modified with at least one cysteine as —SH moiety in the above meaning such that the cationic or polycationic peptide as cationic component carries at least one cysteine, which is capable to form a disulfide bond with other components of the polymeric carrier.

According to another particular preferred embodiment, the cationic or polycationic peptide or protein of the polymeric carrier, when defined according to formula $\{(Arg)_i;(Lys)_m;(His)_n;(Orn)_o;(Xaa)_x\}$ (formula (I)) as shown above, may be, without being restricted thereto, selected from subformula (Ib):

$$Cys^1\{(Arg)_i;(Lys)_m;(His)_n;(Orn)_o;(Xaa)_x\}Cys^2 \quad \text{formula (Ib)}$$

wherein empirical formula $\{(Arg)_i;(Lys)_m;(His)_n;(Orn)_o;(Xaa)_x\}$ (formula (I)) is as defined herein and forms a core of an amino acid sequence according to (semiempirical) formula (I) and wherein $Cys^1$ and $Cys^2$ are Cysteines proximal to, or terminal to $(Arg)_i;(Lys)_m;(His)_n;(Orn)_o;(Xaa)_x$. Exemplary examples may comprise any of the above sequences flanked by two Cys and following sequences:

$CysArg_7Cys$
(SEQ ID NO. 1)
Cys-Arg-Arg-Arg-Arg-Arg-Arg-Arg-Cys $CysArg_8Cys$
(SEQ ID NO. 2)
Cys-Arg-Arg-Arg-Arg-Arg-Arg-Arg-Arg-Cys $CysArg_9Cys$:
(SEQ ID NO. 3)
Cys-Arg-Arg-Arg-Arg-Arg-Arg-Arg-Arg-Arg-Cys $CysArg_{10}Cys$
(SEQ ID NO. 4)
Cys-Arg-Arg-Arg-Arg-Arg-Arg-Arg-Arg-Arg-Arg-Cys $CysArg_{11}Cys$
(SEQ ID NO. 5)
Cys-Arg-Arg-Arg-Arg-Arg-Arg-Arg-Arg-Arg-Arg-Cys $CysArg_{12}Cys$:
(SEQ ID NO. 6)
Cys-Arg-Arg-Arg-Arg-Arg-Arg-Arg-Arg-Arg-Arg-Arg-Cys $CysArg_{13}Cys$:
(SEQ ID NO. 7)
Cys-Arg-Arg-Arg-Arg-Arg-Arg-Arg-Arg-Arg-Arg-Arg-Arg-Cys $CysArg_{14}Cys$:
(SEQ ID NO. 8)
Cys-Arg-Arg-Arg-Arg-Arg-Arg-Arg-Arg-Arg-Arg-Arg-Arg-Arg-Cys $CysArg_{15}Cys$:
(SEQ ID NO. 9)
Cys-Arg-Arg-Arg-Arg-Arg-Arg-Arg-Arg-Arg-Arg-Arg-Arg-Arg-Arg-Cys $CysArg_{16}Cys$:
(SEQ ID NO. 10)
Cys-Arg-Arg-Arg-Arg-Arg-Arg-Arg-Arg-Arg-Arg-Arg-Arg-Arg-Arg-Arg-Cys $CysArg_{17}Cys$:
(SEQ ID NO. 11)
Cys-Arg-Arg-Arg-Arg-Arg-Arg-Arg-Arg-Arg-Arg-Arg-Arg-Arg-Arg-Arg-Arg-Cys $CysArg_{18}Cys$:
(SEQ ID NO. 12)
Cys-Arg-Arg-Arg-Arg-Arg-Arg-Arg-Arg-Arg-Arg-Arg-Arg-Arg-Arg-Arg-Arg-Arg-Cys $CysArg_{19}Cys$:
(SEQ ID NO. 13)
Cys-Arg-Arg-Arg-Arg-Arg-Arg-Arg-Arg-Arg-Arg-Arg-Arg-Arg-Arg-Arg-Arg-Arg-Arg-Cys $CysArg_{20}Cys$:
(SEQ ID NO. 14)
Cys-Arg-Arg-Arg-Arg-Arg-Arg-Arg-Arg-Arg-Arg-Arg-Arg-Arg-Arg-Arg-Arg-Arg-Arg-Arg Cys

This embodiment may apply to situations, wherein the cationic or polycationic peptide or protein of the polymeric carrier, which may be used to complex the at least one mRNA of the inventive vaccine, e.g. when defined according to empirical formula $(Arg)_i;(Lys)_m;(His)_n;(Orn)_o;(Xaa)_x$ (formula (I)) as shown above, has been modified with at least two cysteines as —SH moieties in the above meaning such that the cationic or polycationic peptide of the inventive polymeric carrier carries at least two (terminal) cysteines, which are capable to form a disulfide bond with other components of the polymeric carrier.

According to a second alternative, at least one cationic (or polycationic) component of the polymeric carrier may be selected from e.g. any (non-peptidic) cationic or polycationic polymer suitable in this context, provided that this (non-peptidic) cationic or polycationic polymer exhibits or is modified to exhibit at least one —SH-moiety, which provide for a disulfide bond linking the cationic or polycationic polymer with another component of the polymeric carrier as defined herein. Thus, likewise as defined herein, the polymeric carrier may comprise the same or different cationic or polycationic polymers.

In the specific case that the cationic component of the polymeric carrier comprises a (nonpeptidic) cationic or polycationic polymer the cationic properties of the (non-peptidic) cationic or polycationic polymer may be determined upon its content of cationic charges when compared to the overall charges of the components of the cationic polymer. Preferably, the content of cationic charges in the cationic polymer at a (physiological) pH as defined herein is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 30% to 100%, even preferably in the range of about 50% to 100%, e.g. 50, 60, 70, 80%, 90% or 100%, or in a range formed by any two of the afore mentioned values, provided, that the content of all charges, e.g. positive and negative charges at a (physiological) pH as defined herein, in the entire cationic polymer is 100%.

Preferably, the (non-peptidic) cationic component of the polymeric carrier represents a cationic or polycationic polymer, typically exhibiting a molecular weight of about 0.1 or 0.5 kDa to about 100 kDa, preferably of about 1 kDa to about 75 kDa, more preferably of about 5 kDa to about 50 kDa, even more preferably of about 5 kDa to about 30 kDa, or a molecular weight of about 10 kDa to about 50 kDa, even more preferably of about 10 kDa to about 30 kDa. Additionally, the (non-peptidic) cationic or polycationic polymer typically exhibits at least one —SH-moiety, which is capable to form a disulfide linkage upon condensation with either other cationic components or other components of the polymeric carrier as defined herein.

In the above context, the (non-peptidic) cationic component of the polymeric carrier, which may be used to complex the at least one mRNA of the inventive vaccine may be selected from acrylates, modified acrylates, such as pDMAEMA (poly(dimethylaminoethyl methylacrylate)), chitosanes, aziridines or 2-ethyl-2-oxazoline (forming oligo ethylenimines or modified oligoethylenimines), polymers obtained by reaction of bisacrylates with amines forming oligo beta aminoesters or poly amido amines, or other polymers like polyesters, polycarbonates, etc. Each molecule of these (non-peptidic) cationic or polycationic polymers typically exhibits at least one —SH-moiety, wherein these at least one —SH-moiety may be introduced into the (non-peptidic) cationic or polycationic polymer by chemical modifications, e.g. using imonothiolan, 3-thio propionic acid or introduction of —SH-moieties containing amino acids, such as cysteine or any further (modified) amino acid. Such —SH-moieties are preferably as already defined above.

In the context of the polymeric carrier, the cationic components, which form basis for the polymeric carrier, which may be used to complex the at least one mRNA of the inventive vaccine by disulfide-crosslinkage, may be the same or different from each other. It is also particularly preferred that the polymeric carrier of the present invention comprises mixtures of cationic peptides, proteins or polymers and optionally further components as defined herein, which are crosslinked by disulfide bonds as described herein.

In this context, the inventive polymeric carrier, which may be used to complex the at least one mRNA of the inventive vaccine allows to combine desired properties of different (short) cationic or polycationic peptides, proteins or polymers or other components. The polymeric carrier, e.g., allows to efficiently compact nucleic acids for the purpose of efficient transfection of nucleic acids, for adjuvant therapy, for the purposes of gene therapy, for gene knockdown or others strategies without loss of activity, particularly exhibiting an efficient transfection of a nucleic acid into different cell lines in vitro but particularly transfection in vivo. The polymeric carrier is furthermore not toxic to cells, provides for efficient release of its nucleic acid cargo, is stable during lyophilization and is applicable as immunostimulating agent or adjuvant. In this context the components of the inventive polymeric carrier can be varied in such a way that the cytokine pattern induced can be determined.

In particular, the polymeric carrier formed by disulfide-linked cationic components allows considerably to vary its peptide or polymeric content and thus to modulate its biophysical/biochemical properties, particularly the cationic properties of the polymeric carrier, quite easily and fast, e.g. by incorporating as cationic components the same or different cationic peptide(s) or polymer(s) and optionally adding other components into the polymeric carrier. Even though consisting of quite small non-toxic monomer units the polymeric carrier forms a long cationic binding sequence providing a strong condensation of the mRNA as its nucleic acid cargo and complex stability. Under the reducing conditions of the cytosole (e.g. cytosolic GSH), the complex is rapidly degraded into its (cationic) components, which are further degraded (e.g. oligopeptides). This supports deliberation of the nucleic acid cargo in the cytosol. Due to degradation into small oligopeptides or polymers in the cytosol, no toxicity is observed as known for high-molecular oligopeptides or polymers, e.g. from high-molecular polyarginine.

Accordingly, the polymeric carrier, which may be used to complex the at least one mRNA of the inventive vaccine may comprise different (short) cationic or polycationic peptides, proteins or polymers selected from cationic or polycationic peptides, proteins or (nonpeptidic) polymers as defined above, optionally together with further components as defined herein.

Additionally, the polymeric carrier, which may be used to complex the at least one mRNA of the inventive vaccine as defined above, more preferably at least one of the different (short) cationic or polycationic peptides or (non-peptidic) polymers forming basis for the polymeric carrier via disulfide-crosslinking, may be, preferably prior to the disulfide-crosslinking, modified with at least one further component. Alternatively, the polymeric carrier as such may be modified with at least one further component. It may also optionally comprise at least one further component, which typically forms the polymeric carrier disulfide together with the other the (short) cationic or polycationic peptides as defined above via disulfide crosslinking.

To allow modification of a cationic or polycationic peptide or a (non-peptidic) polymer as defined above, each of the components of the polymeric carrier may (preferably already prior to disulfide-crosslinking) also contain at least one further functional moiety, which allows attaching such further components as defined herein. Such functional moieties may be selected from functionalities which allow the attachment of further components, e.g. functionalities as defined herein, e.g. by amide formation (e.g. carboxylic acids, sulphonic acids, amines, etc.), by Michael addition (e.g. maleinimide moieties, $\alpha,\beta$ unsatured carbonyls, etc.), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g halogenalkans, thiols, alcohols, amines, hydrazines, hydrazides, sulphonic acid esters, oxyphosphonium salts) or other chemical moieties which can be utilized in the attachment of further components.

According to a particularly preferred embodiment, the further component, which may be contained in the polymeric carrier, and which may be used to complex the at least one mRNA of the inventive vaccine or which may be used to modify the different (short) cationic or polycationic peptides or (non-peptidic) polymers forming basis for the polymeric carrier or the biophysical/biochemical properties of the polymeric carrier as defined herein, is an amino acid component (AA). According to the present invention, the amino acid component (AA) comprises a number of amino acids preferably in a range of about 1 to 100, preferably in a range of about 1 to 50, more preferably selected from a number comprising 1, 2, 3, 4, 5, 6, 7, 8, 9, 10, 11, 12, 13, 14 or 15-20, or may be selected from a range formed by any two of the afore mentioned values. In this context the amino acids of amino acid component (AA) can be chosen independently from each other. For example if in the polymeric carrier two or more (AA) components are present they can be the same or can be different from each other.

The amino acid component (AA) may contain or may be flanked (e.g. terminally) by a —SH containing moiety, which allows introducing this component (AA) via a disulfide bond into the polymeric carrier as defined herein. In the specific case that the —SH containing moiety represents a cysteine, the amino acid component (AA) may also be read as -Cys-(AA)-Cys- wherein Cys represents Cysteine and provides for the necessary —SH-moiety for a disulfide bond. The —SH containing moiety may be also introduced into amino acid component (AA) using any of modifications or reactions as shown above for the cationic component or any of its components.

Furthermore, the amino acid component (AA) may be provided with two —SH-moieties (or even more), e.g. in a form represented by formula HS-(AA)—SH to allow binding to two functionalities via disulfide bonds, e.g. if the amino acid component (AA) is used as a linker between two further components (e.g. as a linker between two cationic polymers). In this case, one —SH moiety is preferably protected in a first step using a protecting group as known in the art, leading to an amino acid component (AA) of formula HS-(AA)-S-protecting group. Then, the amino acid component (AA) may be bound to a further component of the polymeric carrier, to form a first disulfide bond via the non-protected —SH moiety. The protected-SH-moiety is then typically deprotected and bound to a further free —SH-moiety of a further component of the polymeric carrier to form a second disulfide bond.

Alternatively, the amino acid component (AA) may be provided with other functionalities as already described above for the other components of the polymeric carrier, which allow binding of the amino acid component (AA) to any of components of the polymeric carrier.

Thus, according to the present invention, the amino acid component (AA) may be bound to further components of the polymeric carrier, which may be used to complex the at least one mRNA of the inventive vaccine with or without using a disulfide linkage. Binding without using a disulfide linkage may be accomplished by any of the reactions described above, preferably by binding the amino acid component (AA) to the other component of the polymeric carrier using an amid-chemistry as defined herein. If desired or necessary, the other terminus of the amino acid component (AA), e.g. the N- or C-terminus, may be used to couple another component, e.g. a ligand L. For this purpose, the other terminus of the amino acid component (AA) preferably comprises or is modified to comprise a further functionality, e.g. an alkyn-species (see above), which may be used to add the other component via e.g. click-chemistry. If the ligand is bound via an acid-labile bond, the bond is preferably cleaved off in the endosome and the polymeric carrier presents amino acid component (AA) at its surface.

The amino acid component (AA) may occur as a further component of the polymeric carrier, which may be used to complex the at least one mRNA of the inventive vaccine as defined above, e.g. as a linker between cationic components e.g. as a linker between one cationic peptide and a further cationic peptide, as a linker between one cationic polymer and a further cationic polymer, as a linker between one cationic peptide and a cationic polymer, all preferably as defined herein, or as an additional component of the polymeric carrier, e.g. by binding the amino acid component (AA) to the polymeric carrier or a component thereof, e.g. via side chains, SH-moieties or via further moieties as defined herein, wherein the amino acid component (AA) is preferably accordingly modified.

According to a further and particularly preferred alternative, the amino acid component (AA), may be used to modify the polymeric carrier, particularly the content of cationic components in the polymeric carrier as defined above.

In this context it is preferable, that the content of cationic components in the polymeric carrier is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 30% to 100%, more preferably in the range of about 50% to 100%, even preferably in the range of about 70% to 100%, e.g. 70, 80, 90 or 100%, or in a range formed by any two of the afore mentioned values, provided, that the content of all components in the polymeric carrier is 100%.

In the context of the present invention, the amino acid component (AA) may be selected from the following alternatives.

According to a first alternative, the amino acid component (AA) may be an aromatic amino acid component (AA). The incorporation of aromatic amino acids or sequences as amino aromatic acid component (AA) into the polymeric carrier of the present invention enables a different (second) binding of the polymeric carrier to the nucleic acid due to interactions of the aromatic amino acids with the bases of the nucleic acid cargo in contrast to the binding thereof by cationic charged sequences of the polymeric carrier molecule to the phosphate backbone. This interaction may occur e.g. by intercalations or by minor or major groove binding. This kind of interaction is not prone to decompaction by anionic complexing partners (e.g. Heparin, Hyaluronic acids) which are found mainly in the extracellular matrix in vivo and is also less susceptible to salt effects.

For this purpose, the amino acids in the aromatic amino acid component (AA) may be selected from either the same or different aromatic amino acids e.g. selected from Trp, Tyr, or Phe. Alternatively, the amino acids (or the entire aromatic amino acid component (AA)) may be selected from following peptide combinations Trp-Tyr, Tyr-Trp, Trp-Trp, Tyr-Tyr, Trp-Tyr-Trp, Tyr-Trp-Tyr, Trp-Trp-Trp, Tyr-Tyr-Tyr, Trp-Tyr-Trp-Tyr, Tyr-Trp-Tyr-Trp, Trp-Trp-Trp-Trp, Phe-Tyr, Tyr-Phe, Phe-Phe, Phe-Tyr-Phe, Tyr-Phe-Tyr, Phe-Phe-Phe, Phe-Tyr-Phe-Tyr, Tyr-Phe-Tyr-Phe, Phe-Phe-Phe-Phe, Phe-Trp, Trp-Phe, Phe-Phe, Phe-Trp-Phe, Trp-Phe-Trp, Phe-Trp-Phe-Trp, Trp-Phe-Trp-Phe, or Tyr-Tyr-Tyr-Tyr, etc. (SEQ ID NOs: 15-42). Such peptide combinations may be repeated e.g. 1, 2, 3, 4, 5, 6, 7, 8, 9, 10, 11, 12, 13, 14 15 or even more times. These peptide combinations may also be combined with each other as suitable.

Additionally, the aromatic amino acid component (AA) may contain or may be flanked by a —SH containing moiety, which allows introducing this component via a disulfide bond as a further part of the polymeric carrier as defined above, e.g. as a linker. Such a —SH containing moiety may be any moiety as defined herein suitable to couple one component as defined herein to a further component as defined herein. As an example, such a —SH containing moiety may be a cysteine. Then, e.g. the aromatic amino acid component (AA) may be selected from e.g. peptide combinations Cys-Tyr-Cys, Cys-Trp-Cys, Cys-Trp-Tyr-Cys, Cys-Tyr-Trp-Cys, Cys-Trp-Trp-Cys, Cys-Tyr-Tyr-Cys, Cys-Trp-Tyr-Trp-Cys, Cys-Tyr-Trp-Tyr-Cys, Cys-Trp-Trp-Trp-Cys, Cys-Tyr-Tyr-Tyr-Cys, Cys-Trp-Tyr-Trp-Tyr-Cys, Cys-Tyr-Trp-Tyr-Trp-Cys, Cys-Trp-Trp-Trp-Trp-Cys, Cys-Tyr-Tyr-Tyr-Tyr-Cys, Cys-Phe-Cys, Cys-Phe-Tyr-Cys, Cys-Tyr-Phe-Cys, Cys-Phe-Phe-Cys, Cys-Tyr-Tyr-Cys, Cys-Phe-Tyr-Phe-Cys, Cys-Tyr-Phe-Tyr-Cys, Cys-Phe-Phe-Phe-Cys, Cys-Tyr-Tyr-Tyr-Cys, Cys-Phe-Tyr-Phe-Tyr-Cys, Cys-Tyr-Phe-Tyr-Phe-Cys, or Cys-Phe-Phe-Phe-Phe-Cys, Cys-Phe-Trp-Cys, Cys-Trp-Phe-Cys, Cys-Phe-Phe-Cys, Cys-Phe-Trp-Phe-Cys, Cys-Trp-Phe-Trp-Cys, Cys-Phe-Phe-Phe-Trp-Cys, Cys-Trp-Phe-Trp-Phe-Cys, etc. Each Cys above may also be replaced by any modified peptide or chemical compound carrying a free —SH-moiety as defined herein. (SEQ ID NOs: 43-75). Such peptide combinations may be repeated e.g. 1, 2, 3, 4, 5, 6, 7, 8, 9, 10, 11, 12, 13, 14, 15 or even more times. These peptide combinations may also be combined with each other as suitable.

Additionally, the aromatic amino acid component (AA) may contain or represent at least one proline, which may serve as a structure breaker of longer sequences of Trp, Tyr and Phe in the aromatic amino acid component (AA), preferably two, three or more prolines.

According to a second alternative, the amino acid component (AA) may be a hydrophilic (and preferably non charged polar) amino acid component (AA). The incorporation of hydrophilic (and preferably non charged polar) amino acids or sequences as amino hydrophilic (and preferably non charged polar) acid component (AA) into the polymeric carrier of the present invention enables a more flexible binding to the nucleic acid cargo. This leads to a more effective compaction of the nucleic acid cargo and hence to a better protection against nucleases and unwanted decompaction. It also allows provision of a (long) polymeric carrier which exhibits a reduced cationic charge over the entire carrier and in this context to better adjusted binding properties, if desired or necessary.

For this purpose, the amino acids in the hydrophilic (and preferably non charged polar) amino acid component (AA) may be selected from either the same or different hydrophilic (and preferably non charged polar) amino acids e.g. selected from Thr, Ser, Asn or Gln. Alternatively, the amino acids (or the entire hydrophilic (and preferably non charged polar) amino acid component (AA)) may be selected from following peptide combinations Ser-Thr, Thr-Ser, Ser-Ser, Thr-Thr, Ser-Thr-Ser, Thr-Ser-Thr, Ser-Ser-Ser, Thr-Thr-Thr, Ser-Thr-Ser-Thr, Thr-Ser-Thr-Ser, Ser-Ser-Ser-Ser, Thr-Thr-Thr-Thr, Gln-Asn, Asn-Gln, Gin-Gln, Asn-Asn, Gln-Asn-Gln, Asn-Gln-Asn, Gln-Gln-Gln, Asn-Asn-Asn, Gin-Asn-Gln-Asn, Asn-Gln-Asn-Gln, Gln-Gln-Gln-Gln, Asn-Asn-Asn-Asn, Ser-Asn, Asn-Ser, Ser-Ser, Asn-Asn, Ser-Asn-Ser, Asn-Ser-Asn, Ser-Ser-Ser, Asn-Asn-Asn, Ser-Asn-Ser-Asn, Asn-Ser-Asn-Ser, Ser-Ser-Ser-Ser, or Asn-Asn-Asn-Asn, etc. (SEQ ID NOs: 76-111) Such peptide combinations may be repeated e.g. 1, 2, 3, 4, 5, 6, 7, 8, 9, 10, 11, 12, 13, 14, 15 or even more times. These peptide combinations may also be combined with each other as suitable.

Additionally, the hydrophilic (and preferably non-charged polar) amino acid component (AA) may contain or may be flanked by a —SH containing moiety, which allows introducing this component via a disulfide bond as a further part of the polymeric carrier as defined above, e.g. as a linker. Such a —SH containing moiety may be any moiety as defined herein suitable to couple one component as defined herein to a further component as defined herein. As an example, such a —SH containing moiety may be a cysteine. Then, e.g. the hydrophilic (and preferably non-charged polar) amino acid component (AA) may be selected from e.g. peptide combinations Cys-Thr-Cys, Cys-Ser-Cys, Cys-Ser-Thr-Cys, Cys-Thr-Ser-Cys, Cys-Ser-Ser-Cys, Cys-Thr-Thr-Cys, Cys-Ser-Thr-Ser-Cys, Cys-Thr-Ser-Thr-Cys, Cys-Ser-Ser-Ser-Cys, Cys-Thr-Thr-Thr-Cys, Cys-Ser-Thr-Ser-Thr-Cys, Cys-Thr-Ser-Thr-Ser-Cys, Cys-Ser-Ser-Ser-Ser-Cys, Cys-Thr-Thr-Thr-Thr-Cys, Cys-Asn-Cys, Cys-Gln-Cys, Cys-Gln-Asn-Cys, Cys-Asn-Gln-Cys, Cys-Gln-Gln-Cys, Cys-Asn-Asn-Cys, Cys-Gln-Asn-Gln-Cys, Cys-Asn-Gln-Asn-Cys, Cys-Gln-Gln-Gln-Cys, Cys-Asn-Asn-Asn-Cys, Cys-Gln-Asn-Gln-Asn-Cys, Cys-Asn-Gln-Asn-Gln-Cys, Cys-Gin-Gln-Gln-Gln-Cys, Cys-Asn-Asn-Asn-Asn-Cys, Cys-Asn-Cys, Cys-Ser-Cys, Cys-Ser-Asn-Cys, Cys-Asn-Ser-Cys, Cys-Ser-Ser-Cys, Cys-Asn-Asn-Cys, Cys-Ser-Asn-Ser-Cys, Cys-Asn-Ser-Asn-Cys, Cys-Ser-Ser-Ser-Cys, Cys-Asn-Asn-Asn-Cys, Cys-Ser-Asn-Ser-Asn-Cys, Cys-Asn-Ser-Asn-Ser-Cys, Cys-Ser-Ser-Ser-Ser-Cys, or Cys-Asn-Asn-Asn-Asn-Cys, etc. Each Cys above may also be replaced by any modified peptide or chemical compound carrying a free —SH-moiety as defined herein. (SEQ ID NOs: 112-153) Such peptide combinations may be repeated e.g. 1, 2, 3, 4, 5, 6, 7, 8, 9, 10, 12, 13, 14, 15 or even more times. These peptide combinations may also be combined with each other as suitable.

Additionally, the hydrophilic (and preferably non-charged polar) amino acid component (AA) may contain at least one proline, which may serve as a structure breaker of longer sequences of Ser, Thr and Asn in the hydrophilic (and preferably non charged polar) amino acid component (AA), preferably two, three or more prolines.

According to a third alternative, the amino acid component (AA) may be a lipophilic amino acid component (AA). The incorporation of lipophilic amino acids or sequences as amino lipophilic acid component (AA) into the polymeric carrier of the present invention enables a stronger compaction of the nucleic acid cargo and/or the polymeric carrier and its nucleic acid cargo when forming a complex. This is particularly due to interactions of one or more polymer strands of the polymeric carrier, particularly of lipophilic sections of lipophilic amino acid component (AA) and the nucleic acid cargo. This interaction will preferably add an additional stability to the complex between the polymeric carrier and its nucleic acid cargo. This stabilization may somehow be compared to a sort of non covalent crosslinking between different polymer strands. Especially in aqueous environment this interaction is typically strong and provides a significant effect.

For this purpose, the amino acids in the lipophilic amino acid component (AA) may be selected from either the same or different lipophilic amino acids e.g. selected from Leu, Val, Ile, Ala, Met. Alternatively, the amino acid AA (or the entire lipophilic amino acid component (AA)) may be selected from following peptide combinations Leu-Val, Val-Leu, Leu-Leu, Val-Val, Leu-Val-Leu, Val-Leu-Val, Leu-Leu- Leu, Val-Val-Val, Leu-Val-Leu-Val, Val-Leu-Val-Leu, Leu-Leu-Leu-Leu, Val-Val-Val-Val, Ile-Ala, Ala-Ile, Ile-Ile, Ala-Ala, Ile-Ala-Ile, Ala-Ile-Ala, Ile-Ile-Ile, Ala-Ala-Ala, Ile-Ala-Ile-Ala, Ala-Ile-Ala-Ile, Ile-Ile-Ile-Ile, Ala-Ala-Ala-Ala, Met-Ala, Ala-Met, Met-Met, Ala-Ala, Met-Ala-Met, Ala-Met-Ala, Met-Met-Met, Ala-Ala-Ala, Met-Ala-Met-Ala, Ala-Met-Ala-Met, or Met-Met-Met-Met etc. (SEQ ID NOs: 154-188) Such peptide combinations may be repeated e.g. 1, 2, 3, 4, 5, 6, 7, 8, 9, 10, 12, 13, 14, 15 or even more times. These peptide combinations may also be combined with each other as suitable.

Additionally, the lipophilic amino acid component (AA) may contain or may be flanked by a —SH containing moiety, which allows introducing this component via a disulfide bond as a further part of the polymeric carrier above, e.g. as a linker. Such a —SH containing moiety may be any moiety as defined herein suitable to couple one component as defined herein to a further component as defined herein. As an example, such a —SH containing moiety may be a cysteine. Then, e.g. the lipophilic amino acid component (AA) may be selected from e.g. peptide combinations Cys-Val-Cys, Cys-Leu-Cys, Cys-Leu-Val-Cys, Cys-Val-Leu-Cys, Cys-Leu-Leu-Cys, Cys-Val-Val-Cys, Cys-Leu-Val-Leu-Cys, Cys-Val-Leu-Val-Cys, Cys-Leu-Leu-Leu-Cys, Cys-Val-Val-Val-Cys, Cys-Leu-Val-Leu-Val-Cys, Cys-Val-Leu-Val-Leu-Cys, Cys-Leu-Leu-Leu-Leu-Cys, Cys-Val-Val-Val-Val-Cys, Cys-Ala-Cys, Cys-Ile-Cys, Cys-Ile-Ala-Cys, Cys-Ala-Ile-Cys, Cys-Ile-Ile-Cys, Cys-Ala-Ala-Cys, Cys-Ile-Ala-Ile-Cys, Cys-Ala-Ile-Ala-Cys, Cys-Ile-Ile-Ile-Cys, Cys-Ala-Ala-Ala-Cys, Cys-Ile-Ala-Ile-Ala-Cys, Cys-Ala-Ile-Ala-Ile-Cys, Cys-Ile-Ile-Ile-Ile-Cys, or Cys-Ala-Ala-Ala-Ala-Cys, Cys-Met-Cys, Cys-Met-Ala-Cys, Cys-Ala-Met-Cys, Cys-Met-Met-Cys, Cys-Ala-Ala-Cys, Cys-Met-Ala-Met-Cys, Cys-Ala-Met-Ala-Cys, Cys-Met-Met-Met-Cys, Cys-Ala-Ala-Ala-Cys, Cys-Met-Ala-Met-Ala-Cys, Cys-Ala-Met-Ala-Met-Cys, Cys-Met-Met-Met-Met-Cys, or Cys-Ala-Ala-Ala-Ala-Cys, etc. Each Cys above may also be replaced by any modified peptide or chemical compound carrying a free —SH-moiety as defined herein. (SEQ ID NOs: 189-229) Such peptide combinations may be repeated e.g. 1, 2, 3, 4, 5, 6, 7, 8, 9, 10, 12, 13, 14, 15 or even more times. These peptide combinations may also be combined with each other as suitable.

Additionally, the lipophilic amino acid component (AA) may contain at least one proline, which may serve as a structure breaker of longer sequences of Leu, Val, Ile, Ala and Met in the lipophilic amino acid component (AA), preferably two, three or more prolines.

Finally, according to a fourth alternative, the amino acid component (AA) may be a weak basic amino acid component (AA). The incorporation of weak basic amino acids or sequences as weak basic amino acid component (AA) into the polymeric carrier of the present invention may serve as a proton sponge and facilitates endosomal escape (also called endosomal release) (proton sponge effect). Incorporation of such a weak basic amino acid component (AA) preferably enhances transfection efficiency.

For this purpose, the amino acids in the weak basic amino acid component (AA) may be selected from either the same or different weak amino acids e.g. selected from histidine or aspartate (aspartic acid). Alternatively, the weak basic amino acids (or the entire weak basic amino acid component (AA)) may be selected from following peptide combinations Asp-His, His-Asp, Asp-Asp, His-His, Asp-His-Asp, His-Asp-His, Asp-Asp-Asp, His-His-His, Asp-His-Asp-His, His-Asp-His-Asp, Asp-Asp-Asp-Asp, or His-His-His-His, etc. (SEQ ID NOs: 230-241) Such peptide combinations may be repeated e.g. 1, 2, 3, 4, 5, 6, 7, 8, 9, 10, 12, 13, 14, 15 or even more times. These peptide combinations may also be combined with each other as suitable.

Additionally, the weak basic amino acid component (AA) may contain or may be flanked by a —SH containing moiety, which allows introducing this component via a disulfide bond as a further part of the polymeric carrier as defined above, e.g. as a linker. Such a —SH containing moiety may be any moiety as defined herein suitable to couple one component as defined herein to a further component as defined herein. As an example, such a —SH containing moiety may be a cysteine. Then, e.g. the weak basic amino acid component (AA) may be selected from e.g. peptide combinations Cys-His-Cys, Cys-Asp-Cys, Cys-Asp-His-Cys, Cys-His-Asp-Cys, Cys-Asp-Asp-Cys, Cys-His-His-Cys, Cys-Asp-His-Asp-Cys, Cys-His-Asp-His-Cys, Cys-Asp-Asp-Asp-Cys, Cys-His-His-His-Cys, Cys-Asp-His-Asp-His-Cys, Cys-His-Asp-His-Asp-Cys, Cys-Asp-Asp-Asp-Asp-Cys, or Cys-His-His-His-His-Cys, etc. Each Cys above may also be replaced by any modified peptide or chemical compound carrying a free —SH-moiety as defined herein. (SEQ ID NOs: 242-255) Such peptide combinations may be repeated e.g. 1, 2, 3, 4, 5, 6, 7, 8, 9, 10, 12, 13, 14, 15 or even more times. These peptide combinations may also be combined with each other as suitable.

Additionally, the weak basic amino acid component (AA) may contain at least one proline, which may serve as a structure breaker of longer sequences of histidine or aspartate (aspartic acid) in the weak basic amino acid component (AA), preferably two, three or more prolines.

According to a fifth alternative, the amino acid component (AA) may be a signal peptide or signal sequence, a localisation signal or sequence, a nuclear localisation signal or sequence (NLS), an antibody, a cell penetrating peptide, (e.g. TAT), etc. Preferably such an amino acid component (AA) is bound to the polymeric carrier or to another component of the polymeric carrier via a (reversible) disulfide bond. In this context the signal peptide or signal sequence, a localisation signal or sequence, a nuclear localisation signal or sequence (NLS), an antibody, a cell penetrating peptide, (e.g. TAT), etc.; additionally comprises at least one —SH-moiety. In this context a signal peptide, a localisation signal or sequence or a nuclear localisation signal or sequence (NLS), may be used to direct the inventive polymeric carrier cargo complex to specific target cells (e.g. hepatocytes or antigen-presenting cells) and preferably allows a translocalisation of the polymeric carrier to a specific target, e.g. into the cell, into the nucleus, into the endosomal compartment, sequences for the mitochondrial matrix, localisation sequences for the plasma membrane, localisation sequences for the Golgi apparatus, the nucleus, the cytoplasm and the cytoskeleton, etc. Such signal peptide, a localisation signal or sequence or a nuclear localisation signal may be used for the transport of any of the herein defined nucleic acids, preferably an RNA or a DNA, more preferably an shRNA or a pDNA, e.g. into the nucleus. Without being limited thereto, such a signal peptide, a localisation signal or sequence or a nuclear localisation signal may comprise, e.g., localisation sequences for the endoplasmic reticulum. Particular localisation signals or sequences or a nuclear localisation signals may include e.g. KDEL (SEQ ID NO: 256), DDEL (SEQ ID NO: 257), DEEL (SEQ ID NO: 258), QEDL (SEQ ID NO: 259), RDEL (SEQ ID NO: 260), and GQNLSTSN (SEQ ID NO: 261), nuclear localisation sequences, including PKKKRKV (SEQ ID NO: 262), PQKKIKS (SEQ ID NO: 263), QPKKP (SEQ ID NO: 264), RKKR (SEQ ID NO: 265), RKKRRQRRRAHQ (SEQ ID NO: 266), RQARRNRRRRWRERQR (SEQ ID NO: 267), MPLTRRRPAASQALAPPTP (SEQ ID NO: 268), GAALTILV (SEQ ID NO: 269), and GAALTLLG (SEQ ID NO: 270), localisation sequences for the endosomal compartment, including MDDQRDLISNNEQLP (SEQ ID NO: 271), localisation sequences for the mitochondrial matrix, including MLFNLRXXLNNAAFRHGHNFMVRN-FRCGQPLX (SEQ ID NO: 272), localisation sequences for the plasma membrane: GCVCSSNP (SEQ ID NO: 273), GQTVITPL (SEQ ID NO: 274), GQELSQHE (SEQ ID NO: 275), GNSPSYNP (SEQ ID NO: 276), GVSGSKGQ (SEQ ID NO: 277), GQTITTPL (SEQ ID NO: 278), GQTLTTPL (SEQ ID NO: 279), GQIFSRSA (SEQ ID NO: 280), GQIHGLSP (SEQ ID NO: 281), GARASVLS (SEQ ID NO: 282), and GCTLSAEE (SEQ ID NO: 283), localisation sequences for the endoplasmic reticulum and the nucleus, including GAQVSSQK (SEQ ID NO: 284), and GAQLSRNT (SEQ ID NO: 285), localisation sequences for the Golgi apparatus, the nucleus, the cytoplasm and the cytoskeleton, including GNAAAAKK (SEQ ID NO: 286), localisation sequences for the cytoplasm and cytoskeleton, including GNEASYPL (SEQ ID NO: 287), localisation sequences for the plasma membrane and cytoskeleton, including GSSKSKPK (SEQ ID NO: 288), etc. Examples of secretory signal peptide sequences as defined herein include, without being limited thereto, signal sequences of classical or non-classical MHC-molecules (e.g. signal sequences of MHC I and II molecules, e.g. of the MHC class I molecule HLA-A*0201), signal sequences of cytokines or immunoglobulins as defined herein, signal sequences of the invariant chain of immunoglobulins or antibodies as defined herein, signal sequences of Lamp1, Tapasin, Erp57, Calreticulin, Calnexin, and further membrane associated proteins or of proteins associated with the endoplasmic reticulum (ER) or the endosomal-lysosomal compartment. Particularly preferably, signal sequences of MHC class I molecule HLA-A*0201 may be used according to the present invention. Such an additional component may be bound e.g. to a cationic polymer or to any other component of the polymeric carrier as defined herein. Preferably this signal peptide, localisation signal or sequence or nuclear localisation signal or sequence (NLS), is bound to the polymeric carrier or to another component of the polymeric carrier via a (reversible) disulfide bond. For this purpose the (AA) component additionally comprises at least one —SH moiety as defined herein. The binding to any of components of the polymeric carrier may also be accomplished using an acid-labile bond, preferably via a side chain of any of components of the polymeric carrier, which allows to detach or release the additional component at lower pH-values, e.g. at physiological pH-values as defined herein.

Additionally, according to another alternative, the amino acid component (AA) may be a functional peptide or protein, which may modulate the functionality of the polymeric carrier accordingly. Such functional peptides or proteins as the amino acid component (AA) preferably comprise any peptides or proteins as defined herein, e.g. as defined below as therapeutically active proteins. According to one alternative, such further functional peptides or proteins may comprise so called cell penetrating peptides (CPPs) or cationic peptides for transportation. Particularly preferred are CPPs, which induce a pH-mediated conformational change in the endosome and lead to an improved release of the polymeric carrier (in complex with a nucleic acid) from the endosome by insertion into the lipid layer of the liposome. These cell penetrating peptides (CPPs) or cationic peptides for transportation, may include, without being limited thereto protamine, nucleoline, spermine or spermidine, oligo- or poly-L-lysine (PLL), basic polypeptides, oligo or poly-arginine, chimeric CPPs, such as Transportan, or MPG peptides, HIV-binding peptides, Tat, HIV-1 Tat (HIV), Tat-derived peptides, members of the penetratin family, e.g. Penetratin, Antennapedia-derived peptides (particularly from *Drosophila antennapedia*), pAntp, plsI, etc., antimicrobial-derived CPPs e.g. Buforin-2, Bac715-24, SynB, SynB(1), pVEC, hCT-derived peptides, SAP, MAP, PpTG20, Loligomere, FGF, Lactoferrin, histones, VP22 derived or analog peptides, Pestivirus Erns, HSV, VP22 (Herpes simplex), MAP, KALA or protein transduction domains (PTDs, PpT620, proline-rich peptides, arginine-rich peptides, lysine-rich peptides, Pep-1, L-oligomers, Calcitonin peptide(s), etc. Such an amino acid component (AA) may also be bound to any component of the polymeric carrier as defined herein. Preferably it is bound to the polymeric carrier or to another component of the polymeric carrier via a (reversible) disulfide bond. For the above purpose, the amino acid component (AA) preferably comprises at least one —SH moiety as defined herein. The binding to any of components of the polymeric carrier may also be accomplished using an SH-moiety or an acid-labile bond, preferably via a side chain of any of components of the polymeric carrier which allows to detach or release the additional component at lower pH-values, e.g. at physiological pH-values as defined herein.

According to a last alternative, the amino acid component (AA) may consist of any peptide or protein which can execute any favourable function in the cell. Particularly preferred are peptides or proteins selected from therapeutically active proteins or peptides, from antigens, e.g. tumour antigens, pathogenic antigens (animal antigens, viral antigens, protozoan antigens, bacterial antigens, allergic antigens), autoimmune antigens, or further antigens, from allergens, from antibodies, from immunostimulatory proteins or peptides, from antigen-specific T cell receptors, or from any other protein or peptide suitable for a specific (therapeutic) application as defined below for coding nucleic acids. Particularly preferred are peptide epitopes from antigens as defined herein.

The polymeric carrier, which may be used to complex the at least one mRNA of the inventive vaccine may comprise at least one of the above mentioned cationic or polycationic peptides, proteins or polymers or further components, e.g. (AA), wherein any of the above alternatives may be combined with each other, and may be formed by polymerizing same in a polymerization condensation reaction via their —SH-moieties.

According to another aspect, the polymeric carrier, which may be used to complex the at least one mRNA of the inventive vaccine or single components thereof, e.g. of the above mentioned cationic or polycationic peptides, proteins or polymers or further components, e.g. (AA), may be further modified with a ligand, preferably a carbohydrate, more preferably a sugar, even more preferably mannose. Preferably this ligand is bound to the polymeric carrier or to a component of the polymeric carrier via a (reversible) disulfide bond or via Michael addition. In the case that the ligand is bound by a disulfide bond the ligand additionally comprises at least one —SH-moiety. These ligands may be used to direct the inventive polymeric carrier cargo complex to specific target cells (e.g. hepatocytes or antigen-presenting cells). In this context mannose is particularly preferred as ligand in the case that dendritic cells are the target especially for vaccination or adjuvant purposes.

According to one specific aspect, the entire inventive polymeric carrier may be formed by a polymerization condensation (of at least one) of the above mentioned cationic or polycationic peptides, proteins or polymers or further components, e.g. (AA), via their —SH-moieties in a first step and complexing the nucleic acid to such a polymeric carrier in a second step. The polymeric carrier may thus contain a number of at least one or even more of the same or different of the above defined cationic or polycationic peptides, proteins or polymers or further components, e.g. (AA), the number preferably determined by the above range.

According to one alternative specific aspect, the inventive polymeric carrier, which may be used to complex the at least one mRNA of the inventive vaccine is formed by carrying out the polymerization condensation of at least one of the above mentioned cationic or polycationic peptides, proteins or polymers or further components, e.g. (AA), via their —SH-moieties simultaneously to complexing the at least one mRNA encoding the at least one antigen to the (in situ prepared) polymeric carrier. Likewise, the polymeric carrier may thus also here contain a number of at least one or even more of the same or different of the above defined cationic or polycationic peptides, proteins or polymers or further components, e.g. (AA), the number preferably determined by the above range.

According to a further alternative aspect, the inventive polymeric carrier may be selected from a polymeric carrier molecule according to generic formula (VI):

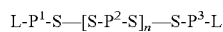

$L-P^1-S—[S-P^2-S]_n—S-P^3-L$ wherein,
- $P^1$ and $P^3$ are different or identical to each other and represent a linear or branched hydrophilic polymer chain, each P1 and P3 exhibiting at least one —SH— moiety, capable to form a disulfide linkage upon condensation with component $P^2$, or alternatively with (AA), $(AA)_x$, or $[(AA)_x]_z$ if such components are used as a linker between $P^1$ and $P^2$ or $P^3$ and $P^2$) and/or with further components (e.g. (AA), $(AA)_x$, $[(AA)_x]_z$ or L), the linear or branched hydrophilic polymer chain selected independent from each other from polyethylene glycol (PEG), poly-N-(2-hydroxypropyl)methacrylamide, poly-2-(methacryloyloxy)ethyl phosphorylcholines, poly(hydroxyalkyl L-asparagine), poly(2-(methacryloyloxy)ethyl phosphorylcholine), hydroxyethyl starch or poly(hydroxyalkyl L-glutamine), wherein the hydrophilic polymer chain exhibits a molecular weight of about 1 kDa to about 100 kDa, preferably of about 2 kDa to about 25 kDa; or more preferably of about 2 kDa to about 10 kDa, e.g. about 5 kDa to about 25 kDa or 5 kDa to about 10 kDa;
- $P^2$ is a cationic or polycationic peptide or protein, e.g. as defined herein, and preferably having a length of about 3 to about 100 amino acids, more preferably having a length of about 3 to about 50 amino acids, even more preferably having a length of about 3 to about 25 amino acids, e.g. a length of about 3 to 10, 5 to 15, 10 to 20 or 15 to 25 amino acids, more preferably a length of about 5 to about 20 and even more preferably a length of about 10 to about 20; or
  - is a cationic or polycationic polymer, e.g. as defined herein, typically having a molecular weight of about 0.5 kDa to about 30 kDa, including a molecular weight of about 1 kDa to about 20 kDa, even more preferably of about 1.5 kDa to about 10 kDa, or having a molecular weight of about 0.5 kDa to about 100 kDa, including a molecular weight of about 10 kDa to about 50 kDa, even more preferably of about 10 kDa to about 30 kDa;
  - each $P^2$ exhibiting at least two —SH-moieties, capable to form a disulfide linkage upon condensation with further components $P^2$ or component(s) $P^1$ and/or P3 or alternatively with further components (e.g. (AA), $(AA)_x$, or $[(AA)_x]_z$);
- —S—S— is a (reversible) disulfide bond (the brackets are omitted for better readability), wherein S preferably represents sulphur or a —SH carrying moiety, which has formed a (reversible) disulfide bond. The (reversible) disulfide bond is preferably formed by condensation of —SH-moieties of either components P1 and P2, P2 and P2, or P2 and P3, or optionally of further components as defined herein (e.g. L, (AA), $(AA)_x$, $[(AA)_x]_z$, etc); The —SH-moiety may be part of the structure of these components or added by a modification as defined below;
- L is an optional ligand, which may be present or not, and may be selected independent from the other from RGD, Transferrin, Folate, a signal peptide or signal sequence, a localization signal or sequence, a nuclear localization signal or sequence (NLS), an antibody, a cell penetrating peptide, (e.g. TAT or KALA), a ligand of a receptor (e.g. cytokines, hormones, growth factors etc), small molecules (e.g. carbohydrates like mannose or galctose or synthetic ligands), small molecule agonists, inhibitors or antagonists of receptors (e.g. RGD peptidomimetic analogues), or any further protein as defined herein, etc.;
- n is an integer, typically selected from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 4 to 9, 4 to 10, 3 to 20, 4 to 20, 5 to 20, or 10 to 20, or a range of about 3 to 15, 4 to 15, 5 to 15, or 10 to 15, or a range of about 6 to 11 or 7 to 10. Most preferably, n is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

As defined above, ligands (L), may be optionally used in the inventive polymeric carrier molecule according to generic formula (VI), e.g. for direction of the inventive carrier polymer and its entire "cargo" (the adjuvant component and/or the antigen of the inventive composition or vaccine composition) into specific cells. They may be selected independent from the other from RGD, Transferrin, Folate, a signal peptide or signal sequence, a localization signal or sequence, a nuclear localization signal or sequence (NLS), an antibody, a cell penetrating peptide (CPP), (e.g. TAT, KALA), a ligand of a receptor (e.g. cytokines, hormones, growth factors etc), small molecules (e.g. carbohydrates like mannose or galactose or synthetic ligands), small molecule agonists, inhibitors or antagonists of receptors (e.g. RGD peptidomimetic analogues) or any such molecule as further defined below, etc. Particularly preferred are cell penetrating peptides (CPPs), which induce a pH-mediated conformational change in the endosome and lead to an improved release of the inventive polymeric carrier (in complex with a nucleic acid) from the endosome by insertion into the lipid layer of the liposome. Such called CPPs or cationic peptides for transportation, may include, without being limited thereto protamine, nucleoline, spermine or spermidine, polyL-lysine (PLL), basic polypeptides, polyarginine, chimeric CPPs, such as Transportan, or MPG peptides, HIV-binding peptides, Tat, HIV-1 Tat (HIV), Tat-derived peptides, oligoargininines, members of the penetratin family, e.g. Penetratin, Antennapedia-derived peptides (particularly from *Drosophila antennapedia*), pAntp, plsI, etc., antimicrobial-derived CPPs e.g. Buforin-2, Bac715-24, SynB, SynB(1), pVEC, hCT-derived peptides, SAP, MAP, PpTG20, Proline-rich peptides, Loligomers, Arginine-rich peptides, Calcitonin-peptides, FGF, Lactoferrin, poly-L-Lysine, poly-Arginine, histones, VP22 derived or analog peptides, Pestivirus Erns, HSV, VP22 (Herpes simplex), MAP, KALA or protein transduction domains (PTDs, PpT620, prolin-rich peptides, arginine-rich peptides, lysine-rich peptides, Pep-1, Loligomers, Calcitonin peptide(s), etc. Particularly preferred in this context is mannose as ligand to target antigen presenting cells which carries on their cell membrane mannose receptors. In a further preferred aspect of the first embodiment of the present invention galactose as optional ligand can be used to target hepatocytes. Such ligands may be attached to component P1 and/or P3 by reversible disulfide bonds as defined below or by any other possible chemical attachment, e.g. by amide formation (e.g. carboxylic acids, sulphonic acids, amines, etc), by Michael addition (e.g. maleinimide moieties, α,β unsaturated carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g halogenalkans, thiols, alcohols, amines, hydrazines, hydrazides, sulphonic acid esters, oxyphosphonium salts) or other chemical moieties which can be utilized in the attachment of further components.

In the context of formula (VI) of the present invention components $P^1$ and $P^3$ represent a linear or branched hydrophilic polymer chain, containing at least one —SH-moiety, each $P^1$ and $P^3$ independently selected from each other, e.g. from polyethylene glycol (PEG), poly-N-(2-hydroxypropyl) methacrylamide, poly-2-(methacryloyloxy)ethyl phosphorylcholines, poly(hydroxyalkyl L-asparagine) or poly(hydroxyalkyl L-glutamine). $P^1$ and $P^3$ may be identical or different to each other. Preferably, each of hydrophilic polymers $P^1$ and $P^3$ exhibits a molecular weight of about 1 kDa to about 100 kDa, preferably of about 1 kDa to about 75 kDa, more preferably of about 5 kDa to about 50 kDa, even more preferably of about 5 kDa to about 25 kDa. Additionally, each of hydrophilic polymers P1 and P3 typically exhibits at least one —SH-moiety, wherein the at least one —SH-moiety is capable to form a disulfide linkage upon reaction with component $P^2$ or with component (AA) or $(AA)_x$, if used as linker between $P^1$ and $P^2$ or $P^3$ and $P^2$ as defined below and optionally with a further component, e.g. L and/or (AA) or $(AA)_x$, e.g. if two or more —SH-moieties are contained. The following subformulae "$P^1$-S—S-$P^2$" and "$P^2$—S—S-$P^3$" within generic formula (VI) above (the brackets are omitted for better readability), wherein any of S, $P^1$ and $P^3$ are as defined herein, typically represent a situation, wherein one-SH-moiety of hydrophilic polymers $P^1$ and $P^3$ was condensed with one —SH-moiety of component $P^2$ of generic formula (VI) above, wherein both sulphurs of these —SH-moieties form a disulfide bond —S—S— as defined herein in formula (VI). These —SH-moieties are typically provided by each of the hydrophilic polymers $P^1$ and $P^3$, e.g. via an internal cysteine or any further (modified) amino acid or compound which carries a —SH moiety. Accordingly, the subformulae "$P^1$-S—S-$P^2$" and "$P^2$-S—S-$P^3$" may also be written as "$P^1$-Cys-Cys-$P^2$" and "$P^2$-Cys-Cys-$P^3$", if the —SH— moiety is provided by a cysteine, wherein the term Cys-Cys represents two cysteines coupled via a disulfide bond, not via a peptide bond. In this case, the term "—S—S—" in these formulae may also be written as "—S-Cys", as "-Cys-S" or as "-Cys-Cys-". In this context, the term "-Cys-Cys-" does not represent a peptide bond but a linkage of two cysteines via their —SH-moieties to form a disulfide bond. Accordingly, the term "-Cys-Cys-" also may be understood generally as "-(Cys-S)—(S-Cys)-", wherein in this specific case S indicates the sulphur of the —SH-moiety of cysteine.

Likewise, the terms "—S-Cys" and "—Cys-S" indicate a disulfide bond between a —SH containing moiety and a cysteine, which may also be written as "—S—(S-Cys)" and "-(Cys-S)—S". Alternatively, the hydrophilic polymers $P^1$ and $P^3$ may be modified with a —SH moiety, preferably via a chemical reaction with a compound carrying a —SH moiety, such that each of the hydrophilic polymers $P^1$ and $P^3$ carries at least one such —SH moiety. Such a compound carrying a —SH moiety may be e.g. an (additional) cysteine or any further (modified) amino acid, which carries a —SH moiety. Such a compound may also be any non-amino compound or moiety, which contains or allows to introduce a —SH moiety into hydrophilic polymers $P^1$ and $P^3$ as defined herein. Such non-amino compounds may be attached to the hydrophilic polymers $P^1$ and $P^3$ of formula (VI) of the polymeric carrier according to the present invention via chemical reactions or binding of compounds, e.g. by binding of a 3-thio propionic acid or thioimolane, by amide formation (e.g. carboxylic acids, sulphonic acids, amines, etc), by Michael addition (e.g maleinimide moieties, α,β unsaturated carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g halogenalkans, thiols, alcohols, amines, hydrazines, hydrazides, sulphonic acid esters, oxyphosphonium salts) or other chemical moieties which can be utilized in the attachment of further components. A particularly preferred PEG derivate in this context is alpha-Methoxy-omega-mercapto poly(ethylene glycol). In each case, the SH-moiety, e.g. of a cysteine or of any further (modified) amino acid or compound, may be present at the terminal ends or internally at any position of hydrophilic polymers $P^1$ and $P^3$. As defined herein, each of hydrophilic polymers $P^1$ and $P^3$ typically exhibits at least one —SH-moiety preferably at one terminal end, but may also contain two or even more —SH-moieties, which may be used to additionally attach further components as defined herein, preferably further functional peptides or proteins e.g. a ligand, an amino acid component (AA) or $(AA)_x$, antibodies, cell penetrating peptides or enhancer peptides (e.g. TAT, KALA), etc.

According to one preferred alternative, such further functional peptides or proteins may comprise so called cell penetrating peptides (CPPs) or cationic peptides for transportation. Particularly preferred are CPPs, which induce a pH-mediated conformational change in the endosome and lead to an improved release of the inventive polymeric carrier (in complex with a nucleic acid) from the endosome by insertion into the lipid layer of the liposome. Such called cell penetrating peptides (CPPs) or cationic peptides for transportation, may include, without being limited thereto protamine, nucleoline, spermine or spermidine, polyL-lysine (PLL), basic polypeptides, poly-arginine, chimeric CPPs, such as Transportan, or MPG peptides, HIV-binding peptides, Tat, HIV-1 Tat (HIV), Tat-derived peptides, oligoarginines, members of the penetratin family, e.g. Penetratin, Antennapedia-derived peptides (particularly from

*Drosophila antennapedia*), pAntp, plsI, etc., antimicrobial-derived CPPs e.g. Buforin-2, Bac715-24, SynB, SynB(1), pVEC, hCT-derived peptides, SAP, MAP, PpTG20, Proline-rich peptides, Loligomers, Arginine-rich peptides, Calcitonin-peptides, FGF, Lactoferrin, poly-L-Lysine, poly-Arginine, histones, VP22 derived or analog peptides, Pestivirus Erns, HSV, VP22 (Herpes simplex), MAP, KALA or protein transduction domains (PTDs, PpT620, prolin-rich peptides, arginine-rich peptides, lysine-rich peptides, Pep-1, L-oligomers, Calcitonin peptide(s), etc.

According to a further preferred aspect of the first embodiment of the present invention, each of hydrophilic polymers $P^1$ and $P^3$ of formula (VI) of the polymeric carrier used according to the present invention may also contain at least one further functional moiety, which allows attaching further components as defined herein, e.g. a ligand as defined above, or functionalities which allow the attachment of further components, e.g. by amide formation (e.g. carboxylic acids, sulphonic acids, amines, etc), by Michael addition (e.g maleinimide moieties, α,β unsaturated carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g halogenalkans, thiols, alcohols, amines, hydrazines, hydrazides, sulphonic acid esters, oxyphosphonium salts) or other chemical moieties which can be utilized in the attachment of further components. Further functional moieties may comprise an amino acid component (AA) as defined herein or $(AA)_x$, wherein (AA) is preferably an amino component as defined above. In the above context, x is preferably an integer and may be selected from a range of about 1 to 100, preferably from a range of about 1 to 50, more preferably 1 to 30, and even more preferably selected from a number comprising 1, 2, 3, 4, 5, 6, 7, 8, 9, 10, 11, 12, 13, 14 or 15-30, e.g. from a range of about 1 to 30, from a range of about 1 to 15, or from a number comprising 1, 2, 3, 4, 5, 6, 7, 8, 9, 10, 11, 12, 13, 14 or 15, or may be selected from a range formed by any two of the afore mentioned values. Most preferably, x is 1. Such an amino acid component (AA) or $(AA)_x$ may be contained in every part of the inventive polymeric carrier according to formula (VI) above and therefore may be attached to all components of the inventive polymeric carrier according to formula (VI). It is particularly preferred that amino acid component (AA) or $(AA)_x$ is present as a ligand or part of the repetitive component $[S-P^2-S]_n$ within formula (VI) of the inventive polymeric carrier.

In the context of the entire formula (VI) of the inventive polymeric carrier may be preferably defined as follows:

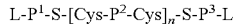

$L-P^1-S-[Cys-P^2-Cys]_n-S-P^3-L$ wherein L, $P^1$, $P^2$, $P^3$ and n are as defined herein, S is sulphur and each Cys provides for one —SH-moiety for the disulfide bond.

According to a particular aspect, the inventive polymeric carrier according to formula (VI) as defined above, may comprise at least one amino acid component (AA) or $(AA)_x$, as defined above. Such an amino acid component (AA) or $(AA)_x$ may be contained in every part of the inventive polymeric carrier according to formula (VI) above and therefore may be attached to all components of the inventive polymeric carrier according to formula (VI). It is particularly preferred that amino acid component (AA) or $(AA)_x$ is present as a ligand or part of the repetitive component $[S-P^2-S]_n$ within formula (VI) of the inventive polymeric carrier. The amino acid component (AA) or $(AA)_x$ preferably contains or is flanked (e.g. terminally) by at least one —SH containing moiety, which allows introducing this component (AA) or $(AA)_x$ via a disulfide bond into the polymeric carrier according to formula (VI) as defined herein. Such a —SH-containing moiety may be any —SH containing moiety (or, of course, one sulphur of a disulfide bond), e.g. a cysteine residue. In the specific case that the —SH containing moiety represents a cysteine, the amino acid component $(AA)_x$ may also be read as -Cys-$(AA)_x$- or -Cys-$(AA)_x$-Cys- wherein Cys represents Cysteine and provides for the necessary —SH-moiety for a disulfide bond. The —SH containing moiety may be also introduced into the amino acid component $(AA)_x$ using any of modifications or reactions as shown above for components $P^1$, $P^2$ or $P^3$. In the specific case that the amino acid component $(AA)_x$ is linked to two components of the inventive polymeric carrier according to formula (VI) it is preferred that (AA) or $(AA)_x$ contains at least two —SH-moieties, e.g. at least two Cysteines, preferably at its terminal ends. This is particularly preferred if (AA) or $(AA)_x$ is part of the repetitive component $[S-P^2-S]_n$. Alternatively, the amino acid component (AA) or $(AA)_x$ is introduced into the inventive polymeric carrier according to formula (VI) as defined herein via any chemical possible addition reaction. Therefore the amino acid component (AA) or $(AA)_x$ contains at least one further functional moiety, which allows attaching same to a further component as defined herein, e.g. component $P^1$ or $P^3$, $P^2$, L, or a further amino acid component (AA) or $(AA)_x$, etc. Such functional moieties may be selected from functionalities which allow the attachment of further components, e.g. functionalities as defined herein, e.g. by amide formation (e.g. carboxylic acids, sulphonic acids, amines, etc), by Michael addition (e.g maleinimide moieties, α,β unsaturated carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g halogenalkans, thiols, alcohols, amines, hydrazines, hydrazides, sulphonic acid esters, oxyphosphonium salts) or other chemical moieties which can be utilized in the attachment of further components.

The amino acid component (AA) or $(AA)_x$ in the polymeric carrier of formula (VI) may also occur as a mixed repetitive amino acid component $[(AA)_x]_z$, wherein the number of amino acid components (AA) or $(AA)_x$ is further defined by integer z. In this context, z may be selected from a range of about 1 to 30, preferably from a range of about 1 to 15, more preferably 1 to 10 or 1 to 5 and even more preferably selected from a number selected from 1, 2, 3, 4, 5, 6, 7, 8, 9, 10, 11, 12, 13, 14 or 15, or may be selected from a range formed by any two of the afore mentioned values.

According to a specific and particularly preferred alternative, the amino acid component (AA) or $(AA)_x$, preferably written as $S-(AA)_x-S$ or $[S-(AA)_x-S]$ may be used to modify component $P^2$, particularly the content of component $S-P^2-S$ in repetitive component $[S-P^2-S]_n$ of the polymeric carrier of formula (VI) above. This may be represented in the context of the entire polymeric carrier according to formula (VI) e.g. by following formula (VIa):

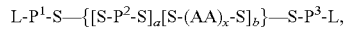

$L-P^1-S-\{[S-P^2-S]_a[S-(AA)_x-S]_b\}-S-P^3-L$, wherein x, S, L, AA, $P^1$, $P^2$ and $P^3$ are preferably as defined herein. In formula (VIa) above, any of the single components $[S-P^2-S]$ and $[S-(AA)_x-S]$ may occur in any order in the subformula $\{[S-P^2-S]_a[S-(AA)_x-S]_b\}$. The numbers of single components [S-P²-S] and [S-(AA)ₓ-S] in the subformula {[S-P²-S]ₐ[S-(AA)ₓ-S]ᵦ} are determined by integers a and b, wherein a+b=n. n is an integer and is defined as above for formula (VI).

a is an integer, typically selected independent from integer b from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 3 to 20, 4 to 20, 5 to 20, or 10 to 20, or a range of about 3 to 15, 4 to 15, 5 to 15, or 10 to 15, or a range of about 6 to 11 or 7 to 10. Most preferably, a is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

b is an integer, typically selected independent from integer a from a range of about 0 to 50 or 1 to 50, preferably from a range of about 0, 1, 2 or 3 to 30, more preferably from a range of about 0, 1, 2, 3, 4, or 5 to 25, or a range of about 0, 1, 2, 3, 4, or 5 to 20, or a range of about 0, 1, 2, 3, 4, or 5 to 15, or a range of about 0, 1, 2, 3, 4, or 5 to 10, including e.g. a range of about 3 to 20, 4 to 20, 5 to 20, or 10 to 20, or a range of about 3 to 15, 4 to 15, 5 to 15, or 10 to 15, or a range of about 6 to 11 or 7 to 10. Most preferably, b is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

According to one preferred aspect, the mRNA of the inventive vaccine encoding at least one antigen as defined above may be formulated together with a cationic or polycationic compound and/or with a polymeric carrier, preferably as defined herein.

According to a further preferred aspect, the mRNA of the inventive vaccine encoding at least one antigen as defined above may be formulated together with an (adjuvant) component. According to a particularly preferred aspect, the mRNA of the inventive vaccine encoding at least one antigen as defined above may be formulated to comprise a) an (adjuvant) component, comprising or consisting of at least one immunostimulatory nucleic acid, complexed with a cationic or polycationic compound and/or with a polymeric carrier, preferably as defined herein, and b) at least one free mRNA, encoding an antigen, preferably as defined herein for the inventive vaccine.

In the above context, a cationic or polycationic compound and/or a polymeric carrier used to complex the at least one immunostimulatory nucleic acid in the adjuvant component, may be selected from a cationic or polycationic compound and/or a polymeric carrier as defined above.

Furthermore, an immunostimulatory nucleic acid as defined above for the adjuvant component may be preferably selected from an mRNA as defined herein for the inventive vaccine, encoding at least one antigen. Alternatively, such an immunostimulatory nucleic acid may be selected from an immunostimulatory nucleic acid, as defined herein, preferably an immunostimulatory RNA (isRNA) as defined herein.

In this context, an immunostimulatory nucleic acid, as used herein, is preferably selected from immunostimulatory nucleic acids which are known to bind to TLR receptors. Such an immunostimulatory nucleic acid can be in the form of a(n) (immunostimulatory) CpG nucleic acid, in particular CpG-RNA or CpG-DNA, which preferably induces an innate immune response. A CpG-RNA or CpG-DNA used according to the invention can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid used according to the invention is preferably in the form of CpG-RNA, more preferably in the form of single-stranded CpG-RNA (ss CpG-RNA). Also preferably, such CpG nucleic acids have a length as described above. Preferably, the CpG motifs are unmethylated.

Furthermore, an immunostimulatory nucleic acid, as used herein, is preferably selected from an immunostimulatory RNA (isRNA), which preferably elicits an innate immune response. Preferably, the immunostimulatory RNA may be a single-stranded, a double-stranded or a partially double-stranded RNA, more preferably a single-stranded RNA, and/or a circular or linear RNA, more preferably a linear RNA. More preferably, the immunostimulatory RNA may be a (linear) single-stranded RNA. Even more preferably, the immunostimulatory RNA may be a (long) (linear) (single-stranded) non-coding RNA. In this context it is particular preferred that the isRNA carries a triphosphate at its 5'-end which is the case for in vitro transcribed RNA. An immunostimulatory RNA may also occur as a short RNA oligonucleotide as defined herein. An immunostimulatory RNA as used herein may furthermore be selected from any class of RNA molecules, found in nature or being prepared synthetically, and which can induce an innate immune response and may support an adaptive immune response induced by an antigen. In this context, an immune response may occur in various ways. A substantial factor for a suitable (adaptive) immune response is the stimulation of different T cell sub-populations. T-lymphocytes are typically divided into two subpopulations, the T-helper 1 (Th1) cells and the T-helper 2 (Th2) cells, with which the immune system is capable of destroying intracellular (Th1) and extracellular (Th2) pathogens (e.g. antigens). The two Th cell populations differ in the pattern of the effector proteins (cytokines) produced by them. Thus, Th1 cells assist the cellular immune response by activation of macrophages and cytotoxic T cells. Th2 cells, on the other hand, promote the humoral immune response by stimulation of B-cells for conversion into plasma cells and by formation of antibodies (e.g. against antigens). The Th1/Th2 ratio is therefore of great importance in the induction and maintenance of an adaptive immune response. In connection with the present invention, the Th1/Th2 ratio of the (adaptive) immune response is preferably shifted in the direction towards the cellular response (Th1 response) and a cellular immune response is thereby induced. According to one example, the innate immune system which may support an adaptive immune response may be activated by ligands of Toll-like receptors (TLRs). TLRs are a family of highly conserved pattern recognition receptor (PRR) polypeptides that recognize pathogen-associated molecular patterns (PAMPs) and play a critical role in innate immunity in mammals. Currently at least thirteen family members, designated TLR1-TLR13 (Toll-like receptors: TLR1, TLR2, TLR3, TLR4, TLR5, TLR6, TLR7, TLR8, TLR9, TLR10, TLR11, TLR12 or TLR13), have been identified. Furthermore, a number of specific TLR ligands have been identified. It was e.g. found that unmethylated bacterial DNA and synthetic analogs thereof (CpG DNA) are ligands for TLR9 (Hemmi H et al. (2000) Nature 408:740-5; Bauer S et al. (2001) Proc Natl. Acad. Sci. USA 98, 9237-42). Furthermore, it has been reported that ligands for certain TLRs include certain nucleic acid molecules and that certain types of RNA are immunostimulatory in a sequence-independent or sequence-dependent manner, wherein these various immunostimulatory RNAs may e.g. stimulate TLR3, TLR7, or TLR8, or intracellular receptors such as RIG-I, MDA-5, etc.

Preferably, an immunostimulatory nucleic acid, preferably an immunostimulatory RNA (isRNA), as used herein, may comprise any RNA sequence known to be immunostimulatory, including, without being limited thereto, RNA sequences representing and/or encoding ligands of TLRs, preferably selected from human family members TLR1-TLR10 or murine family members TLR1-TLR13, more preferably selected from (human) family members TLR1-TLR10, even more preferably from TLR7 and TLR8, ligands for intracellular receptors for RNA (such as RIG-I or MDA-5, etc.) (see e.g. Meylan, E., Tschopp, J. (2006). Toll-like receptors and RNA helicases: two parallel ways to trigger antiviral responses. Mol. Cell 22, 561-569), or any other immunostimulatory RNA sequence. Furthermore, (classes of) immunostimulatory RNA molecules, used as a further compound of the inventive vaccine, may include any other RNA capable of eliciting an immune response. Without being limited thereto, such an immunostimulatory RNA may include ribosomal RNA (rRNA), transfer RNA (tRNA), messenger RNA (mRNA), and viral RNA (vRNA). Such an immunostimulatory RNA may comprise a length of 1000 to 5000, of 500 to 5000, of 5 to 5000, or of 5 to 1000, 5 to 500, 5 to 250, of 5 to 100, of 5 to 50 or of 5 to 30 nucleotides.

According to a particularly preferred embodiment, an immunostimulatory nucleic acid sequence, particularly an isRNA, as used herein, may consist of or comprise a nucleic acid of formula (I) or (II):

$$G_l X_m G_n,  \quad \text{(formula (I))}$$

wherein:
G is guanosine, uracil or an analogue of guanosine or uracil;
X is guanosine, uracil, adenosine, thymidine, cytosine or an analogue of the abovementioned nucleotides;
l is an integer from 1 to 40,
  wherein
  when l=1 G is guanosine or an analogue thereof,
  when l>1 at least 50% of the nucleotides are guanosine or an analogue thereof;
m is an integer and is at least 3;
  wherein
  when m=3 X is uracil or an analogue thereof,
  when m>3 at least 3 successive uracils or analogues of uracil occur;
n is an integer from 1 to 40,
  wherein
  when n=1 G is guanosine or an analogue thereof,
  when n>1 at least 50% of the nucleotides are guanosine or an analogue thereof.

$$C_l X_m C_n, \quad \text{(formula (II))}$$

wherein:
C is cytosine, uracil or an analogue of cytosine or uracil;
X is guanosine, uracil, adenosine, thymidine, cytosine or an analogue of the abovementioned nucleotides;
l is an integer from 1 to 40,
  wherein
  when l=1 C is cytosine or an analogue thereof,
  when l>1 at least 50% of the nucleotides are cytosine or an analogue thereof;
m is an integer and is at least 3;
  wherein
  when m=3 X is uracil or an analogue thereof,
  when m>3 at least 3 successive uracils or analogues of uracil occur;
n is an integer from 1 to 40,
  wherein
  when n=1 C is cytosine or an analogue thereof,
  when n>1 at least 50% of the nucleotides are cytosine or an analogue thereof.

The nucleic acids of formula (I) or (II), which may be used as an immunostimulatory nucleic acid sequence, particularly an isRNA, may be relatively short nucleic acid molecules with a typical length of approximately from 5 to 100 (but may also be longer than 100 nucleotides for specific embodiments, e.g. up to 200 nucleotides), from 5 to 90 or from 5 to 80 nucleotides, preferably a length of approximately from 5 to 70, more preferably a length of approximately from 8 to 60 and, more preferably a length of approximately from 15 to 60 nucleotides, more preferably from 20 to 60, most preferably from 30 to 60 nucleotides. If the nucleic acid of formula (I) or (II) has a maximum length of e.g. 100 nucleotides, m will typically be <=98. The number of nucleotides G in the nucleic acid of formula (I) is determined by l or n. l and n, independently of one another, are each an integer from 1 to 40, wherein when l or n=1 G is guanosine or an analogue thereof, and when l or n>1 at least 50% of the nucleotides are guanosine or an analogue thereof. For example, without implying any limitation, when l or n=4 G, or $G_n$ can be, for example, a GUGU, GGUU, UGUG, UUGG, GUUG, GGGU, GGUG, GUGG, UGGG or GGGG, etc.; when l or n=5 $G_l$ or $G_n$ can be, for example, a GGGUU, GGUGU, GUGGU, UGGGU, UGGUG, UGUGG, UUGGG, GUGUG, GGGGU, GGGUG, GGUGG, GUGGG, UGGGG, or GGGGG, etc.; etc. A nucleotide adjacent to $X_m$ in the nucleic acid of formula (I) according to the invention is preferably not a uracil. Similarly, the number of nucleotides C in the nucleic acid of formula (II) according to the invention is determined by l or n. l and n, independently of one another, are each an integer from 1 to 40, wherein when l or n=1 C is cytosine or an analogue thereof, and when l or n>1 at least 50% of the nucleotides are cytosine or an analogue thereof. For example, without implying any limitation, when l or n=4, C, or $C_n$ can be, for example, a CUCU, CCUU, UCUC, UUCC, CUUC, CCCU, CCUC, CUCC, UCCC or CCCC, etc.; when l or n=5 $C_l$ or $C_n$ can be, for example, a CCCUU, CCUCU, CUCCU, UCCCU, UCCUC, UCUCC, UUCCC, CUCUC, CCCCU, CCCUC, CCUCC, CUCCC, UCCCC, or CCCCC, etc.; etc. A nucleotide adjacent to $X_m$ in the nucleic acid of formula (II) according to the invention is preferably not a uracil. Preferably, for formula (I), when l or n>1, at least 60%, 70%, 80%, 90% or even 100% of the nucleotides are guanosine or an analogue thereof, as defined above. The remaining nucleotides to 100% (when guanosine constitutes less than 100% of the nucleotides) in the flanking sequences $G_l$ and/or $G_n$ are uracil or an analogue thereof, as defined hereinbefore. Also preferably, l and n, independently of one another, are each an integer from 2 to 30, more preferably an integer from 2 to 20 and yet more preferably an integer from 2 to 15. The lower limit of l or n can be varied if necessary and is at least 1, preferably at least 2, more preferably at least 3, 4, 5, 6, 7, 8, 9 or 10. This definition applies correspondingly to formula (II).

According to a particularly preferred embodiment, a nucleic acid according to any of formulas (I) or (II) above, which may be used as an immunostimulatory nucleic acid sequence, particularly an isRNA, may be selected from a sequence consisting or comprising any of the following sequences:

GGUUUUUUUUUUUUUUGGG; (SEQ ID NO: 289)

GGGGGUUUUUUUUUGGGGG; (SEQ ID NO: 290)

GGGGGUUUUUUUUUUUUUUUUUUUUUUUUUUUGGGGG; (SEQ ID NO: 291)

GUGUGUGUGUGUUUUUUUUUUUUUUUGUGUGUGUGUGU; (SEQ ID NO: 292)

GGUUGGUUGGUUUUUUUUUUUUUUUUGGUUGGUUGGUU; (SEQ ID NO: 293)

GGGGGGGGGUUUGGGGGGGG; (SEQ ID NO: 294)

GGGGGGGGUUUGGGGGGGG; (SEQ ID NO: 295)

GGGGGGGUUUUUGGGGGGG; (SEQ ID NO: 296)

GGGGGGGUUUUUGGGGGGG; (SEQ ID NO: 297)

GGGGGGUUUUUUGGGGGGG; (SEQ ID NO: 298)

GGGGGGUUUUUUUGGGGGG; (SEQ ID NO: 299)

GGGGGGUUUUUUUUGGGGG; (SEQ ID NO: 300)

GGGGGUUUUUUUUUUGGGG; (SEQ ID NO: 301)

GGGGGUUUUUUUUUUUGGGG; (SEQ ID NO: 302)

GGGUUUUUUUUUUUUUGGG; (SEQ ID NO: 303)

GGGGUUUUUUUUUUUUUGG; (SEQ ID NO: 304)

GGUUUUUUUUUUUUUUUGG; (SEQ ID NO: 305)

GUUUUUUUUUUUUUUUUUG; (SEQ ID NO: 306)

GGGGGGGGGUUUGGGGGGGG; (SEQ ID NO: 307)

GGGGGGGGGUUUGGGGGGGG; (SEQ ID NO: 308)

GGGGGGGGGUUUUGGGGGGGG; (SEQ ID NO: 309)

GGGGGGGGGUUUUGGGGGGGG; (SEQ ID NO: 310)

GGGGGGGUUUUUUGGGGGGG; (SEQ ID NO: 311)

GGGGGGGUUUUUUUGGGGGG; (SEQ ID NO: 312)

GGGGGGGUUUUUUUUGGGGG; (SEQ ID NO: 313)

GGGGGGUUUUUUUUUGGGGG; (SEQ ID NO: 314)

GGGGGGUUUUUUUUUUGGGG; (SEQ ID NO: 315)

GGGGGUUUUUUUUUUUGGGG; (SEQ ID NO: 316)

GGGGGUUUUUUUUUUUUUGGG; (SEQ ID NO: 317)

GGGUUUUUUUUUUUUUUGGG; (SEQ ID NO: 318)

GGUUUUUUUUUUUUUUUGG; (SEQ ID NO: 319)

GGGGGGGGGGUUUGGGGGGGGGG; (SEQ ID NO: 320)

GGGGGGGGGGUUUGGGGGGGGGG; (SEQ ID NO: 321)

GGGGGGGGGUUUUUGGGGGGGGG; (SEQ ID NO: 322)

GGGGGGGGGUUUUUGGGGGGGGG; (SEQ ID NO: 323)

GGGGGGGGUUUUUUGGGGGGGG; (SEQ ID NO: 324)

GGGGGGGGUUUUUUUGGGGGGG; (SEQ ID NO: 325)

GGGGGGGGUUUUUUUUGGGGGG; (SEQ ID NO: 326)

GGGGGGGUUUUUUUUUGGGGGG; (SEQ ID NO: 327)

GGGGGGGUUUUUUUUUUGGGGG; (SEQ ID NO: 328)

GGGGGGUUUUUUUUUUUGGGGG; (SEQ ID NO: 329)

GGGGGGUUUUUUUUUUUUGGGG; (SEQ ID NO: 330)

GGGGGUUUUUUUUUUUUUGGGG; (SEQ ID NO: 331)

GGGUUUUUUUUUUUUUUUGGG; (SEQ ID NO: 332)

GUUUUUUUUUUUUUUUUUUUUUUUUUG; (SEQ ID NO: 333)

GGUUUUUUUUUUUUUUUUUUUUUUUUUUGG; (SEQ ID NO: 334)

GGGUUUUUUUUUUUUUUUUUUUUUUUUUUUGGG; (SEQ ID NO: 335)

GGGGUUUUUUUUUUUUUUUUUUUUUUUUUUUUGGG; (SEQ ID NO: 336)

GGGGUUUUUUUUUUUUUUUUUUUUUUUUUUUUUGGGG; (SEQ ID NO: 337)

GGGGGGUUUUUUUUUUUUUUUUUUUUUUUUUUUUGGGGG; (SEQ ID NO: 338)

-continued

GGGGGGGUUUUUUUUUUUUUUUUUUUUUUUUUUUGGGGGG; (SEQ ID NO: 339)

GGGGGGGGUUUUUUUUUUUUUUUUUUUUUUUUUUUGGGGGGG; (SEQ ID NO: 340)

GGGGGGGGGUUUUUUUUUUUUUUUUUUUUUUUUUUUGGGGGGGG; (SEQ ID NO: 341)

GGUUUGG; (SEQ ID NO: 342)

GGUUUUGG; (SEQ ID NO: 343)

GGUUUUUGG; (SEQ ID NO: 344)

GGUUUUUUGG; (SEQ ID NO: 345)

GGUUUUUUUGG; (SEQ ID NO: 346)

GGUUUUUUUUGG; (SEQ ID NO: 347)

GGUUUUUUUUUGG; (SEQ ID NO: 348)

GGUUUUUUUUUUGG; (SEQ ID NO: 349)

GGUUUUUUUUUUUGG; (SEQ ID NO: 350)

GGUUUUUUUUUUUUGG; (SEQ ID NO: 351)

GGUUUUUUUUUUUUUGG; (SEQ ID NO: 352)

GGUUUUUUUUUUUUUUGG; (SEQ ID NO: 353)

GGUUUUUUUUUUUUUUUGG; (SEQ ID NO: 354)

GGGUUUGGG; (SEQ ID NO: 355)

GGGUUUUGGG; (SEQ ID NO: 356)

GGGUUUUUGGG; (SEQ ID NO: 357)

GGGUUUUUUGGG; (SEQ ID NO: 358)

GGGUUUUUUUGGG; (SEQ ID NO: 359)

GGGUUUUUUUUGGG; (SEQ ID NO: 360)

GGGUUUUUUUUUGGG; (SEQ ID NO: 361)

GGGUUUUUUUUUUGGG; (SEQ ID NO: 362)

GGGUUUUUUUUUUUGGG; (SEQ ID NO: 363)

GGGUUUUUUUUUUUUGGG; (SEQ ID NO: 364)

GGGUUUUUUUUUUUUUGGG; (SEQ ID NO: 365)

GGGUUUUUUUUUUUUUGGGUUUUUUUUUUUUUUUGG-GUUUUUUUUUUUUUGGG; (SEQ ID NO: 366)

GGGUUUUUUUUUUUUUGGGGGUUUUUUUUUUUUUUUGGG; (SEQ ID NO: 367)

GGGUUUGGUUGGGUUUGGGUUUGGGUUUGGGUUUGGGUUUGG-GUUUGGG; (SEQ ID NO: 368)

GGUUUUUUUUUUUUUUGGG (short GU-rich, SEQ ID NO: 369)

or

CCCUUUUUUUUUUUUUUCCCUUUUUUUUUUUUUUUCCC-UUUUUUUUUUUUUUCCC (SEQ ID NO: 370)

CCCUUUCCCUUUCCCUUUCCCUUUCCCUUUCCCUUUCCCUUUCCCUUUCCC (SEQ ID NO: 371)
C

CCCUUUUUUUUUUUUUUCCCCCUUUUUUUUUUUUUUUCCC (SEQ ID NO: 372)

or from a sequence having at least 60%, 70%, 80%, 90%, or even 95% sequence identity with any of these sequences.

According to a further particularly preferred embodiment, an immunostimulatory nucleic acid sequence, particularly an isRNA, as used herein, may consist of or comprise a nucleic acid of formula (III) or (IV):

$$(N_uG_lX_mG_nN_v)_a,$$ (formula (III))

wherein:

G is guanosine (guanine), uridine (uracil) or an analogue of guanosine (guanine) or uridine (uracil), preferably guanosine (guanine) or an analogue thereof;

x is guanosine (guanine), uridine (uracil), adenosine (adenine), thymidine (thymine), cytidine (cytosine), or an analogue of these nucleotides (nucleosides), preferably uridine (uracil) or an analogue thereof;

N is a nucleic acid sequence having a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);

a is an integer from 1 to 20, preferably from 1 to 15, most preferably from 1 to 10;

l is an integer from 1 to 40, l
  wherein
  when l=1, G is guanosine (guanine) or an analogue thereof,
  when l>1, at least 50% of these nucleotides (nucleosides) are guanosine (guanine) or an analogue thereof;

m is an integer and is at least 3;
  wherein
  when m=3, X is uridine (uracil) or an analogue thereof, and
  when m>3, at least 3 successive uridines (uracils) or analogues of uridine (uracil) occur;

n is an integer from 1 to 40,
wherein
when n=1, G is guanosine (guanine) or an analogue thereof,
when n>1, at least 50% of these nucleotides (nucleosides) are guanosine (guanine) or an analogue thereof;
u,v may be independently from each other an integer from 0 to 50,
preferably wherein when u=0, v≥1, or
when v=0, u≥1;
wherein the nucleic acid molecule of formula (III) has a length of at least 50 nucleotides, preferably of at least 100 nucleotides, more preferably of at least 150 nucleotides, even more preferably of at least 200 nucleotides and most preferably of at least 250 nucleotides.

$$(N_u C_l X_m C_n N_v)_a \quad \text{(formula (IV))}$$

wherein:
C is cytidine (cytosine), uridine (uracil) or an analogue of cytidine (cytosine) or uridine (uracil), preferably cytidine (cytosine) or an analogue thereof;
X is guanosine (guanine), uridine (uracil), adenosine (adenine), thymidine (thymine), cytidine (cytosine) or an analogue of the above-mentioned nucleotides (nucleosides), preferably uridine (uracil) or an analogue thereof;
N is each a nucleic acid sequence having independent from each other a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);
a is an integer from 1 to 20, preferably from 1 to 15, most preferably from 1 to 10;
l is an integer from 1 to 40,
wherein
when l=1, C is cytidine (cytosine) or an analogue thereof,
when l>1, at least 50% of these nucleotides (nucleosides) are cytidine (cytosine) or an analogue thereof;
m is an integer and is at least 3;
wherein
when m=3, X is uridine (uracil) or an analogue thereof,
when m>3, at least 3 successive uridines (uracils) or analogues of uridine (uracil) occur;
n is an integer from 1 to 40,
wherein
when n=1, C is cytidine (cytosine) or an analogue thereof,
when n>1, at least 50% of these nucleotides (nucleosides) are cytidine (cytosine) or an analogue thereof.
u, v may be independently from each other an integer from 0 to 50,
preferably wherein when u=0, v≥1, or
when v=0, u≥1;
wherein the nucleic acid molecule of formula (IV) according to the invention has a length of at least 50 nucleotides, preferably of at least 100 nucleotides, more preferably of at least 150 nucleotides, even more preferably of at least 200 nucleotides and most preferably of at least 250 nucleotides.
Any of the definitions given above in formulae (I) and (II), e.g. for elements N (i.e. $N_u$ and $N_v$) and X ($X_m$), particularly the core structure as defined above, as well as for integers a, l, m, n, u and v, similarly apply to elements of formula (III) and (IV) correspondingly. The definition of bordering elements $N_u$ and $N_v$ in formula (IV) is identical to the definitions given above for $N_u$ and $N_v$ in formula (IV).

According to a very particularly preferred embodiment, the inventive nucleic acid molecule according to formula (IV), which may be used as an immunostimulatory nucleic acid sequence, particularly an isRNA, may be selected from e.g. any of the following sequences:

```
                                       (SEQ ID NO: 373)
UAGCGAAGCUCUUGGACCUAGGUUUUUUUUUUUUUUGGGUGCGUUCCUA

GAAGUACACG (SEQ ID NO: 374)
UAGCGAAGCUCUUGGACCUAGGUUUUUUUUUUUUUUGGGUGCGUUCCUA

GAAGUACACG AUCGCUUCGA GAACCUGGAUCCAAAAAAAAAAAAAAAC

CCACGCAAGGAUCUUCAUGUGC (SEQ ID NO: 375)
GGGAGAAAGCUCAAGCUUGGAGCAAUGCCCGCACAUUGAGGAAACCGAGU

UGCAUAUCUCAGAGUAUUGGCCCCCGUGUAGGUUAUUCUUGACAGACAGU

GGAGCUUAUUCACUCCCAGGAUCCGAGUCGCAUACUACGGUACUGGUGAC

AGACCUAGGUCGUCAGUUGACCAGUCCGCCACUAGACGUGAGUCCGUCAA

AGCAGUUAGAUGUUACACUCUAUUAGAUC (SEQ ID NO: 376)
GGGAGAAAGCUCAAGCUUGGAGCAAUGCCCGCACAUUGAGGAAACCGAGU

UGCAUAUCUCAGAGUAUUGGCCCCCGUGUAGGUUAUUCUUGACAGACAGU

GGAGCUUAUUCACUCCCAGGAUCCGAGUCGCAUACUACGGUACUGGUGAC

AGACCUAGGUCGUCAGUUGACCAGUCCGCCACUAGACGUGAGUCCGUCAA

AGCAGUUAGAUGUUACACUCUAUUAGAUCUCGGAUUACAGCUGGAAGGAG

CAGGAGUAGUGUUCUUGCUCUAAGUACCGAGUGUGCCCAAUACCCGAUCA

GCUUAUUAACGAACGGCUCCUCCUCUUAGACUGCAGCGUAAGUGCGGAAU

CUGGGGAUCAAAUUACUGACUGCCUGGAUUACCCUCGGACAUAUAACCUU

GUAGCACGCUGUUGCUGUAUAGGUGACCAACGCCCACUCGAGUAGACCAG

CUCUCUUAGUCCGGACAAUGAUAGGAGGCGCGGUCAAUCUACUUCUGGCU

AGUUAAGAAUAGGCUGCACCGACCUCUAUAAGUAGCGUGUCCUCUAG (SEQ ID NO: 377)
GGGAGAAAGCUCAAGCUUGGAGCAAUGCCCGCACAUUGAGGAAACCGAGU

UGCAUAUCUCAGAGUAUUGGCCCCCGUGUAGGUUAUUCUUGACAGACAGU

GGAGCUUAUUCACUCCCAGGAUCCGAGUCGCAUACUACGGUACUGGUGAC

AGACCUAGGUCGUCAGUUGACCAGUCCGCCACUAGACGUGAGUCCGUCAA

AGCAGUUAGAUGUUACACUCUAUUAGAUCUCGGAUUACAGCUGGAAGGAG

CAGGAGUAGUGUUCUUGCUCUAAGUACCGAGUGUGCCCAAUACCCGAUCA

GCUUAUUAACGAACGGCUCCUCCUCUUAGACUGCAGCGUAAGUGCGGAAU

CUGGGGAUCAAAUUACUGACUGCCUGGAUUACCCUCGGACAUAUAACCUU

GUAGCACGCUGUUGCUGUAUAGGUGACCAACGCCCACUCGAGUAGACCAG

CUCUCUUAGUCCGGACAAUGAUAGGAGGCGCGGUCAAUCUACUUCUGGCU

AGUUAAGAAUAGGCUGCACCGACCUCUAUAAGUAGCGUGUCCUCUAGAGC

UACGCAGGUUCGCAAUAAAAGCGUUGAUUAGUGUGCAUAGAACAGACCUC
```

-continued

UUAUUCGGUGAAACGCCAGAAUGCUAAAUUCCAAUAACUCUUCCCAAAAC

GCGUACGGCCGAAGACGCGCGCUUAUCUUGUGUACGUUCUCGCACAUGGA

AGAAUCAGCGGGCAUGGUGGUAGGGCAAUAGGGGAGCUGGGUAGCAGCGA

AAAAGGGCCCCUGCGCACGUAGCUUCGCUGUUCGUCUGAAACAACCCGGC

AUCCGUUGUAGCGAUCCCGUUAUCAGUGUUAUUCUUGUGCGCACUAAGAU

UCAUGGUGUAGUCGACAAUAACAGCGUCUUGGCAGAUUCUGGUCACGUGC

CCUAUGCCCGGGCUUGUGCCUCUCAGGUGCACAGCGAUACUUAAAGCCUU

CAAGGUACUCGACGUGGGUACCGAUUCGUGACACUUCCUAAGAUUAUUCC

ACUGUGUUAGCCCCGCACCGCCGACCUAAACUGGUCCAAUGUAUACGCAU

UCGCUGAGCGGAUCGAUAAUAAAAGCUUGAAUU (SEQ ID NO: 378)
GGGAGAAAGCUCAAGCUUAUCCAAGUAGGCUGGUCACCUGUACAACGUAG

CCGGUAUUUUUUUUUUUUUUUUUUUUUUUGACCGUCUCAAGGUCCAAGUUA

GUCUGCCUAUAAAGGUGCGGAUCCACAGCUGAUGAAAGACUUGUGCGGUA

CGGUUAAUCUCCCCUUUUUUUUUUUUUUUUUUUUUAGUAAAUGCGUCUAC

UGAAUCCAGCGAUGAUGCUGGCCCAGAUC (R 722 SEQ ID NO: 379)
GGGAGAAAGCUCAAGCUUAUCCAAGUAGGCUGGUCACCUGUACAACGUAG

CCGGUAUUUUUUUUUUUUUUUUUUUUUUUGACCGUCUCAAGGUCCAAGUUA

GUCUGCCUAUAAAGGUGCGGAUCCACAGCUGAUGAAAGACUUGUGCGGUA

CGGUUAAUCUCCCCUUUUUUUUUUUUUUUUUUUUUAGUAAAUGCGUCUAC

UGAAUCCAGCGAUGAUGCUGGCCCAGAUCUUCGACCACAAGUGCAUAUAG

UAGUCAUCGAGGGUCGCCUUUUUUUUUUUUUUUUUUUUUUGGCCCAGUU

CUGAGACUUCGCUAGAGACUACAGUUACAGCUGCAGUAGUAACCACUGCG

GCUAUUGCAGGAAAUCCCGUUCAGGUUUUUUUUUUUUUUUUUUUCCGC

UCACUAUGAUUAAGAACCAGGUGGAGUGUCACUGCUCUCGAGGUCUCACG

AGAGCGCUCGAUACAGUCCUUGGAAGAAUCUUUUUUUUUUUUUUUUUUU

UUGUGCGACGAUCACAGAGAACUUCUAUUCAUGCAGGUCUGCUCUA (SEQ ID NO: 380)
GGGAGAAAGCUCAAGCUUAUCCAAGUAGGCUGGUCACCUGUACAACGUAG

CCGGUAUUUUUUUUUUUUUUUUUUUUUUUGACCGUCUCAAGGUCCAAGUUA

GUCUGCCUAUAAAGGUGCGGAUCCACAGCUGAUGAAAGACUUGUGCGGUA

CGGUUAAUCUCCCCUUUUUUUUUUUUUUUUUUUUUAGUAAAUGCGUCUAC

UGAAUCCAGCGAUGAUGCUGGCCCAGAUCUUCGACCACAAGUGCAUAUAG

UAGUCAUCGAGGGUCGCCUUUUUUUUUUUUUUUUUUUUUUGGCCCAGUU

CUGAGACUUCGCUAGAGACUACAGUUACAGCUGCAGUAGUAACCACUGCG

GCUAUUGCAGGAAAUCCCGUUCAGGUUUUUUUUUUUUUUUUUUUCCGC

UCACUAUGAUUAAGAACCAGGUGGAGUGUCACUGCUCUCGAGGUCUCACG

AGAGCGCUCGAUACAGUCCUUGGAAGAAUCUUUUUUUUUUUUUUUUUUU

UUGUGCGACGAUCACAGAGAACUUCUAUUCAUGCAGGUCUGCUCUAGAAC

GAACUGACCUGACGCCUGAACUUAUGAGCGUGCGUAUUUUUUUUUUUUU

UUUUUUUUUCCUCCCAACAAAUGUCGAUCAAUAGCUGGGCUGUUGGAGAC

GCGUCAGCAAAUGCCGUGGCUCCAUAGGACGUGUAGACUUCUAUUUUUUU

UUUUUUUUUUUUUUCCCGGGACCACAAAUAAUAUUCUUGCUUGGUUGGGC

GCAAGGGCCCCGUAUCAGGUCAUAAACGGGUACAUGUUGCACAGGCUCCU

UUUUUUUUUUUUUUUUUUUUUUCGCUGAGUUAUUCCGGUCUCAAAAGACG

GCAGACGUCAGUCGACAACACGGUCUAAAGCAGUGCUACAAUCUGCCGUG

UUCGUGUUUUUUUUUUUUUUUUUUUGUGAACCUACACGGCGUGCACUGU

AGUUCGCAAUUCAUAGGGUACCGGCUCAGAGUUAUGCCUUGGUUGAAAAC

UGCCCAGCAUACUUUUUUUUUUUUUUUUUUCAUAUUCCCAUGCUAAGC

AAGGGAUGCCGCGAGUCAUGUUAAGCUUGAAUU

According to another very particularly preferred embodiment, the nucleic acid molecule according to formula (V) may be selected from e.g. any of the following sequences:

(SEQ ID NO: 381)
UAGCGAAGCUCUUGGACCUACCUUUUUUUUUUUUUUUCCCUGCGUUCCUAG

AAGUACACG or (SEQ ID NO: 382)
UAGCGAAGCUCUUGGACCUACCUUUUUUUUUUUUUUUCCCUGCGUUCCUA

GAAGUACACGAUCGCUUCGAGAACCUGGAUGGAAAAAAAAAAAAAAAGGG

ACGCAAGGAUCUUCAUGUGC or from a sequence having at least 60%, 70%, 80%, 90%, or even 95% sequence identity with any of these sequences.

Finally, the so called "(adjuvant) component", which may be used to together with the mRNA in the inventive vaccine, is preferably prepared according to a first step by complexing the at least one (m)RNA of the (adjuvant) component with a cationic or polycationic compound and/or with a polymeric carrier, preferably as defined herein, in a specific ratio to form a stable complex. In this context, it is highly preferable, that no free cationic or polycationic compound or polymeric carrier or only a neglectably small amount thereof remains in the (adjuvant) component after complexing the (m)RNA. Accordingly, the ratio of the (m)RNA and the cationic or polycationic compound and/or the polymeric carrier in the (adjuvant) component is typically selected in a range that the (m)RNA is entirely complexed and no free cationic or polycationic compound or polymeric carrier or only a neglectably small amount thereof remains in the composition. Preferably the ratio of the (adjuvant) component, i.e. the ratio of the (m)RNA to the cationic or polycationic compound and/or the polymeric carrier, preferably as defined herein, is selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w). Alternatively, the ratio of the (m)RNA to the cationic or polycationic compound and/or the polymeric carrier, preferably as defined herein, in the (adjuvant) component, may also be calculated on the basis of the nitrogen/phosphate ratio (N/P-ratio) of the entire complex of the (adjuvant) component. In the context of the present invention, an N/P-ratio is preferably in the range of about 0.1-10, preferably in a range of about 0.3-4 and most preferably in a range of about 0.5-2 or 0.7-2 regarding the ratio of (m)RNA: cationic or polycationic compound and/or polymeric carrier, preferably as defined herein, in the complex, and most preferably in the range of about 0.7-1.5, preferably provided the cationic or polycationic compound in the complex is a cationic or polycationic cationic or polycationic protein or peptide and/or the polymeric carrier is as defined above. Such ratios, particularly weight and/or N/P ratios may also be applied to ratios of the at least one mRNA encoding at least one antigen as defined herein to a cationic or polycationic polymer or a polymeric carrier as defined herein used to complex the at least one mRNA.

According to a further preferred aspect, the mRNA of the inventive vaccine encoding at least one antigen as defined above may be formulated together with an (adjuvant) component as defined above, wherein the inventive vaccine may comprise a) an (adjuvant) component, comprising or consisting of at least one (m)RNA, complexed with a cationic or polycationic compound and/or with a polymeric carrier, preferably as defined herein, and b) at least one free mRNA, encoding an antigen, preferably as defined herein. This formulation is preferably as defined above. Furthermore, the entire formulation of a) and b) may be additionally packaged with a carrier molecule to allow combined packaging the (adjuvant) component and the antigen. Such a carrier molecule may be selected from any polymer suitable for packaging and preferably transporting the entire formulation of a) and b) into cells, tissue, etc., of a patient as defined herein, e.g. from a cationic or polycationic polymer as defined herein or from any further polymer suitable for this purpose, e.g. a polymeric carrier as defined above.

The ratio of all components of the entire inventive vaccine composition, as defined above, preferably, an adjuvant component comprising or consisting of at least one immunostimulatory nucleic acid sequence, complexed with a cationic or polycationic compound, the at least one mRNA encoding at least one antigen, and/or a carrier molecule, formulated in the inventive vaccine, may be calculated on the basis of the nitrogen/phosphate ratio (N/P-ratio) of all these components. In the context of the present invention, an N/P-ratio is preferably in the range of about 0.01-4, 0.01-2, 0.1-2 or 0.1-1.5 regarding the ratio of nucleic acids:cationic or polycationic peptide contained in the inventive vaccine, and most preferably in the range of about 0.1-1. Such an N/P ratio is preferably designed to provide good transfection properties in vivo and transport into and through cell membranes. Preferably, for this purpose, cationic or polycationic compound and/or polymeric carriers as used herein, are based on peptide sequences.

In a further preferred aspect of the present invention the inventive vaccine may comprise a pharmaceutically acceptable carrier and/or vehicle. In the context of the present invention, a pharmaceutically acceptable carrier typically includes the liquid or non-liquid basis of a composition comprising the components of the inventive vaccine. If the composition is provided in liquid form, the carrier will typically be pyrogen-free water; isotonic saline or buffered (aqueous) solutions, e.g. phosphate, citrate etc. buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds, which are suitable for administration to a patient to be treated, may be used as well for the inventive vaccine. The term "compatible" as used here means that these constituents of the inventive vaccine are capable of being mixed with the components of the inventive vaccine in such a manner that no interaction occurs which would substantially reduce the pharmaceutical effectiveness of the inventive vaccine under typical use conditions.

According to a specific aspect, the inventive vaccine may comprise an adjuvant. In this context, an adjuvant may be understood as any compound, which is suitable to initiate or increase an immune response of the innate immune system, i.e. a non-specific immune response. With other words, when administered, the vaccine preferably elicits an innate immune response due to the adjuvant, optionally contained therein. Preferably, such an adjuvant may be selected from an adjuvant known to a skilled person and suitable for the present case, i.e. supporting the induction of an innate immune response in a mammal, e.g. an adjuvant protein as defined above or an adjuvant as defined in the following.

According to one aspect such an adjuvant may be selected from an (adjuvant) component as defined above.

According to one further aspect such an adjuvant may be selected from any adjuvant known to a skilled person and suitable for the present case, i.e. supporting the induction of an innate immune response in a mammal and/or suitable for depot and delivery of the components of the inventive vaccine. Preferred as adjuvants suitable for depot and delivery are cationic or polycationic compounds as defined above. Likewise, the adjuvant may be selected from the group consisting of, without being limited thereto, cationic or polycationic compounds as defined above, from chitosan, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylaminob-D-glucopyranosyl)-N-octadecyl-dodecanoyl-amide hydroacetate); CALCITRIOL™ (1-alpha,25-dihydroxy-vitamin D3); calcium phosphate gel; CAP™ (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D35 glutamine (GMDP), ii) dimethyldioctadecylammonium chloride (DDA), iii) zinc-L-proline salt complex (ZnPro-8); (N-acetylglucosaminyl-(b1-4)-N-acetylmuramyl-L47 alanyl-D-GM-CSF); GMDP isoglutamine); imiquimod (1-(2-methylpropyl)-1H-imidazo[4,5-c]quinoline-4-amine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); inter-ferongamma; interleukin-1beta; interleukin-2; interleukin-7; interleukin-12; ISCOMS™; ISCOPREP 7.0.3.™; liposomes; LOXORIBINE™ (7-allyl-8-oxoguanosine); LT 5 oral adjuvant (*E. coli* labile enterotoxin-protoxin); microspheres and microparticles of any composition; MF59™; (squalenewater emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))ethylamide, monosodium salt); MURAMETIDE™ (Nac-Mur-L-Ala-D-Gln-OCH3); MURAPALMITINE™ and DMURAPALMITINE™ (Nac-Mur-L-Thr-D-isoGln-sn-glyceroldipalmitoyl); NAGO (neuraminidase-galactose oxidase); nanospheres or nanoparticles of any composition; NISVs (non-ionic surfactant vesicles); PLEURAN™ (-glucan); PLGA, PGA and PLA (homo- and co-polymers of lactic acid and glycolic acid; microspheres/nanospheres); PLURONIC L121™; PMMA (polymethylmethacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, AL); STIMULON™ (QS-21); Quil-A (Quil-A saponin); S-28463 (4-amino-otecdimethyl-2-ethoxymethyl-1H-imidazo[4,5-c]quinoline-1-ethanol); SAF-1™ ("Syntex adjuvant formulation"); Sendai proteoliposomes and Sendai-containing lipid matrices; Span-85 (sorbitan trioleate); Specol (emulsion of Marcol 52, Span 85 and Tween 85); squalene or Robane® (2,6,10,15, 19,23-hexamethyltetracosan and 2,6,10,15,19,23-hexamethyl-2,6,10,14,18,22-tetracosahexane); stearyltyrosine (octadecyltyrosine hydrochloride); Theramid® (N-acetylglucosaminyl-N-acetylmuramyl-L-Ala-D-isoGluL-Aladipalmitoxypropylamide); Theronyl-MDP (Termurtide™ or [thr 1]-MDP; N-acetylmuramyl-L-threonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adju-phos, Alhydrogel, Rehydragel; emulsions, including CFA, SAF, IFA, MF59, Provax, TiterMax, Montanide, Vaxfectin; copolymers, including Optivax (CRL1005), L121, Poloaxmer4010), etc.; liposomes, including Stealth, cochleates, including BIORAL; plant derived adjuvants, including QS21, Quil A, Iscomatrix, ISCOM; adjuvants suitable for costimulation including Tomatine, biopolymers, including PLG, PMM, Inulin, microbe derived adjuvants, including Romurtide, DETOX, MPL, CWS, Mannose, CpG nucleic acid sequences, CpG7909, ligands of human TLR 1-10, ligands of murine TLR 1-13, ISS-1018, 35 IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; and adjuvants suitable as antagonists including CGRP neuropeptide.

Particularly preferred, an adjuvant may be selected from adjuvants, which support induction of a Th1-immune response or maturation of naïve T-cells, such as GM-CSF, IL-12, IFNg, any RNA as defined herein, preferably an immunostimulatory RNA, CpG DNA, etc.

The inventive vaccine may additionally contain a further immunotherapeutic agent selected from immunoglobulins, preferably IgGs, monoclonal or polyclonal antibodies, polyclonal serum or sera, etc. Preferably, such a further immunotherapeutic agent may be provided as a peptide/protein or may be encoded by a nucleic acid, preferably by a DNA or an RNA, more preferably an mRNA. Such an immunostimulatory agent allows providing passive vaccination additional to active vaccination triggered by the mRNA encoded antigen of the inventive composition or vaccine composition.

The inventive vaccine can additionally contain one or more auxiliary substances in order to increase its immunogenicity or immunostimulatory capacity, if desired. A synergistic action of the inventive vaccine and of an auxiliary substance, which may be optionally contained in the vaccine or may be formulated with the inhibitor, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta or TNF-alpha, growth factors, such as hGH.

The inventive vaccine can also additionally contain any further compound, which is known to be immunostimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13, a ligand of a NOD-like receptor, or a ligand of a RIG-I like receptor.

In this context the inventive vaccine may also additionally contain an immunostimulatory nucleic acid, preferably an immunostimulatory RNA (isRNA), as defined above.

The inventive vaccine as defined according to the first embodiment of the present invention may furthermore comprise further additives or additional compounds. Further additives which may be included in the inventive vaccine are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

One further additive, which may be contained in the inventive vaccine, may be an antibacterial agent. In this context, any anti-bacterial agents known to one of skill in the art may be used in combination with the components of the inventive vaccine as defined herein. Non-limiting examples of anti-bacterial agents include Amikacin, Amoxicillin, Amoxicillin-clavulanic acid, Amphothericin-B, Ampicillin, Ampicllin-sulbactam, Apramycin, Azithromycin, Aztreonam, Bacitracin, Benzylpenicillin, Caspofungin, Cefaclor, Cefadroxil, Cefalexin, Cefalothin, Cefazolin, Cefdinir, Cefepime, Cefixime, Cefmenoxime, Cefoperazone, Cefoperazone-sulbactam, Cefotaxime, Cefoxitin, Cefbirome, Cefpodoxime, Cefpodoxime-clavulanic acid, Cefpodoxime-sulbactam, Cefbrozil, Cefquinome, Ceftazidime, Ceftibutin, Ceftiofur, Ceftobiprole, Ceftriaxon, Cefuroxime, Chloramphenicole, Florfenicole, Ciprofloxacin, Clarithromycin, Clinafloxacin, Clindamycin, Cloxacillin, Colistin, Cotrimoxazol (Trimthoprim/sulphamethoxazole), Dalbavancin, Dalfopristin/Quinopristin, Daptomycin, Dibekacin, Dicloxacillin, Doripenem, Doxycycline, Enrofloxacin, Ertapenem, Erythromycin, Flucloxacillin, Fluconazol, Flucytosin, Fosfomycin, Fusidic acid, Garenoxacin, Gatifloxacin, Gemifloxacin, Gentamicin, Imipenem, Itraconazole, Kanamycin, Ketoconazole, Levofloxacin, Lincomycin, Linezolid, Loracarbef, Mecillnam (amdinocillin), Meropenem, Metronidazole, Meziocillin, Mezlocillin-sulbactam, Minocycline, Moxifloxacin, Mupirocin, Nalidixic acid, Neomycin, Netilmicin, Nitrofurantoin, Norfloxacin, Ofloxacin, Oxacillin, Pefloxacin, Penicillin V, Piperacillin, Piperacillin-sulbactam, Piperacillin-tazobactam, Rifampicin, Roxythromycin, Sparfloxacin, Spectinomycin, Spiramycin, Streptomycin, Sulbactam, Sulfamethoxazole, Teicoplanin, Telavancin, Telithromycin, Temocillin, Tetracyklin, Ticarcillin, Ticarcillin-clavulanic acid, Tigecycline, Tobramycin, Trimethoprim, Trovafloxacin, Tylosin, Vancomycin, Virginiamycin, and Voriconazole.

Another additive, which may be contained in the inventive vaccine, may be an anti-viral agents, preferably, but are not limited to, nucleoside analogs (e.g., zidovudine, acyclovir, gangcyclovir, vidarabine, idoxuridine, trifluridine, and ribavirin), foscarnet, amantadine, peramivir, rimantadine, saquinavir, indinavir, ritonavir, alpha-interferons and other interferons, AZT, t-705, zanamivir (Relenza®), and oseltamivir (Tamiflu®). Other anti-viral agents include influenza virus vaccines, e.g., Fluarix® (Glaxo SmithKline), FluMist® (MedImmune Vaccines), Fluvirin® (Chiron Corporation), Flulaval® (GlaxoSmithKline), Afluria® (CSL Biotherapies Inc.), Agriflu® (Novartis) or Fluzone® (Aventis Pasteur).

The inventive vaccine typically comprises a "safe and effective amount" of the components of the inventive vaccine as defined herein. As used herein, a "safe and effective amount" preferably means an amount of the components, preferably of the at least one mRNA, that is sufficient to significantly induce a positive modification of a disease or disorder as defined herein. At the same time, however, a "safe and effective amount" is small enough to avoid serious side-effects and to permit a sensible relationship between advantage and risk. The determination of these limits typically lies within the scope of sensible medical judgment.

As defined according to the first embodiment, the inventive vaccine comprising at least one mRNA encoding at least one antigen may be used in the prophylaxis and treatment of a disease in an elderly patient preferably exhibiting an age of at least 50 years, more preferably of at least 55 years, 60 years, 65 years, 70 years, or older. In this context, an elderly patient is preferably a mammal, more preferably a human, even more preferably a human adult, likewise more preferably an elderly (adult) human patient exhibiting an age of at least 50 years, 55 years, 60 years, 65 years, 70 years, or older. The elderly patient may be male or female.

As furthermore defined in the first embodiment of the present invention, the treatment comprises vaccination of the patient and eliciting an immune response in said patient. In this context, vaccination typically occurs via administration of the inventive vaccine. Administration may occur parenterally, orally, nasally, pulmonary, by inhalation (e.g. via an aerosol or spray), topically, rectally, buccally, vaginally, or via an implanted reservoir. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques. Preferably, the inventive vaccine may be administered intradermally to reach APCs in the dermis. Likewise preferably, the inventive vaccine as defined herein may be administered orally in any orally acceptable dosage form including, but not limited to, capsules, tablets, aqueous suspensions or solutions. Likewise preferably, the inventive vaccine may be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive vaccine may be formulated in a suitable ointment, containing the inventive vaccine and optionally further components as defined herein suspended or dissolved in one or more carriers. Pulmonary administration can also be employed, e.g., by use of an inhaler or nebulizer, and formulation with an aerosolizing agent for use as a spray.

The inventive vaccine may be used in combination with other therapies, preferably with a therapy for a disease as defined herein, or further therapies. As used herein, the term "in combination," in the context of the administration of two or more therapies to an elderly patient as defined herein, refers to the use of more than one therapy, preferably two therapies or even more. The use of the term "in combination" does not restrict the order in which therapies are administered to an elderly patient as defined herein. For example, a first therapy (e.g., a first prophylactic or therapeutic agent) can be administered at any time prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to an elderly patient as defined herein. In some aspects, the one or more other therapies are conventional tumour therapies, surgery, chemotherapies, immunotherapies, gene therapies, pain treatments, anti-fever medications, therapies that alleviate or assist with breathing, other (active or passive) vaccinations/immunizations, antiviral therapies, antibacterial therapies, antifungal therapies, anti-parasite therapies, anti-allergic therapies etc.

In certain aspects, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart. In specific aspects, two or more therapies are administered within the same patient visit.

Exemplary doses for mRNAs encoding at least one antigen as defined herein may range, without being limited thereto, from about 10 ng to 1 g, 100 ng to 100 mg, 1 μg to 10 μg, or 30-300 μg mRNA per patient. Preferably, the inventive vaccine is formulated accordingly to comprise one dose, two doses, three or even more doses.

According to a specific aspect, the inventive vaccine may be administered to an elderly patient as a single dose. In certain aspects, the inventive vaccine may be administered to an elderly patient as a single dose followed by a second dose later and optionally even a third, fourth (or more) dose subsequent thereto etc. In accordance with this aspect, booster inoculations with the inventive vaccine may be administered to an elderly patient at specific time intervals, preferably as defined below, following the second (or third, fourth, etc.) inoculation. In certain aspects, such booster inoculations with the inventive vaccine may utilize an additional compound or component as defined for the inventive vaccine as defined herein. In some aspects, the administration of the same inventive vaccine and/or booster administrations may be repeated and such administrations may be separated by at least 1 day, 2 days, 3 days, 4 days, 5 days, 10 days, 15 days, 30 days, 45 days, 2 months, 75 days, e.g. 1 to 5 days, 1 to 10 days, 5 to 15 days, 10 to 20 days, 15 to 25 days, 20 to 30 days, 25 to 35 days, 30 to 50 days, 40 to 60 days, 50 to 70 days, 1 to 75 days, or 1 month, 2 months, 3 months, 4 months, 5 months, or at least 6, 7, 8, 9, 10, 11, 12 months, 18 months, 24 months, 30 months, 36 months, 1 year, 2 years, 3 years, 5 years, 10 years, 15 years, 20 years, 30 years, 40 years, 50 years, 60 years, or even more. In certain aspects, the inventive vaccine may be administered to a subject as a single dose once per year.

In particular aspects, the inventive vaccine may be administered to an elderly patient in the fall or winter, i.e., prior to or during the influenza season in each hemisphere. In one aspect, an elderly patient is administered his/her first dose early in the season, e.g., late September or early October, so that the second dose (if necessary) can be given prior to the peak of the influenza season.

In particular aspects, the inventive vaccine may be administered at least once, preferably twice or more to an elderly patient prior to a treatment of a disease as defined herein, preferably at least 1 day, 2 days, 3 days, 4 days, 5 days, 10 days, 15 days, 30 days, 45 days, 2 months, 75 days, e.g. 1 to 5 days, 1 to 10 days, 5 to 15 days, 10 to 20 days, 15 to 25 days, 20 to 30 days, 25 to 35 days, 30 to 50 days, 40 to 60 days, 50 to 70 days, 1 to 75 days, or 1 month, 2 months, 3 months, 4 months, 5 months, or at least 6, 7, 8, 9, 10, 11, or 12 months prior to a treatment of a disease as defined herein. A second or further dose may then be administered directly prior to treatment, concurrent with or subsequent to treatment.

Furthermore, a disease as defined according to the first embodiment of the present invention is any disease selected from infectious diseases, preferably (viral, bacterial or protozoological) infectious diseases, autoimmune diseases, or allergies or allergic diseases or cancer or tumour diseases.

Such diseases include cancer or tumour diseases, preferably selected from melanomas, malignant melanomas, colon carcinomas, lymphomas, sarcomas, blastomas, renal carcinomas, gastrointestinal tumours, gliomas, prostate tumours, bladder cancer, rectal tumours, stomach cancer, oesophageal cancer, pancreatic cancer, liver cancer, mammary carcinomas (=breast cancer), uterine cancer, cervical cancer, acute myeloid leukaemia (AML), acute lymphoid leukaemia (ALL), chronic myeloid leukaemia (CML), chronic lymphocytic leukaemia (CLL), hepatomas, various virus-induced tumours such as, for example, papilloma virus-induced carcinomas (e.g. cervical carcinoma=cervical cancer), adenocarcinomas, herpes virus-induced tumours (e.g. Burkitt's lymphoma, EBV-induced B-cell lymphoma), hepatitis B-induced tumours (hepatocell carcinomas), HTLV-1- and HTLV-2-induced lymphomas, acoustic neuroma, lung carcinomas (=lung cancer=bronchial carcinoma), small-cell lung carcinomas, pharyngeal cancer, anal carcinoma, glioblastoma, rectal carcinoma, astrocytoma, brain tumours, retinoblastoma, basalioma, brain metastases, medulloblastomas, vaginal cancer, pancreatic cancer, testicular cancer, Hodgkin's syndrome, meningiomas, Schneeberger disease, hypophysis tumour, Mycosis fungoides, carcinoids, neurinoma, spinalioma, Burkitt's lymphoma, laryngeal cancer, renal cancer, thymoma, corpus carcinoma, bone cancer, non-Hodgkin's lymphomas, urethral cancer, CUP syndrome, head/neck tumours, oligodendroglioma, vulval cancer, intestinal cancer, colon carcinoma, oesophageal carcinoma (=oesophageal cancer), wart involvement, tumours of the small intestine, craniopharyngeomas, ovarian carcinoma, genital tumours, ovarian cancer (=ovarian carcinoma), pancreatic carcinoma (=pancreatic cancer), endometrial carcinoma, liver metastases, penile cancer, tongue cancer, gall bladder cancer, leukaemia, plasmocytoma, lid tumour, prostate cancer (=prostate tumours), etc.

According to one further specific aspect, diseases as defined herein comprise infectious diseases, preferably (viral, bacterial or protozoological) infectious diseases. Such infectious diseases, preferably viral, bacterial or protozoological infectious diseases, are typically selected from viral infectious diseases such as influenza, preferably influenza A, influenza B, influenza C or thogotovirus, more preferably influenza A comprising e.g. haemagglutinin subtypes H1, H2, H3, H4, H5, H6, H7, H8, H9, H10, H11, H12, H13, H14 or H15, and/or neuraminidase subtypes N1, N2, N3, N4, N5, N6, N7, N8 or N9, or preferably influenza-A subtypes H1N1, H1N2, H2N2, H2N3, H3N1, H3N2, H3N3, H5N1, H5N2, H7N7 or H9N2, etc., or any further combination, malaria, severe acute respiratory syndrome (SARS), yellow fever, AIDS, Lyme borreliosis, Leishmaniasis, anthrax, meningitis, Condyloma acuminata, hollow warts, Dengue fever, three-day fever, Ebola virus, cold, early summer meningoencephalitis (FSME), shingles, hepatitis, herpes simplex type I, herpes simplex type II, Herpes zoster, human herpes virus 8 (HHV-8; Kaposi-Sarcoma-herpesvirus (KSHV)); Human Papilloma virus infection, Japanese encephalitis, Arenavirus-associated diseases (Lassa fever infection), Marburg virus, measles, foot-and-mouth disease, mononucleosis infectiosa (Pfeiffer's glandular fever), mumps, Norwalk virus infection, smallpox, polio (childhood lameness), pseudo-croup, Erythema infectiosum (fifth disease), rabies, warts, West Nile fever, chickenpox, cytomegalic virus (CMV), bacterial infectious diseases such as miscarriage (prostate inflammation), anthrax, appendicitis, borreliosis, botulism, Camphylobacter, *Chlamydia trachomatis* (inflammation of the urethra, conjunctivitis), cholera, diphtheria, donavanosis, epiglottitis, typhus fever, gas gangrene, gonorrhoea, rabbit fever, *Heliobacter pylori*, whooping cough, climatic bubo, osteomyelitis, Legionnaire's disease, leprosy, listeriosis, pneumonia, meningitis, bacterial meningitis, anthrax, otitis media, *Mycoplasma hominis*, neonatal sepsis (Chorioamnionitis), noma, paratyphus, plague, Reiter's syndrome, Rocky Mountain spotted fever, *Salmonella paratyphus, Salmonella typhus*, scarlet fever, syphilis, tetanus, tripper, tsutsugamushi disease, tuberculosis, typhus, vaginitis (colpitis), soft chancre, and infectious diseases caused by parasites, protozoa or fungi, such as amoebiasis, bilharziosis, Chagas disease, *Echinococcus*, fish tapeworm, fish poisoning (Ciguatera), fox tapeworm, athlete's foot, canine tapeworm, candidosis, yeast fungus spots, scabies, cutaneous Leishmaniosis, lambliasis (giardiasis), lice, malaria, microscopy, onchocercosis (river blindness), fungal diseases, bovine tapeworm, schistosomiasis, porcine tapeworm, toxoplasmosis, trichomoniasis, trypanosomiasis (sleeping sickness), visceral Leishmaniosis, nappy/diaper dermatitis or miniature tapeworm.

According to another specific aspect, diseases as defined herein comprise autoimmune diseases as defined in the following. Autoimmune diseases can be broadly divided into systemic and organ-specific or localised autoimmune disorders, depending on the principal clinico-pathologic features of each disease. Autoimmune diseases may be divided into the categories of systemic syndromes, including systemic lupus erythematosus (SLE), Sjögren's syndrome, Scleroderma, Rheumatoid Arthritis and polymyositis or local syndromes which may be endocrinologic (type I diabetes (Diabetes mellitus Type 1), Hashimoto's thyroiditis, Addison's disease etc.), dermatologic (pemphigus vulgaris), haematologic (autoimmune haemolytic anaemia), neural (multiple sclerosis) or can involve virtually any circumscribed mass of body tissue. The autoimmune diseases to be treated may be selected from the group consisting of type I autoimmune diseases or type II autoimmune diseases or type Ill autoimmune diseases or type IV autoimmune diseases, such as, for example, multiple sclerosis (MS), rheumatoid arthritis, diabetes, type I diabetes (Diabetes mellitus Type 1), chronic polyarthritis, Basedow's disease, autoimmune forms of chronic hepatitis, colitis ulcerosa, type I allergy diseases, type II allergy diseases, type III allergy diseases, type IV allergy diseases, fibromyalgia, hair loss, Bechterew's disease, Crohn's disease, Myasthenia gravis, neurodermitis, Polymyalgia rheumatica, progressive systemic sclerosis (PSS), Reiter's syndrome, rheumatic arthritis, psoriasis, vasculitis, etc, or type II diabetes. While the exact mode as to why the immune system induces an immune reaction against autoantigens has not been elucidated so far, there are several findings with regard to the etiology. Accordingly, the autoreaction may be due to a T cell bypass. A normal immune system requires the activation of B cells by T cells before the former can produce antibodies in large quantities. This requirement of a T cell can be by-passed in rare instances, such as infection by organisms producing superantigens, which are capable of initiating polyclonal activation of B cells, or even of T cells, by directly binding to the ß-subunit of T cell receptors in a non-specific fashion. Another explanation deduces autoimmune diseases from a "Molecular Mimicry": an exogenous antigen may share structural similarities with certain host antigens; thus, any antibody produced against this antigen (which mimics the self-antigens) can also, in theory, bind to the host antigens and amplify the immune response. Autoimmune diseases based on molecular mimicry are known to a skilled person for various viral and bacterial antigens. The most striking form of molecular mimicry is observed in Group A beta-haemolytic streptococci, which shares antigens with human myocardium, and is responsible for the cardiac manifestations of rheumatic fever.

Additionally, according to one further specific aspect, diseases as defined herein comprise allergies or allergic diseases, i.e. diseases related to allergies. Allergy is a condition that typically involves an abnormal, acquired immunological hypersensitivity to certain foreign antigens or allergens, such as the allergy antigens as defined herein. Such allergy antigens or allergens may be selected from allergy antigens as defined herein antigens derived from different sources, e.g. from animals, plants, fungi, bacteria, etc. Allergens in this context include e.g. danders, grasses, pollens, molds, drugs, or numerous environmental triggers, etc. Allergies normally result in a local or systemic inflammatory response to these antigens or allergens and lead to immunity in the body against these allergens. Without being bound to theory, several different disease mechanisms are supposed to be involved in the development of allergies. According to a classification scheme by P. Gell and R. Coombs the word "allergy" was restricted to type I hypersensitivities, which are caused by the classical IgE mechanism. Type I hypersensitivity is characterised by excessive activation of mast cells and basophils by IgE, resulting in a systemic inflammatory response that can result in symptoms as benign as a runny nose, to life-threatening anaphylactic shock and death. Well known types of allergies include, without being limited thereto, asthma, allergic asthma (leading to swelling of the nasal mucosa), allergic conjunctivitis (leading to redness and itching of the conjunctiva), allergic rhinitis ("hay fever"), anaphylaxis, angiodema, atopy, atopic dermatitis (eczema), urticaria (hives), eosinophilia, respiratory, allergies to insect stings, skin allergies (leading to and including various rashes, such as eczema, hives (urticaria) and (contact) dermatitis), food allergies, allergies to medicine, etc.; etc. Treatment of such allergic disorders or diseases may occur preferably by desensitizing the immune reaction which triggers a specific immune response. Such a desensitizing may be carried out by administering an effective amount of the allergen or allergic antigen encoded by the nucleic acid as defined herein, preferably, when formulated as a pharmaceutical composition, to induce a slight immune reaction. The amount of the allergen or allergic antigen may then be raised step by step in subsequent administrations until the immune system of the patient to be treated tolerates a specific amount of allergen or allergic antigen.

Diseases in the context of the present invention may also include type II hypersensitivity reactions (cytotoxic, antibody-dependent), including e.g. autoimmune hemolytic anemia, thrombocytopenia, erythroblastosis fetalis, Goodpasture's syndrome, Graves' disease, Myasthenia Gravis, etc.; type Ill hypersensitivity reactions (immune complex disease), including e.g. serum sickness, Arthus reaction, Systemic lupus erythematosus (SLE), etc.; type IV hypersensitivity reactions (delayed-type hypersensitivity (DTH), cell-mediated immune memory response, antibody-independent), including e.g. contact dermatitis, Mantoux test, chronic transplant rejection, multiple sclerosis, etc.; and type V hypersensitivity reactions (receptor mediated autoimmune disease), including e.g. Graves' disease, Myasthenia Gravis, etc.;

In a further preferred embodiment, the inventive vaccine may be formulated as a kit, preferably as a kit of part. Accordingly, the present invention also provides kits, particularly kits of parts, comprising the components of the inventive vaccine either alone or in combination with further ingredients as defined above, and optionally technical instructions with information on the administration and dosage of the inventive vaccine. The components of the inventive vaccine either alone or in combination with further ingredients as defined above may be contained in the kit in either one part of the kit or in different parts of the kit, e.g. each at least one mRNA encoding at least one antigen as defined above in one part of the kit, and preferably further components admixed to the each at least one mRNA encoding at least one antigen or separately in a further part of the kit. Such kits, preferably kits of parts, may be applied, e.g., for any of the above mentioned applications or uses.

In the present invention, if not otherwise indicated, different features of alternatives and embodiments may be combined with each other, where suitable. Furthermore, the term "comprising" shall not be construed as meaning "consisting of", if not specifically mentioned. However, in the context of the present invention, term "comprising" may be substituted with the term "consisting of", where suitable.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

FIGURES

The following Figures are intended to illustrate the invention further. They are not intended to limit the subject matter of the invention thereto.

FIGS. 1A, B: show the result of the vaccination of 18 months or 8 weeks old mice. The mice were vaccinated twice intradermally with 80 μg mRNA coding for PR8 H1 HA (Hemagglutinin of influenza virus A/Puerto Rico/8/1934) or with mRNA coding for *Gallus gallus* ovalbumine as a control (control mRNA). Injections were done with an interval of 7 days. 5 weeks after the last vaccination the mice were challenged with a 10fold lethal dose of PR8 virus (10 LD50). The weight of the mice was controlled over 2 weeks and the mice were killed when they have lost more than 25% of their original weight. FIG. 1A shows the overall survival of the mice. FIG. 1B shows the weight of the mice.

FIGS. 1 C, D: show the coding sequence of the mRNAs used for vaccination of 18 months or 8 weeks old mice (see FIGS. 1A, B) coding for PR8 H1 HA (Hemagglutinin of influenza virus A/Puerto Rico/8/1934) (SEQ ID NO: 384) (FIG. 2C) or for *Gallus gallus* ovalbumine as a control (control mRNA) (SEQ ID NO: 385) (FIG. 2D)

FIGS. 2A, B: show the results of the vaccination of 32 patients with an age between 52 and 74 with histologically confirmed diagnosis of adenocarcinoma of the prostate. These patients were vaccinated intradermally 5 times with a total of 1280 μg mRNA per treatment coding for the tumour antigens PSA, PSCA, PSMA, and STEAP-1. Injections were done in study weeks 1, 3, 7, 15, and 23.2 weeks after the 3rd, 4th, and 5th vaccination blood samples of the patients were collected and analysed for the presence of an antigen specific immune response against the tumour antigens PSA, PSCA, PSMA and STEAP-1. As can be seen, patients older than 70 shows at least the same efficiency in generation of an antigen specific immune response as patients younger than 70. In FIG. 2B antigens against which a specific immune response was detected by ELISPOT, Tetramer staining, Intracellular Cytokine Staining (ICS) or ELISA are indicated for each patient included in the study.

FIGS. 2 C-F: show the coding sequence of the mRNAs used for vaccination of 32 patients with an age between 52 and 74 with histologically confirmed diagnosis (see FIGS. 2A, B). The mRNA sequences code for the tumour antigens PSA, PSMA, PSCA, STEAP-1 (SEQ ID NOS: 386, 387, 388 and 389).

EXAMPLES

The following examples are intended to illustrate the invention further. They are not intended to limit the subject matter of the invention thereto.

Example 1—Preparation of mRNA Constructs

For the present examples DNA sequences, encoding PR8 H1 HA (Haemagglutinin of A/Puerto Rico/8/1934) (SEQ ID NO: 384), and *Gallus gallus* ovalbumine, respectively, as a control (control mRNA) (SEQ ID NO: 385), were prepared and used for subsequent in vitro transcription reactions.

According to a first preparation, the DNA sequence termed PR8 H1 HA (Haemagglutinin of A/Puerto Rico/8/1934) (SEQ ID NO: 384) (see FIG. 1C) was prepared by modifying the wildtype Haemagglutinin encoding DNA sequence by introducing a GC-optimized sequence for a better codon usage and stabilization. In SEQ ID NO: 384 (see FIG. 1C) the sequence of the corresponding mRNA is shown. The sequence was furthermore introduced into a pCV19 vector and modified to comprise stabilizing sequences derived from alpha-globin-3'-UTR (muag (mutated alpha-globin-3'-UTR)), a stretch of 70× adenosine at the 3'-terminal end (poly-A-tail) and a stretch of 30× cytosine at the 3'-terminal end (poly-C-tail). The sequence of the final DNA construct was termed "PR8 H1 HA".

According to a second preparation, the DNA sequence termed *Gallus gallus* ovalbumine, respectively, as a control (control mRNA) (SEQ ID NO: 385) (see FIG. 1D) was prepared by modifying the wildtype *Gallus gallus* ovalbumine encoding DNA sequence by introducing a GC-optimized sequence for a better codon usage and stabilization. In SEQ ID NO: 385 (see FIG. 1D) the sequence of the corresponding mRNA is shown. The sequence was furthermore introduced into a pCV19 vector and modified to comprise stabilizing sequences derived from alpha-globin-3'-UTR (muag (mutated alpha-globin-3'-UTR)), a stretch of 70× adenosine at the 3'-terminal end (poly-A-tail) and a stretch of 30× cytosine at the 3'-terminal end (poly-C-tail). The sequence of the final DNA construct was termed "*Gallus gallus* ovalbumine".

Likewise, DNA plasmids coding for the tumour antigens PSA, PSMA, PSCA, STEAP-1 were prepared. In SEQ ID NOs: 386, 387, 388 and 389, the sequence of the corresponding mRNAs are shown (see also FIGS. 2 C-F).

In a further step, the respective DNA plasmids prepared above were transcribed into mRNA in vitro using T7-Polymerase. Subsequently the obtained mRNA was purified using PureMessenger® (CureVac, Tübingen, Germany).

All obtained mRNAs used herein were furthermore complexed with protamine prior to use. The RNA complexation consisted of a mixture of 50% free mRNA and 50% mRNA complexed with protamine at a weight ratio of 2:1. First, mRNA was complexed with protamine by slow addition of protamine-Ringer's lactate solution to mRNA. As soon as the complexes were stably generated, free mRNA was added, stirred shortly and the final concentration of the vaccine was adjusted with Ringer's lactate solution.

Example 2—Vaccination of 18 Months or 8 Weeks Old Mice

In this experiment 18 months or 8 weeks old mice were vaccinated twice intradermally with 80 µg mRNA coding for PR8 H1 HA (Hemagglutinin of A/Puerto Rico/8/1934; FIG. 1C) or with mRNA coding for *Gallus gallus* ovalbumine as a control (control mRNA; FIG. 1D). Injections were done with an interval of 7 days. 5 weeks after the last vaccination the mice were challenged with a 10fold lethal dose of PR8 virus (10 LD50). The weight of the mice was controlled over 2 weeks and the mice were killed when they have lost more than 25% of their original weight. The results are shown in FIGS. 1A and B. FIG. 1A shows the overall survival of the mice. FIG. 1B shows the weight of the mice. As can be seen in FIG. 1A, mice vaccinated with mRNA coding for PR8 H1 Hemagglutinin exhibited a significantly better survival (all mice survived) against influenza challenge infection with control mRNA only (all mice died about 7 days subsequent to vaccination with control mRNA encoding chicken ovalbumin, when vaccinated with 8 weeks and died about 9 days subsequent to vaccination with control mRNA, when vaccinated with 18 months).

Example 3—Vaccination of Human Prostate Carcinoma Patients

In this experiment 32 patients with an age between 52 and 74 with histologically confirmed diagnosis of adenocarcinoma of the prostate were vaccinated intradermally 5 times with a total of 1280 µg mRNA per treatment coding for the tumour antigens PSA, PSCA, PSMA, STEAP-1. Injections were done in study weeks 1, 3, 7, 15, and 23. 22 weeks after the 3rd, 4th, and 5th vaccination blood samples of the patients were collected and analysed for the presence of an antigen specific immune response against the tumour antigens PSA, PSCA, PSMA and STEAP-1. The results are shown in FIGS. 2A and 2B. As can be seen in FIG. 2A, patients older than 70 show at least the same efficiency in generation of an antigen specific immune response as patients younger than 70. In FIG. 2B antigens against which a specific immune response was detected by ELISPOT, Tetramer staining, Intracellular Cytokine Staining (ICS) or ELISA are indicated for each patient included in the study.

The invention claimed is:

1. A method for stimulating a protective anti-influenza immune response in a patient, the method comprising administering an effective amount of a composition comprising at least two RNA molecules, wherein the RNA molecules encode influenza haemagglutinin (HA) antigens from at least three different strains of influenza, wherein the RNA comprises a G/C content in the coding sequence that is elevated relative to wild type RNA encoding the HA antigen, wherein the method stimulates a protective immune response in the patient, wherein said protective immune response in the patient comprises an enhanced T cell-mediated immune response as compared to an inactivated influenza vaccine, and wherein the enhanced T cell-mediated immune response is a CD8+ T cell-mediated immune response.

2. The method of claim 1, wherein the composition is administered by intradermal or intramuscular injection.

3. The method of claim 1, wherein the HA antigens are each independently a H2, H3, H4, H5, H6, H7, H8, H9, H10, H11, H12, H13, H14 or H15 subtype.

4. The method of claim 1, wherein at least one of the HA antigens is a H1 subtype.

5. The method of claim 1, further comprising administering an effective amount of a composition comprising an RNA encoding at least a second influenza antigen.

6. The method of claim 5, wherein the at least a second influenza antigen is an influenza neuraminidase, matrix protein, or nucleoprotein antigen.

7. The method of claim 5, comprising administering an RNA encoding an influenza haemagglutinin (HA) antigen and an RNA encoding an influenza neuraminidase (NA) antigen.

8. The method of claim 7, comprising administering RNAs encoding HA antigens and NA antigens from at least one H1N1 strain, at least one H3N2 strain, and at least one Influenza B strain.

9. The method of claim 1, wherein the RNA molecules each comprise at least one nucleotide substituted with an analog of the naturally occurring nucleotide.

10. The method of claim 8, wherein the at least one nucleotide substituted with an analog of the naturally occurring nucleotide comprises a backbone modification, a sugar modification, or a base modification.

11. The method of claim 1, wherein the RNA molecules are mRNA molecules and comprise a 5' cap structure.

12. The method of claim 11, wherein the mRNA molecules further comprise a poly-A sequence positioned 3' of the coding region.

13. The method of claim 12, wherein the mRNA molecules comprise a 5' nontranslated region and/or a 3' nontranslated region.

14. The method of claim 12, wherein the mRNA molecules comprise at least three of the following features:
 (i) a 5' cap structure;
 (ii) a 5' non-translated region;
 (iii) a 3' non-translated region;
 (iv) a poly-A positioned 3' of the coding region; and
 (v) optionally, a poly-C sequence positioned 3' of the coding region.

15. The method of claim 12, wherein the HA antigens from at least four three different strains of influenza comprise an HA antigen from at least one H1N1 strain and an HA antigen from at least one H3N2 strain.

16. The method of claim 12, wherein the HA antigens from at least four three different strains of influenza comprise an HA antigen from at least one Influenza A strain and an HA antigen from at least one Influenza B strain.

17. The method of claim 16, wherein the HA antigens from at least four three different strains of influenza comprise HA antigens from at least one H1N1 strain, at least one H3N2 strain, and at least one Influenza B strain.

18. The method of claim 12, wherein the mRNA molecules are associated with a vehicle, transfection, or complexation agent suitable for increasing the transfection efficiency of the mRNA molecules.

19. The method of claim 18, wherein the vehicle, transfection, or complexation agent comprises cationic or polycationic compounds selected from cationic or polycationic peptides or polypeptides, cationic or polycationic polymers, or cationic or polycationic lipids.

20. The method of claim 18, wherein the vehicle, transfection, or complexation agent are lipid particles.

21. The method of claim 18, wherein the vehicle, transfection, or complexation agent is protamine.

22. The method of claim 1, wherein the RNA molecules comprise a G/C content in the coding sequence that is increased at least 7% relative to a wild type mRNA encoding the HA antigen.

23. The method of claim 1, further comprising administering the composition at least two times.

24. The method of claim 1, wherein each of the influenza HA antigens is encoded on a separate RNA molecule.

* * * * *